United States Patent
Zhou et al.

(10) Patent No.: US 10,577,346 B2
(45) Date of Patent: Mar. 3, 2020

(54) BENZOBICYCLOALKANE DERIVATIVES, THEIR PREPARATION AND PHARMACEUTICAL USE THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Fusheng Zhou, Shanghai (CN); Shuchun Guo, Shanghai (CN); Jinzhu Zhao, Shanghai (CN); Hui Xu, Shanghai (CN); Xia Shi, Shanghai (CN); Yi Hu, Shanghai (CN); Yufeng Li, Shanghai (CN); Jiong Lan, Shanghai (CN)

(73) Assignees: SHANGHAI HAIYAN PHARMACEUTICAL TECHNOLOGY CO., LTD. (CN); YANGTZE RIVER PHARMACEUTICAL GROUP CO., LTD. (CN)

( * ) Notice: Subject to any disclaimer, the term of this patent is extended or adjusted under 35 U.S.C. 154(b) by 0 days.

(21) Appl. No.: 16/308,790

(22) PCT Filed: Nov. 17, 2017

(86) PCT No.: PCT/CN2017/111684
§ 371 (c)(1),
(2) Date: Dec. 10, 2018

(87) PCT Pub. No.: WO2018/090982
PCT Pub. Date: May 24, 2018

(65) Prior Publication Data
US 2019/0161468 A1 May 30, 2019

(30) Foreign Application Priority Data
Nov. 17, 2016 (CN) .......................... 2016 1 1027675

(51) Int. Cl.
| | | |
|---|---|---|
| C07D 401/04 | (2006.01) |
| C07D 205/04 | (2006.01) |
| C07D 207/12 | (2006.01) |
| C07D 207/08 | (2006.01) |
| C07D 305/08 | (2006.01) |
| C07D 295/10 | (2006.01) |
| C07C 271/44 | (2006.01) |
| C07C 271/50 | (2006.01) |
| A61P 25/04 | (2006.01) |
| C07D 305/06 | (2006.01) |

(52) U.S. Cl.
CPC ............ *C07D 401/04* (2013.01); *A61P 25/04* (2018.01); *C07C 271/44* (2013.01); *C07C 271/50* (2013.01); *C07D 205/04* (2013.01); *C07D 207/08* (2013.01); *C07D 207/12* (2013.01); *C07D 295/10* (2013.01); *C07D 305/06* (2013.01); *C07D 305/08* (2013.01); *C07C 2603/80* (2017.05)

(58) Field of Classification Search
CPC .............................. C07D 401/04; A61P 25/04
See application file for complete search history.

(56) References Cited

U.S. PATENT DOCUMENTS

| | | |
|---|---|---|
| 3,976,696 A | 8/1976 | Freed et al. |
| 3,979,434 A | 9/1976 | Freed et al. |
| 4,001,331 A | 1/1977 | Freed et al. |
| 4,540,806 A | 9/1985 | Freed et al. |
| 2012/0165520 A1 | 6/2012 | McGee et al. |

FOREIGN PATENT DOCUMENTS

| | | |
|---|---|---|
| WO | 2011/007247 A1 | 1/2011 |
| WO | 2011/083304 A1 | 7/2011 |

OTHER PUBLICATIONS

International Search Report for PCT/CN2017/111684, dated Feb. 14, 2018, 3 pages.

*Primary Examiner* — Golam M Shameem
(74) *Attorney, Agent, or Firm* — Adsero IP

(57) ABSTRACT

It is provided herein a benzobicycloalkane derivative, and a preparation method and use thereof. In particular, it is provided herein a compound of Formula (I), or a pharmaceutically acceptable salt, stereoisomer or solvate thereof, a preparation method, and a use thereof in preparation of drugs for treating pain.

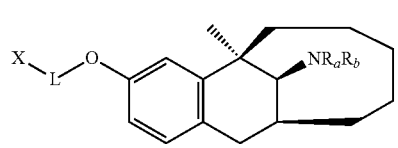

(I)

19 Claims, No Drawings

BENZOBICYCLOALKANE DERIVATIVES, THEIR PREPARATION AND PHARMACEUTICAL USE THEREOF

CROSS-REFERENCE TO RELATED APPLICATION

This application claims priority to and is a 35 U.S.C. § 371 national phase application of PCT/CN2017/111684 (WO 2018/090982 A1), filed on Nov. 17, 2017 entitled "BENZODICYCLOALKANE DERIVATIVE, PREPARATION METHOD AND USE THEREOF", which application claims priority to and the benefit of Chinese Application CN 201611027675.0 filed Nov. 17, 2016; the disclosures of which are incorporated herein by reference in their entirety.

TECHNICAL FIELD

The present disclosure relates to the field of medical technology, in particular to benzo bicycloalkane derivatives, preparation methods, and applications thereof as analgesic drugs, as well as pharmaceutical compositions and medical compositions prepared therefrom.

BACKGROUND

Pain is a most common clinical condition and most disturbing symptom for patients, especially for postoperative patients and patients suffering from chronic paining diseases or cancer. Postoperative analgesia currently is still dominated by opioid analgesics alone, with high incidences of respiratory depression, nausea, vomiting, pruritus and other complications, which add new concerns to patients with postoperative analgesia.

In recent years, dezocine has been widely used both at home and abroad as a novel mixed agonistic antagonist of opioid receptor. It has a good analgesic effect and less adverse reactions. Dezocine is an artificially synthesized compound having a benzobicycloalkane structure and is a mixed opioid receptor agonist-antagonist. Dezocine reduces the incidence of respiratory depression and addiction with extremely weak activity on δ opioid receptor and thus no irritability and anxiety. Therefore, it is widely used in clinical postoperative analgesia.

However, one of the main disadvantages of dezocine is poor oral bioavailability (no greater than 5%), which leads to the current use of dezocine as an injection form. Another disadvantage of dezocine is small administration window, with no obvious effect at low doses and enhanced effect yet also significantly increased risk of adverse reactions as the dose is gradually increased. Therefore, in order to ensure a stable dosing concentration, it is typically a perfusion administration in clinical practice. However, the injections are not only inconvenient, but also have a short onset time of about 2-3 hours, after which the plasma concentration drops below the effective level and the drug effect disappears. In addition, large doses increase clinically risk of respiratory depression, nausea, vomiting, pruritus and other adverse reactions due to fast elimination of plasma concentration.

Therefore, it is of great necessity to develop novel dezocine analogues to increase oral bioavailability, prolong onset time, maintain constant plasma concentrations, reduce clinical adverse reactions, and provide better drug selection and better compliance for clinical patients.

SUMMARY OF THE INVENTION

One object of the present disclosure is to provide a class of dezocine analogs with novel structures, and their preparation methods and uses.

In a first aspect, the present disclosure provides a compound represented by Formula (I), or a pharmaceutically acceptable salt, solvate, or stereoisomer thereof:

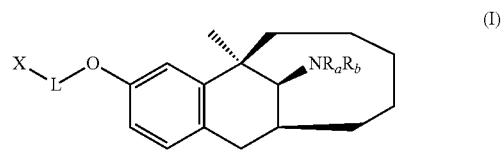

wherein,

L is —CO— or —(C($R_4R_5$)$_2$)$_k$—; k is 1, 2 or 3;

X is —N($R_1R_2$), —O$R_3$ or —CH$_2$O—(CH$_2$)$_r$—O)$_t$—CH$_3$; r is 2, 3 or 4; t is 1, 2, 3, 4, 5, 6, 7, 8 or 9;

$R_a$, $R_b$ are each independently hydrogen, methyl, —CHO, —C(O)OC$_{1-10}$ alkyl (preferably —C(O)OC$_{1-6}$ alkyl, more preferably —C(O)OC$_{1-3}$ alkyl) or —C(O)C$_{1-10}$ alkyl (preferably —C(O)C$_{1-6}$ alkyl, more preferably —C(O)C$_{1-3}$ alkyl);

$R_4$, $R_5$ are each independently hydrogen or methyl;

$R_1$, $R_2$ are each independently hydrogen, C$_{1-10}$ alkyl (preferably C$_{1-6}$ alkyl, more preferably C$_{1-3}$ alkyl), C$_{3-8}$ cycloalkyl (preferably C$_{3-6}$ cycloalkyl), C$_{6-10}$ aryl (preferably phenyl), 5 to 6 membered single heteroaryl ring (preferably pyridine), 4 to 6 membered saturated single heterocycle, spiro, spiroheterocycle, bridged ring, bridged heterocycle or —((CH$_2$)$_n$—O)$_m$—CH$_3$; wherein n is 2, 3 or 4; m is 1, 2, 3, 4, 5, 6, 7, 8 or 9;

or $R_1$, $R_2$, together with the nitrogen atom to which they are attached, form a 4 to 6 membered saturated single heterocycle; and $R_3$ is C$_{1-10}$ alkyl (preferably C$_{1-6}$ alkyl, more preferably C$_{1-3}$ alkyl), C$_{3-8}$ cycloalkyl (preferably C$_{3-6}$ cycloalkyl), —((CH$_2$)$_p$—O)$_q$—CH$_3$, —C(O)O—((CH$_2$)$_p$—O)$_q$—CH$_3$, —C(O)OC$_{1-10}$ alkyl (preferably —C(O)OC$_{1-6}$ alkyl, more preferably —C(O)OC$_{1-3}$ alkyl), —C(O)OC$_{3-8}$ cycloalkyl (preferably —C(O)OC$_{3-6}$ cycloalkyl), —C(O)C$_{1-10}$ alkyl (preferably —C(O)C$_{1-6}$ alkyl, more preferably —C(O)C$_{1-3}$ alkyl); wherein p is 2, 3 or 4; q is 1, 2, 3 or 4.

The alkyl, cycloalkyl, alkoxy, alkynyl, aryl, 4 to 6 membered saturated single heterocycle, 5 to 6 membered single heteroaryl ring, spiro, spiroheterocycle, bridged ring, bridged heterocycle are unsubstituted or substituted with 1, 2 or 3 substituents selected from the group consisting of NR$_{a0}$R$_{b0}$, halogen, acetyl, hydroxy, hydroxymethyl, hydroxyethyl, carboxyl, C$_{1-8}$ alkyl (preferably C$_{1-6}$ alkyl, more preferably C$_{1-3}$ alkyl), C$_{1-8}$ alkoxy (preferably C$_{1-6}$ alkoxy, more preferably C$_{1-3}$ alkoxy), halogenated C$_{1-8}$ alkyl (preferably halogenated C$_{1-6}$ alkyl, more preferably halogenated C$_{1-3}$ alkyl), C$_{3-8}$ cycloalkyl (preferably C$_{3-6}$ cycloalkyl), C$_{3-8}$ cycloalkoxy (preferably C$_{3-6}$ cycloalkoxy), C$_{2-10}$ alkenyl (preferably C$_{2-6}$ alkenyl, more preferably C$_{2-4}$ alkenyl), C$_{2-10}$ alkynyl (preferably C$_{2-6}$ alkynyl, more preferably C$_{2-4}$ alkynyl), halogenated C$_{1-8}$ alkoxy (preferably halogenated C$_{1-6}$ alkoxy, more preferably halogenated C$_{1-3}$ alkoxy), C$_{6-10}$ aryl, 4 to 6 membered saturated single heterocycle, —C(O)C$_{1-10}$ alkyl (preferably —C(O)C$_{1-6}$ alkyl, more preferably —C(O)C$_{1-3}$ alkyl), —C(O)C$_{1-10}$ alkyl (preferably —C(O)OC$_{1-6}$ alkyl, more preferably —C(O)OC$_{1-3}$ alkyl), —OC(O)C$_{1-10}$ alkyl (preferably —OC(O)C$_{1-6}$ alkyl, more preferably —OC(O)C$_{1-3}$ alkyl), —CONR$_{a0}$R$_{b0}$; R$_{a0}$, R$_{b0}$ are each independently hydrogen, C$_{1-8}$ alkyl (preferably C$_{1-6}$ alkyl, more preferably C$_{1-3}$ alkyl), C$_{1-8}$ alkyl substituted with C$_{1-8}$ alkoxy (preferably C$_{1-6}$ alkyl substituted with C$_{1-6}$ alkoxy, more preferably C$_{1-3}$ alkyl substituted with C$_{1-3}$ alkoxy).

In another preferred example, R$_a$, R$_b$ are hydrogen. In another preferred example, R$_1$ is hydrogen, C$_{1-10}$ alkyl (preferably C$_{1-6}$ alkyl, more preferably C$_{1-3}$ alkyl), C$_{3-8}$ cycloalkyl (preferably C$_{3-6}$ cycloalkyl) or —((CH$_2$)$_{n1}$—O)$_{m1}$—CH$_3$;

R$_2$ is C$_{1-10}$ alkyl (preferably C$_{1-6}$ alkyl, more preferably C$_{1-3}$ alkyl), C$_{3-8}$ cycloalkyl (preferably C$_{3-6}$ cycloalkyl), C$_{6-10}$ aryl (preferably phenyl), 5 to 6 membered single heteroaryl ring (preferably pyridine), 4 to 6 membered saturated single heterocycle, spiro, spiroheterocycle, bridged ring, bridged heterocycle or —((CH$_2$)$_{n2}$—O)$_{m2}$—CH$_3$; wherein n1, n2 are each independently 2, 3 or 4; m1, m2 are each independently 1, 2, 3, 4, 5, 6, 7, 8 or 9;

or R$_1$, R$_2$, together with the nitrogen atom to which they are attached, form a 4 to 6 membered saturated single heterocycle; and the alkyl, cycloalkyl, aryl, 4 to 6 membered saturated single heterocycle, 5 to 6 membered single heteroaryl ring, spiro, spiroheterocycle, bridged ring, bridged heterocycle are unsubstituted or substituted with 1, 2 or 3 substituents selected from the group consisting of NR$_{a0}$R$_{b0}$, halogen, acetyl, hydroxy, hydroxymethyl, hydroxyethyl, carboxyl, C$_{1-8}$ alkyl (preferably C$_{1-6}$ alkyl, more preferably C$_{1-3}$ alkyl), C$_{1-8}$ alkoxy (preferably C$_{1-6}$ alkoxy, more preferably C$_{1-3}$ alkoxy), halogenated C$_{1-8}$ alkyl (preferably halogenated C$_{1-6}$ alkyl, more preferably halogenated C$_{1-3}$ alkyl), C$_{3-8}$ cycloalkyl (preferably C$_{3-6}$ cycloalkyl), C$_{3-8}$ cycloalkoxy (preferably C$_{3-6}$ cycloalkoxy), C$_{2-10}$ alkenyl (preferably C$_{2-6}$ alkenyl, more preferably C$_{2-4}$ alkenyl), C$_{2-10}$ alkynyl (preferably C$_{2-6}$ alkynyl, more preferably C$_{2-4}$ alkynyl), halogenated C$_{1-8}$ alkoxy (preferably halogenated C$_{1-6}$ alkoxy, more preferably halogenated C$_{1-3}$ alkoxy), C$_{6-10}$ aryl, 4 to 6 membered saturated single heterocycle, —C(O)C$_{1-10}$ alkyl (preferably —C(O)C$_{1-6}$ alkyl, more preferably —C(O)C$_{1-3}$ alkyl), —C(O)OC$_{1-10}$ alkyl (preferably —C(O)OC$_{1-6}$ alkyl, more preferably —C(O)OC$_{1-3}$ alkyl), —OC(O)C$_{1-10}$ alkyl (preferably —OC(O)C$_{1-6}$ alkyl, more preferably —OC(O)C$_{1-3}$ alkyl), —CONR$_{a0}$R$_{b0}$; R$_{a0}$, R$_{b0}$ are each independently hydrogen, C$_{1-8}$ alkyl (preferably C$_{1-6}$ alkyl, more preferably C$_{1-3}$ alkyl), C$_{1-8}$ alkyl substituted with C$_{1-8}$ alkoxy (preferably C$_{1-6}$ alkyl substituted with C$_{1-6}$ alkoxy, more preferably C$_{1-3}$ alkyl substituted with C$_{1-3}$ alkoxy).

In another preferred example, the 4 to 6 membered saturated single heterocycle is azetidine, oxetane, tetrahydrofuran, tetrahydrothiophene, pyrrolidine, piperidine, piperazine, morpholine, thiomorpholine, thiomorpholine-1,1-dioxide or tetrahydropyrane, or is represented by the structure of

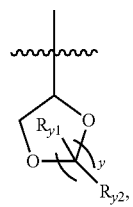

wherein y is 1 or 2; R$_{y1}$, R$_{y2}$ are each independently hydrogen or C$_{1-3}$ alkyl.

In another preferred example, the spiro is a 4 membered/5 membered, 5 membered/5 membered or 5 membered/6 membered bicyclic spiro.

In another preferred example, the spiroheterocycle is a 4 membered/5 membered, 5 membered/5 membered or 5 membered/6 membered bicyclic spiroheterocycle.

In another preferred example, the bridged ring is a bicyclic or tricyclic bridged ring.

In another preferred example, the bridged heterocycle is a bicyclic or tricyclic bridged heterocycle.

In another preferred example, the spiroheterocycle is selected from the following structures:

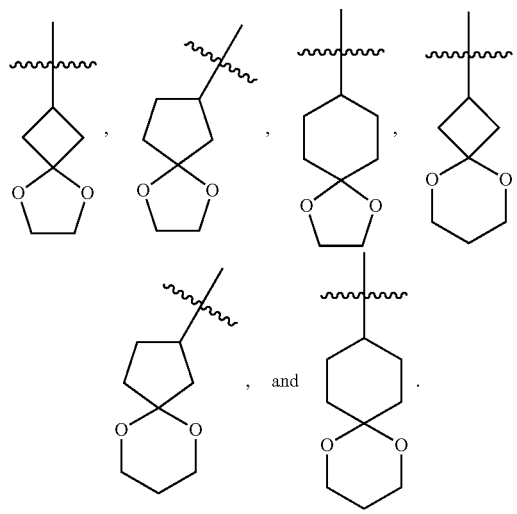

In another preferred example, the 4 to 6 membered saturated single heterocycle formed by R$_1$, R$_2$ together with the nitrogen atom to which they are attached is selected from azetidine, pyrrolidine, piperidine, piperazine, morpholine, thiomorpholine or thiomorpholine-1,1-dioxide.

In another preferred example, the 4 to 6 membered saturated single heterocycle is unsubstituted or substituted with 1, 2 or 3 substituents selected from the group consisting of NR$_{a0}$R$_{b0}$, acetyl, hydroxy, hydroxymethyl, hydroxyethyl, carboxyl, C$_{1-8}$ alkyl (preferably C$_{1-6}$ alkyl, more preferably C$_{1-3}$ alkyl), C$_{1-8}$ alkoxy (preferably C$_{1-6}$ alkoxy, more preferably C$_{1-3}$ alkoxy), C$_{6-10}$ aryl (preferably phenyl), 4 to 6 membered saturated single heterocycle, —C(O)C$_{1-10}$ alkyl (preferably —C(O)C$_{1-6}$ alkyl, more preferably —C(O)C$_{1-3}$ alkyl), —C(O)OC$_{1-10}$ alkyl (preferably —C(O)OC$_{1-6}$ alkyl, more preferably —C(O)OC$_{1-3}$ alkyl); R$_{a0}$, R$_{b0}$ are each independently hydrogen, C$_{1-8}$ alkyl (preferably C$_{1-6}$ alkyl, more preferably C$_{1-3}$ alkyl), and C$_{1-8}$ alkyl substituted with C$_{1-8}$ alkoxy (preferably C$_{1-6}$ alkyl substituted with C$_{1-6}$ alkoxy, more preferably C$_{1-3}$ alkyl substituted with C$_{1-3}$ alkoxy).

In another preferred example, the 4 to 6 membered saturated single heterocycle in the substituent is unsubstituted or substituted with 1, 2 or 3 substituents selected from the group consisting of acetyl, hydroxy, hydroxymethyl, hydroxyethyl, carboxyl, C$_{1-3}$ alkyl, C$_{1-3}$ alkoxy, halogenated C$_{1-3}$ alkyl, C$_{3-6}$ cycloalkyl, halogenated C$_{1-3}$ alkoxy, —C(O)OC$_{1-6}$ alkyl, and NR$_{a0}$R$_{b0}$; wherein R$_{a0}$, R$_{b0}$ are each independently hydrogen or C$_{1-3}$ alkyl.

In another preferred example, the aryl and the 5 to 6 membered single heteroaryl ring are unsubstituted or substituted with 1, 2 or 3 substituents selected from the group consisting of halogen, hydroxy, carboxyl, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), —OC(O)$C_{1-10}$ alkyl (preferably —OC(O)$C_{1-6}$ alkyl, more preferably —OC(O)$C_{1-3}$ alkyl), —CONR$_{a0}$R$_{b0}$; R$_{a0}$, R$_{b0}$ are each independently hydrogen, $C_{1-8}$ alkyl (preferably $C_{1-6}$ alkyl, more preferably $C_{1-3}$ alkyl), $C_{1-8}$ alkyl substituted with $C_{1-8}$ alkoxy (preferably $C_{1-6}$ alkyl substituted with $C_{1-6}$ alkoxy, more preferably $C_{1-3}$ alkyl substituted with $C_{1-3}$ alkoxy).

In another preferred example, the alkyl are unsubstituted or substituted with 1, 2 or 3 substituents selected from the group consisting of NR$_{a0}$R$_{b0}$, hydroxy, hydroxymethyl, carboxyl, $C_{1-8}$ alkoxy (preferably $C_{1-6}$ alkoxy, more preferably $C_{1-3}$ alkoxy), 4 to 6 membered saturated single heterocycle, —C(O)O$C_{1-10}$ alkyl (preferably —C(O)O$C_{1-6}$ alkyl, more preferably —C(O)O$C_{1-3}$ alkyl); R$_{a0}$, R$_{b0}$ are each independently hydrogen, $C_{1-8}$ alkyl (preferably $C_{1-6}$ alkyl, more preferably $C_{1-3}$ alkyl), and $C_{1-8}$ alkyl substituted with $C_{1-8}$ alkoxy (preferably $C_{1-6}$ alkyl substituted with $C_{1-6}$ alkoxy, more preferably $C_{1-3}$ alkyl substituted with $C_{1-3}$ alkoxy).

In another preferred example, the cycloalkyl is unsubstituted or substituted with one substituent selected from the group consisting of hydroxy and hydroxymethyl.

In another preferred example, when n1 is 2, m1 is 1, 2, 3, 4, 5, 6, 7, 8 or 9 (preferably m is 1, 2, 3, 4 or 9); when n1 is 3, m1 is 1; and when n1 is 4; m1 is 2.

In another preferred example, when n2 is 2, m2 is 1, 2, 3, 4, 5, 6, 7, 8 or 9 (preferably m2 is 1, 2, 3, 4 or 9); when n2 is 3, m2 is 1; and when n2 is 4; m2 is 2.

In another preferred example, R$_1$ and R$_2$ are each independently hydrogen, $C_{1-10}$ alkyl (preferably $C_{1-6}$ alkyl, more preferably $C_{1-3}$ alkyl), and $C_{3-8}$ cycloalkyl (preferably $C_{3-6}$ cycloalkyl);

the alkyl or cycloalkyl is unsubstituted or substituted with 1, 2 or 3 substituents selected from the group consisting of R$_{a0}$R$_{b0}$, hydroxy, hydroxymethyl, carboxyl, $C_{2-10}$ alkenyl (preferably $C_{2-6}$ alkenyl, more preferably $C_{2-4}$ alkenyl, and most preferably vinyl), $C_{1-8}$ alkoxy (preferably $C_{1-6}$ alkoxy, more preferably $C_{1-3}$ alkoxy), 4 to 6 membered saturated single heterocycle, —C(O)O$C_{1-10}$ alkyl (preferably —C(O)O$C_{1-6}$ alkyl, more preferably —C(O)O$C_{1-3}$ alkyl); R$_{a0}$ and R$_{b0}$ are each independently hydrogen, $C_{1-8}$ alkyl (preferably $C_{1-6}$ alkyl, more preferably $C_{1-3}$ alkyl), $C_{1-8}$ alkyl substituted with $C_{1-8}$ alkoxy (preferably $C_{1-6}$ alkyl substituted with $C_{1-6}$ alkoxy, more preferably $C_{1-3}$ alkyl substituted with $C_{1-3}$ alkoxy).

In another preferred example, the 4 to 6 membered saturated single heterocycle is selected from azetidine, oxetane, tetrahydrofuran, tetrahydrothiophene, pyrrolidine, piperidine, piperazine, morpholine, thiomorpholine, thiomorpholine-1,1-dioxide, tetrahydropyrane, or is represented by the structure of

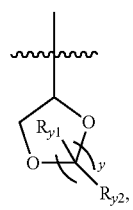

wherein y is 1 or 2; R$_{y1}$ and R$_{y2}$, are each independently hydrogen or $C_{1-3}$ alkyl.

In another preferred example, the substituted $C_{1-10}$ alkyl (preferably $C_{1-6}$ alkyl, more preferably $C_{1-3}$ alkyl) or the substituted $C_{3-8}$ cycloalkyl (preferably $C_{3-6}$ cycloalkyl) is preferably selected from the following structures:

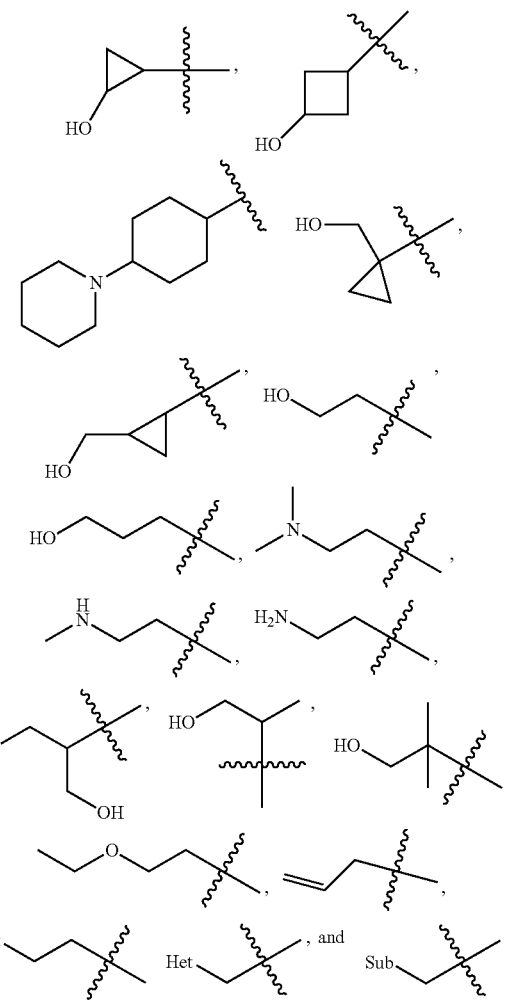

wherein "Het" represents a substituted or unsubstituted 4 to 6 membered saturated single heterocycle, and "Sub" each independently represents the various types of substituents described herein.

In another preferred example, —N(R$_1$R$_2$) is selected from the following structures:

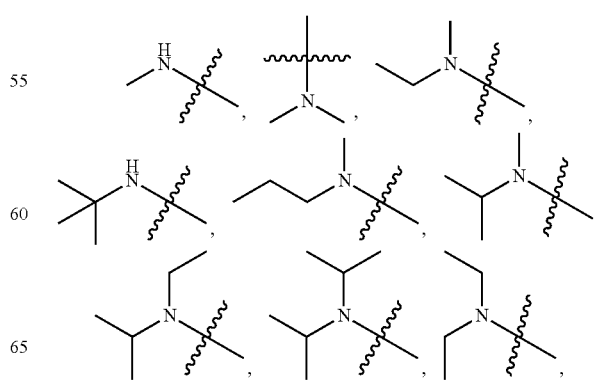

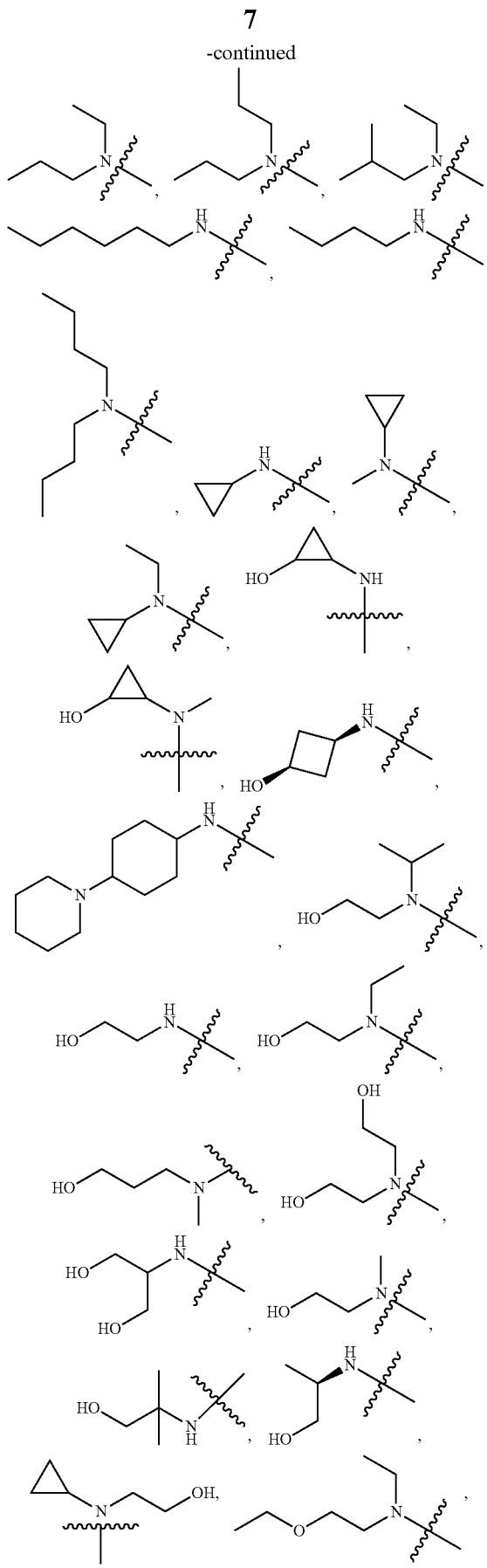

In another preferred example, the 4 to 6 membered saturated single heterocycle is unsubstituted or substituted with 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)O$C_{1-6}$ alkyl, and $NR_{a0}R_{b0}$; wherein $R_{a0}$ and $R_{b0}$ are each independently hydrogen or $C_{1-3}$ alkyl.

In another preferred example, the alkyl is unsubstituted or substituted with 1, 2 or 3 substituents selected from the group consisting of $NH_2$, $N(CH_3)_2$, hydroxy, carboxyl, methoxy, ethoxy, propoxy, isopropoxy, azetidine, oxetane, tetrahydrofuran, tetrahydrothiophene, pyrrolidine, piperidine, piperazine, morpholine, thiomorpholine, thiomorpholine-1,1-dioxide, tetrahydropyrane, —C(O)OCH$_3$, —C(O)OCH$_2$CH$_3$, —C(O)OCH(CH$_3$)$_2$, and —C(O)OC(CH$_3$)$_3$; wherein the cycloalkyl is unsubstituted or substituted with one hydroxy or hydroxymethyl.

In another preferred example, $R_1$ is hydrogen, $C_{1-10}$ alkyl (preferably $C_{1-6}$ alkyl, more preferably $C_{1-3}$ alkyl) or $C_{3-8}$ cycloalkyl (preferably $C_{3-6}$ cycloalkyl); $R_2$ is —CH($R_{11}$)—

C(O)OC$_{1-10}$ alkyl (preferably —CH(R$_{11}$)—C(O)OC$_{1-6}$ alkyl, more preferably —CH(R$_{11}$)—C(O)OC$_{1-3}$ alkyl) or —CH(R$_{11}$)—C(O)OH; R$_{11}$ is hydrogen or C$_{1-3}$ alkyl.

In another preferred example, —N(R$_1$R$_2$) is selected from the following structures:

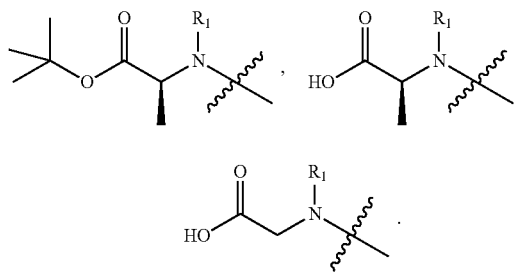

In another preferred example, R$_{11}$ is hydrogen or methyl.

In another preferred example, R$_1$ is hydrogen, C$_{1-10}$ alkyl (preferably C$_{1-6}$ alkyl, more preferably C$_{1-3}$ alkyl), C$_{3-8}$ cycloalkyl (preferably C$_{3-6}$ cycloalkyl) or —((CH$_2$)$_{n1}$—O)$_{m1}$—CH$_3$; and, R$_2$ is —((CH$_2$)$_{n2}$—O)$_{m2}$—CH$_3$; wherein, n1 and n2 are each independently 2, 3 or 4; and wherein m1 and m2 are each independently 1, 2, 3, 4, 5, 6, 7, 8 or 9.

In another preferred example, n1 is 2; and m1 is 1, 2, 3, 4, 5, 6, 7, 8 or 9 (preferably m1 is 1, 2, 3, 4 or 9).

In another preferred example, n1 is 3; and m1 is 1, 2, 3, 4, 5, 6, 7, 8 or 9 (preferably m1 is 1).

In another preferred example, n1 is 4; and m1 is 1, 2, 3, 4, 5, 6, 7, 8 or 9 (preferably m1 is 2).

In another preferred example, n2 is 2; and m2 is 1, 2, 3, 4, 5, 6, 7, 8 or 9 (preferably m2 is 1, 2, 3, 4 or 9).

In another preferred example, n2 is 3; and m2 is 1, 2, 3, 4, 5, 6, 7, 8 or 9 (preferably m2 is 1).

In another preferred example, n2 is 4; and m2 is 1, 2, 3, 4, 5, 6, 7, 8 or 9 (preferably m2 is 2).

In another preferred example, —((CH$_2$)$_{n1}$—O)$_{m1}$—CH$_3$ or —((CH$_2$)$_{n2}$—O)$_{m2}$—CH$_3$ is —(CH$_2$)$_2$—O—CH$_3$, —((CH$_2$)$_2$—O)$_2$—CH$_3$, —((CH$_2$)$_2$—O)$_3$—CH$_3$, —((CH$_2$)$_2$—O)$_4$—CH$_3$, —((CH$_2$)$_2$—O)$_9$—CH$_3$, —(CH$_2$)$_3$—O—CH$_3$ or —((CH$_2$)$_4$—O)$_2$—CH$_3$.

In another preferred example, —CH(R$_{11}$)—C(O)OC$_{1-10}$ alkyl is —CH(CH$_3$)—C(O)OC(CH$_3$)$_3$.

In another preferred example, —N(R$_1$R$_2$) is selected from the following structures:

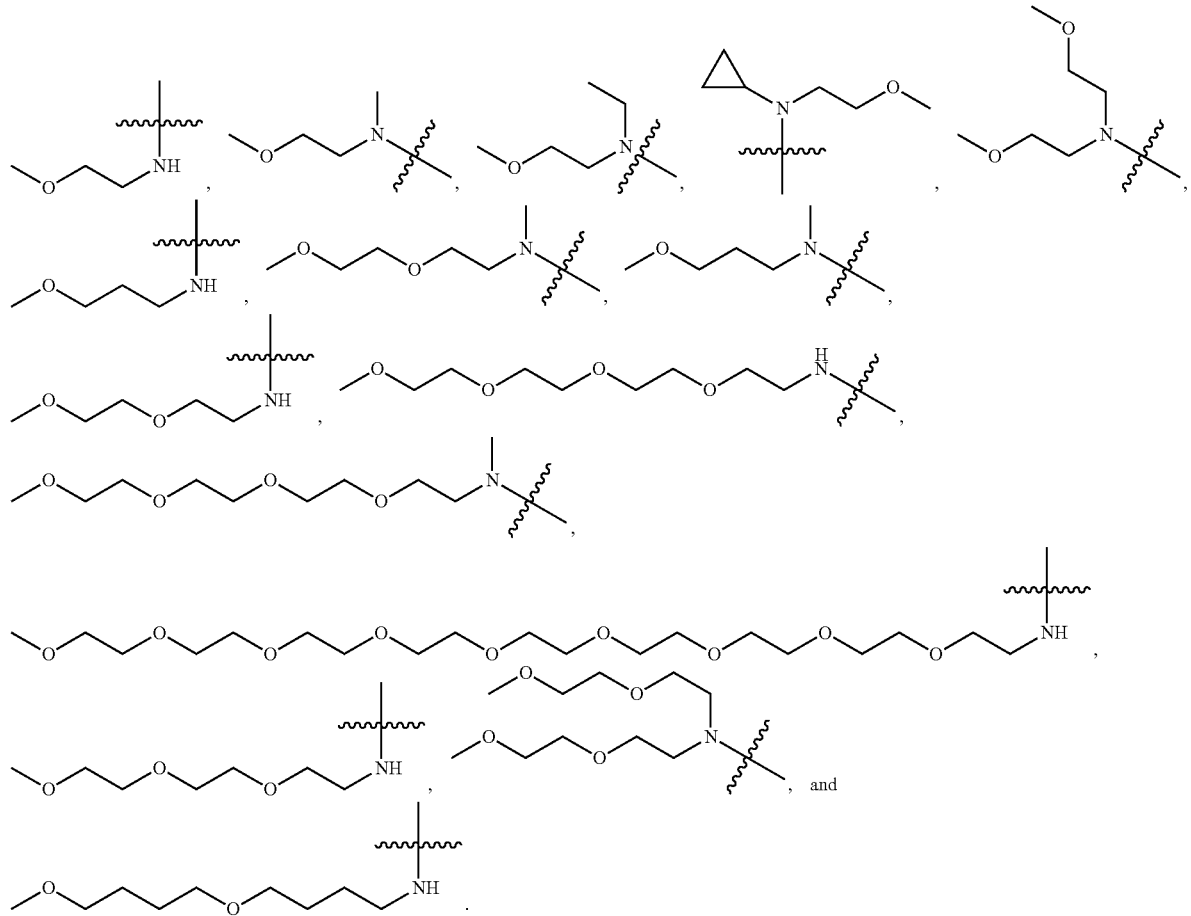

In another preferred example, R$_1$ is hydrogen, C$_{1-10}$ alkyl (preferably C$_{1-6}$ alkyl, more preferably C$_{1-3}$ alkyl) or C$_{3-8}$ cycloalkyl (preferably C$_{3-6}$ cycloalkyl); and R$_2$ is C$_{6-10}$ aryl (preferably phenyl); and the aryl is unsubstituted or substituted with 1, 2 or 3 substituents selected from the group consisting of halogen, hydroxy, carboxyl, C$_{1-8}$ alkyl (preferably C$_{1-6}$ alkyl, more preferably C$_{1-3}$ alkyl), C$_{1-8}$ alkoxy (preferably C$_{1-6}$ alkoxy, more preferably C$_{1-3}$ alkoxy), —OC(O)C$_{1-10}$ alkyl (preferably —OC(O)C$_{1-6}$ alkyl, more preferably —OC(O)C$_{1-3}$ alkyl), —CONR$_{a0}$R$_{b0}$; R$_{a0}$, R$_{b0}$ are each independently hydrogen, C$_{1-8}$ alkyl (preferably C$_{1-6}$ alkyl, more preferably C$_{1-3}$ alkyl), and C$_{1-8}$ alkyl substituted with C$_{1-8}$ alkoxy (preferably C$_{1-6}$ alkyl substituted with C$_{1-6}$ alkoxy, more preferably C$_{1-3}$ alkyl substituted with C$_{1-3}$ alkoxy).

The cycloalkyl is unsubstituted or substituted with one substituent selected from the group consisting of hydroxy and hydroxymethyl. In another preferred example, the aryl is unsubstituted or substituted with 1, 2 or 3 substituents selected from the group consisting of fluorine, chlorine, bromine, iodine, hydroxy, methyl, ethyl, n-propyl, isopropyl, n-butyl, isobutyl, tert-butyl, pentyl, n-hexyl, methoxy, ethoxy, —OC(O)CH$_2$CH$_3$, —CONH$_2$, and —CON(CH$_3$)$_2$.

In another preferred example, R$_1$ is hydrogen or C$_{1-10}$ alkyl (preferably C$_{1-6}$ alkyl, more preferably C$_{1-3}$ alkyl) or C$_{3-8}$ cycloalkyl (preferably C$_{3-6}$ cycloalkyl); and R$_2$ is 5 to 6 membered single heteroaryl ring (preferably pyridine); and the 5 to 6 membered single heteroaryl ring are unsubstituted or substituted with 1, 2 or 3 substituents selected from the group consisting of halogen, hydroxy, carboxyl, C$_{1-8}$ alkyl (preferably C$_{1-6}$ alkyl, more preferably C$_{1-3}$ alkyl), C$_{1-8}$ alkoxy (preferably C$_{1-6}$ alkoxy, more preferably C$_{1-3}$ alkoxy), —OC(O)C$_{1-10}$ alkyl (preferably —OC(O)C$_{1-6}$ alkyl, more preferably —OC(O)C$_{1-3}$ alkyl), —CONR$_{a0}$R$_{b0}$; R$_{a0}$, R$_{b0}$ are each independently hydrogen, C$_{1-8}$ alkyl (preferably C$_{1-6}$ alkyl, more preferably C$_{1-3}$ alkyl), and C$_{1-8}$ alkyl substituted with C$_{1-8}$ alkoxy (preferably C$_{1-6}$ alkyl substituted with C$_{1-6}$ alkoxy, more preferably C$_{1-3}$ alkyl substituted with C$_{1-3}$ alkoxy).

In another preferred example, —N(R$_1$R$_2$) is selected from the following structures:

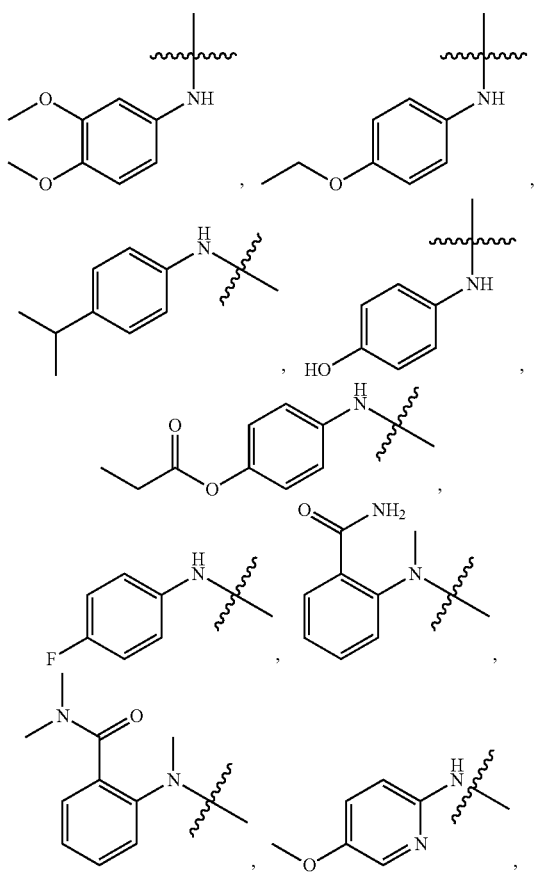

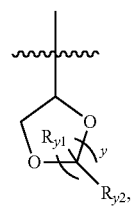

, and

In another preferred example, R$_1$ is hydrogen or C$_{1-10}$ alkyl (preferably C$_{1-6}$ alkyl, more preferably C$_{1-3}$ alkyl) or C$_{3-8}$ cycloalkyl (preferably C$_{3-6}$ cycloalkyl); and R$_2$ is 4 to 6 membered saturated single heterocycle; and the 4 to 6 membered saturated single heterocycle is unsubstituted or substituted with 1, 2 or 3 substituents selected from the group consisting of NR$_{a0}$R$_{b0}$, acetyl, hydroxy, hydroxymethyl, hydroxyethyl, carboxyl, C$_{1-8}$ alkyl (preferably C$_{1-6}$ alkyl, more preferably C$_{1-3}$ alkyl), C$_{1-8}$ alkoxy (preferably C$_{1-6}$ alkoxy, more preferably C$_{1-3}$ alkoxy), C$_{6-10}$ aryl (preferably phenyl), 4 to 6 membered saturated single heterocycle, —C(O)C$_{1-10}$ alkyl (preferably —C(O)C$_{1-6}$ alkyl, more preferably —C(O)C$_{1-3}$ alkyl), —C(O)OC$_{1-10}$ alkyl (preferably —C(O)OC$_{1-6}$ alkyl, more preferably —C(O)OC$_{1-3}$ alkyl); R$_{a0}$ and R$_{b0}$ are each independently hydrogen, C$_{1-8}$ alkyl (preferably C$_{1-6}$ alkyl, more preferably C$_{1-3}$ alkyl), and C$_{1-8}$ alkyl substituted with C$_{1-8}$ alkoxy (preferably C$_{1-6}$ alkyl substituted with C$_{1-6}$ alkoxy, more preferably C$_{1-3}$ alkyl substituted with C$_{1-3}$ alkoxy).

In another preferred example, the 4 to 6 membered saturated single heterocycle in the substituent is unsubstituted or substituted with 1, 2 or 3 substituents selected from the group consisting of acetyl, hydroxy, hydroxymethyl, hydroxyethyl, carboxyl, C$_{1-3}$ alkyl, C$_{1-3}$ alkoxy, halogenated C$_{1-3}$ alkyl, C$_{3-6}$ cycloalkyl, halogenated C$_{1-3}$ alkoxy, —C(O)OC$_{1-6}$ alkyl, and NR$_{a0}$R$_{b0}$; wherein R$_{a0}$ and R$_{b0}$ are each independently hydrogen or C$_{1-3}$ alkyl.

In another preferred example, the 4 to 6 membered saturated single heterocycle is azetidine, oxetane, tetrahydrofuran, tetrahydrothiophene, pyrrolidine, piperidine, piperazine, morpholine, thiomorpholine, thiomorpholine-1,1-dioxide or tetrahydropyrane, or is represented by the structure of wherein y is 1 or 2; and wherein R$_{y1}$, R$_{y2}$ are each independently hydrogen or C$_{1-3}$ alkyl.

In another preferred example, the 4 to 6 membered saturated single heterocycle is selected from the following structures:

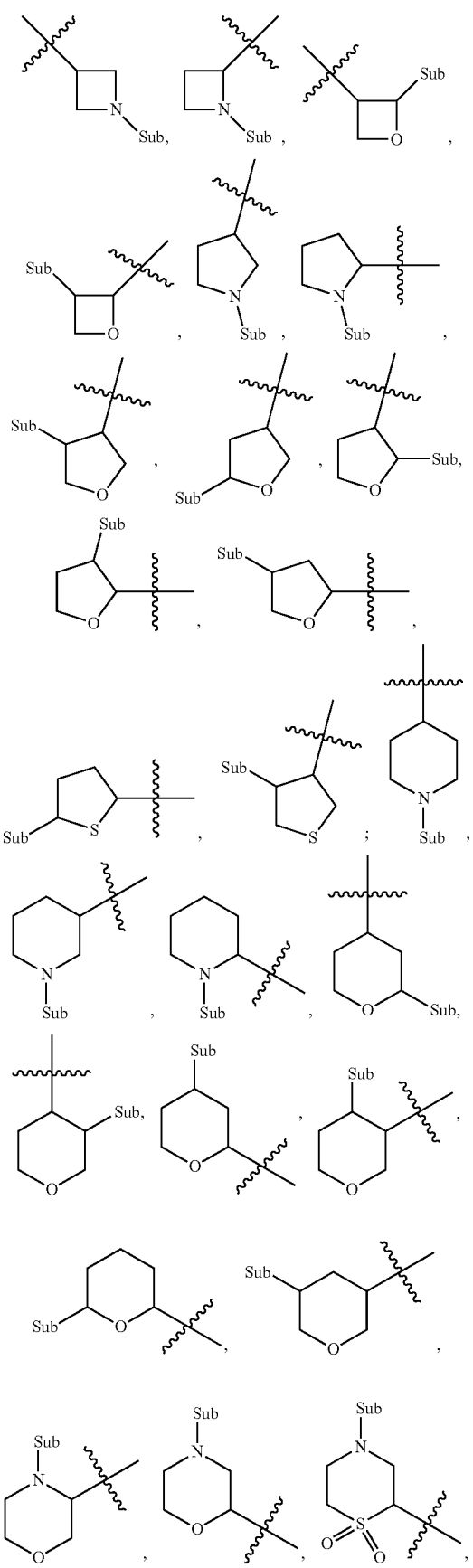

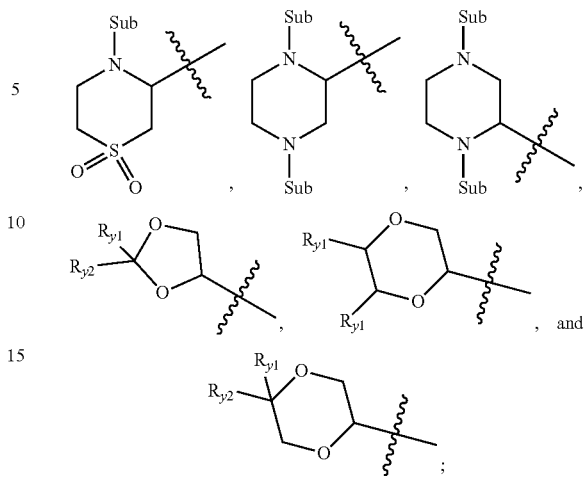

wherein "Sub" represents the various types of substituents described herein, each of which independently and optionally exists; and "∼" represents a connection with other atoms.

In another preferred example, the 4 to 6 membered saturated single heterocycle is selected from the following structures:

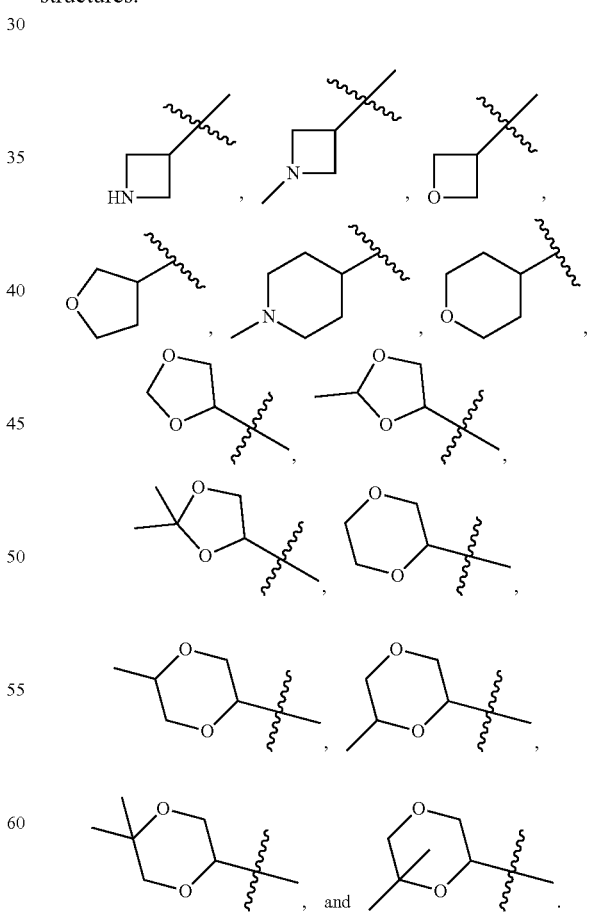

In another preferred example, —N(R₁R₂) is selected from the following structures:

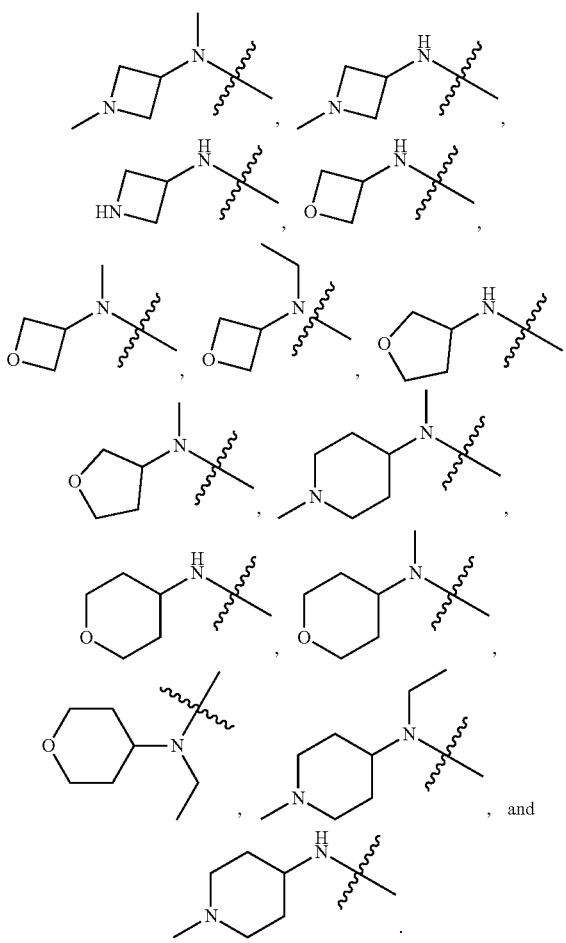

In another preferred example, $R_1$, $R_2$, together with the nitrogen atom to which they are attached, form a 4 to 6 membered nitrogen-containing saturated single heterocycle; and the 4 to 6 membered nitrogen-containing saturated single heterocycle is unsubstituted or substituted with 1, 2 or 3 substituents selected from the group consisting of $NR_{a0}R_{b0}$, acetyl, hydroxy, hydroxymethyl, carboxyl, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), $C_{6-10}$ aryl (preferably phenyl), 4 to 6 membered saturated single heterocycle, —C(O)$C_{1-10}$ alkyl (preferably —C(O)$C_{1-6}$ alkyl, more preferably —C(O)$C_{1-3}$ alkyl), —C(O)O$C_{1-10}$ alkyl (preferably —C(O)O$C_{1-6}$ alkyl, more preferably —C(O)O$C_{1-3}$ alkyl); $R_{a0}$ and $R_{b0}$ are each independently hydrogen, $C_{1-8}$ alkyl (preferably $C_{1-6}$ alkyl, more preferably $C_{1-3}$ alkyl), and $C_{1-3}$ alkyl substituted with $C_{1-8}$ alkoxy (preferably $C_{1-6}$ alkyl substituted with $C_{1-6}$ alkoxy, more preferably $C_{1-3}$ alkyl substituted with $C_{1-3}$ alkoxy).

In another preferred example, the 4 to 6 membered saturated single heterocycle in the substituent is unsubstituted or substituted with 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)O$C_{1-6}$ alkyl, and $R_{a0}R_{b0}$; wherein $R_{a0}$ and $R_{b0}$ are each independently hydrogen or $C_{1-3}$ alkyl.

In another preferred example, the 4 to 6 membered nitrogen-containing saturated single heterocycle is azetidine, pyrrolidine, piperidine, piperazine, morpholine, thiomorpholine or thiomorpholine-1,1-dioxide.

In another preferred example, the 4 to 6 membered saturated single heterocycle is azetidine, oxetane, tetrahydrofuran, tetrahydrothiophene, pyrrolidine, piperidine, piperazine, morpholine, thiomorpholine, thiomorpholine-1,1-dioxide or tetrahydropyrane.

In another preferred example, the 4 to 6 membered saturated single heterocycle is selected from the following structures:

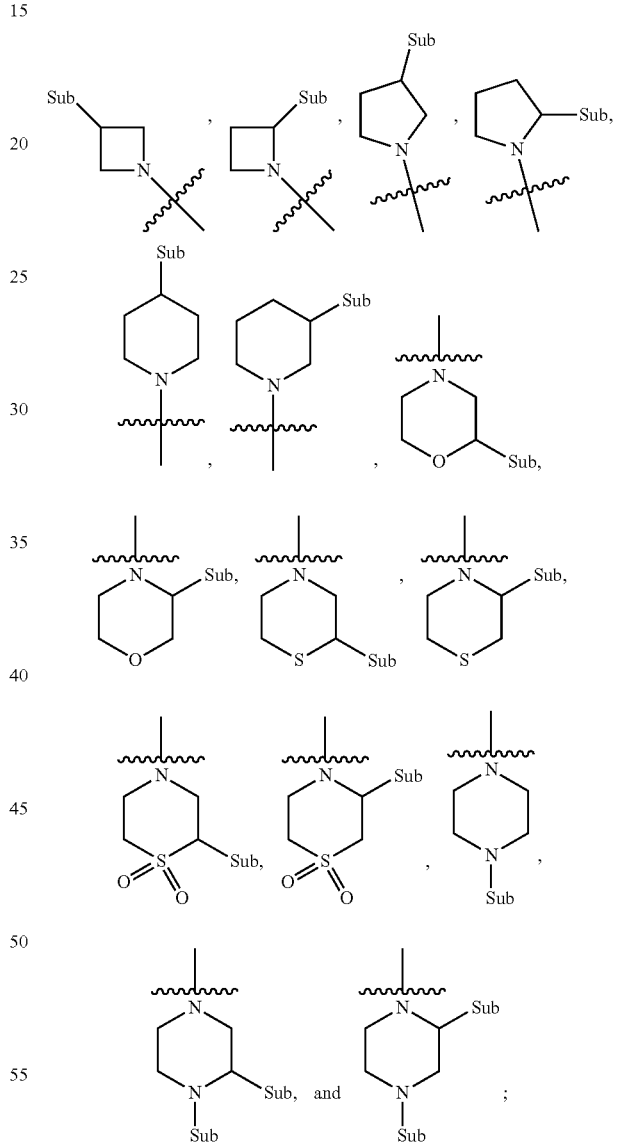

wherein "Sub" represents the various types of substituents described herein, each of which independently and optionally exists; and " ~~~ " represents a connection with other atoms.

In another preferred example, the 4 to 6 membered saturated single heterocycle is selected from the following structures:

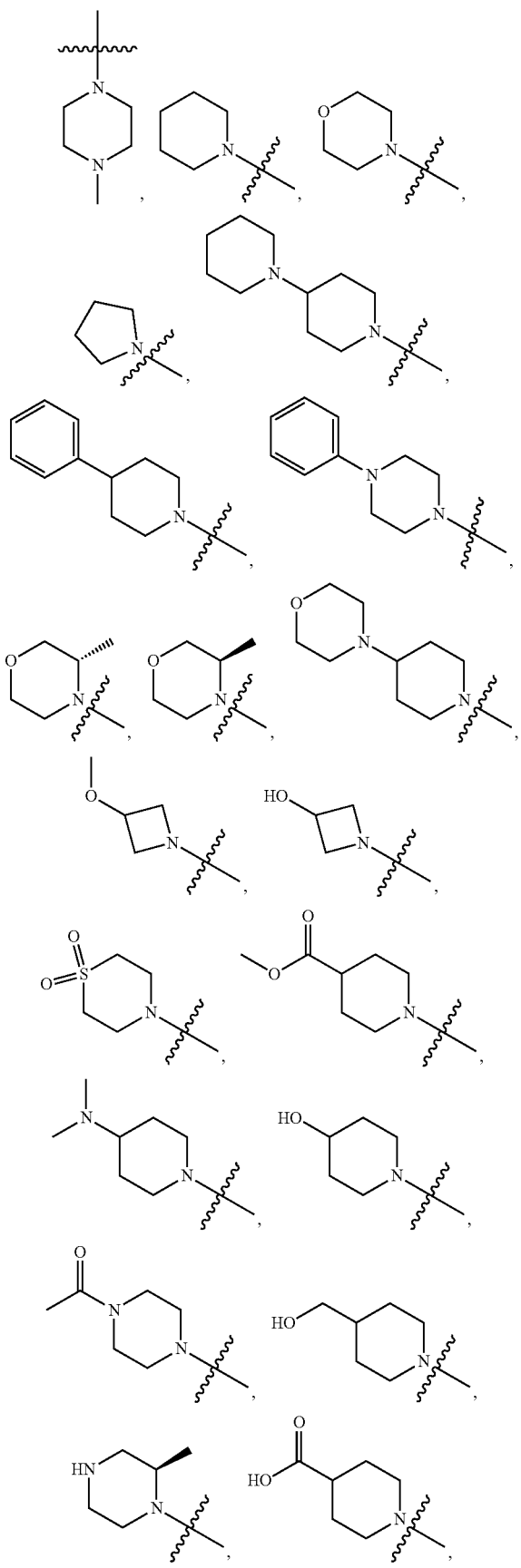

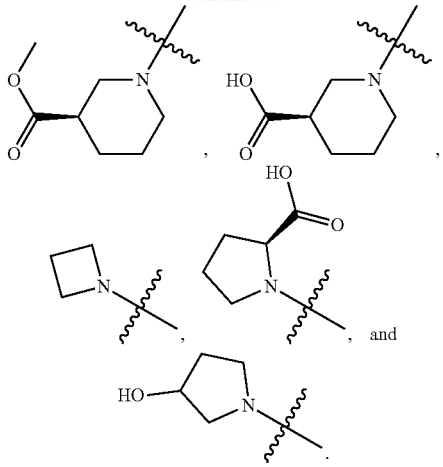

In another preferred example, n is 2; and m is 1, 2, 3, 4, 5, 6, 7, 8 or 9 (preferably m is 1, 2, 3, 4 or 9).

In another preferred example, n is 3; and m is 1, 2, 3, 4, 5, 6, 7, 8 or 9 (preferably m is 1).

In another preferred example, n is 4; and m is 1, 2, 3, 4, 5, 6, 7, 8 or 9 (preferably m is 2).

In another preferred example, r is 2; and t is 1, 2, 3, 4, 5, 6, 7, 8 or 9.

In another preferred example, k is 1.

In another preferred example, p is 2; and q is 1, 2, 3 or 4.

In another preferred example, $R_1$ is hydrogen, $C_{1-10}$ alkyl (preferably $C_{1-6}$ alkyl, more preferably $C_{1-3}$ alkyl) or $C_{3-8}$ cycloalkyl (preferably $C_{3-6}$ cycloalkyl); and $R_2$ is spiro, spiroheterocycle, bridged ring or bridged heterocycle.

In another preferred example, $R_2$ is spiroheterocycle.

In another preferred example, the spiroheterocycle is a 4 membered/5 membered, 5 membered/5 membered or 5 membered/6 membered bicyclic spiroheterocycle.

In another preferred example, the spiroheterocycle is selected from the following structures:

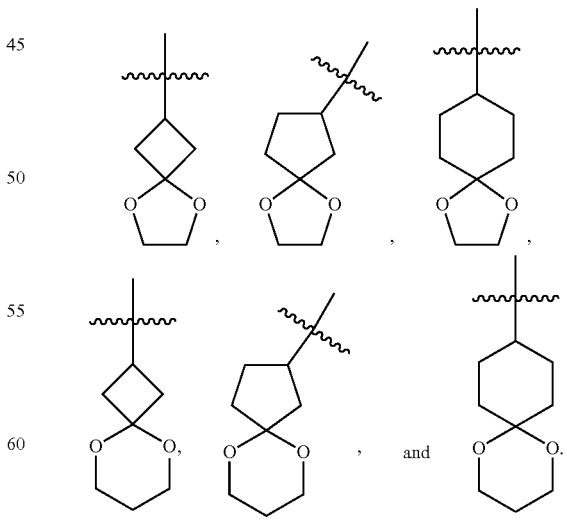

In another preferred example, L is —CO—; X is —N($R_1R_2$), —$OR_3$ or —$CH_2O$—$((CH_2)_r$—O$)_t$—$CH_3$; and r, t, $R_1$, $R_2$, and $R_3$ are as defined previously.

In another preferred example, L is —CO—; X is —N(R₁R₂); R₁ and R₂ are as defined previously.

In another preferred example, L is —CO—; X is —OR₃ or —CH₂O—((CH₂)ᵣO)ₜ—CH₃; and r, t, and R₃ are as defined previously.

In another preferred example, $R_3$ is $C_{1-10}$ alkyl (preferably $C_{1-6}$ alkyl, more preferably $C_{1-3}$ alkyl) or $C_{3-8}$ cycloalkyl (preferably $C_{3-6}$ cycloalkyl), —((CH₂)ₚ—O)_q—CH₃; wherein, p is 2, 3 or 4; q is 1, 2, 3 or 4.

In another preferred example, $R_3$ is selected from the group consisting of methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, cyclopropyl, cyclobutyl, cyclopentyl, cyclohexyl, —(CH₂)₂—O—CH₃, —((CH₂)₂—O)₂—CH₃, —((CH₂)₂—O)₃—CH₃, and —((CH₂)₂—O)₄—CH₃.

In another preferred example, L is —(C(R₄R₅)₂)_k—; X is —OR₃; k, R₃, R₄, and R₅ are as defined previously.

In another preferred example, $R_3$ is selected from the group consisting of $C_{1-10}$ alkyl (preferably $C_{1-6}$ alkyl, more preferably $C_{1-3}$ alkyl), $C_{3-8}$ cycloalkyl (preferably $C_{3-6}$ cycloalkyl), —((CH₂)ₚ—O)_q—CH₃, —C(O)O—(CH₂)ₚ—O_q—CH₃, —C(O)OC$_{1-10}$ alkyl (preferably —C(O)OC$_{1-6}$ alkyl, more preferably —C(O)OC$_{1-3}$ alkyl), —C(O)OC$_{3-8}$ cycloalkyl (preferably —C(O)OC$_{3-6}$ cycloalkyl), and —C(O)C$_{1-10}$ alkyl (preferably —C(O)C$_{1-6}$ alkyl, more preferably —C(O)C$_{1-3}$ alkyl); wherein, p is 2, 3 or 4; q is 1, 2, 3 or 4.

In another preferred example, $R_3$ is selected from the group consisting of methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, cyclopropyl, cyclobutyl, cyclopentyl, cyclohexyl, —(CH₂)₂—O—CH₃, —((CH₂)₂—O)₂—CH₃, —((CH₂)₂—O)₃—CH₃, —((CH₂)₂—O)₄—CH₃, —C(O)O—(CH₂)₂—O—CH₃, —C(O)O—((CH₂)₂—O)₂—CH₃, —C(O)O—((CH₂)₂—O)₃—CH₃, —C(O)O—((CH₂)₂—O)₄—CH₃, —C(O)O-cyclopropyl, —C(O)O-cyclopentyl, —C(O)O-cyclohexyl, —C(O)OC$_{1-10}$ alkyl, —C(O)CH₃, —C(O)-propyl, —C(O)-n-butyl, and —C(O)-tert-butyl.

In another preferred example, the compound of Formula (I) is selected from the group consisting of:

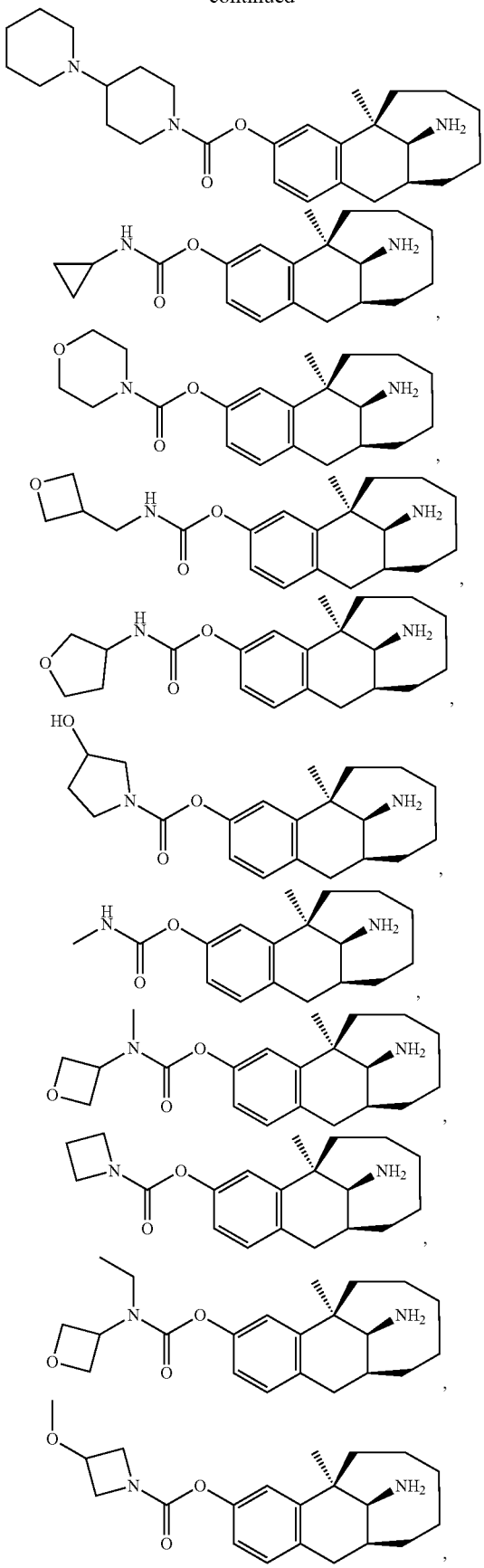

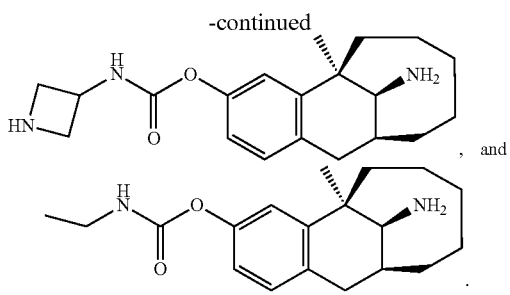
, and

In a second aspect of the present disclosure, a pharmaceutical composition is provided, comprising a compound of the first aspect of the disclosure, or a pharmaceutically acceptable salt, solvate, or stereoisomer thereof and a pharmaceutically acceptable carrier.

In a third aspect of the present disclosure, a use of a compound of the first aspect of the present disclosure, or a pharmaceutically acceptable salt, solvate, or stereoisomer thereof, or a pharmaceutical composition of the second aspect of the disclosure, in the manufacture of a medicament for the treatment of pain, is provided.

In a fourth aspect of the present disclosure, a method for treating pain is provided, comprising administering to a subject in need a therapeutically effective amount of the compound of the first aspect of the disclosure, or a pharmaceutically acceptable salt, solvate, or stereoisomer thereof, or the pharmaceutical composition of the second aspect of the disclosure.

In another preferred example, the pain is selected from acute pain, chronic pain, postoperative pain, pain caused by neuralgia (optionally post-herpetic neuralgia or trigeminal neuralgia), pain caused by diabetic neuropathy, oral pain, pain associated with arthritis or osteoarthritis, or pain associated with cancer or its treatment.

In another preferred example, the pain is neuropathic pain or nociceptive pain.

It should be understood that each technical feature of the disclosure described above and specified below (such as in Examples) can be combined with each other so as to constitute new or preferred technical solutions, without departing from the scope of the present disclosure.

DETAILED DESCRIPTION OF EMBODIMENTS

After long and thorough studies, the inventors have unexpectedly discovered a class of benzobicycloalkane derivatives, which have a prolonged drug effect time of more than 3 times as compared with the existing dezocine, a greatly increased oral bioavailability, a constant plasma concentration, and smaller side effects, providing better drug choice and better compliance for clinical patients.

Definition of Terms

As used herein, "alkyl" refers to a straight and branched saturated aliphatic hydrocarbon group. $C_{1-8}$ alkyl is an alkyl containing 1 to 8 carbon atoms, preferably $C_{1-6}$ alkyl, more preferably $C_{1-3}$ alkyl with similar definitions. Non-limiting examples of alkyl include: methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-decyl, 2-methyl-2-ethylhexyl, 2-methyl-3-ethylhexyl, 2,2-diethylpentyl, n-decyl, 3,3-diethylhexyl, 2,2-diethylhexyl, and their various branched isomers.

As used herein, "cycloalkyl" refers to a saturated or partially unsaturated monocyclic hydrocarbon group. "$C_{3-8}$ cycloalkyl" refers to a cyclic hydrocarbon group containing 3 to 8 carbon atoms, preferably a $C_{3-6}$ cycloalkyl with similar definition. Non-limiting examples of cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, preferably cyclopropyl, cyclopentyl, and cyclohexenyl.

As used herein, "spiro" refers to a polycyclic group which shares one carbon atom (spiro atom) between the single rings. These rings may contain one or more double bonds, but none of the rings has a completely conjugated π electron system. According to the number of rings, the spiro is categorized into bicyclic spiro or polycyclic spiro. The bicyclic spiro is preferable, more preferably a 4 membered/5 membered, 5 membered/5 membered, or 5 membered/6 membered bicyclic spiro, e.g., selected from the following:

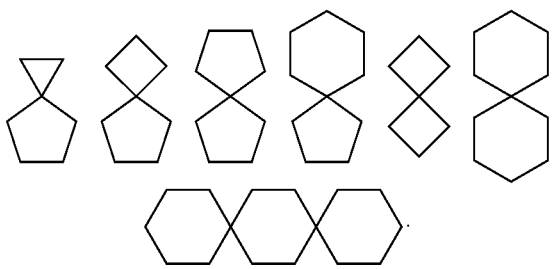

As used herein, "spiroheterocycle" refers to a polycyclic hydrocarbon which shares one atom (spiro atom) between the single rings, wherein one or two ring atoms are selected from heteroatoms such as nitrogen, oxygen, or $S(O)_n$ (wherein n is an integer from 0 to 2), the remaining ring atoms being carbon atoms. These may contain one or more double bonds, but none of the rings have a completely conjugated π-electron system. According to the number of rings, the spiroheterocycle is categorized into bicyclic spiroheterocycle or polycyclic spiroheterocycle. The bicyclic spiro is preferable, more preferably a 4 membered/5 membered, 5 membered/5 membered, or 5 membered/6 membered bicyclic spiroheterocycle, e.g., selected from the following:

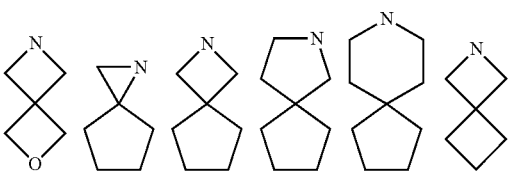

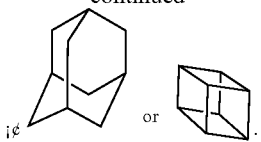

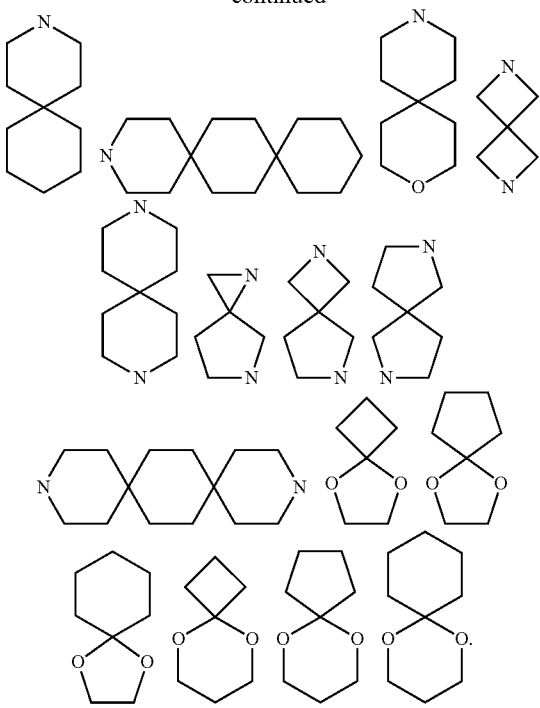

As used herein, "bridged heterocycle" refers to a polycyclic group that shares two or more atoms, wherein one or more ring atoms are selected from heteroatoms such as nitrogen, oxygen, or S(O)$_n$ (wherein n is an integer from 0 to 2) and the remaining ring atoms are carbon atoms. Such rings may contain one or more double bonds, but none of the rings has a completely conjugated π-electron system. Bicyclic or tricyclic bridged heterocycles are preferred, e.g., selected from the following:

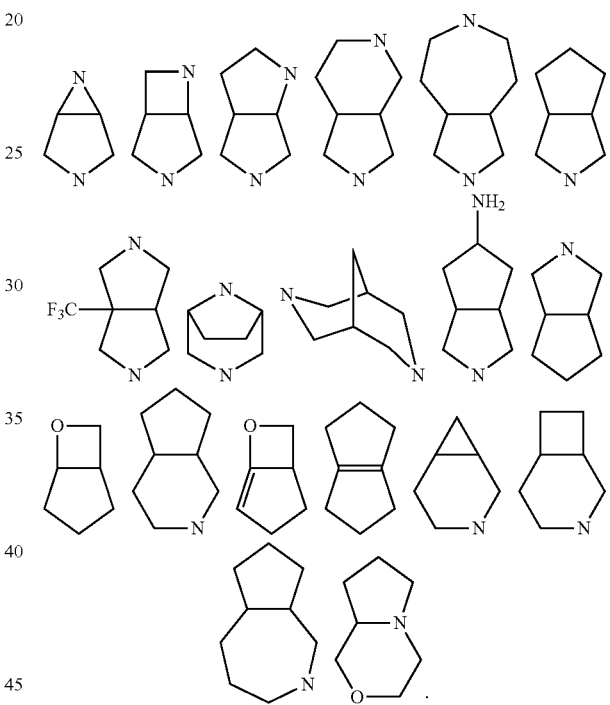

As used herein, "bridged ring" refers to a polycyclic group which shares two or more carbon atoms. The shared carbon atoms are known as bridgehead carbons. There may be a carbon chain or a bond between two bridgehead carbons, known as the bridge. Such rings may contain one or more double bonds, but none of the rings have a completely conjugated π-electron system. Bicyclic or tricyclic bridged rings are preferred, e.g., selected from the following:

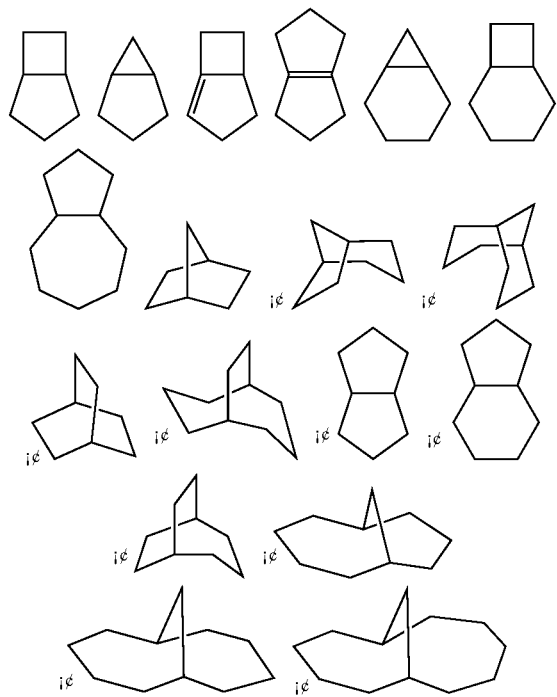

As used herein, "8 to 10 membered bicyclic ring" refers to a bridged ring with two rings, containing 8 to 10 ring atoms. The bicyclic ring may be a saturated full-carbon bicyclic or partially unsaturated full-carbon bicyclic ring. Examples of bicyclic ring include (but not limited to):

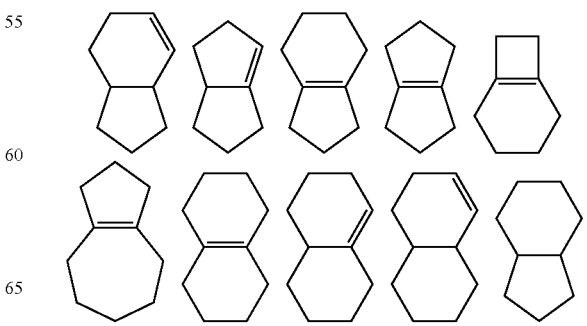

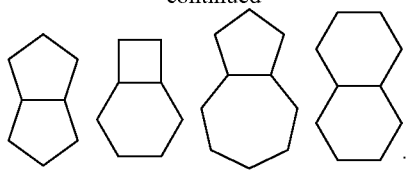

As used herein, "8 to 10 membered bicyclic heterocycle" refers to a bridged heterocycle with two rings, containing 8 to 10 ring atoms, wherein 1, 2, 3, 4 or 5 carbon ring atoms are substituted with heteroatoms selected from nitrogen, oxygen or sulfur. Examples of bicyclic heterocycles include, but are not limited to, tetrahydroquinoline, tetrahydroisoquinoline, decahydroquinoline, and the like.

As used herein, "$C_{1-8}$ alkoxy" refers to —O—($C_{1-8}$ alkyl), wherein alkyl is as defined above. $C_{1-6}$ alkoxy is preferred, and $C_{1-3}$ alkoxy is more preferred. Non-limiting examples include methoxy, ethoxy, propoxy, isopropoxy, butoxy, tert-butoxy, isobutoxy, pentoxy, and the like.

As used herein, "$C_{3-8}$ cycloalkoxy" refers to —O—($C_{3-8}$ cycloalkyl), wherein cycloalkyl is as defined above. $C_{3-6}$ cycloalkoxy is preferred. Non-limiting examples include cyclopropyloxy, cyclobutyloxy, cyclopentoxy, cyclohexyloxy, and the like.

As used herein, "$C_{6-10}$ aryl" refers to a full-carbon monocyclic or fused polycyclic (i.e., a ring that shares an adjacent pair of carbon atoms) group having a conjugated π-electron system, and refers to an aryl containing 6 to 10 carbon atoms. Phenyl and naphthyl are preferred, while phenyl is more preferred.

As used herein, "a bond" means that two groups connected therewith are linked by a covalent bond.

As used herein, "halogen" refers to fluorine, chlorine, bromine, or iodine.

As used herein, "halogenated" means that one or more (e.g., 1, 2, 3, 4 or 5) hydrogens in a group are substituted with a halogen.

For example, "halogenated $C_{1-8}$ alkyl" means that the alkyl is substituted with one or more (e.g., 1, 2, 3, 4 or 5) halogens, wherein the alkyl is as defined above. Halogenated $C_{1-6}$ alkyl is preferred, and halogenated $C_{1-3}$ alkyl is more preferred. Examples of halogenated $C_{1-8}$ alkyl include, but not limited to, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, and the like.

As another example, "halogenated $C_{1-8}$ alkoxy" means that the alkoxy is substituted with one or more (e.g., 1, 2, 3, 4 or 5) halogens, wherein the alkoxy is as defined above. Halogenated $C_{1-6}$ alkoxy is preferred, and halogenated $C_{1-3}$ alkoxy is more preferred. Examples of $C_{1-8}$ alkoxy include, but not limited to, trifluoromethoxy, trifluoroethoxy, monofluoromethoxy, monofluoroethoxy, difluoromethoxy, difluoroethoxy, and the like.

As another example, "halogenated $C_{3-8}$ cycloalkyl" means that a cycloalkyl is substituted with one or more (e.g., 1, 2, 3, 4 or 5) halogens, wherein the cycloalkyl is as defined above. Halogenated $C_{3-6}$ cycloalkyl is preferred. Examples of halogenated $C_{3-8}$ cycloalkyl include, but not limited to, trifluorocyclopropyl, monofluorocyclopropyl, monofluorocyclohexyl, difluorocyclopropyl, difluorocyclohexyl and the like.

As used herein, "deuterated $C_{1-8}$ alkyl" means that an alkyl is substituted with one or more (e.g., 1, 2, 3, 4, or 5) deuterium atoms, wherein the alkyl is as defined above. Deuterated $C_{1-6}$ alkyl is preferred, and deuterated $C_{1-3}$ alkyl is more preferred. Examples of deuterated $C_{1-8}$ alkyl include, but not limited to, monodeuterated methyl, monodeuterated ethyl, dideuterated methyl, dideuterated ethyl, trideuterated methyl, trideuterated ethyl and the like.

As used herein, "amino" refers to $NH_2$, "cyano" refers to CN, "nitro" refers to $NO_2$, "benzyl" refers to —$CH_2$-phenyl, "oxo" refers to =O, "carboxyl" refers to —C(O)OH, "acetyl" refers to —C(O)$CH_3$, "hydroxymethyl" refers to —$CH_2$OH, "hydroxyethyl" refers to —$CH_2CH_2$OH, "hydroxy" refers to —OH, "thiol" refers to SH, and the structure of "cyclopropylene" is:

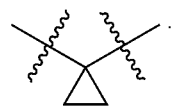

As used herein, "heteroaryl ring" and "heteroaryl" can be used interchangeably, and refer to a monocyclic heteroaryl group having 5 to 10 ring atoms, preferably 5 or 6 membered, or refer to an 8 to 10 membered bicyclic heteroaryl; 6,10 or 14 π electrons are shared in the ring array; and have 1 to 5 heteroatoms in addition to the carbon atoms. "Heteroatom" refers to nitrogen, oxygen or sulfur.

As used herein, "3 to 6 membered saturated or partially unsaturated monocyclic ring" refers to a saturated or partially unsaturated full-carbon monocyclic ring containing 3 to 6 ring atoms. Examples of 3 to 6 membered saturated or partially unsaturated monocyclic rings include, but not limited to, cyclopropyl ring, cyclobutyl ring, cyclopentyl ring, cyclopentenyl ring, cyclohexyl ring, cyclohexenyl ring, cyclohexadienyl ring, cycloheptyl ring, cycloheptatrienyl ring, cyclooctyl ring, and the like.

As used herein, "3 to 6 membered saturated single heterocycle" means a 3 to 6 membered monocyclic ring with 1, 2 or 3 carbon atoms in substituted with heteroatoms selected from nitrogen, oxygen, or S(O)$_t$ (wherein t is an integer from 0 to 2), but not including —O—O—, —O—S— or —S—S— as part of the ring the remaining ring atoms being carbon. A 4 to 6 membered ring is preferred, and a 5 to 6 membered ring is more preferred. Examples of 3 to 6 membered saturated single heterocycles include, but not limited to, epoxypropane, azetidine, oxetane, tetrahydrofuran, tetrahydrothiophene, pyrrolidine, piperidine, pyrroline, oxazolidine, piperazine, dioxolane, dioxane, morpholine, thiomorpholine, thiomorpholine-1,1-dioxide, tetrahydropyran and the like, or represented by the structure:

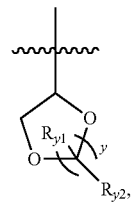

wherein y is 1 or 2, and $R_{y1}$ and $R_{y2}$ are each independently hydrogen or $C_{1-3}$ alkyl.

As used herein, "5 to 6 membered single heteroaryl ring" refers to a single heteroaryl ring containing 5 to 6 ring atoms, include but not limited to, for example, thiophene ring, N-alkylpyrrole ring, furan ring, thiazole ring, imidazole ring, oxazole ring, pyrrole ring, pyrazole ring, triazole ring, tetrazole ring, isoxazole ring, oxadiazole ring, thiadiazole ring, pyridine ring, pyridazine ring, pyrimidine ring, pyrazine ring and the like.

As used herein, "8 to 10 membered bicyclic heteroaryl ring" refers to a bicyclic heteroaryl ring containing 8 to 10 ring atoms, including, for example, but not limited to, benzofuran, benzothiophene, indole, isoindole, quinoline, isoquinoline, indazole, benzothiazole, benzimidazole, quinazoline, quinoxaline, cinnoline, and phthalizine.

As used herein, "substituted" means that one or more hydrogen atoms, preferably 1 to 5 hydrogen atoms in a group are independently substituted with a corresponding number of substituents, and more preferably 1 to 3 hydrogen atoms are independently substituted with a corresponding number of substituents. Of course, the substituents are only in their possible chemical positions, and those skilled in the art can determine (by experiment or theory) the possible or impossible substitutions without undue effort. For example, an amino or hydroxy with a free hydrogen may be unstable when combined with a carbon atom having an unsaturated (e.g., olefinic) bond.

As used herein, any one of the above groups may be substituted or unsubstituted. When the above groups are substituted, the substituents are preferably independently selected from 1 to 5 groups consisting of CN, halogen, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), halogenated $C_{1-8}$ alkoxy (preferably halogenated $C_{1-6}$ alkoxy, more preferably halogenated $C_{1-3}$ alkoxy), amino substituted with $C_{1-8}$ alkyl, amino, amino substituted with halogenated $C_{1-8}$ alkyl, 4 to 6 membered saturated single heterocycle, 5 to 6 membered single heteroaryl ring, 8 to 10 membered bicyclic heteroaryl ring, spiro, spiroheterocycle, bridged ring or bridged heterocycle.

The above-mentioned various substituents themselves of the present disclosure can also be substituted with the groups described herein.

When 4 to 6 membered saturated single heterocycles described herein are substituted, the positions of the substituents may be at their possible chemical positions, and representative substitutions of the exemplary single heterocycles are shown below:

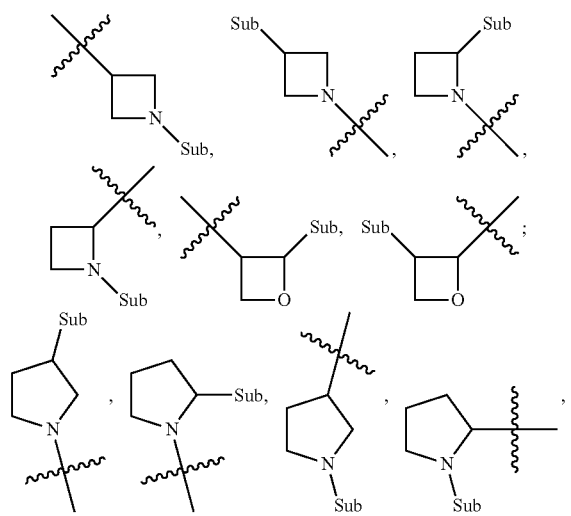

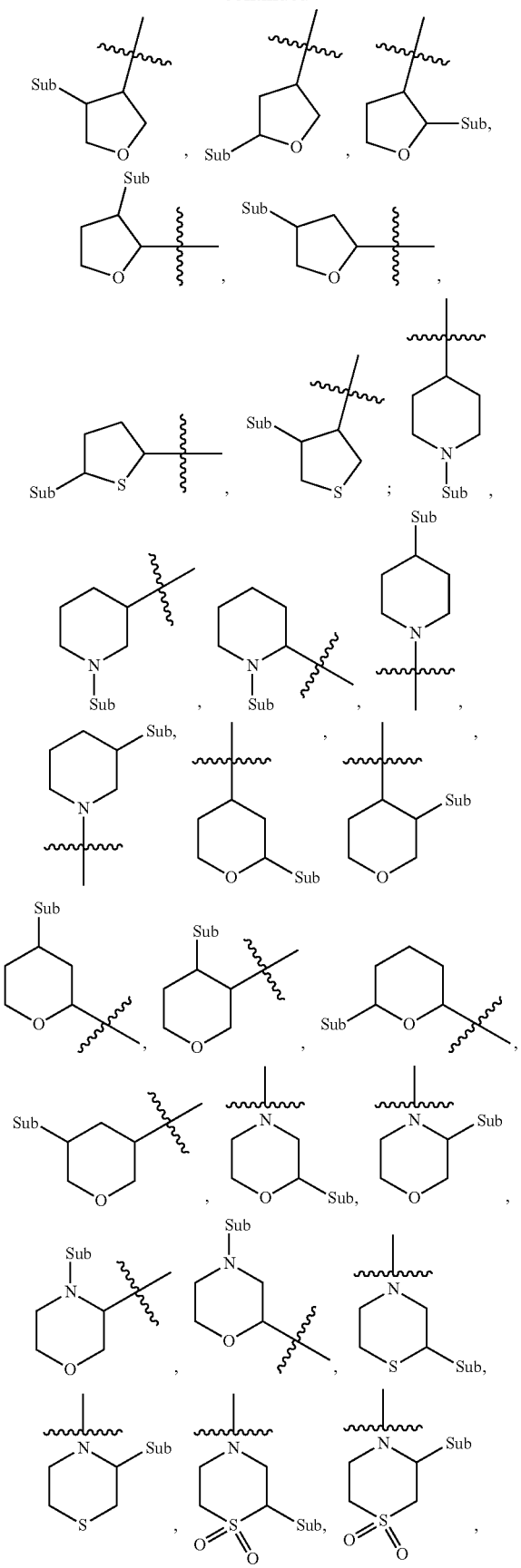

29

-continued

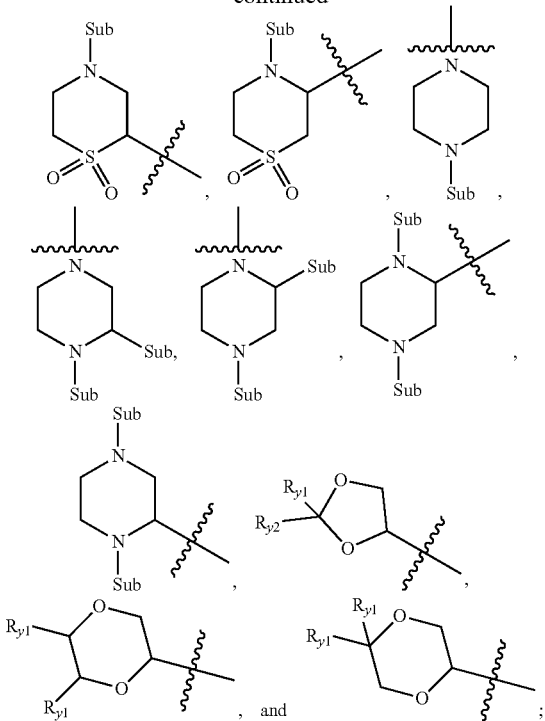

wherein "Sub" each independently represents the various types of substituents described herein; and "〜〜" represents a connection with other atoms.

When the cycloalkyl described herein are substituted, the positions of the substituents can be at their possible chemical positions, representative substitutions of the exemplary single heterocycles are as follows:

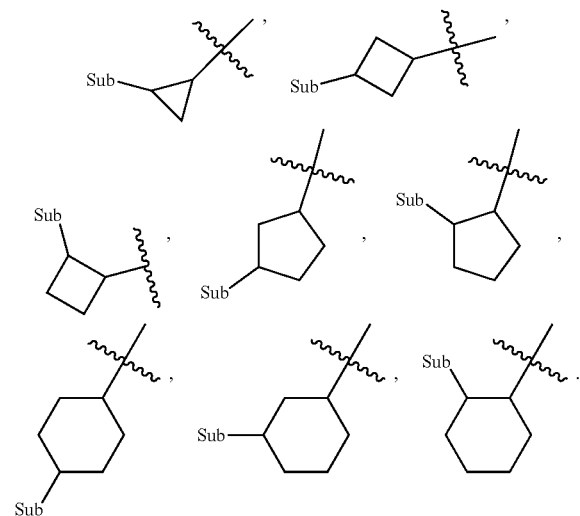

Wherein "Sub" each independently represents the various types of substituents described herein; "〜〜" represents connections with other atoms.

As used herein, the compounds of Formula (I) may be present in one or more crystalline forms, and the active compounds of the present disclosure include various crystalline forms and mixtures thereof.

30

"Solvate" mentioned in the present disclosure refers to a complex formed by the compound of the present disclosure with a solvent. They either react in a solvent, or precipitate or crystallize out of the solvent. For example, a complex formed with water is called a "hydrate". Solvates of the compounds of Formula (I) are within the scope of this disclosure.

The compounds represented by Formula (I) of the present disclosure may contain one or more chiral centers and exist in different optically active forms. When the compound contains one chiral center, the compound comprises an enantiomer. The present disclosure includes both isomers and mixtures thereof, such as racemic mixtures. Enantiomers can be resolved by methods known in the art, such as crystallization, chiral chromatography and the like. When the compound of Formula (I) contains more than one chiral centers, diastereomers may be present. The present disclosure includes optically-pure specific isomers which have been resolved, as well as mixtures of diastereomers. Diastereomers can be resolved by methods known in the art, such as crystallization and preparative chromatography.

Preparation Method

The present disclosure provides the preparation method of compounds of Formula (I). The compounds of the present disclosure can be prepared by a variety of synthetic processes. Exemplary preparation methods of these compounds may include (but not limited to) the procedures described below.

Preferably, the compounds of Formula (I) according to the present disclosure can be prepared from the following schemes and exemplary processes described in the embodiments as well as relevant literature available to those skilled in the art.

The steps of the processes can be extended or combined as desired in practice.

Route 1

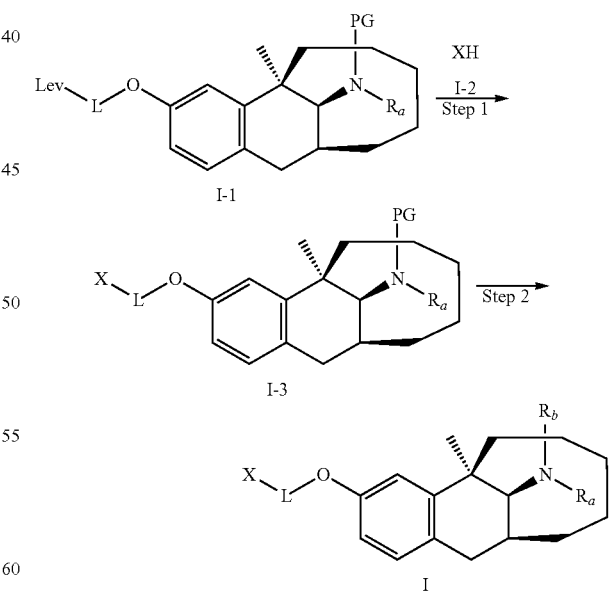

Step 1: When L is —CO—, a compound of Formula (I-1) reacts with a compound of Formula (I-2) to produce a compound of Formula (I-3) in an alkaline system, wherein suitable bases include a series of organic amine reagents that do not affect the production of the compound, preferably DIPEA or a suitable compound of Formula (I-2) such as —N(R₁R₂) and the like. The reaction solvent may be an aprotic solvent, preferably tetrahydrofuran, the reaction temperature may be from room temperature to 80° C., and the reaction time may be 1 to 24 h. Lev in Formula (I-1) refers to a leaving group including, but not limited to, chlorine, p-nitrophenol, and the like. PG in Formula (I-1) is an amino protecting group, and the amino protecting group includes but does not limited to: tert-butoxycarbonyl (Boc); aryl methoxycarbonyl, benzyloxycarbonyl (Cbz) and 9-fluorenylmethyloxycarbonyl (Fmoc); benzyl (Bn), 2,4-dimethoxybenzyl (DMB), triphenylmethyl (Tr), 1,1-bis-(4'-methoxyphenyl)methyl; trimethylsilylalkyl (TMS) and tert-butyl dimethylsilylalkyl (TBS), and the like.

Step 2: The compound of Formula (I-3) undergoes a deprotection reaction and a substitution reaction under suitable conditions to give compound of Formula (I). The method of deprotection can be adopted from conventional methods in the art, and the substitution reaction can be performed by referring to the conventional method in the art according to the structure of the $R_b$ group.

Route 2

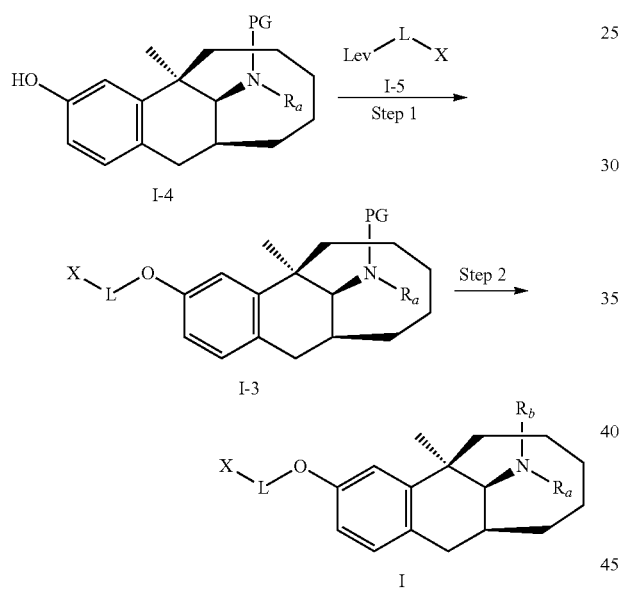

The compound of Formula (I-4) may undergo a condensation reaction or a substitution reaction in an alkaline system with the compound of Formula (I-5) to give the compound of Formula (I-3), followed by deprotection and substitution to produce the compound of Formula (I). The condensation reaction method can be adopted from the conventional method in the art; and suitable base systems include potassium t-butoxide in DMSO, sodium hydride in DMF, potassium carbonate in DMF, and the like. Lev in Formula (I-5) refers to a leaving group including, but are not limited to, chlorine, bromine, iodine, sulfonate groups, such as mesylate, tosylate, p-bromobenzenesulfonate, p-toluenesulfonate, and the like; and acyloxy groups may be, such as acetoxy, trifluoroacetoxy, and the like. The definition of the other groups is the same as in route 1.

The raw materials and the compounds of Formula (I-1), Formula (I-2), Formula (I-4) and Formula (I-5) in the route, depending on their specific structures, may be obtained commercially or prepared by methods known to those skilled in the art.

The compound of Formula (I-4) can be prepared by Process (A) including the following steps:

Process (A)

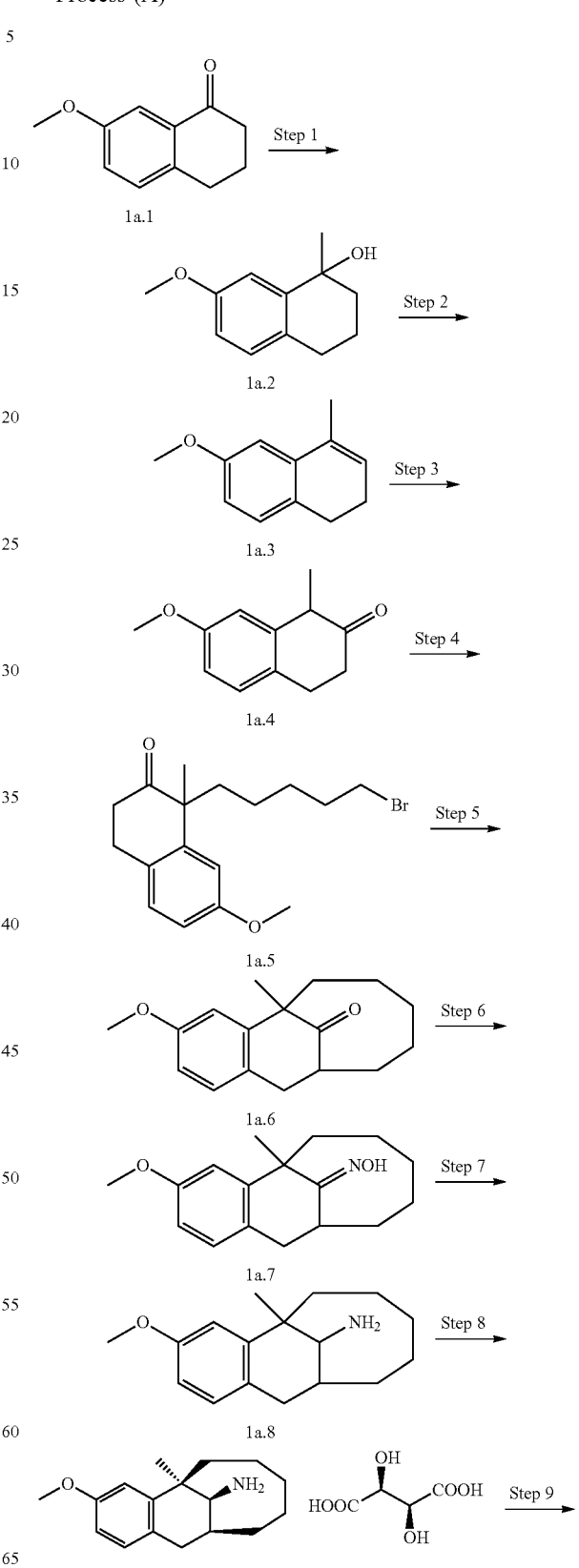

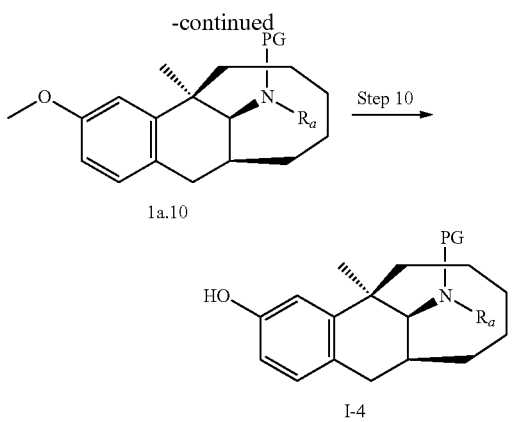

The compound of Formula (1a.1) reacts with methylated Grignard reagent under anhydrous and anaerobic conditions to obtain the compound of Formula (1a.2); the compound of Formula (1a.2) undergoes an elimination reaction to obtain the compound of Formula (1a.3); the compound of Formula (1a.3) undergoes an oxidation reaction to obtain the compound of Formula (1a.4), wherein mCPBA is preferably used as an oxidant; the compound of Formula (1a.4) reacts with 1,5-dibromopentane to obtain the compound of Formula (1a.5), and then undergoes an ring closing reaction using a suitable base such as sodium hydride to give the compound of the Formula (1a.6); the compound of Formula (1a.6) reacts with hydroxylamine hydrochloride to give the compound of Formula (1a.7); the compound of Formula (1a.7) is subjected to pressure hydrogenation to give the compound of Formula (1a.8); the compound of Formula (1a.8) is subjected to chiral resolution to obtain the compound of Formula (1a.9) with desired configuration, wherein the chiral resolution methods can be adopted from the conventional methods known in the art; the amino group in the compound of Formula (1a.9) is protected to obtain the compound of Formula (1a.10), wherein the protecting group that can be used includes, but is not limited to, the protecting group mentioned in Route 1, while methods for introducing the protecting group can be adopted from the conventional methods known in the art; and, the compound of Formula (I-4) is obtained by demethylation of the compound of Formula (1a.10).

The compound of Formula (I-1) can be prepared by Process (B) including the following steps:

Process (B)

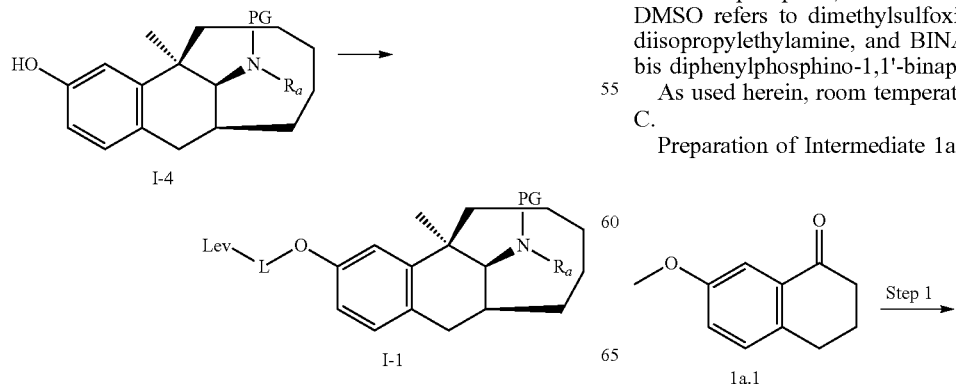

When L is —CO—, the compound of Formula (I-4) is carbonylated to obtain the compound of Formula (I-1). Depending on different compounds of Formula (I-1), the preferred carbonylation reagents may be bi(p-nitrophenyl) carbonate or triphosgene, and the like. The carbonate of the compound of Formula (I-4) is obtained carrying an easy-to-leave group Lev. Lev may include, but not limited to, chlorine, p-nitrophenol, and the like.

The reactions in the above steps are all conventional reactions known to those skilled in the art. Unless otherwise specified, the reagents and raw material compounds used in the synthetic route are all commercially available or can be prepared by those skilled in the art by referring to known methods according to the different compound structures designed.

The present disclosure is advantageous as compared with the prior art, mainly in a prolonged drug effect time of more than 2 times as compared with dezocine, a greatly increased oral bioavailability, a constant plasma concentration, and smaller side effects.

The present disclosure will be further illustrated below with reference to the specific embodiments. It should be understood that these embodiments are only to illustrate the present disclosure but not to limit the scope thereof in any way. The experimental methods without specific conditions in the following embodiments are generally carried out according to conventional conditions, or in accordance with the conditions recommended by the manufacturer. Unless indicated otherwise, parts and percentage are calculated by weight. Unless otherwise defined, terms used herein are of the same meanings that are familiar to those skilled in the art. In addition, any methods and materials similar with or equivalent to those described herein can be applied to the present disclosure.

As used herein, DMB refers to 2,4-dimethoxybenzyl, THF refers to tetrahydrofuran, EA refers to ethyl acetate, PE refers to petroleum ether, Ac$_2$O refers to acetic anhydride, NBS refers to N-bromosuccinimide, DCM refers to dichloromethane, AIBN refers to azodiisobutyronitrile, Pd(dppf)Cl$_2$ refers to [1,1'-bis(diphenylphosphino)ferrocene]palladium dichloride, TFA refers to trifluoroacetic acid, TBSCI refers to tert-butyldimethylchlorosilane, NCS refers to N-chlorosuccinimide, DHP refers to dihydrogenpyran, LiAlH$_4$ refers to lithium aluminium hydride, PMB refers to p-methoxybenzyl, LiHMDS refers to lithium bistrimethylsilylamide, Pd$_2$(dba)$_3$ refers to tris(dibenzylideneacetone) dipalladium, RuPhos refers to 2-dicyclohexylphosphoryl-2', 6'-diisopropoxy-1,1'-biphenyl, DMAP refers to 4-dimethylaminopyridine, THP refers to tetrahydropyran, n-BuLi refers to n-butyllithium, TMsOTf refers to trimethylsilyl trifluoromethanesulfonate, TEBAC refers to triethylbenzylammonium chloride, HATU refers to 2-(7-azobenzotriazole)-N,N,N',N'-tetramethyluronium hexafluorophosphate, DMF refers to dimethylformamide, DMSO refers to dimethylsulfoxide, DIEA refers to N,N-diisopropylethylamine, and BINAP refers to (2R,3S)-2,2'-bis diphenylphosphino-1,1'-binaphthyl.

As used herein, room temperature refers to about 20-25° C.

Preparation of Intermediate 1a

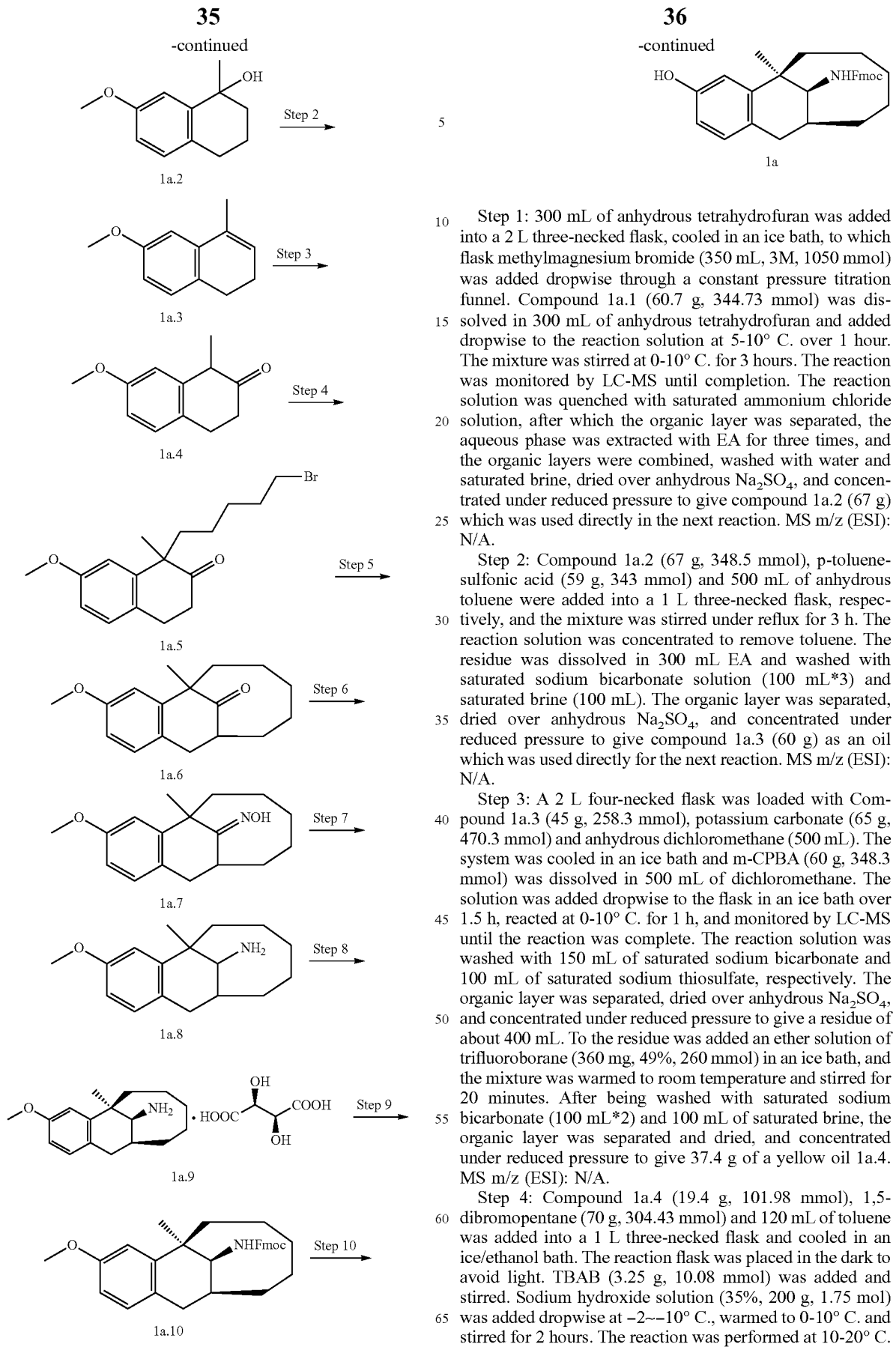

Step 1: 300 mL of anhydrous tetrahydrofuran was added into a 2 L three-necked flask, cooled in an ice bath, to which flask methylmagnesium bromide (350 mL, 3M, 1050 mmol) was added dropwise through a constant pressure titration funnel. Compound 1a.1 (60.7 g, 344.73 mmol) was dissolved in 300 mL of anhydrous tetrahydrofuran and added dropwise to the reaction solution at 5-10° C. over 1 hour. The mixture was stirred at 0-10° C. for 3 hours. The reaction was monitored by LC-MS until completion. The reaction solution was quenched with saturated ammonium chloride solution, after which the organic layer was separated, the aqueous phase was extracted with EA for three times, and the organic layers were combined, washed with water and saturated brine, dried over anhydrous $Na_2SO_4$, and concentrated under reduced pressure to give compound 1a.2 (67 g) which was used directly in the next reaction. MS m/z (ESI): N/A.

Step 2: Compound 1a.2 (67 g, 348.5 mmol), p-toluenesulfonic acid (59 g, 343 mmol) and 500 mL of anhydrous toluene were added into a 1 L three-necked flask, respectively, and the mixture was stirred under reflux for 3 h. The reaction solution was concentrated to remove toluene. The residue was dissolved in 300 mL EA and washed with saturated sodium bicarbonate solution (100 mL*3) and saturated brine (100 mL). The organic layer was separated, dried over anhydrous $Na_2SO_4$, and concentrated under reduced pressure to give compound 1a.3 (60 g) as an oil which was used directly for the next reaction. MS m/z (ESI): N/A.

Step 3: A 2 L four-necked flask was loaded with Compound 1a.3 (45 g, 258.3 mmol), potassium carbonate (65 g, 470.3 mmol) and anhydrous dichloromethane (500 mL). The system was cooled in an ice bath and m-CPBA (60 g, 348.3 mmol) was dissolved in 500 mL of dichloromethane. The solution was added dropwise to the flask in an ice bath over 1.5 h, reacted at 0-10° C. for 1 h, and monitored by LC-MS until the reaction was complete. The reaction solution was washed with 150 mL of saturated sodium bicarbonate and 100 mL of saturated sodium thiosulfate, respectively. The organic layer was separated, dried over anhydrous $Na_2SO_4$, and concentrated under reduced pressure to give a residue of about 400 mL. To the residue was added an ether solution of trifluoroborane (360 mg, 49%, 260 mmol) in an ice bath, and the mixture was warmed to room temperature and stirred for 20 minutes. After being washed with saturated sodium bicarbonate (100 mL*2) and 100 mL of saturated brine, the organic layer was separated and dried, and concentrated under reduced pressure to give 37.4 g of a yellow oil 1a.4. MS m/z (ESI): N/A.

Step 4: Compound 1a.4 (19.4 g, 101.98 mmol), 1,5-dibromopentane (70 g, 304.43 mmol) and 120 mL of toluene was added into a 1 L three-necked flask and cooled in an ice/ethanol bath. The reaction flask was placed in the dark to avoid light. TBAB (3.25 g, 10.08 mmol) was added and stirred. Sodium hydroxide solution (35%, 200 g, 1.75 mol) was added dropwise at −2~−10° C., warmed to 0-10° C. and stirred for 2 hours. The reaction was performed at 10-20° C. for 2 hours. The reaction was monitored by LC-MS until completion. The system was added with water (100 ml) and extracted with toluene (200 mL*3). The organic layer was washed with 2N HCl (100 mL*3) and saturated brine (100 mL*2), respectively, dried over anhydrous Na$_2$SO$_4$, concentrated to remove the toluene, had 1,5-dibromopentane was distilled off under reduced pressure, and had the remaining residue purified by Preparative Liquid Chromatography to give Compound 1a.5 as a yellow oil (12.8 g, 37%). MS m/z (ESI): 356.1 [M+NH4]$^+$.

Step 5: Compound 1a.5 (59.2 g, 174.5 mmol) and 600 mL of anhydrous DMF were added into a 2 L three-necked flask, stirred, and added with sodium hydride (15 g, 60%, 375 mmol) in batches in an ice bath. The reaction was slowly heated to 100° C. and stirred for 1 hour. The reaction was monitored by LC-MS until completion. After the heating was stopped, the mixed solution was cooled in an ice bath, quenched with saturated ammonium chloride solution, added with 2 L of water. The organic layers were separated, extracted with EA (400 mL*3), combined, washed with water (500 mL*2), washed with saturated brine (500 mL), dried over Na$_2$SO$_4$, concentrated, and purified by Preparative Liquid Chromatography to obtain a white solid 1a.6 (24 g, 51.1%). MS m/z(ESI): 259.2 [M+H]$^+$.

Step 6: To a 500 mL three-necked flask was added Compound 1a.6 (5.9 g, 22.84 mmol), hydroxylamine hydrochloride (15.9 g, 228.8 mmol) and 100 mL of pyridine/The system was stirred at 135° C. overnight. The reaction was monitored by LC-MS until completion. The reaction solution was concentrated under reduced pressure to remove pyridine, after which the residue was added with 100 mL of water and extracted with EA (100 mL*2). The organic layers were combined, washed with 100 mL of saturated brine, dried over anhydrous Na$_2$SO$_4$ and concentrated. The concentrate was beaten with petroleum ether/EA=1:1 and filtered to give a white solid 1a.7 (4.93 g, 79%). MS m/z (ESI): 274.2 [M+H]$^+$.

Step 7: To a 1 L autoclave were added Compound 1a.7 (20 g, 73.16 mmol), Raney Ni (23 g), 400 mL of ethanol and 160 mL of ammonia (28%-30%). The system was stirred at 60° C. under 60 atm hydrogen for 48 hours. The reaction solution was filtered through celite and the filtrate was concentrated to remove the solvent. EA (400 mL) and hydrochloric acid/1,4-dioxane (4M, 40 mL) were added to the residue and stirred at room temperature for 2 hours. The reaction solution was filtered and the filter cake was washed with EA, dried to give 21 g white solid. The white solid was dissolved in 500 mL EA, added with saturated sodium bicarbonate solution (30 mL) dropwise in an ice bath. The organic layer was separated, and the aqueous layer was extracted with EA (300 mL). The organic layers were combined, dried and concentrated under reduced pressure to give an oily compound 1a.8 (17.4 g, 91.7%). MS m/z (ESI): 260.3 [M+H]$^+$.

Step 8: Compound 1a.8 (41.6 g, 160.38 mmol) was dissolved in 820 mL of methanol, added with L-tartaric acid (24.1 g, 160.57 mmol), and stirred at room temperature for 1 hour. The system was added with (+)-(L)-seeds, allowed to stand still for two days, and filtered. The filtrate was concentrated, added with saturated sodium bicarbonate solution/EA to release free base, reconcentrated, dissolved with addition of 20× volumes of methanol, added with D-tartaric acid (17.6 g, 117.26 mmol), stirred at room temperature for 1 hour, added with (−)-(D)-seeds, allowed to stand still for 1 day, and filtered. The filtered cake was recrystallized with methanol to give a white solid 1a.9 (17 g, 25.9%). MS m/z (ESI): 410 [M+H]$^+$.

Step 9: To a 250 mL round-bottom flask were added Compound 1a.9 (5.01 g, 12.235 mmol), Fmoc-Cl (3.96 g, 15.307 mmol), sodium carbonate (4.28 g, 40.381 mmol), 50 mL of 1,4-dioxane and 50 mL of water, and the mixture was stirred at room temperature for 3 hours. The reaction was monitored by LC-MS until completion. 200 mL of water was added to the system and extracted with EA (100 mL*2). The organic layers were combined, washed with 100 mL of saturated saline, dried over anhydrous Na$_2$SO$_4$, concentrated, and purified under medium pressure Preparative Liquid Chromatography to obtain a white solid compound 1a.10 (5.7 g, 96.8%). MS m/z (ESI): 482.3 [M+H]$^+$.

Step 10: To a 250 mL round-bottom flask were added Compound 1a.10 (5.7 g, 11.8 mmol) and 80 mL of anhydrous dichloromethane, added with boron tribromide (5.9 g, 23.55 mmol) in an ice bath, and stirred while warming to room temperature for 3 hrs. The reaction was monitored by LC-MS until completion. The reaction was quenched with saturated ammonium chloride solution. The organic layer was separated, and the aqueous layer was extracted with dichloromethane. The organic layers were combined, washed with saturated brine, dried over anhydrous Na$_2$SO$_4$, concentrated and purified under medium pressure Preparative Liquid Chromatography to obtain a white solid compound 1a (3.77 g, 68.2%). MS m/z (ESI): 466.3 [MH]$^-$.

Preparation of Intermediate 2a

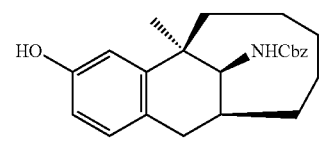

2a

The preparation process was the same as that of Compound 1a, except that Fmoc-Cl, sodium carbonate and 1,4-dioxane in step 9 of Compound 1a were replaced with Cbz-Cl, potassium carbonate and tetrahydrofuran, respectively. MS m/z (ESI): 394.3 [M+H]$^+$.

Preparation of Intermediate 3a

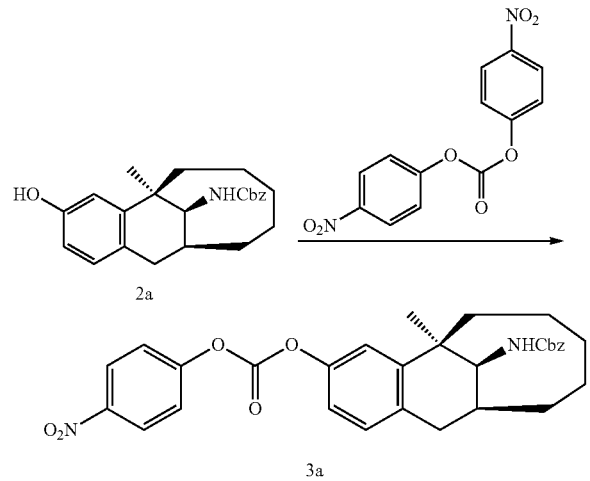

A 50 mL three-neck flask was loaded with 2a (4 g, 10.54 mmol), bis(p-nitrophenyl)carbonate (3.53 g, 11.6 mmol), DIPEA (2.74 g, 21.2 mmol) and 50 mL tetrahydrofuran, and the mixture was stirred overnight at room temperature. The reaction was monitored by LC-MS until completion. The reaction solution was concentrated to remove the solvent. The residue was dissolved in 100 mL of EA, washed with 1M sodium hydroxide solution (100 mL*4), 1M hydrochloric acid solution (100 mL*4) and 100 mL of saturated brine, respectively. The organic layer was separated, dried over anhydrous Na₂SO₄, concentrated to give 5.9 g of a yellow solid compound 3a. MS m/z (ESI): N/A.

Preparation of Intermediate 4a

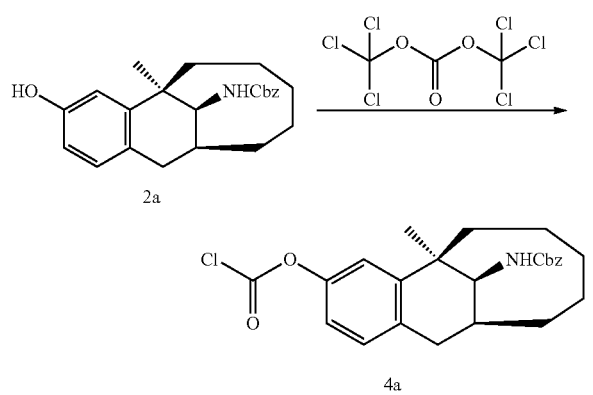

A 50 mL round-bottom flask was loaded with bis(trichloromethyl) carbonate (311 mg, 1.048 mmol) and 5 mL of dried tetrahydrofuran, cooled in an ice bath, added with triethylamine (162 mg, 1.601 mmol), added dropwise with a solution of 2a (200 mg, 0.527 mmol) in tetrahydrofuran (1 mL), stirred in an ice bath for 1 hour. The reaction was monitored by LC-MS until completion. The reaction solution was quenched with water, extracted with EA, and the organic layer was dried and concentrated to give 280 mg of Compound 4a as a colorless oil. The methyl ester of Compound 4a: MS m/z (ESI): 438.0 [M+H]+.

Preparation of Intermediate 5a

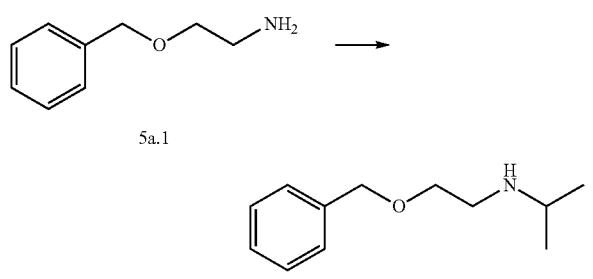

Compound 5a.1 (451 mg, 2.98 mmol), acetone (1.74 g, 29.96 mmol), and a solution of acetic acid (180 mg, 3 mmol) in dichloromethane (20 mL) were stirred at room temperature for 20 minutes, added with sodium triacetoxyborohydride (1.9 g, 8.96 mmol), and then stirred at room temperature for 1 hour. The reaction was monitored by LC-MS until completion. The reaction solution was poured into water, adjusted to pH 8 with sodium bicarbonate solution, extracted with EA, dried, and concentrated to obtain 90 mg of Compound 5a. MS m/z (ESI): 194.2 [M+H]⁺.

Preparation of Intermediate 6a

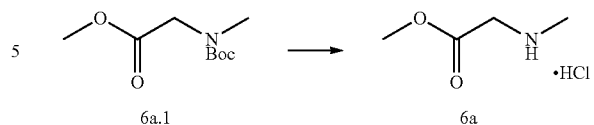

To a solution of Compound 6a.1 (500 mg, 2.644 mmol) in methanol (10 mL) was added hydrochloric acid/1,4-dioxane (2.6 mL), and the mixture was stirred at room temperature overnight. The reaction solution was concentrated and used directly in the next reaction.

Preparation of Intermediate 7a

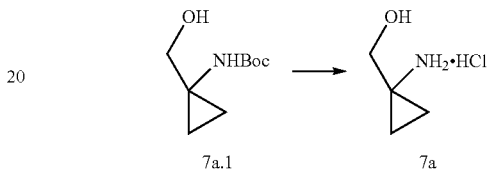

Intermediate 7a was prepared by using Compound 7a.1 as a raw material and referring to preparation method of Compound 6a.

Preparation of Intermediate 8a

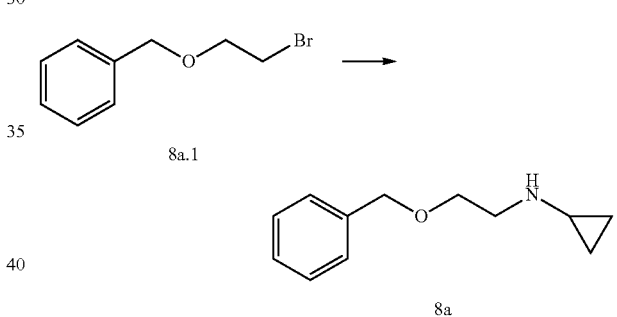

A solution of Compound 8a.1 (1 g, 4.649 mmol) and cyclopropylamine (265 mg, 4.649 mmol) in 10 mL of ethanol was stirred at 70° C. overnight. The reaction solution was cooled to room temperature, concentrated and purified by combiflash to give 120 mg of Compound 8a. MS m/z (ESI): 192.2 [M+H]⁺.

Preparation of Intermediate 9a

Step 1: Intermediate 9a was prepared by using Compounds 9a.1 and 9a.3 as a raw materials and referring to preparation method of Compound 1a.6. Compound 9a.2 was obtained by Combiflash purification.

Step 2: The preparation method was the same as that of Compound 6a, except that Compound 6a.1 in the preparation method of Compound 6a was replaced with Compound 9a.2.

Example 1

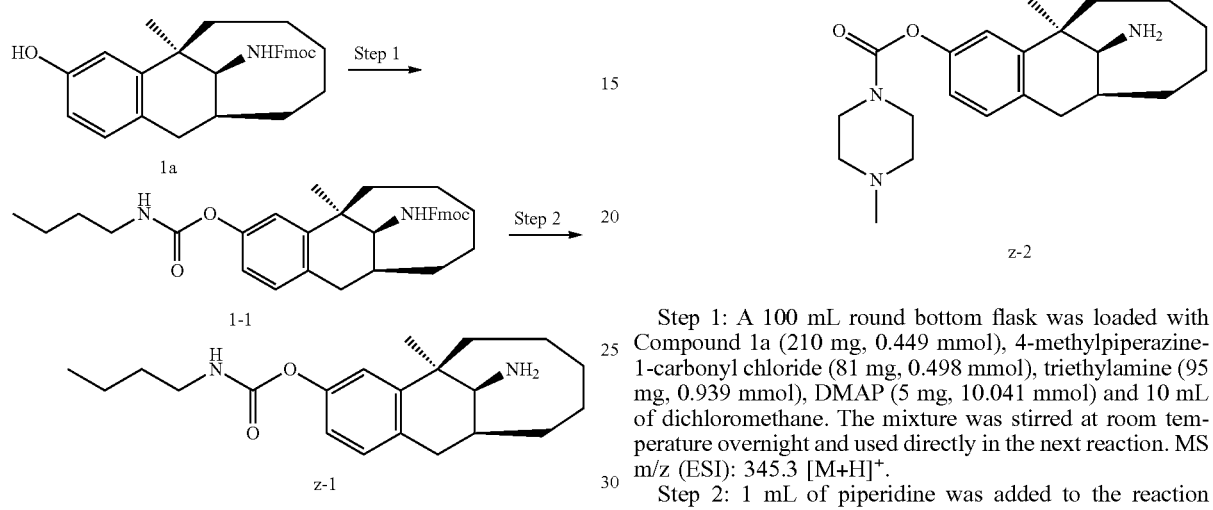

1a 1-1 z-1

Step 1: A 100 mL round bottom flask was loaded with Compound 1a (270 mg, 0.577 mmol), n-butylisocyanate (86 mg, 0.868 mmol), triethylamine (95 mg, 0.939 mmol) and dichloromethane (10 mL). The system was stirred at room temperature for 2 hours. The reaction was monitored by LC-MS until completion. The reaction solution was washed with saturated ammonium chloride solution and concentrated to give 322 mg of a white solid compound 1-1.MS m/z (ESI): 567.3 [M+H]$^+$.

Step 2: To a 100 mL round bottom flask were added 1-1 (153 mg, 0.27 mmol), piperidine (115 mg, 1.351 mmol) and 10 mL of dichloromethane, and the mixture was stirred at room temperature for 24 hours. The reaction was monitored by LC-MS until completion. The reaction solution was washed with water (20 mL*3), underwent reverse extraction with dichloromethane (20 mL), after which the organic layers were combined, dried, concentrated, purified by preparative high-performance liquid chromatography to give a yellow solid compound z-1 (17.1 mg, 18.4%). MS m/z (ESI): 345.3 [M+H]$^+$; $^1$H NMR (500 MHz, DMSO-d$_6$) δ 8.35 (s, 3H), 7.67 (m, 1H), 7.09 (d, 1H), 6.96 (d, 1H), 6.86-6.88 (dd, 1H), 3.52 (m, 1H), 3.15-3.18 (m, 1H), 3.04 (m, 2H), 2.68 (m, 1H), 1.77 (m, 4H), 1.31-1.44 (m, 12H), 0.89 (m, 3H), 0.68 (m, 2H).

Example 2

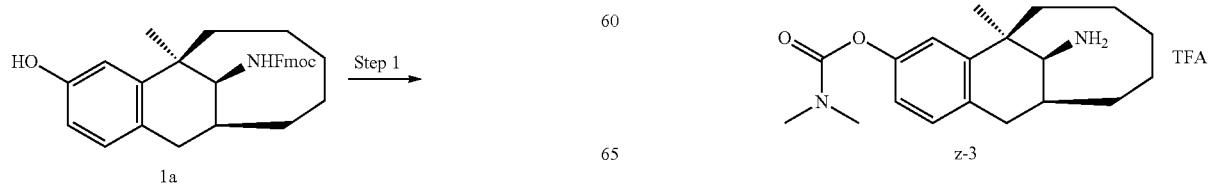

1a 2-1 z-2

Step 1: A 100 mL round bottom flask was loaded with Compound 1a (210 mg, 0.449 mmol), 4-methylpiperazine-1-carbonyl chloride (81 mg, 0.498 mmol), triethylamine (95 mg, 0.939 mmol), DMAP (5 mg, 10.041 mmol) and 10 mL of dichloromethane. The mixture was stirred at room temperature overnight and used directly in the next reaction. MS m/z (ESI): 345.3 [M+H]$^+$.

Step 2: 1 mL of piperidine was added to the reaction solution of Step 1, and the mixture was stirred at room temperature for 3 hours. The reaction was monitored by LC-MS until completion. The reaction solution was washed with saturated ammonium chloride, and the organic layer was separated, concentrated and purified by preparative HPLC to give a white solid compound z-2 (125 mg, 60.7%). MS m/z (ESI): 372.4 [M+H]$^+$; $^1$H NMR (500 MHz, DMSO-d$_6$) δ 7.03 (d, 1H), 6.93 (d, 1H), 6.80-6.82 (dd, 1H), 3.57 (m, 1H), 3.34-3.41 (m, 2H), 3.01-3.09 (m, 2H), 2.61 (m, 1H), 2.35 (m, 4H), 2.22 (s, 3H), 2.14 (m, 1H), 2.03-2.08 (m, 2H), 1.76-1.81 (m, 1H), 1.40-1.57 (m, 5H), 1.28 (s, 3H), 1.08 (m, 1H), 0.68 (m, 2H).

Example 3

1a 3-1 z-3

Step 1: The preparation method of Compound 3-1 was the same as that of Compound 2-1, except that 4-methylpiperazine-1-carbonyl chloride was replaced with dimethylcarbamoyl chloride. MS m/z (ESI): 539.3 [M+H]$^+$.

Step 2: Compound z-3 (101.51 mg, 75%) was prepared by using Compound 3-1 as the raw material and by referring to the process of Step 2 of Example 1. MS m/z (ESI): 304 [M+H]$^+$; $^1$H NMR (500 MHz, DMSO-d$_6$) δ 8.30 (s, 1H), 7.03 (d, 1H), 6.93 (d, 1H), 6.79-6.82 (dd, 1H), 3.26 (m, 1H), 3.04-3.10 (m, 1H), 2.99 (s, 3H), 2.86 (s, 3H), 2.60 (m, 1H), 2.28 (m, 1H), 1.82-1.88 (m, 1H), 1.61-1.71 (m, 3H), 1.35-1.50 (m, 3H), 1.31 (s, 3H), 1.12 (m, 1H), 0.65 (m, 2H).

Example 4

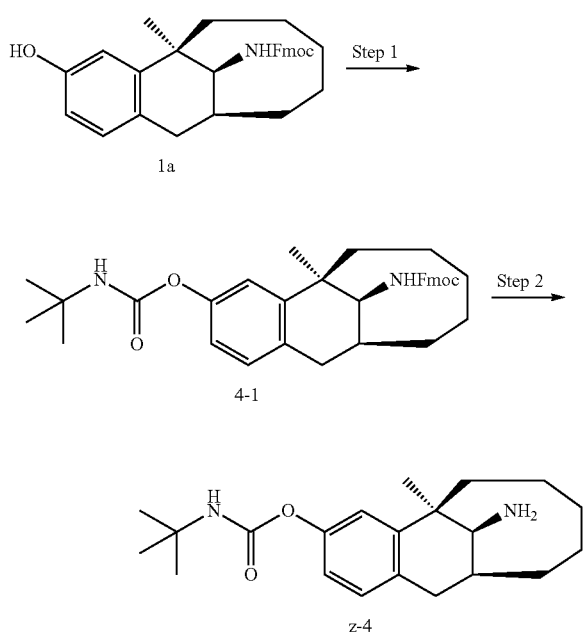

Step 1: Compound 1a (200 mg, 0.44 mmol), tert-butyl isocyanate (120 mg, 0.88 mmol) and cuprous chloride (80 mg, 0.88 mmol) were added to 5 mL of DMF, and the mixture was stirred at room temperature for 2 hours. The reaction was monitored by LC-MS until completion. The reaction solution was filtered, extracted with EA/water system, and had the organic layer separated, concentrated and purified by medium pressure Preparative Liquid Chromatography to give Compound 4-1 (200 mg, 77.3%). MS m/z (ESI): 589 [M+H]$^+$.

Step 2: Compound z-4 (30 mg, 34.1%) was prepared by using Compound 4-1 as the raw material and by referring to the method of Step 2 of Example 1. MS m/z (ESI): 345 [M+H]$^+$; 1H NMR (500 MHz, DMSO-d$_6$) δ 8.38 (s, 1H), 7.45 (s, 1H), 7.04 (d, 1H), 6.89 (d, 1H), 6.79-6.82 (dd, 1H), 3.19 (m, 1H), 3.05-3.11 (m, 1H), 2.62 (m, 1H), 2.25 (m, 1H), 1.92-1.98 (m, 1H), 1.73-1.76 (m, 1H), 1.61-1.65 (m, 2H), 1.35-1.50 (m, 3H), 1.33 (s, 3H), 1.27 (s, 9H), 1.11 (m, 1H), 0.68 (m, 2H).

Example 5

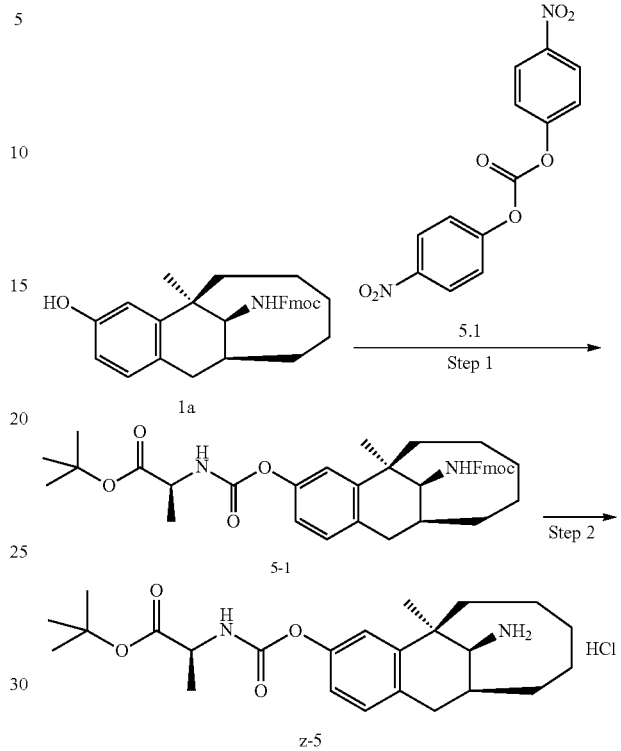

Step 1: A 100 mL round-bottomed flask was loaded with Compound 1a (100 mg, 0.214 mmol), bis(p-nitrophenyl) carbonate (71 mg, 0.235 mmol), DIPEA (61 mg, 0.47 mmol) and 10 mL of tetrahydrofuran. The mixture was stirred at room temperature overnight, added with (S)-tert-butyl-2-aminopropyl ester (39 mg, 0.214 mmol), stirred overnight at room temperature. The reaction was monitored by LC-MS until completion. The mixture was extracted with EA/water, and the organic layer was concentrated and purified by the medium pressure Preparative Liquid Chromatography to give compound 5-1 (70 mg, 51.3%). MS m/z (ESI): 639 [M+H]$^+$.

Step 2: Compound z-5 (9.53 mg, 24.3%) was prepared by using Compound 5-1 (60 mg, 0.094 mmol) as the raw material and referring to the method of Step 2 of Example 1. MS m/z (ESI): 417 [M+H]$^+$; $^1$H NMR (500 MHz, DMSO-d$_6$) δ 8.06 (m, 1H), 7.09 (d, 1H), 6.93 (d, 1H), 6.82-6.84 (dd, 1H), 4.17 (m, 1H), 3.25 (m, 1H), 3.10 (m, 1H), 2.65 (m, 1H), 2.33 (m, 1H), 1.90-1.95 (m, 1H), 1.74-1.78 (m, 1H), 1.64-1.67 (m, 2H), 1.35-1.50 (m, 3H), 1.42 (s, 9H), 1.35 (s, 3H), 1.31 (d, J=7.5 Hz, 3H), 1.15 (m, 1H), 0.69 (m, 2H).

Example 6

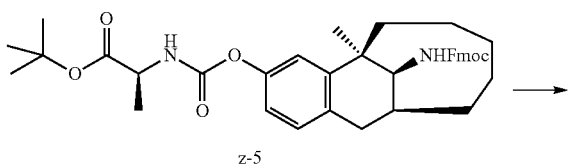

-continued

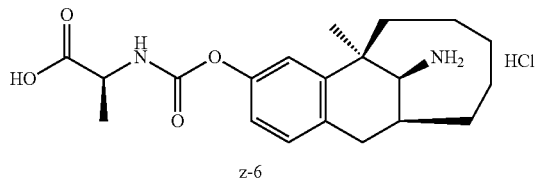

z-6

A 50 mL round-bottomed flask was loaded with Compound z-5 (90 mg, 0.216 mmol) and acetic acid (5 mL). The mixture was stirred at room temperature for 2 hours, concentrated under reduced pressure, and purified by preparative HPLC to give Compound z-6 (9.25 mg, 11.8%). MS m/z (ESI): 361 [M+H]$^+$; $^1$H NMR (400 MHz, DMSO-d$_6$) δ 8.23 (s, 1H), 7.69 (m, 1H), 7.06 (d, 1H), 6.94 (d, 1H), 6.82-6.84 (dd, 1H), 3.91 (m, 1H), 3.25 (m, 1H), 3.09 (m, 1H), 2.64 (m, 1H), 2.24 (m, 1H), 1.92-1.97 (m, 1H), 1.72-1.74 (m, 1H), 1.65 (m, 2H), 1.35-1.50 (m, 3H), 1.33 (s, 3H), 1.31 (d, J=5.6 Hz, 3H), 1.13 (m, 1H), 0.69 (m, 2H).

Example 7

Step 1: A 50 mL round bottom flask was loaded with Compound 3a (830 mg, 1.524 mmol), 2,5,8,11-tetraethylene glycol monomethylether-13-amine (540 mg, 2.605 mmol), 10 mL of tetrahydrofuran and DMAP (204 mg, 1.67 mmol, respectively).), and the mixture was stirred at room temperature for 1 h. The reaction was monitored by LC-MS until completion. The reaction solution was concentrated and purified by combi-flash (0-100% EA in n-hexane) to give Compound 7-1 (660 mg, 81.8%) as a colorless oil. MS m/z (ESI): 613.4 [M+H]$^+$.

Step 2: A 100 mL round bottom flask was loaded with compound 7-1 (660 mg, 1.077 mmol), 20 mL of EA and 70 mg of palladium/carbon (5%), and the mixture was stirred under hydrogen atmosphere at 50° C. overnight. The reaction was monitored by LC-MS until completion. The mixture was filtered, and the filtrate was concentrated to remove the solvent, while the residue was dissolved in 50 mL of water. 40 mg of formic acid was dissolved in 5 mL of water and was added dropwise to the residue. The mixture was extracted with EA (50 mL*2), and the water layer was freeze-dried to obtain a yellow solid Z-7 (360 mg, 69.9%). MS m/z (ESI): 479.4 [M+H]$^+$; $^1$H NMR (400 MHz, DMSO-d$_6$) δ 8.34 (s, 1H), 7.69 (t, 1H), 7.06 (d, 1H), 6.93 (d, 1H), 6.82-6.85 (dd, 1H), 3.07-3.53 (m, 20H), 2.63 (m, 1H), 2.29 (m, 1H), 1.86-1.93 (m, 1H), 1.63-1.78 (m, 3H), 1.35-1.50 (m, 3H), 1.34 (s, 3H), 1.15 (m, 1H), 0.68 (m, 2H).

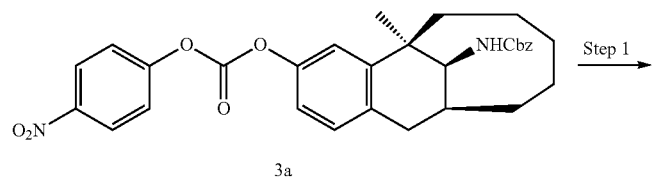

3a

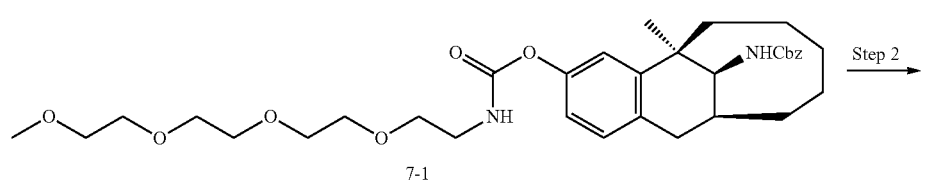

7-1

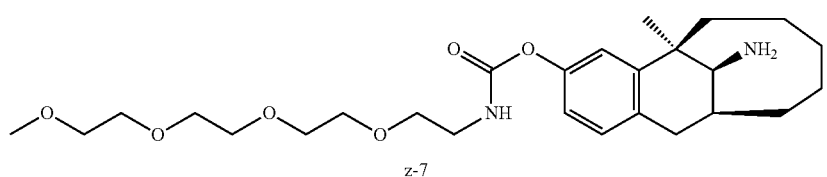

z-7

Example 8

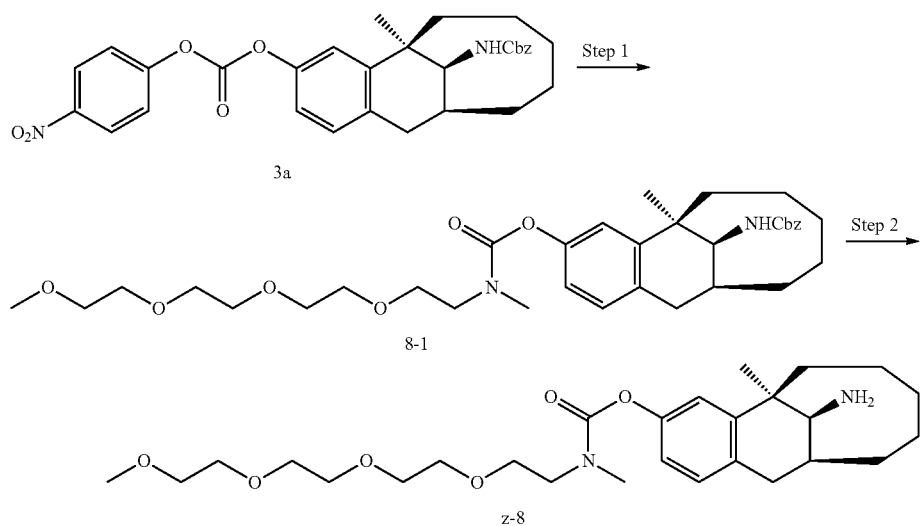

Step 1: The preparation method was the same as that of Compound 7-1, except that 2,5,8,11-tetraethylene glycol monomethyl ether-13-amine in the preparation method of Compound 7-1 was replaced with N-methyl-2,5,8,11-tetraethylene glycol monomethyl ether-13-amine MS m/z (ESI): 627.4 [M+H]$^+$.

Step 2: A 100 mL round bottom flask was loaded with Compound 8-1 (870 mg, 1.388 mmol), 20 mL of EA and palladium/carbon (500 mg, 5%), and the mixture was stirred at room temperature under hydrogen atmosphere overnight. The reaction was monitored by LC-MS until completion. The reaction solution was filtered through celite, concentrated and purified by prep-HPLC to give Compound z-8 (436 mg, 63.7%) as a white solid. MS m/z (ESI): 493.4 [M+H]$^+$; $^1$H NMR (400 MHz, DMSO-d$_6$) δ 8.38 (s, 1H), 7.05 (d, 1H), 6.93 (d, 1H), 6.81-6.83 (dd, 1H), 3.42-3.64 (m, 16H), 3.23 (s, 3H), 3.17 (m, 1H), 3.09-3.13 (m, 1H), 3.06 (s, 1.5H), 2.92 (s, 1.5H), 2.62 (m, 1H), 2.24 (m, 1H), 1.93-2.00 (m, 1H), 1.73-1.80 (m, 1H), 1.60-1.63 (m, 2H), 1.35-1.50 (m, 3H), 1.32 (s, 3H), 1.13 (m, 1H), 0.69 (m, 2H).

Example 9

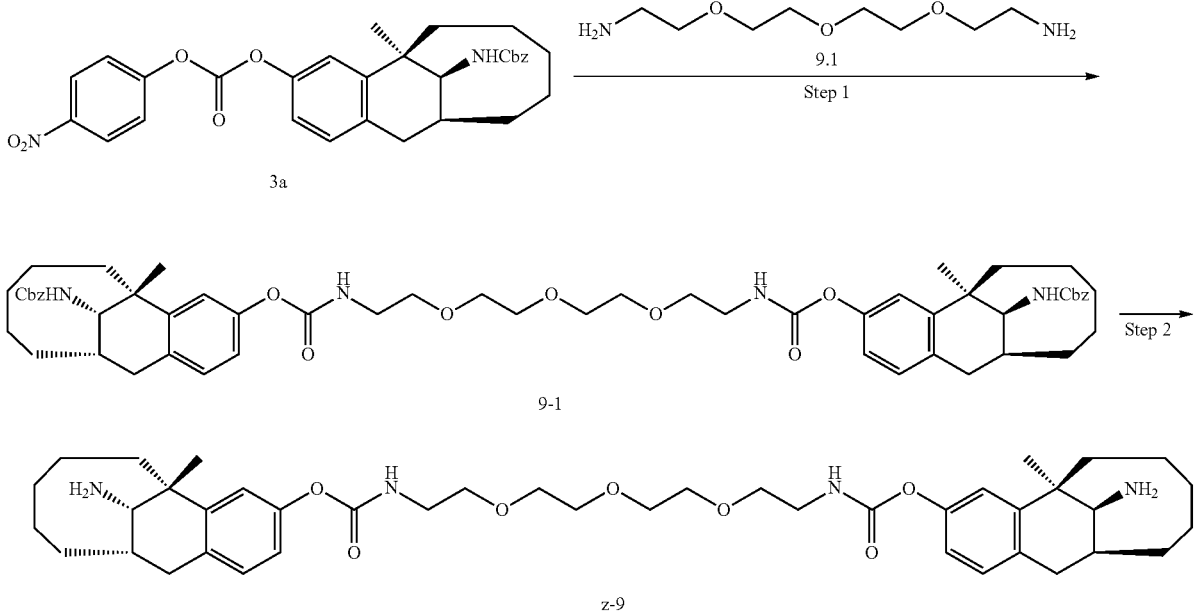

Step 1: The preparation method was the same as that of Compound 7-1, except that 2,5,8,11-tetraethylene glycol monomethyl ether-13-amine in the preparation method of 7-1 was replaced with Compound 9.1 and stirred at room temperature overnight. MS m/z (ESI): 502.1 [M+2H]⁺/2.

Step 2: Compound z-9 (220 mg, 39.5%) was prepared by using Compound 9-1 as a raw material and referring to the method of Step 2 in Example 8. MS m/z (ESI): 736.5 [M+H]⁺; $^1$H NMR (400 MHz, DMSO-$d_6$) δ 8.36 (s, 2H), 7.70 (t, 2H), 7.06 (d, 2H), 6.93 (d, 2H), 6.82-6.85 (dd, 2H), 3.09-3.54 (m, 20H), 2.63 (m, 2H), 2.32 (m, 2H), 1.85-1.91 (m, 2H), 1.68-1.78 (m, 6H), 1.35-1.50 (m, 6H), 1.33 (s, 6H), 1.14 (m, 2H), 0.69 (m, 4H).

Example 10

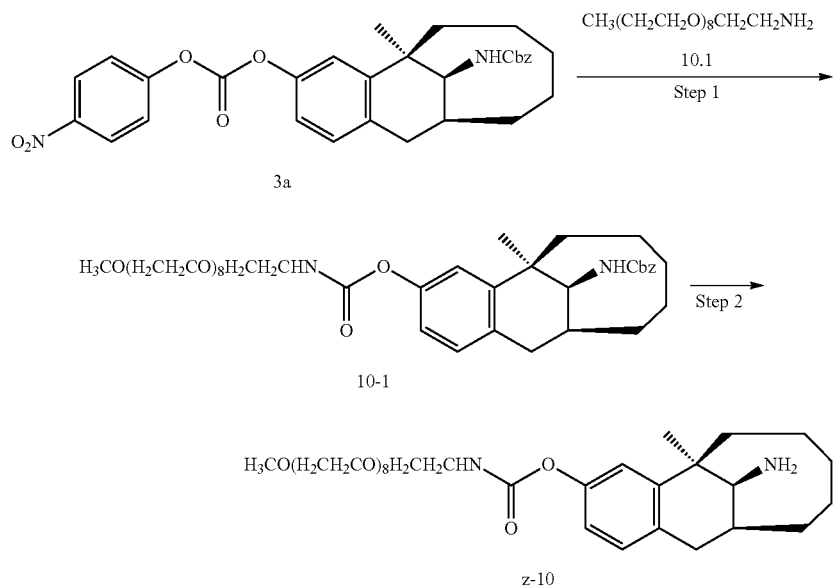

Step 1: The preparation method was the same as that of Compound 9-1, except that Compound 9.1 in the preparation method of Compound 9-1 was replaced with Compound 10.1. MS m/z (ESI): 417.4 [M+H]⁺.

Step 2: Compound z-10 (100 mg, 21.7%) was prepared by using Compound 9-1 as a raw material and referring to the method of Step 2 in Example 8. MS m/z (ESI): 699.5 [M+H]⁺; $^1$H NMR (400 MHz, DMSO-$d_6$) δ 8.34 (s, 1H), 7.66 (t, 1H), 7.05 (d, 1H), 6.92 (d, 1H), 6.81-6.84 (dd, 1H), 3.06-3.53 (m, 38H), 2.63 (m, 1H), 2.27 (m, 1H), 1.89-1.96 (m, 1H), 1.68-1.78 (m, 3H), 1.35-1.50 (m, 3H), 1.33 (s, 3H), 1.14 (m, 1H), 0.69 (m, 2H).

Example 11

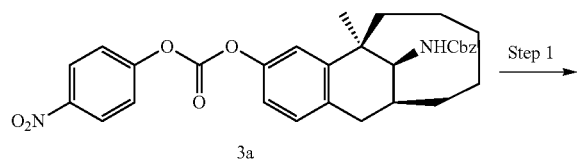

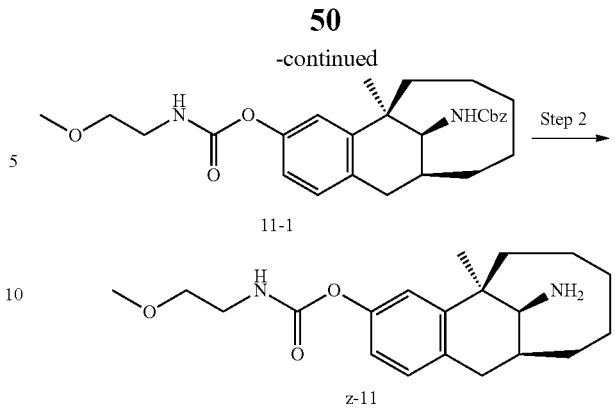

Step 1: A 50 mL round bottom flask was loaded with Compound 3a (873 mg, 1.603 mmol), 2-methoxyethylamine (120 mg, 1.598 mmol), 10 mL of tetrahydrofuran and DMAP (220 mg, 1.801 mmol), and the mixture was stirred at room temperature for 1 hour. The reaction was monitored by LC-MS until completion. EA (50 mL) was added to the reaction solution, and washed with NaOH (1 M, 30 mL*3) and HCl (1 M, 30 mL*3), and the organic layer was dried, concentrated and purified by combi-flash (0-40% EA and n-hexane) to give Compound 11-1 (750 mg, 83.7%) as a colorless oil. MS m/z (ESI): 481.3 [M+H]⁺.

Step 2: Compound z-11 (550 mg, 89.8%) was prepared by using Compound 11-1 as a raw material and referring to the method of Step 2 in Example 7. MS m/z (ESI): 347.3 [M+H]⁺; $^1$H NMR (400 MHz, DMSO-$d_6$) δ 8.32 (s, 1H), 7.68 (t, 1H), 7.02 (d, 1H), 6.90 (d, 1H), 6.78-6.81 (dd, 1H), 3.15-3.37 (m, 8H), 3.03-3.10 (m, 1H), 2.60 (m, 1H), 2.26 (m, 1H), 1.83-1.90 (m, 1H), 1.60-1.71 (m, 3H), 1.35-1.50 (m, 3H), 1.31 (s, 3H), 1.12 (m, 1H), 0.65 (m, 2H).

Example 12

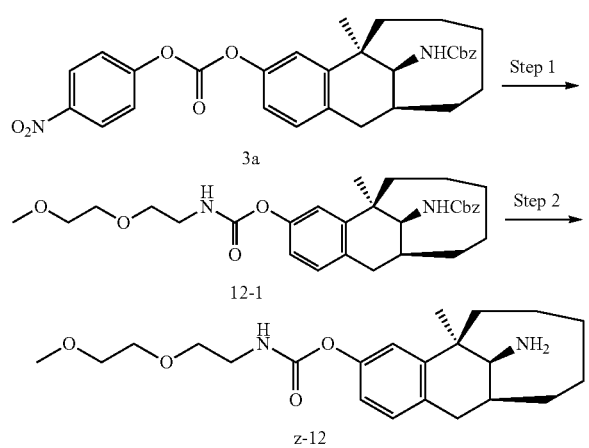

Step 1: The preparation method is the same as that of Compound 11-1, except that 2-methoxyethylamine in the preparation method of 11-1 is replaced with Compound 2-(2-methoxyethoxy)-ethylamine MS m/z (ESI): 525.3 [M+H]$^+$.

Step 2: Compound z-12 (470 mg, 83.1%) was prepared by using Compound 12-1 as a raw material and referring to the method of Step 2 in Example 7. MS m/z (ESI): 391.3 [M+H]$^+$; $^1$H NMR (400 MHz, DMSO-d$_6$) δ 8.35 (s, 1H), 7.70 (t, 1H), 7.06 (d, 1H), 6.93 (d, 1H), 6.82-6.85 (dd, 1H), 3.44-3.54 (m, 6H), 3.30 (m, 1H), 3.25 (3, 3H), 3.18-3.22 (m, 1H), 3.07-3.13 (m, 1H), 2.63 (m, 1H), 2.31 (m, 1H), 1.86-1.93 (m, 1H), 1.64-1.74 (m, 3H), 1.35-1.50 (m, 3H), 1.34 (s, 3H), 1.16 (m, 1H), 0.68 (m, 2H).

Example 13

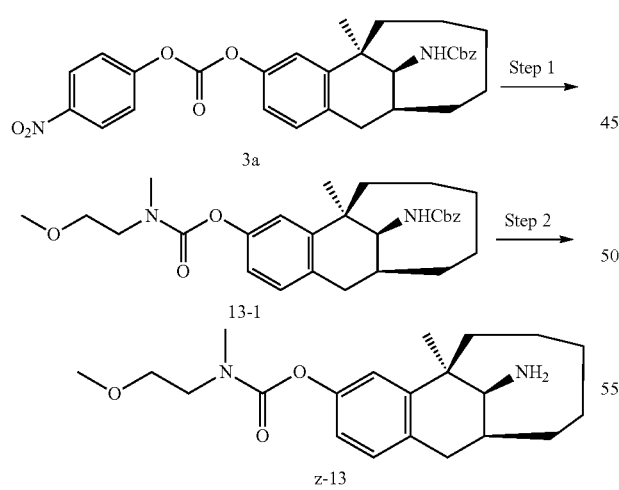

Step 1: The preparation method was the same as that of Compound 11-1, except that 2-methoxyethylamine in the preparation method of 11-1 was replaced with Compound 2-methoxy-N-methylethylamine MS m/z (ESI): 495.3 [M+H]$^+$.

Step 2: Compound z-13 (365 mg, 83.5%) was prepared by using Compound 13-1 as a raw material and referring to the method of Step 2 in Example 7. MS m/z (ESI): 361.3 [M+H]$^+$; $^1$H NMR (400 MHz, DMSO-d$_6$) δ 8.33 (s, 1H), 7.07 (d, 1H), 6.94 (d, 1H), 6.82-6.85 (dd, 1H), 3.42-3.45 (m, 4H), 3.27-3.30 (m, 4H), 3.23 (m, 1H), 3.09-3.13 (m, 1H), 3.05 (s, 1.5H), 2.91 (s, 1.5H), 2.63 (m, 1H), 2.29 (m, 1H), 1.88-1.94 (m, 1H), 1.72-1.78 (m, 1H), 1.62-1.66 (m, 2H), 1.35-1.50 (m, 3H), 1.33 (s, 3H), 1.11 (m, 1H), 0.69 (m, 2H).

Example 14

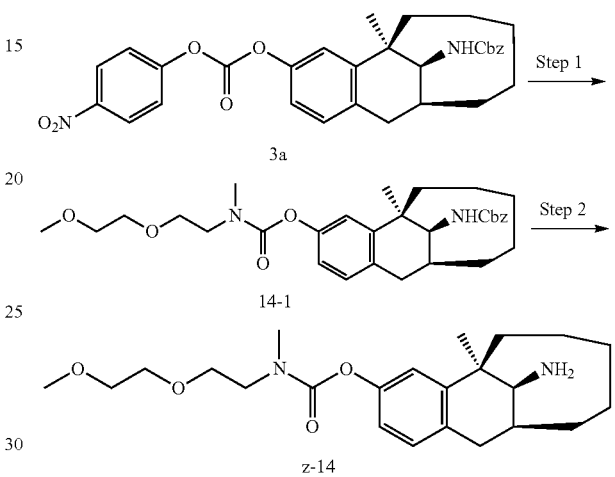

Step 1: The preparation method was the same as that of Compound 11-1, except that 2-methoxyethylamine in the preparation method of 11-1 was replaced with Compound 2-(2-methoxyethoxy)-N-methylethylamine. MS m/z (ESI): 539.3 [M+H]$^+$.

Step 2: Compound z-14 (610 mg, 83.3%) was prepared by using Compound 14-1 as a raw material and referring to the method of Step 2 in Example 7. MS m/z (ESI): 405.3 [M+H]$^+$; $^1$H NMR (400 MHz, DMSO-d$_6$) δ 8.32 (s, 1H), 7.07 (d, 1H), 6.94 (d, 1H), 6.82-6.84 (dd, 1H), 3.42-3.64 (m, 8H), 3.25 (s, 3H), 3.23 (m, 1H), 3.09-3.13 (m, 1H), 3.06 (s, 1.5H), 2.92 (s, 1.5H), 2.63 (m, 1H), 2.25 (m, 1H), 1.90-1.96 (m, 1H), 1.72-1.78 (m, 1H), 1.62-1.66 (m, 2H), 1.35-1.50 (m, 3H), 1.33 (s, 3H), 1.11 (m, 1H), 0.69 (m, 2H).

Example 15

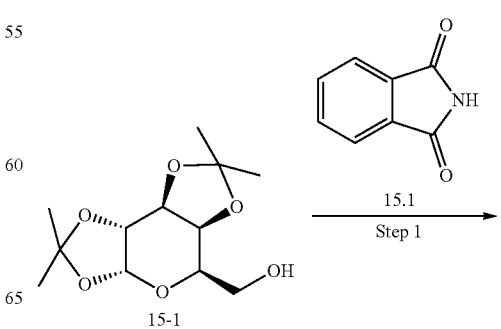

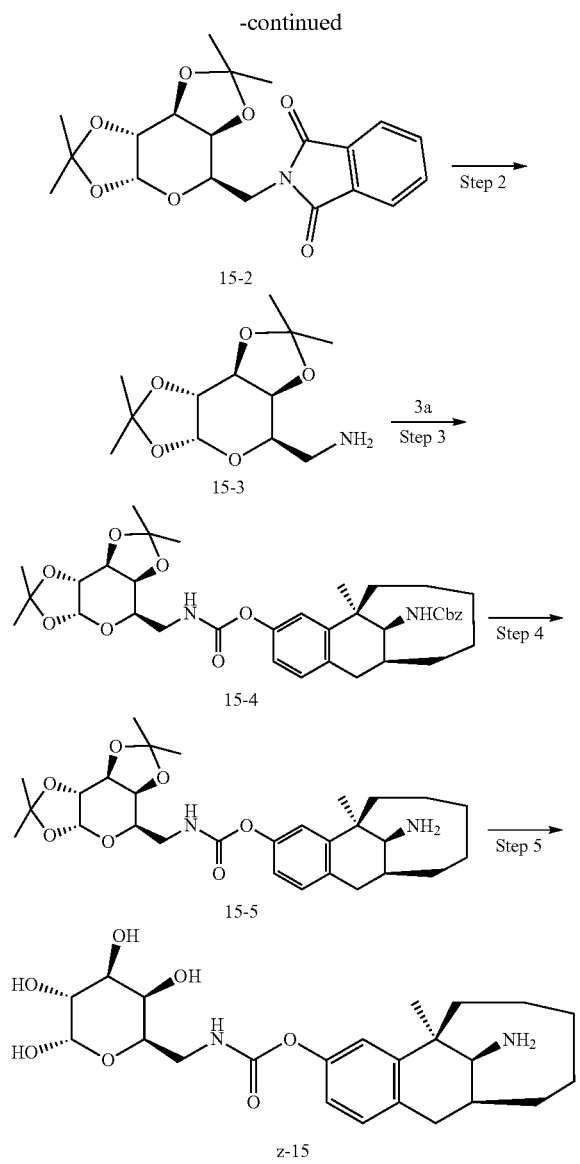

Step 1: A 250 mL three-necked flask was filled with nitrogen gas and loaded with Compound 15-1 (2.5 g, 9.605 mmol), Compound 15.1 (1.41 g, 9.583 mmol), and 60 mL of tetrahydrofuran, and triphenylphosphine (7.55 g, 28.785 mmol), respectively, cooled in an ice bath, and added dropwise with DIAD (5.83 g, 28.83 mmol), after which it was allowed to warm to room temperature and react for 5 hours. The reaction was monitored by LC-MS until completion. The reaction solution was concentrated and purified by combiflash (0-30% EA in n-hexane) to give Compound 15-2 (3.76 g, 90.4%) as a colorless oil. MS m/z (ESI): 390.3 $[M+H]^+$.

Step 2: A 100 mL round-bottomed flask was loaded with Compound 15-2 (3.55 g, 9.12 mmol), ethanol (20 mL) and hydrazine hydrate (600 mg, 85%, 10.19 mmol), and the system was stirred at 80° C. for 3 hours. The reaction was monitored by LC-MS until completion. The reaction solution was filtered, and the filtrate was concentrated, dissolved by adding 30 mL of EA and then filtered. The filtrate (pH=2-3) was washed with water (50 mL), the aqueous layer was adjusted to a pH of 9-10, concentrated to remove water, and had the residue washed with EA, filtered and concentrated to give a yellow oily Compound 15-3 (1.9 g, 76%). MS m/z (ESI): 260.2 $[M+H]^+$.

Step 3: The preparation method was the same as that of Compound 11-1, except that 2-methoxyethylamine in the preparation method of Compound 11-1 was replaced with Compound 15-3. MS m/z (ESI): 687.3 $[M+Na]^+$.

Step 4: To a 100 mL round-bottom flask were added Compound 15-4 (1.28 g, 1.925 mmol), 20 mL of EA and palladium/carbon (285 mg, 10%), respectively, and the system was stirred at room temperature under hydrogen atmosphere overnight. The reaction solution was filtered and concentrated to give Compound 15-5 (950 mg, 93%) as a white solid. MS m/z (ESI): 531.4 $[M+H]^+$.

Step 5: To a 100 mL round bottom flask were added Compound 15-5 (825 mg, 1.56 mmol), 9 mL of trifluoroacetic acid and 1 mL of water, and the mixture was stirred at room temperature for 30 minutes. The reaction was monitored by LC-MS until completion. The reaction solution was concentrated and purified by preparative high-performance liquid chromatography to give Compound z-15 (220 mg, 28.5%) as a white solid. MS m/z (ESI): 451.3 $[M+H]^+$; $^1$H NMR (400 MHz, DMSO-$d_6$) δ 8.22 (s, 1H), 7.52-7.59 (m, 1H), 7.02 (d, 1H), 6.89 (d, 1H), 6.79-6.81 (dd, 1H), 4.90 (m, 1H), 4.19 (m, 1H), 3.35-3.80 (m, 5H), 3.05-3.25 (m, 5H), 2.59 (m, 1H), 2.22 (m, 1H), 1.85-1.92 (m, 1H), 1.63-1.70 (m, 3H), 1.35-1.49 (m, 3H), 1.30 (s, 3H), 1.11 (m, 1H), 0.66 (m, 2H).

Example 16

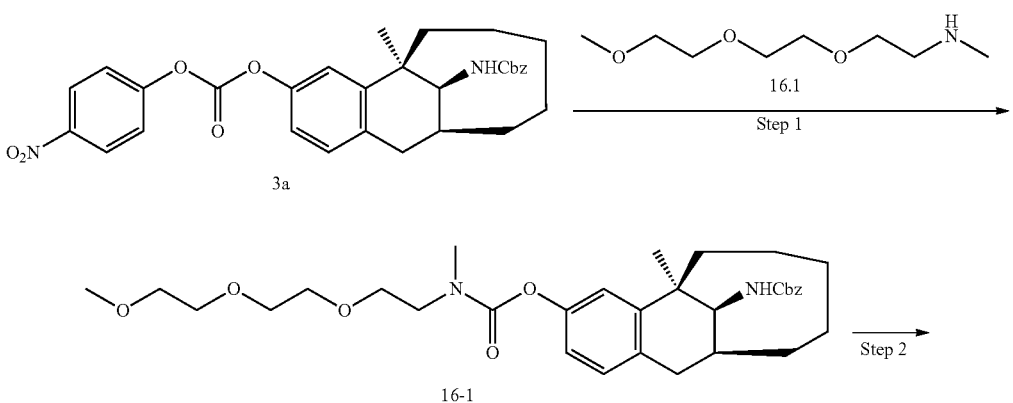

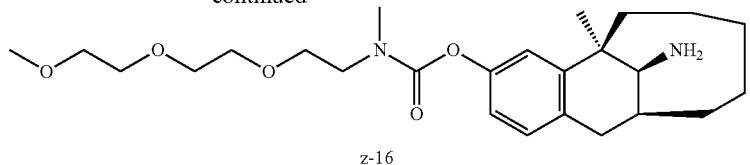

z-16

Step 1: The preparation method was the same as that of Compound 11-1, except that 2-methoxyethylamine in the preparation method of Compound 11-1 was replaced with Compound 16.1. MS m/z (ESI): 583.4 [M+H]⁺.

Step 2: Compound z-16 (420 mg, 63.7%) was prepared by using Compound 16-1 as a raw material and referring to the method of Step 2 in Example 7. MS m/z (ESI): 449.4 [M+H]⁺; ¹H NMR (400 MHz, DMSO-d₆) δ 8.32 (s, 1H), 7.07 (d, 1H), 6.94 (d, 1H), 6.82-6.84 (dd, 1H), 3.35-3.70 (m, 12H), 3.24 (m, 1H), 3.23 (s, 3H), 3.09-3.13 (m, 1H), 3.06 (s, 1.5H), 2.92 (s, 1.5H), 2.63 (m, 1H), 2.25 (m, 1H), 1.90-1.96 (m, 1H), 1.72-1.78 (m, 1H), 1.62-1.66 (m, 2H), 1.35-1.50 (m, 3H), 1.33 (s, 3H), 1.11 (m, 1H), 0.69 (m, 2H).

Example 17

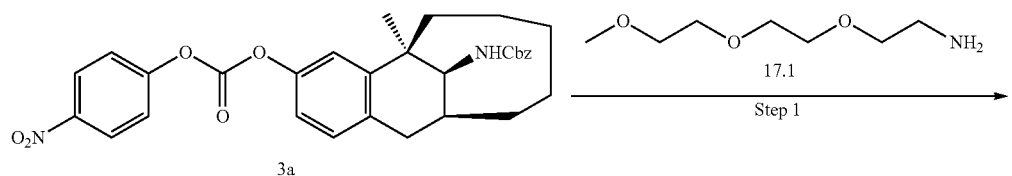

3a

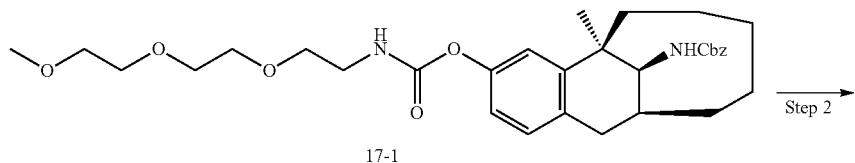

17-1

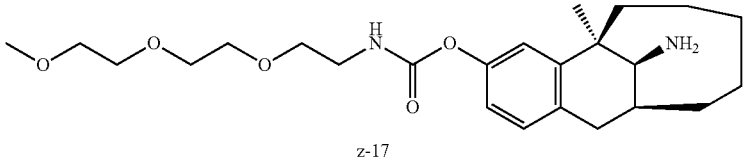

z-17

Step 1: The preparation method was the same as that of Compound 11-1, except that 2-methoxyethylamine in the preparation method of Compound 11-1 was replaced with Compound 17.1. MS m/z (ESI): 569.3 [M+H]⁺.

Step 2: Compound z-17 (208.9 mg, 59.3%) was prepared by using Compound 17-1 as a raw material and referring to the method of Step 2 in Example 8. MS m/z (ESI): 435.4 [M+H]⁺; ¹H NMR (400 MHz, DMSO-d₆) δ 7.67 (t, 1H), 7.07 (d, 1H), 6.93 (d, 2.0 Hz, 1H), 6.83 (dd, 1H), 3.53-3.42 (m, 11H), 3.24-3.19 (m, 5H), 3.10 (dd, 1H), 2.65 (d, 1H), 2.32 (br. s., 1H), 1.93-1.60 (m, 4.5H), 1.52-1.10 (m, 6.8H), 0.80-0.65 (m, 1.7H).

Example 18

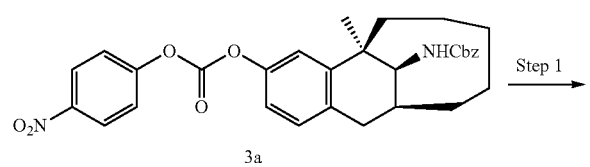

3a

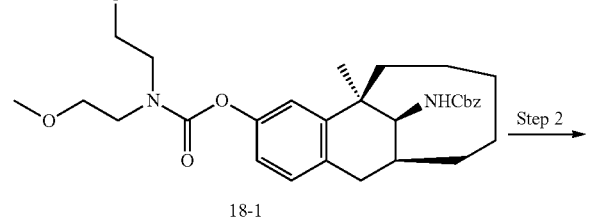

18-1

-continued

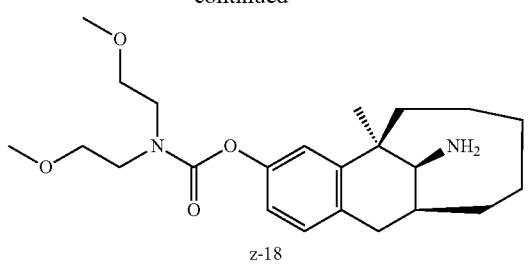

z-18

Step 1: The preparation method was the same as that of Compound 11-1, except that 2-methoxyethylamine in the preparation method of Compound 11-1 was replaced with bis(2-methoxyethyl) amine MS m/z (ESI): 539.3 [M+H]$^+$.

Step 2: Compound z-18 (252 mg, 90.6%) was prepared by using Compound 18-1 as a raw material and referring to the method of Step 2 in Example 7. MS m/z (ESI): 376.3 [M+H]$^+$; $^1$H NMR (400 MHz, DMSO-d$_6$) δ 7.04 (d, 1H), 6.92 (d, 1H), 6.80 (dd, 8.4 Hz, 1H), 3.52-3.42 (m, 8H), 3.25-3.22 (m, 7H), 3.07 (dd, 1H), 2.62 (d, 1H), 2.77 (br. s., 1H), 1.90-1.83 (m, 1H), 1.75-1.60 (m, 3H), 1.46-1.37 (m, 3H), 1.31 (s, 3H), 1.18-1.09 (m, 1H), 0.71-0.59 (m, 2H).

Example 19

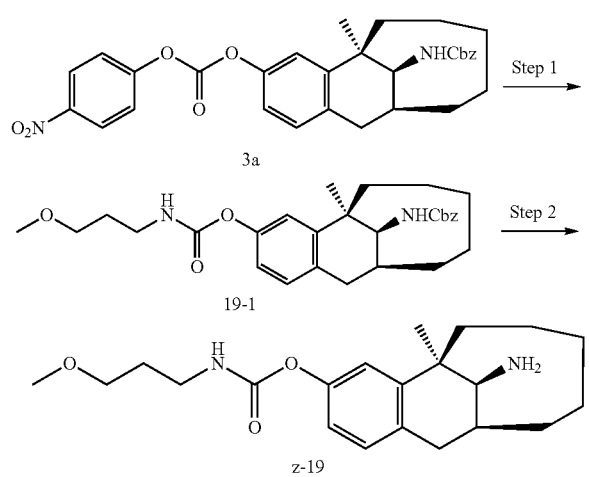

Step 1: The preparation method was the same as that of Compound 11-1, except that 2-methoxyethylamine in the preparation method of 11-1 was replaced with 3-methoxypropylamine MS m/z (ESI): 495.0 [M+H]$^+$.

Step 2: Compound z-19 (320 mg, 72.7%) was prepared by using Compound 19-1 as a raw material and referring to the method of Step 2 in Example 7. MS m/z (ESI): 361.1 [M+H]$^+$; $^1$H NMR (400 MHz, DMSO-d$_6$) δ 8.33 (s, 1H), 7.65 (t, 1H), 7.07 (d, 1H), 6.92 (d, 1H), 6.81-6.83 (dd, 1H), 3.36 (t, 2H), 3.23 (s, 3H), 3.20 (m, 1H), 3.06-3.11 (m, 3H), 2.63 (m, 1H), 2.24 (m, 1H), 1.91-1.94 (m, 1H), 1.61-1.76 (m, 5H), 1.35-1.50 (m, 3H), 1.32 (s, 3H), 1.13 (m, 1H), 0.66 (m, 2H).

Example 20

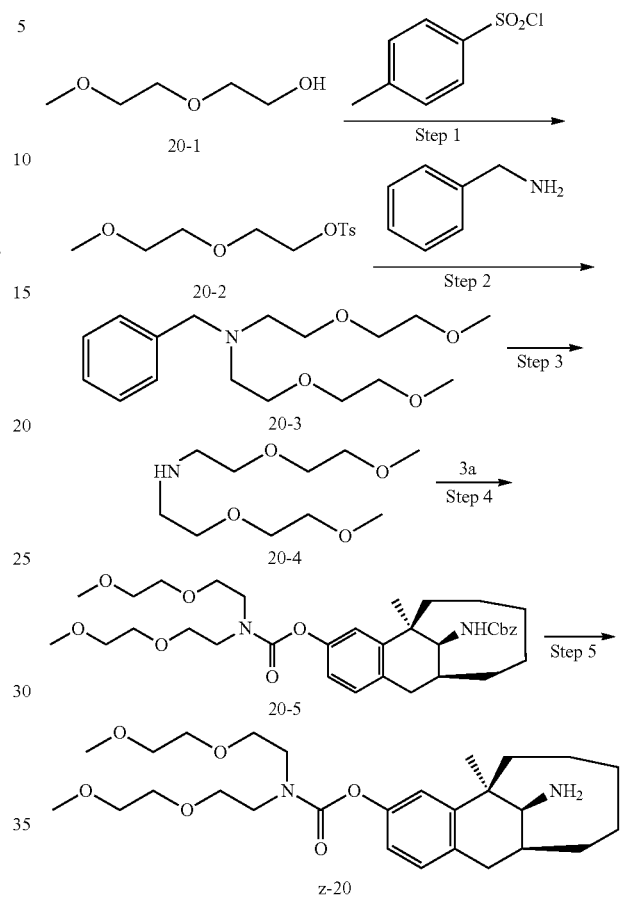

Step 1: To a 100 mL round-bottom flask were added Compound 20-1 (5 g, 41.61 mmol), 15 mL of tetrahydrofuran, 15 mL of water and sodium hydroxide (3.33 g, 83.25 mmol). The system was cooled in an ice bath and added dropwise with a solution of tosyl chloride (8.7 g, 45.63 mmol) dissolved in 20 mL tetrahydrofuran. The mixture was stirred at room temperature for 2 hours. The reaction was monitored by LC-MS until completion. The reaction solution was washed with water, extracted with EA, and the combined organic layers were dried and concentrated to give 10.2 g of a colorless oil Compound 20-2. MS m/z (ESI): 275.0 [M+H]$^+$.

Step 2: A 250 mL three-necked flask was loaded with phenylethylamine (1.8 g, 16.8 mmol), Compound 20-2 (10.2 g, 37.18 mmol), potassium carbonate (7 g, 50.65 mmol) and 100 mL of acetonitrile, and the system was stirred under reflux overnight. The reaction was monitored by LC-MS until completion. The reaction solution was filtered and distilled under reduced pressure to remove acetonitrile, after which 100 mL of 1 M hydrochloric acid solution was added to the residue.

After EA extraction, the pH of the aqueous layer was adjusted to 9-10 and then again extracted with EA. The organic layers were combined, dried and concentrated to give 4.6 g of Compound 20-3 as a colorless oil. MS m/z (ESI): 312.1 [M+H]$^+$.

Step 3: To a 100 mL round-bottomed flask were added Compound 20-3 (1.08 g, 3.418 mmol), 20 mL of methanol and palladium/carbon (200 mg, 10%), and the system was stirred at room temperature under hydrogen atmosphere overnight. The reaction was monitored by LC-MS until completion. The reaction solution was filtered and concentrated to give 715 mg of Compound 20-4 as a colorless oil. MS m/z (ESI): 222.1 [M+H]$^+$.

Step 4: The preparation method was the same as that of Compound 11-1, except that 2-methoxyethylamine in the preparation method of 11-1 was replaced with Compound 20-4. MS m/z (ESI): 627.0 [M+H]$^+$.

Step 5: Compound z-20 (330 mg, 76.5%) was prepared by using Compound 20-4 as a raw material and referring to the method of Step 2 in Example 7. MS m/z (ESI): 493.1 [M+H]$^+$; $^1$H NMR (400 MHz, DMSO-d$_6$) δ 8.32 (s, 1H), 7.09 (d, 1H), 6.95 (d, 1H), 6.82-6.85 (dd, 1H), 3.45-3.63 (m, 16H), 3.25 (s, 3H), 3.24 (s, 3H), 3.23 (m, 1H), 3.07-3.13 (m, 1H), 2.63 (m, 1H), 2.27 (m, 1H), 1.90-1.97 (m, 1H), 1.72-1.78 (m, 1H), 1.63-1.67 (m, 1H), 1.35-1.50 (m, 3H), 1.34 (s, 3H), 1.15 (m, 1H), 0.68 (m, 2H).

Example 21

Step 1: To a 50 mL round bottom flask were added Compound 21-1 (290 mg, 1.053 mmol), 10 mL of methanol, and hydrochloric acid/1,4-dioxane (2 mL, 4 M), and the mixture was stirred at room temperature for 10 hours. The reaction solution was concentrated to remove the solvent. 250 mg colorless oil Compound 21-2 was obtained. MS m/z (ESI): 493.1 [M+H]$^+$.

Step 2: The preparation method was the same as that of Compound 11-1, except that 2-methoxyethylamine in the preparation method of 11-1 was replaced with Compound 21-2. MS m/z (ESI): 581.0 [M+H]$^+$.

Step 3: Compound z-21 (390 mg, 76.6%) was prepared by using Compound 21-2 as a raw material and referring to the method of Step 2 in Example 7. MS m/z (ESI): 447.1 [M+H]$^+$; $^1$H NMR (400 MHz, DMSO-d$_6$) δ 8.29 (s, 1H), 7.62 (t, 1H), 7.04 (d, 1H), 6.89 (d, 1H), 6.77-6.80 (dd, 1H), 3.26-3.33 (m, 6H), 3.18 (s, 3H), 3.17 (m, 1H), 3.01-3.09 (m, 3H), 2.59 (m, 1H), 2.21 (m, 1H), 1.88-1.95 (m, 1H),

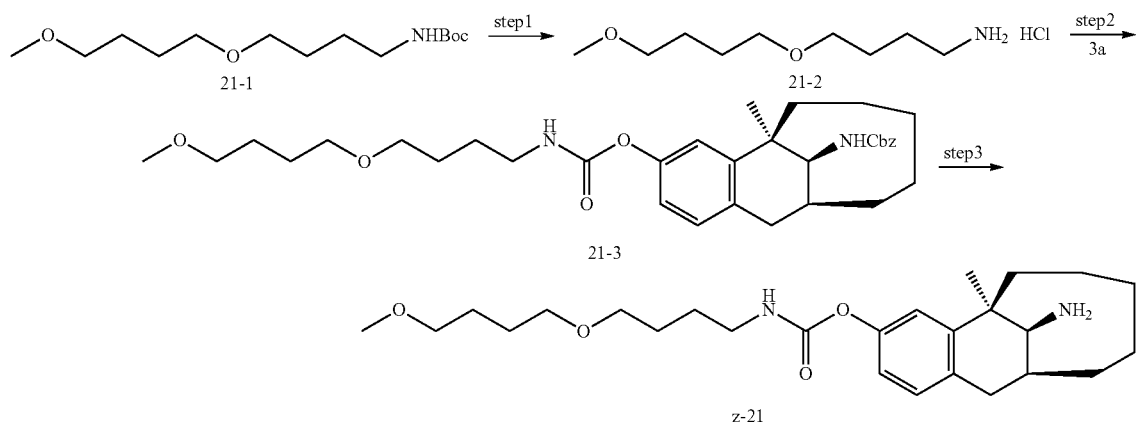

1.69-1.76 (m, 1H), 1.57-1.65 (m, 1H), 1.35-1.55 (m, 11H), 1.30 (s, 3H), 1.11 (m, 1H), 0.66 (m, 2H).

Example 22

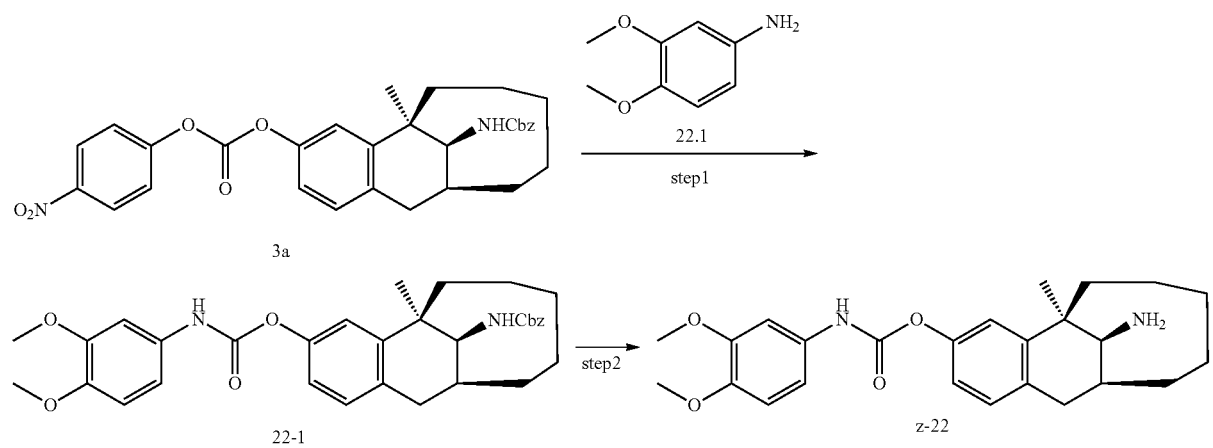

Step 1: The preparation method was the same as that of Compound 11-1, except that 2-methoxyethylamine in the preparation method of 11-1 was replaced with Compound 22.1 and stirred at 50° C. overnight. MS m/z (ESI): 559.0 [M+H]⁺.

Step 2: Compound z-22 (110 mg, 38.5%) was prepared by using Compound 22-1 as a raw material and referring to the method of Step 2 in Example 8. MS m/z (ESI): 425.0 [M+H]⁺; $^1$H NMR (400 MHz, DMSO-$d_6$) δ 9.95 (s, 1H), 8.34 (s, 1H), 7.19 (s, 1H), 7.11 (d, 1H), 7.04 (d, 1H), 6.88-7.04 (m, 3H), 3.71 (s, 6H), 3.23 (m, 1H), 3.08-3.14 (m, 1H), 2.65 (m, 1H), 2.27 (m, 1H), 1.92-1.99 (m, 1H), 1.73-1.80 (m, 1H), 1.67 (m, 2H), 1.35-1.50 (m, 3H), 1.31 (s, 3H), 1.14 (m, 1H), 0.68 (m, 2H).

Example 23

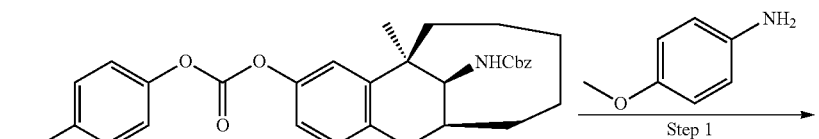

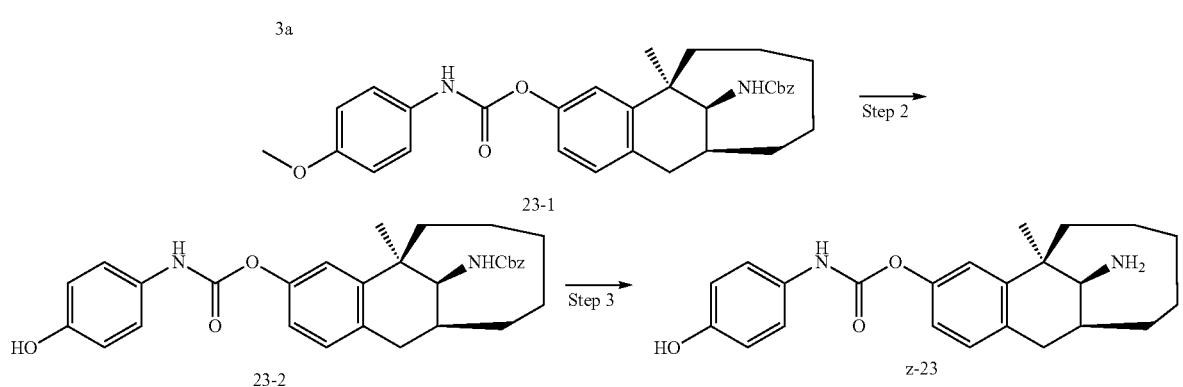

Step 1: The preparation method was the same as that of Compound 11-1, except that 2-methoxyethylamine in the preparation method of 11-1 was replaced with p-methoxyaniline and stirred at 45° C. for 3 hours. MS m/z (ESI): 529.0 [M+H]⁺.

Step 2: To a 50 mL round bottom flask were added Compound 23-1 (460 mg, 0.87 mmol) and dry dichloromethane (10 mL). The mixture was cooled in an ice bath and added with boron tribromide (4 mL, 4 M, 4 mmol) dropwise. The mixture was stirred in an ice bath for 2 hours. The reaction was monitored by LC-MS until completion. The reaction solution was quenched with methanol in an ice bath, the pH was adjusted to 9-10 (ammonia), and the aqueous layer was extracted with dichloromethane. The organic layers were combined, dried, concentrated, and purified by combiflash (0-20% EA/n-hexane) to give Compound 23-2 (290 mg, 64.7%) as a white solid. MS m/z (ESI): 515.0 [M+H]⁺.

Step 3: Compound z-23 (205 mg, 85.4%) was prepared by using Compound 23-2 as a raw material and referring to the method of Step 2 in Example 7. MS m/z (ESI): 381.0 [M+H]⁺; $^1$H NMR (400 MHz, DMSO-$d_6$) δ 9.81 (s, 1H), 8.35 (s, 1H), 7.25 (d, 2H), 7.11 (d, 1H), 7.03 (d, 1H), 6.91-6.93 (dd, 1H), 6.70 (d, 2H), 3.25 (m, 1H), 3.08-3.14 (m, 1H), 2.68 (m, 1H), 2.27 (m, 1H), 1.89-1.98 (m, 1H), 1.73-1.80 (m, 1H), 1.60-1.70 (m, 2H), 1.35-1.52 (m, 3H), 1.35 (s, 3H), 1.11 (m, 1H), 0.68 (m, 2H).

Example 24

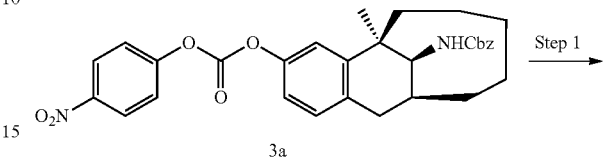

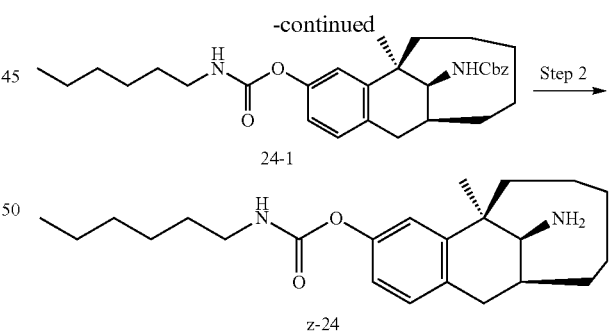

Step 1: The preparation method was the same as that of Compound 11-1, except that 2-methoxyethylamine in the preparation method of 11-1 was replaced with hexylamine MS m/z (ESI): 507.0 [M+H]⁺.

Step 2: Compound z-24 (132.4 mg, 56%) was prepared by using Compound 24-1 as a raw material and referring to the method of Step 2 in Example 7. MS m/z (ESI): 373.1 [M+H]⁺; $^1$H NMR (400 MHz, DMSO-$d_6$) δ 7.64 (t, 1H), 7.05 (d, 1H), 6.91 (d, 1H), 6.81 (dd, 1H), 3.22 (d, 1H), 3.13-3.00 (m, 3H), 2.64 (d, 1H), 2.65 (br. s., 1H), 1.98-1.90

(m, 1H), 1.82-1.70 (m, 1H), 1.68-1.58 (m, 2H), 1.48-1.37 (m, 5H), 1.33-1.25 (m, 9H), 1.20-1.05 (m, 1H), 0.87 (t, 3H), 0.78-0.60 (m, 2H).

Example 25

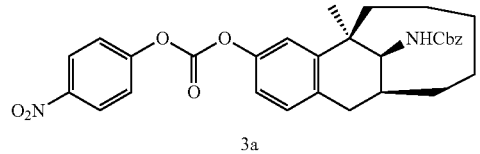

3a

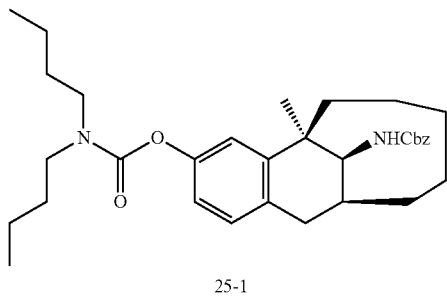

25-1

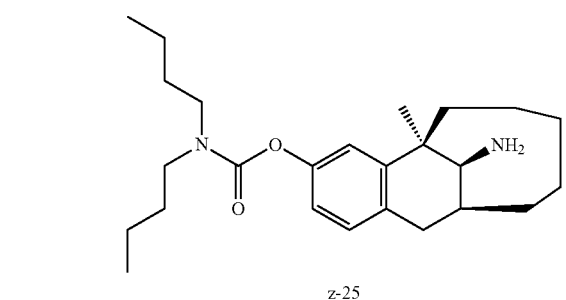

z-25

Step 1: The preparation method was the same as that of Compound 11-1, except that 2-methoxyethylamine in the preparation method of 11-1 was replaced with di-n-butylamine. MS m/z (ESI): 535.1 [M+H]$^+$.

Step 2: Compound z-25 (63.4 mg, 9%) was prepared by using Compound 25-1 as a raw material and referring to the method of Step 2 in Example 7. MS m/z (ESI): 401.1 [M+H]$^+$; $^1$H NMR (400 MHz, DMSO-d$_6$) δ 7.07 (d, 1H), 6.93 (d, 1H), 6.80 (dd, 1H), 3.38-3.18 (m, 5H), 3.10 (dd, 1H), 2.65 (d, 1H), 2.29 (br. s., 1H), 1.97-1.90 (m, 1H), 1.82-1.70 (m, 1H), 1.70-1.40 (m, 9H), 1.48-1.20 (m, 8H), 0.95-0.87 (m, 6H), 0.78-0.61 (m, 2H).

Example 26

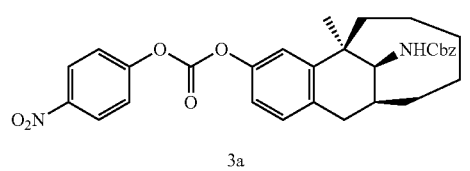

3a

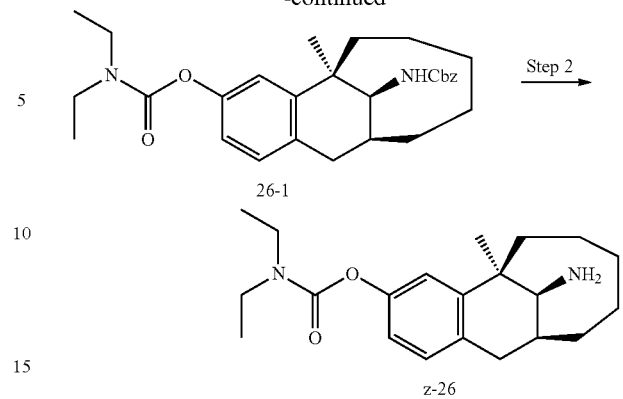

Step 1: The preparation method was the same as that of Compound 11-1, except that 2-methoxyethylamine in the preparation method of 11-1 was replaced with diethylamine MS m/z (ESI): 479.0 [M+H]$^+$.

Step 2: Compound z-26 (170.5 mg, 81%) was prepared by using Compound 26-1 as a raw material and referring to the method of Step 2 in Example 7. MS m/z (ESI): 345.1 [M+H]$^+$; $^1$H NMR (500 MHz, DMSO-d$_6$) δ 7.08 (d, 1H), 6.96 (d, 1H), 6.84 (dd, 1H), 3.42-3.34 (m, 2H), 3.32-3.24 (m, 3H), 3.11 (dd, 1H), 2.66 (d, 1H), 2.32 (br. s., 1H), 1.94-1.85 (m, 1H), 1.79-1.61 (m, 3H), 1.51-1.38 (m, 3H), 1.36 (s, 3H), 1.24-1.07 (m, 7H). 0.76-0.60 (m, 2H).

Example 27

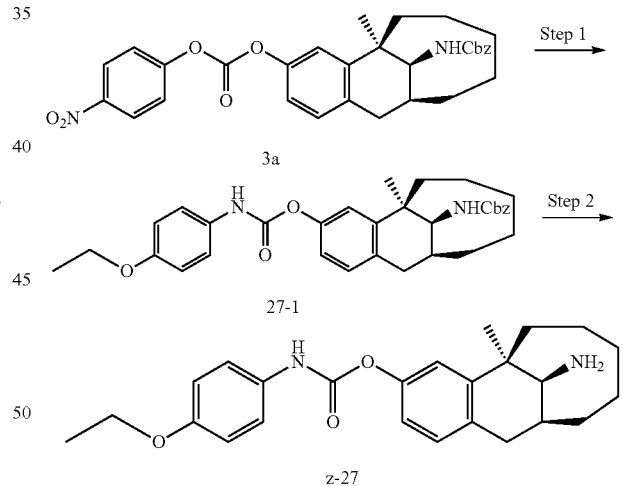

Step 1: The preparation method was the same as that of Compound 11-1, except that 2-methoxyethylamine in the preparation method of 11-1 was replaced with p-ethoxyaniline MS m/z (ESI): 543.0 [M+H]$^+$.

Step 2: Compound z-27 (82.5 mg, 38%) was prepared by using Compound 27-1 as a raw material and referring to the method of Step 2 in Example 8. MS m/z (ESI): 409.0 [M+H]$^+$; $^1$H NMR (400 MHz, DMSO-d$_6$) δ 9.93 (s, 1H), 7.38 (d, 2H), 7.10 (d, 1H), 7.03 (d, 1H), 6.92 (dd, 1H), 6.90-6.85 (m, 2H), 3.97 (q, 2H), 3.18 (d, 1H), 3.10 (dd, 1H), 2.66 (d, 1H), 2.36 (br. s., 1H), 2.02-1.92 (m, 1H), 1.82-1.72 (m, 1H), 1.68-1.56 (m, 2H), 1.55-1.38 (m, 3H), 1.36-1.27 (m, 6H), 1.21-1.07 (m, 1H), 0.80-0.64 (m, 2H).

Example 28

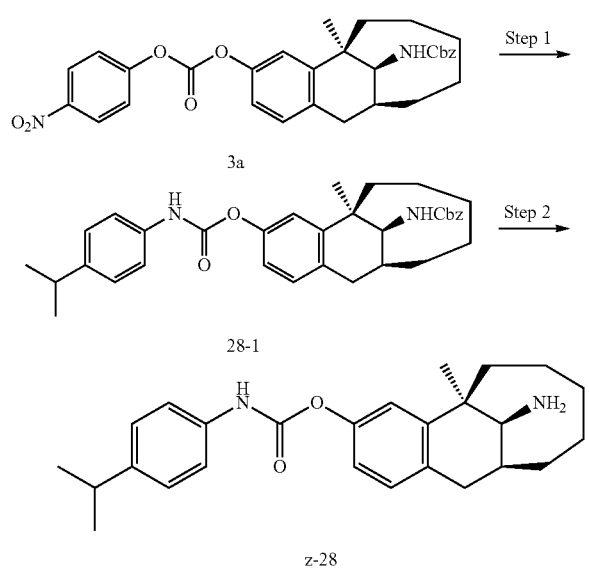

Step 1: The preparation method was the same as that of Compound 11-1, except that 2-methoxyethylamine in the preparation method of 11-1 was replaced with 4-isopropylaniline MS m/z (ESI): 541.0 [M+H]$^+$.

Step 2: Compound z-28 (35.8 mg, 47%) was prepared by using Compound 28-1 as a raw material and referring to the method of Step 2 in Example 8. MS m/z (ESI): 407.1 [M+H]$^+$; $^1$H NMR (400 MHz, DMSO-d$_6$) δ 10.05 (s, 1H), 7.40 (d, 2H), 7.18 (d, 2H), 7.11 (d, 1H), 7.04 (d, 1H), 6.93 (dd, 1H), 3.21 (d, 1H), 3.11 (dd, 1H), 2.87-2.80 (m, 1H), 2.67 (d, 1H), 2.58 (br. s., 1H), 2.01-1.94 (m, 1H), 1.82-1.72 (m, 1H), 1.70-1.60 (m, 2H), 1.52-1.38 (m, 3H), 1.35 (s, 3H), 1.17 (d, 7H), 0.80-0.64 (m, 2H).

Example 29

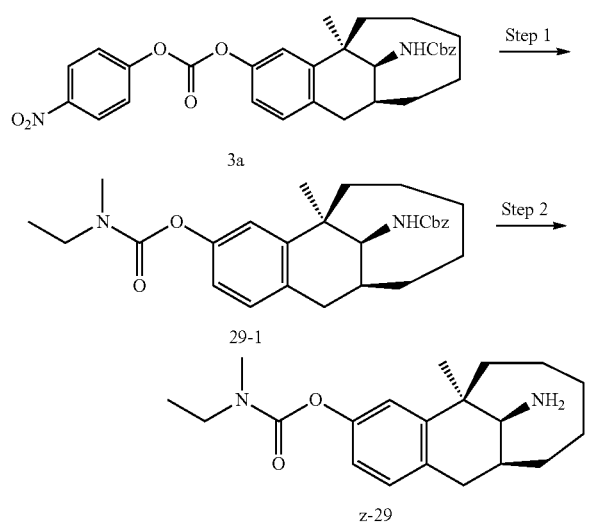

Step 1: The preparation method was the same as that of Compound 11-1, except that 2-methoxyethylamine in the preparation method of 11-1 was replaced with N-ethylmethylamine. MS m/z (ESI): 465.0 [M+H]$^+$.

Step 2: Compound z-29 (92.7 mg, 47%) was prepared by using Compound 29-1 as a raw material and referring to the method of Step 2 in Example 7. MS m/z (ESI): 331.1 [M+H]$^+$; $^1$H NMR (400 MHz, DMSO-d$_6$) δ 7.08 (d, J=8.4 Hz, 1H), 6.97 (s, 1H), 6.85 (d, J=8.4 Hz, 1H), 3.47-3.24 (m, 3H), 3.11 (dd, J=7.2 Hz, 16.8 Hz, 1H), 3.01 (s, 1.5H), 2.88 (s, 1.5H), 2.66 (d, J=17.2 Hz, 1H), 2.34 (br. s., 1H), 1.94-1.83 (m, 1H), 1.79-1.62 (m, 3H), 1.52-1.34 (m, 6H), 1.24-1.06 (m, 4H), 0.78-0.60 (m, 2H).

Example 30

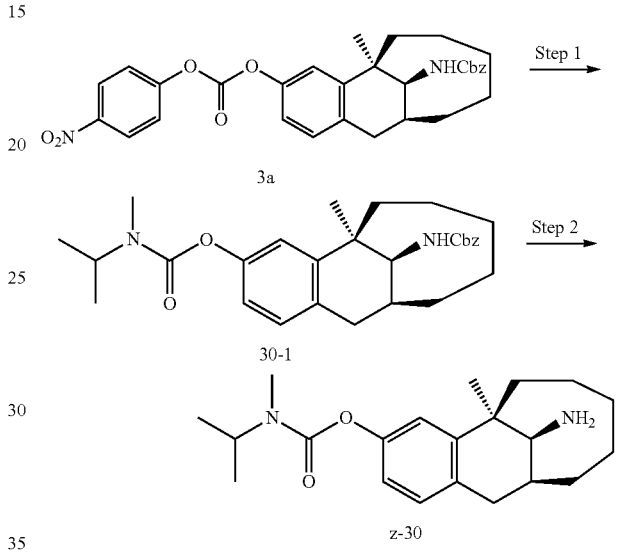

Step 1: The preparation method was the same as that of Compound 11-1, except that 2-methoxyethylamine in the preparation method of 11-1 was replaced with N-isopropylmethylamine MS m/z (ESI): 479.0 [M+H]$^+$.

Step 2: Compound z-30 (113.6 mg, 62%) was prepared by using Compound 30-1 as a raw material and referring to the method of Step 2 in Example 7. MS m/z (ESI): 345.1 [M+H]$^+$; $^1$H NMR (400 MHz, DMSO-d$_6$) δ 7.08 (d, 1H), 6.97 (d, 1H), 6.85 (dd, 1H), 4.48-4.22 (m, 1H), 3.35 (d, 1H), 3.12 (dd, 1H), 2.87 (s, 1.5H), 2.76 (s, 1.5H), 2.67 (d, 1H), 2.35 (br. s., 1H), 1.93-1.82 (m, 1H), 1.80-1.62 (m, 3H), 1.50-1.34 (m, 6H), 1.24-1.08 (m, 7H), 0.76-0.60 (m, 2H).

Example 31

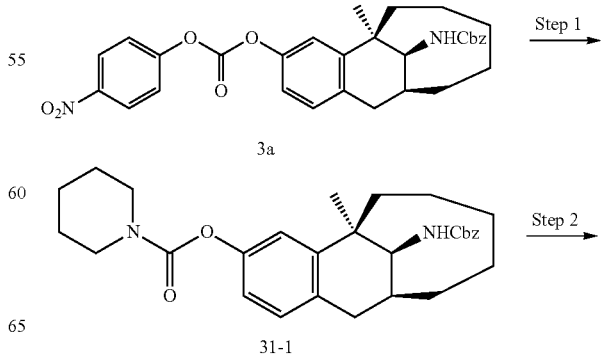

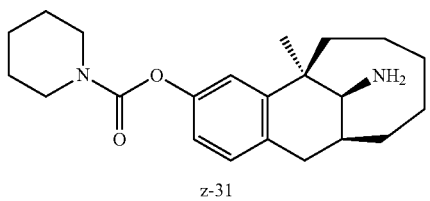

z-31

Step 1: The preparation method was the same as that of Compound 11-1, except that 2-methoxyethylamine in the preparation method of 11-1 was replaced with piperidine. MS m/z (ESI): 491.0 [M+H]$^+$.

Step 2: Compound z-31 (44.8 mg, 26%) was prepared by using Compound 31-1 as a raw material and referring to the method of Step 2 in Example 8. MS m/z (ESI): 357.3 [M+H]$^+$; $^1$H NMR (400 MHz, DMSO-d$_6$) δ 7.06 (d, 1H), 6.95 (d, 1H), 6.83 (dd, 1H), 3.53 (s, 2H), 3.88 (s, 2H), 3.22 (d, 1H), 3.09 (dd, 1H), 2.65 (d, 1H), 2.66 (br.s., 1H), 1.98-1.89 (m, 1H), 1.81-1.78 (m, 1H), 1.78-1.37 (m, 11H), 1.33 (s, 3H), 1.22-1.08 (m, 1H), 0.78-0.61 (m, 2H).

Example 32

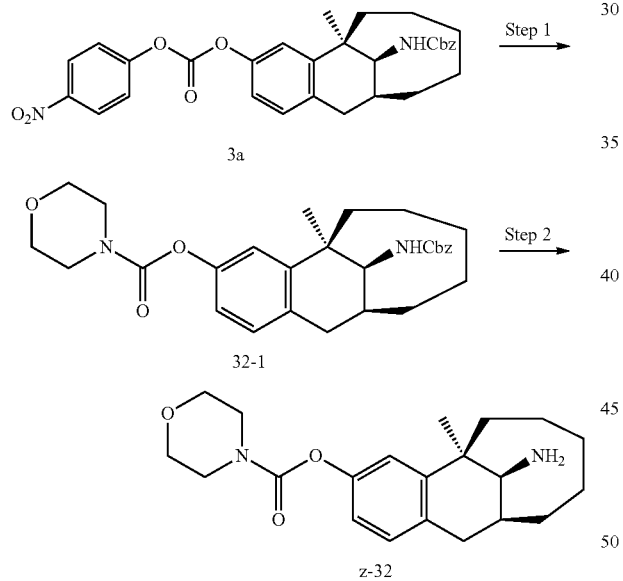

z-32

Step 1: The preparation method was the same as that of Compound 11-1, except that 2-methoxyethylamine in the preparation method of 11-1 was replaced with morpholine. MS m/z (ESI): 493.3 [M+H]$^+$.

Step 2: Compound z-32 (103.9 mg, 71%) was prepared by using Compound 32-1 as a raw material and referring to the method of Step 2 in Example 7. MS m/z (ESI): 359.2 [M+H]$^+$; $^1$H NMR (400 MHz, DMSO-d$_6$) δ 7.06 (d, 1H), 6.96 (d, 1H), 6.84 (dd, 1H), 3.64-3.58 (m, 4H), 3.53 (s, 2H), 3.37 (s, 2H), 3.30-3.24 (m, 1H), 3.08 (dd, 1H), 2.63 (d, 1H), 2.29 (br. s., 1H), 1.92-1.88 (m, 1H), 1.77-1.64 (m, 3H), 1.49-1.32 (m, 6H), 1.22-1.06 (m, 1H), 0.74-0.56 (m, 2H).

Example 33

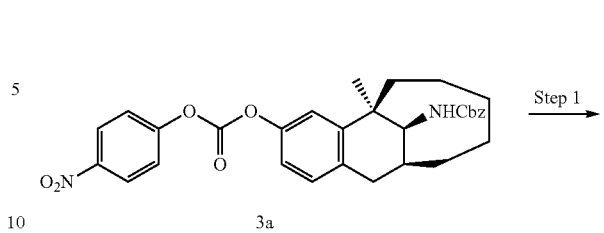

z-33

Step 1: The preparation method was the same as that of Compound 11-1, except that 2-methoxyethylamine in the preparation method of 11-1 was replaced with dipropylamine MS m/z (ESI): 507.3 [M+H]$^+$.

Step 2: Compound z-33 (89.9 mg, 50%) was prepared by using Compound 33-1 as a raw material and referring to the method of Step 2 in Example 7. MS m/z (ESI): 373.3 [M+H]$^+$; $^1$H NMR (400 MHz, DMSO-d$_6$) δ 7.04 (d, 1H), 6.90 (d, 1H), 6.78 (dd, 1H), 3.32-3.12 (m, 5H), 3.07 (dd, 1H), 2.62 (d, 1H), 2.27 (br. s., 1H), 1.94-1.84 (m, 1H), 1.78-1.68 (m, 1H), 1.67-1.34 (m, 9H), 1.31 (s, 3H), 1.20-1.08 (m, 1H), 0.89-0.80 (m, 6H), 0.74-0.59 (m, 2H).

Example 34

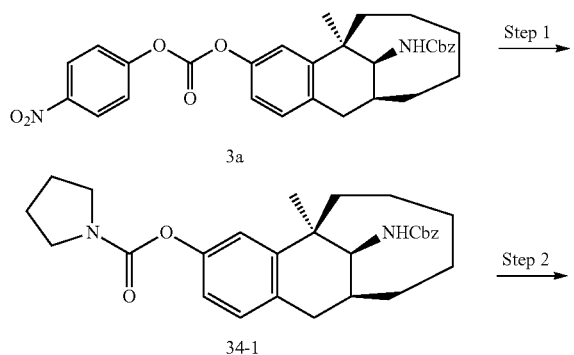

-continued

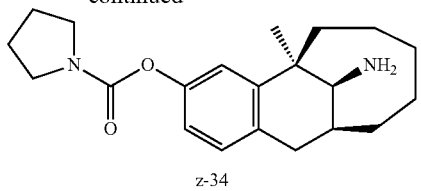

z-34

Step 1: The preparation method was the same as that of Compound 11-1, except that 2-methoxyethylamine in the preparation method of 11-1 was replaced with pyrrolidine. MS m/z (ESI): 477.3 [M+H]$^+$.

Step 2: Compound z-34 (25 mg, 23%) was prepared by using Compound 34-1 as a raw material and referring to the method of Step 2 in Example 8. MS m/z (ESI): 343.3 [M+H]$^+$; $^1$H NMR (400 MHz, DMSO-d$_6$) δ 7.03 (d, 1H), 6.93 (d, 1H), 6.81 (dd, 1H), 3.45 (t, 2H), 3.29 (t, 2H), 3.20 (br. s., 1H), 3.06 (dd, 1H), 2.62 (d, 1H), 2.32 (br. s., 1H), 1.97-1.54 (m, 8H), 1.50-1.34 (m, 3H), 1.30 (s, 3H), 1.19-1.05 (m, 1H), 0.75-0.57 (m, 2H).

Example 35

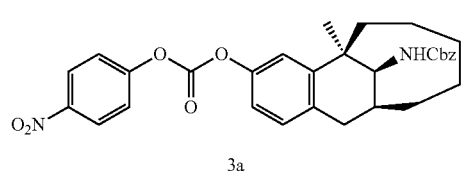

3a

Step 1 →

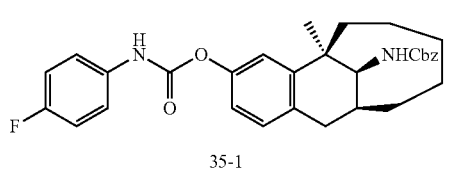

35-1

Step 2 →

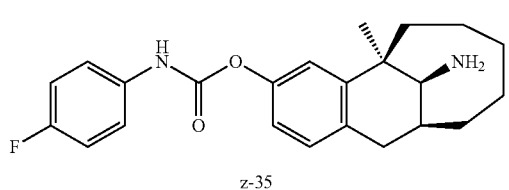

z-35

Step 1: The preparation method was the same as that of Compound 11-1, except that 2-methoxyethylamine in the preparation method of 11-1 was replaced with 4-fluoroaniline, stirred at room temperature for 2 days. MS m/z (ESI): 517.2 [M+H]$^+$.

Step 2: Compound z-35 (32 mg, 17%) was prepared by using Compound 35-1 as a raw material and referring to the method of Step 2 in Example 8. MS m/z (ESI): 383.3 [M+H]$^+$; $^1$H NMR (400 MHz, DMSO-d$_6$) δ 10.18 (s, 1H), 7.52-7.45 (m, 2H), 7.16-7.10 (m, 2H), 7.08 (d, 1H), 7.03 (d, 1H), 3.91 (dd, 1H), 3.08 (d, 1H), 2.64 (d, 1H), 2.30-2.15 (br. s., 1H), 2.10-1.89 (m, 1H), 1.81-1.21 (m, 10H), 1.19-1.05 (m, 1H), 0.75-0.62 (m, 2H).

Example 36

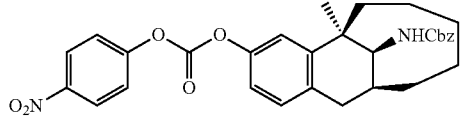

3a

Step 1 →

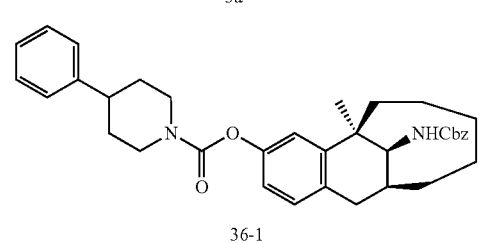

36-1

Step 2 →

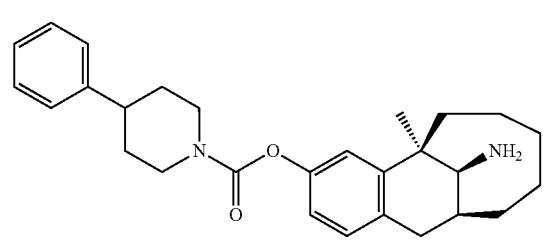

z-36

Step 1: The preparation method was the same as that of Compound 11-1, except that 2-methoxyethylamine in the preparation method of 11-1 was replaced with 4-phenylpiperidine. MS m/z (ESI): 567.3 [M+H]$^+$.

Step 2: Compound z-36 (69.4 mg, 34%) was prepared by using Compound 36-1 as a raw material and referring to the method of Step 2 in Example 8. MS m/z (ESI): 433.3 [M+H]$^+$; $^1$H NMR (400 MHz, DMSO-d$_6$) δ 7.31-7.24 (m, 4H), 7.20-7.14 (m, 1H), 7.05 (d, 1H), 6.95 (d, 1H), 6.84 (dd, 1H), 4.32-4.08 (m, 2H), 3.20 (d, 1H), 3.07 (dd, 1H), 2.98-2.95 (m, 1H), 2.78-0.69 (m, 1H), 2.62 (d, 1H), 2.25 (br. s., 1H), 2.00-1.52 (m, 9H), 1.45-1.35 (m, 3H), 1.31 (s, 3H), 1.21-1.06 (m, 1H), 0.76-0.59 (m, 2H).

Example 37

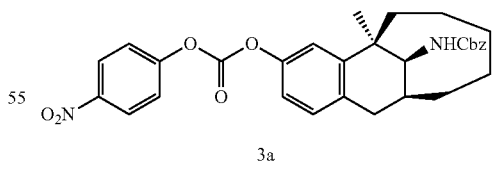

3a

Step 1 →

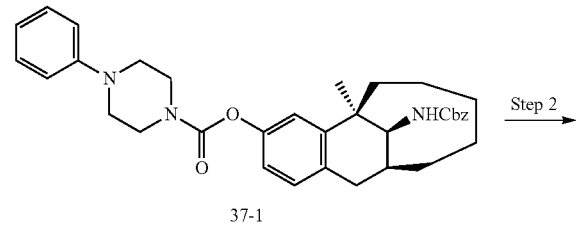

37-1

Step 2 →

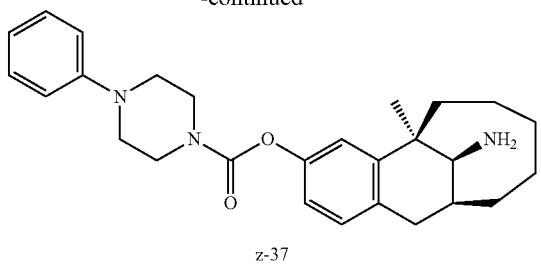

z-37

Step 1: The preparation method was the same as that of Compound 11-1, except that 2-methoxyethylamine in the preparation method of 11-1 was replaced with 1-phenylpiperazine. MS m/z (ESI): 568.3 [M+H]+.

Step 2: Compound z-37 (157 mg, 63%) was prepared by using Compound 37-1 as a raw material and referring to the method of Step 2 in Example 8. MS m/z (ESI): 434.2 [M+H]+; 1H NMR (400 MHz, DMSO-d6) δ 7.24-7.19 (m, 2H), 7.06 (d, 1H), 6.98 (d, 1H), 6.95 (d, 2H), 6.85 (dd, 1H), 6.80 (t, 1H), 3.69 (s, 2H), 3.54 (m, 2H), 3.23 (d, 1H), 3.22-3.12 (m, 4H), 3.08 (dd, 1H), 2.63 (d, 1H), 2.27 (br. s., 1H), 1.96-1.86 (m, 1H), 1.77-1.57 (m, 3H), 1.50-1.34 (m, 3H), 1.32 (s, 3H), 1.21-1.06 (m, 1H), 0.74-0.62 (m, 2H).

Example 38

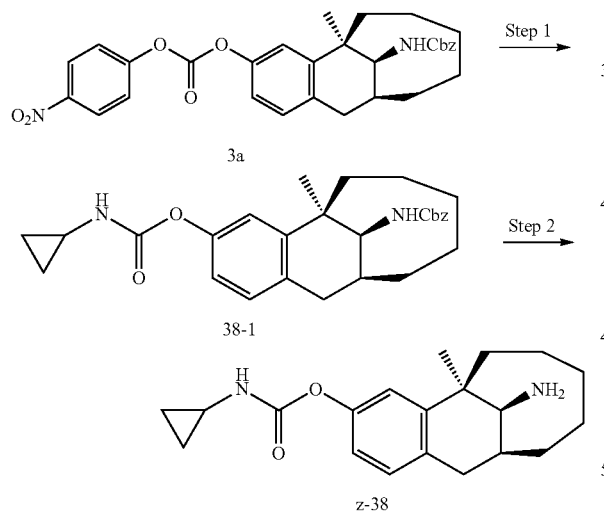

z-38

Step 1: The preparation method was the same as that of Compound 11-1, except that 2-methoxyethylamine in the preparation method of 11-1 was replaced with cyclopropylamine MS m/z (ESI): 463.3 [M+H]+.

Step 2: Compound z-38 (131.8 mg, 80%) was prepared by using Compound 38-1 as a raw material and referring to the method of Step 2 in Example 8. MS m/z (ESI): 329.3 [M+H]+; 1H NMR (400 MHz, DMSO-d6) δ 7.82 (d, 1H), 7.06 (d, 1H), 6.92 (d, 1H), 6.82 (dd, 1H), 3.20 (d, 1H), 3.09 (dd, 1H), 2.64 (d, 1H), 2.57-58 (m, 1H), 2.54 (br. s., 1H), 1.99-1.90 (m, 1H), 1.81-1.71 (m, 1H), 1.68-1.58 (m, 2H), 1.57-1.36 (m, 3H), 1.33 (s, 3H), 1.20-1.07 (m, 1H), 0.77-0.61 (m, 4H), 0.65-0.45 (m, 2H).

Example 39

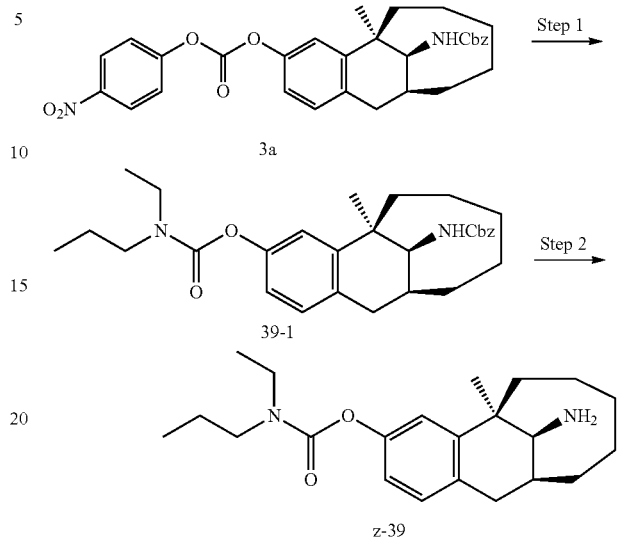

z-39

Step 1: The preparation method was the same as that of Compound 11-1, except that 2-methoxyethylamine in the preparation method of 11-1 was replaced with N-ethylpropylamine MS m/z (ESI): 493.4 [M+H]+.

Step 2: Compound z-39 (80.2 mg, 42%) was prepared by using Compound 39-1 as a raw material and referring to the method of Step 2 in Example 8. MS m/z (ESI): 359.3 [M+H]+; 1H NMR (400 MHz, DMSO-d6) δ 7.04 (d, 1H), 6.91 (s, 1H), 6.79 (d, 1H), 3.41-3.12 (m, 5H), 3.07 (dd, 1H), 2.62 (d, 1H), 2.27 (br. s., 1H), 1.91-1.82 (m, 1H), 1.78-1.72 (m, 1H), 1.68-1.34 (m, 7H), 1.31 (s, 3H), 1.20-1.04 (m, 4H), 0.89-0.81 (m, 3H), 0.74-0.59 (m, 2H).

Example 40

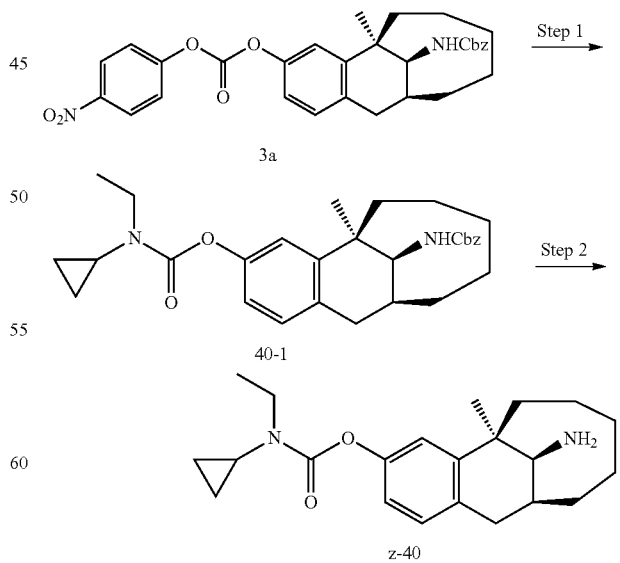

z-40

Step 1: The preparation method was the same as that of Compound 11-1, except that 2-methoxyethylamine in the preparation method of 11-1 was replaced with N-cyclopropyl-N-ethylamine. MS m/z (ESI): 491.3 [M+H]+.

Step 2: Compound z-40 (142 mg, 78%) was prepared by using Compound 40-1 as a raw material and referring to the method of Step 2 in Example 8. MS m/z (ESI): 357.3 [M+H]+; $^1$H NMR (400 MHz, DMSO-$d_6$) δ 7.07 (d, 1H), 6.96 (d, 1H), 6.83 (dd, 1H), 3.4-3.28 (m, 2H), 3.26 (d, 1H), 3.11 (dd, 1H), 2.76-2.63 (m, 2H), 2.29 (br. s., 1H), 1.96-1.88 (m, 1H), 1.80-1.72 (m, 1H), 1.69-1.63 (m, 2H), 1.52-1.38 (m, 3H), 1.35 (s, 3H), 1.22-1.10 (m, 4H), 0.82-0.63 (m, 6H).

Example 41

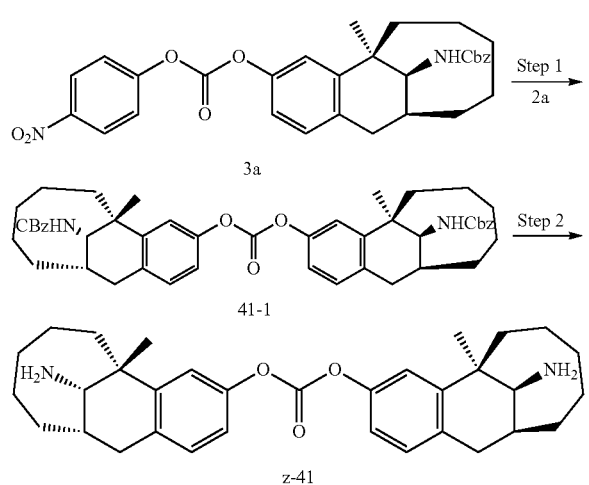

Step 1: The preparation method was the same as that of Compound 11-1, except that 2-methoxyethylamine in the preparation method of 11-1 was replaced with Compound 2a. MS m/z (ESI): N/A.

Step 2: Compound z-41 (64.2 mg, 32%) was prepared by using Compound 41-1 as a raw material and referring to the method of Step 2 in Example 8. MS m/z (ESI): 517.4 [M+H]+.

Example 42

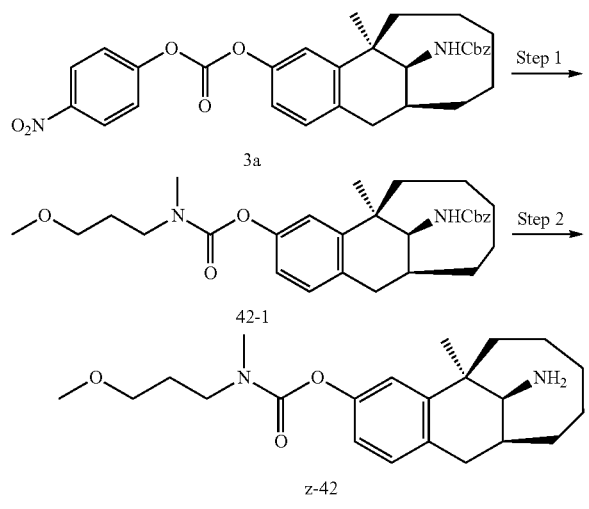

Step 1: The preparation method was the same as that of Compound 11-1, except that 2-methoxyethylamine in the preparation method of 11-1 was replaced with 3-methoxy-N-methylpropylamine hydrochloride. MS m/z (ESI): 509.0 [M+H]+.

Step 2: Compound z-42 (220 mg, 63.6%) was prepared by using Compound 42-1 as a raw material and referring to the method of Step 2 in Example 8. MS m/z (ESI): 375.4 [M+H]+; $^1$H NMR (400 MHz, DMSO-$d_6$): δ 8.30 (s, 1H), 7.05 (d, 1H), 6.92 (m, 1H), 6.79 (m, 1H), 3.28-3.42 (m, 4H), 3.22 (m, 1H), 3.20 (s, 3H), 3.04-3.10 (m, 1H), 2.98 (s, 1.5H), 2.85 (s, 1.5H), 2.60 (m, 1H), 2.25 (m, 1H), 1.60-1.92 (m, 6H), 1.35-1.42 (m, 3H), 1.31 (s, 3H), 1.11 (m, 1H), 0.66 (m, 2H).

Example 43

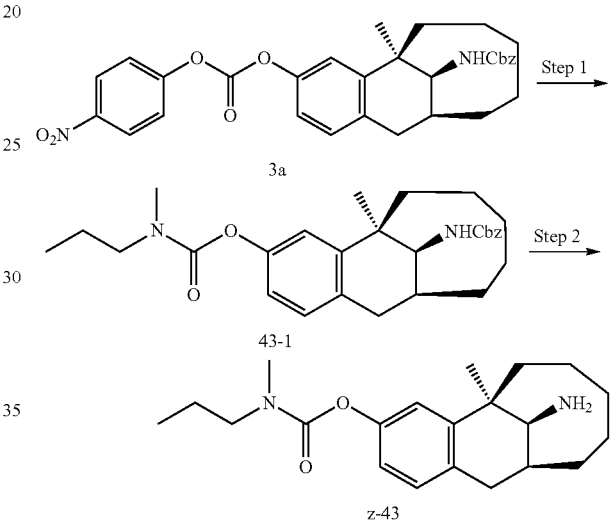

Step 1: The preparation method was the same as that of Compound 11-1, except that 2-methoxyethylamine in the preparation method of 11-1 was replaced with N-methylpropylamine MS m/z (ESI): N/A.

Step 2: Compound z-43 (310 mg, 78.3%) was prepared by using Compound 43-1 as a raw material and referring to the method of Step 2 in Example 7. MS m/z (ESI): 345.3 [M+H]+; $^1$H NMR (400 MHz, DMSO-$d_6$): δ 8.29 (s, 1H), 7.05 (d, 1H), 6.92 (m, 1H), 6.79 (m, 1H), 3.32 (m, 1H), 3.29-3.31 (m, 2H), 3.04-3.10 (m, 1H), 2.98 (s, 1.5H), 2.85 (s, 1.5H), 2.60 (m, 1H), 2.25 (m, 1H), 1.85-1.92 (m, 1H), 1.69-1.75 (m, 1H), 1.48-1.64 (m, 7H), 1.31 (s, 3H), 1.11 (m, 1H), 0.81-0.89 (m, 3H), 0.66 (m, 2H).

Example 44

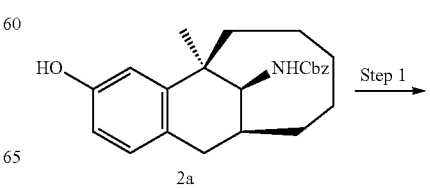

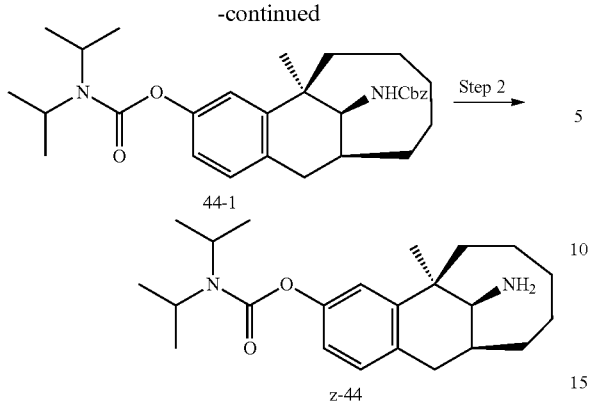

Step 1: To a solution of diisopropylmethanechloride (129 mg, 0.79 mmol) in dichloromethane (2 mL) was added Compound 2a (300 mg, 0.79 mmol), DIPEA (204 mg, 1.581 mmol), DMAP (97 mg, 0.79 mmol) and 8 mL of dichloromethane. The mixture was stirred at room temperature overnight. The reaction was monitored by LC-MS until completion. The reaction solution was washed three times with 1M hydrochloric acid solution. The organic layer was dried, concentrated and purified by combiflash (0-15% EA/petroleum ether) to give a colourless oil, i.e., Compound 44-1 (329 mg, 61%). MS m/z (ESI): 507.0 [M+H]$^+$.

Step 2: Compound z-44 (182 mg, 67%) was prepared by using Compound 44-1 as a raw material and referring to the method of Step 2 in Example 7. MS m/z (ESI): 373.1 [M+H]$^+$; $^1$H NMR (400 MHz, DMSO-d$_6$) δ 7.06 (d, 1H), 6.92 (d, 1H), 6.80 (dd, 1H), 4.02-3.94 (m, 2H), 3.20 (d, 1H), 3.09 (dd, 1H), 2.65 (d, 1H), 2.53 (br. s., 1H), 2.00-1.92 (m, 1H), 1.82-1.69 (m, 1H), 1.70-1.58 (m, 2H), 1.54-1.38 (m, 3H), 1.33 (s, 3H), 1.24 (s, 12H), 1.18-1.08 (m, 1H), 0.80-0.62 (m, 2H).

Example 45

Step 1: Compound 2a (300 mg, 0.79 mmol), 2-chloroethylmethylether (112 mg, 1.186 mmol), potassium tert-butoxide (89 mg, 0.79 mmol) and potassium iodide (14 mg, 0.079 mmol) were dissolved in 10 mL of DMF, respectively, and the mixture was heated to 80° C., and stirred overnight. The reaction was monitored by LC-MS until completion. The reaction solution was cooled to room temperature, poured into water, and extracted with EA. The organic layer was washed with water, dried over anhydrous sodium sulfate, concentrated, and then purified by combiflash (0-10% EA/petroleum ether) to give Compound 45-1 (128 mg, 37%) as a colorless oil. MS m/z (ESI): 347.3 [M+H]$^+$.

Step 2: Compound z-45 (15 mg, 15%) was prepared by using Compound 45-1 as a raw material and referring to the method of Step 2 in Example 8. MS m/z (ESI): 304.1 [M+H]$^+$.

Example 46

Step 1: A mixed solution of Compound 46.1 (200 mg, 0.701 mmol), Compound 2a (266 mg, 0.701 mmol), DMAP (10 mg, 0.07 mmol) and dichloromethane (10 mL) was stirred in an ice bath and added with DCC (145 mg, 0.701 mmol). The system was warmed to room temperature and stirred overnight. The reaction solution was washed with saturated brine, dried over anhydrous sodium sulfate, concentrated and purified by combiflash (0-15% EA/petroleum ether) to give Compound 46-1 as a colorless oil (252 mg, 47%). MS m/z (ESI): 668.9 [M+H]$^+$.

Step 2: Compound z-46 (32 mg, 19%) was prepared by using Compound 46-1 as a raw material and referring to the method of Step 2 in Example 8. MS m/z (ESI): 379.0 [M+H]$^+$.

Example 47

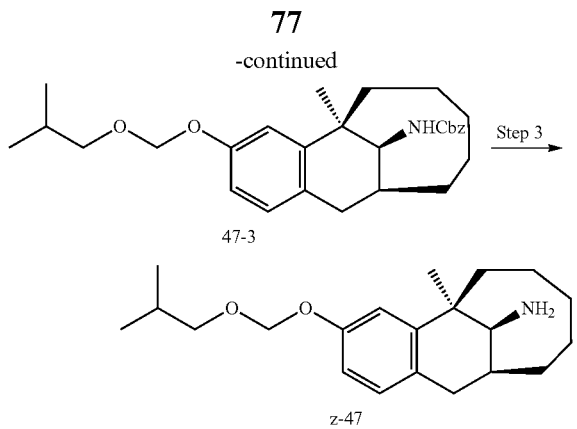

47-3

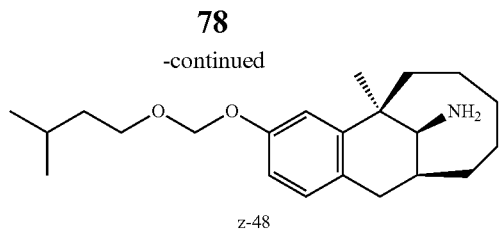

z-48

Step 1: 1.1 g of colorless oil of Compound 48-2 was prepared by using Compound 48-1 as a raw material and referring to the method of Step 1 in Example 47. MS m/z (ESI): N/A.

Step 2: The colorless oil of Compound 48-3 (490 mg, 77.5%) was prepared by using Compound 48-2 as a raw material and referring to the method of Step 2 in Example 47. MS m/z (ESI): 480.0 [M+H]$^+$.

Step 3: Compound z-48 (115 mg, 28.8%) was prepared by using Compound 48-3 as a raw material and referring to the method of Step 2 in Example 8. MS m/z (ESI): 346.1 [M+H]$^+$.

z-47

Step 1: A 50 mL round bottom flask was loaded with isobutanol (741 mg, 10 mmol), TMSCI (5 mL) and para-formaldehyde (3.5 mg, 10.5 mmol), and the mixture was stirred at room temperature for 2.5 hours. The reaction solution was concentrated under reduced pressure at room temperature to give 800 mg of colorless oil, i.e., Compound 47-2. MS m/z (ESI): N/A.

Step 2: To a 50 mL round bottom flask were added sodium hydride (165 mg, 60%, 4.125 mmol) and 6 mL of tetrahydrofuran, and added with a solution of Compound 2a (390 mg, 1.028 mmol) in tetrahydrofuran (3 mL) dropwise at room temperature. The mixture was stirred at room temperature for 10 minutes, then added with a solution of Compound 47-2 (700 mg, 5.71 mmol) in tetrahydrofuran (3 mL) dropwise, and finally added with 3 mL of DMF, after which the mixture was reacted at room temperature for 30 minutes. The reaction was monitored by LC-MS until completion. The reaction solution was quenched with water. The aqueous layers were subjected to EA extraction, after which the organic layers were combined, dried, concentrated, and then purified by combiflash (0-10% EA/n-hexane) to give Compound 47-3 (385 mg, 80.5%) as a colorless oil. MS m/z (ESI): 466.0 [M+H]$^+$. Step 3: Compound z-47 (230 mg, 73.7%) was prepared by using Compound 47-3 as a raw material and referring to the method of Step 2 in Example 7. MS m/z (ESI): 332.1 [M+H]$^+$.

Example 48

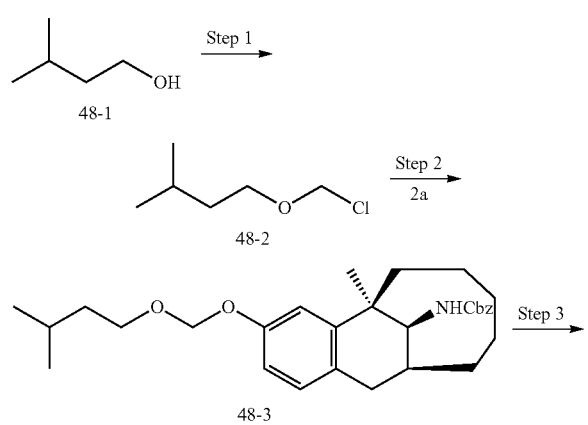

Example 49

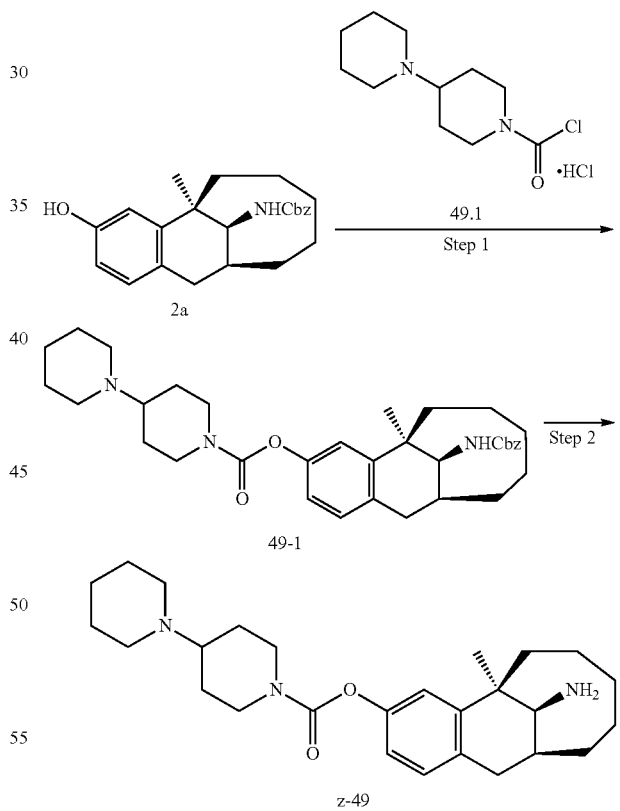

Step 1: Colorless oil Compound 49-1 (258 mg, 34%) was prepared by using Compound 49.1 as a raw material and referring to the method of Step 1 in Example 44. MS m/z (ESI): 574.0 [M+H]$^+$. Step 2: Compound z-49 (150 mg, 62.8%) was prepared by using Compound 49-1 as a raw material and referring to the method of Step 2 in Example 7. MS m/z (ESI): 440.1 [M+H]$^+$; $^1$H NMR (DMSO-d$_6$, 400 MHz) δ 8.27 (s, 2H), 7.05 (d, 1H), 6.94 (d, 1H), 6.83 (dd, 1H), 3.93-4.13 (m, 2H), 3.32 (d, 1H), 3.09 (dd, 1H), 2.79-2.94 (m, 2H), 2.64 (d, 1H), 2.49-2.57 (m, 5H), 2.30 (br. s., 1H), 1.59-1.88 (m, 5H), 1.32-1.57 (m, 12H), 1.25-1.43 (m, 8H), 1.07-1.21 (m, 1H), 0.65 (m, 2H).

Example 50

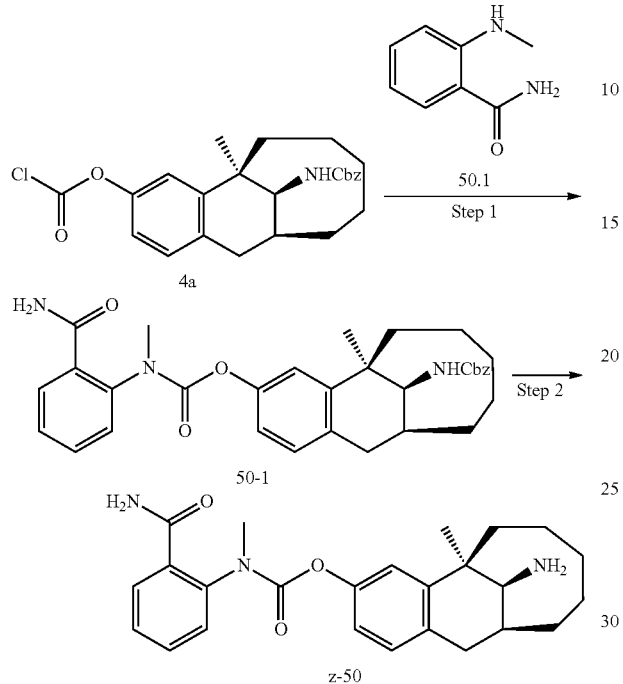

Step 1: A 50 mL round bottom flask was loaded with 4a (900 mg, 2.036 mmol), Compound 50.1 (150 mg, 1 mmol) and 10 mL of tetrahydrofuran. The mixture was stirred at room temperature for 30 minutes, added with 10 drops of triethylamine, and stirred for 1 hour at room temperature. The reaction was monitored by LC-MS until completion. The reaction solution was washed with 1 M hydrochloric acid solution, extracted with EA, after which the organic layer was dried, concentrated and purified by combiflash (0-70% EA/n-hexane) to give Compound 50-1 (570 mg, 84.6%) as a white solid. MS m/z (ESI): 556.0 [M+H]$^+$.

Step 2: Compound z-50 (420 mg, 87.5%) was prepared by using Compound 50-1 as a raw material and referring to the method of Step 2 in Example 7. MS m/z (ESI): 422.4 [M+H]$^+$; $^1$H NMR (400 MHz, DMSO-d$_6$) δ 8.30 (s, 1H), 7.37-7.84 (m, 6H), 7.04 (d, 1H), 6.80-6.87 (m, 2H), 3.24 (m, 1H), 3.21 (s, 3H), 3.05-3.11 (m, 1H), 2.65 (m, 1H), 2.26 (m, 1H), 1.84-1.91 (m, 1H), 1.64-1.72 (m, 3H), 1.35-1.41 (m, 3H), 1.31 (s, 3H), 1.11 (m, 1H), 0.66 (m, 2H).

Example 51

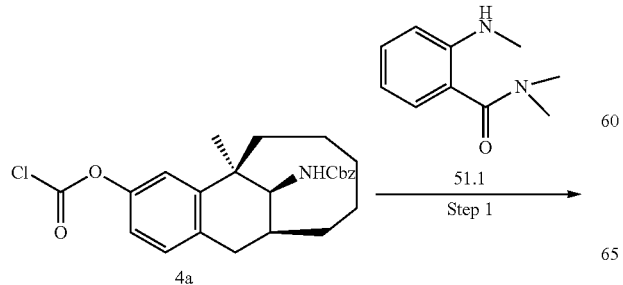

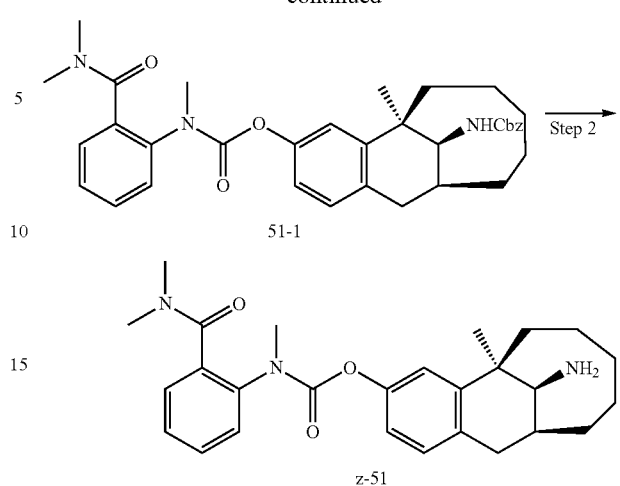

Step 1: A 100 mL round bottom flask was loaded with 4a (1.6 g, 3.625 mmol), Compound 51.1 (238 mg, 1.335 mmol) and 10 mL of tetrahydrofuran, and DIPEA (864 mg, 6.685 mmol) in tetrahydrofuran (5 mL) was added dropwise while stirring at room temperature. The mixture was stirred at room temperature for 30 minutes. The reaction was monitored by LC-MS until completion. The reaction solution was washed with 1 M hydrochloric acid solution, extracted with EA, and the organic layer was dried, concentrated and purified by combiflash (0-50% EA/n-hexane) to give a white solid Compound 51-1 (745 mg, 89.2%). MS m/z (ESI): 584.2 [M+H]$^+$. Step 2: Compound z-51 (420 mg, 63.2%) was prepared by using Compound 51-1 as a raw material and referring to the method of Step 2 in Example 7. MS m/z (ESI): 450.2 [M+H]$^+$; $^1$H NMR (400 MHz, DMSO-d$_6$) δ 8.29 (s, 1H), 7.35-7.54 (m, 4H), 6.67-7.04 (m, 3H), 3.29 (m, 1H), 3.15 (s, 3H), 3.05 (m, 1H), 2.97 (s, 3H), 2.71 (s, 3H), 2.60 (m, 1H), 2.20 (m, 1H), 1.92 (m, 1H), 1.71 (m, 1H), 1.59 (m. 2H), 1.28-1.45 (m, 3H), 1.27 (s, 3H), 1.11 (m, 1H), 0.63 (m, 2H).

Example 52

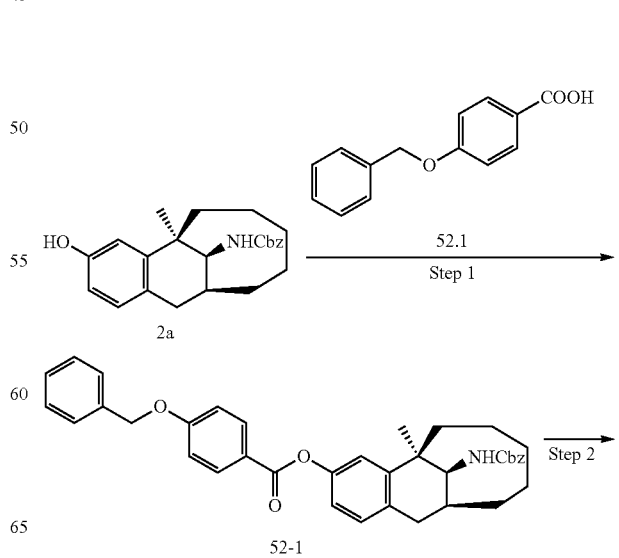

81
-continued

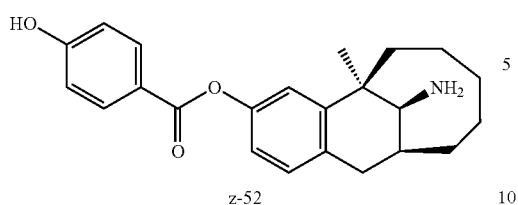
z-52

Step 1: A 100 mL round-bottomed flask was loaded with Compound 52.1 (343 mg, 1.503 mmol), Compound 2a (572 mg, 1.507 mmol), DIPEA (585 mg, 4.526 mmol), 10 mL of dichloromethane and HATU (630 mg, 1.657 mmol). The mixture was stirred at room temperature overnight. The reaction was monitored by LC-MS until completion. The reaction solution was concentrated and purified by combi-flash (0-15% EA/hexane) to give Compound 52-1 (700 mg, 69.1%) as a colorless oil. MS m/z (ESI): 590.2 [M+H]$^+$.

Step 2: Compound z-52 (270 mg, 55.3%) was prepared by using Compound 52-1 as a raw material and referring to the method of Step 2 in Example 7. MS m/z (ESI): 366.2 [M+H]$^+$.

Example 53

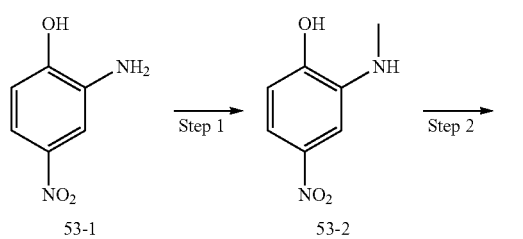

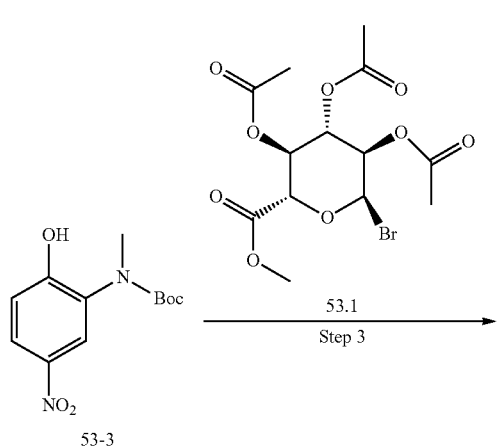

82
-continued

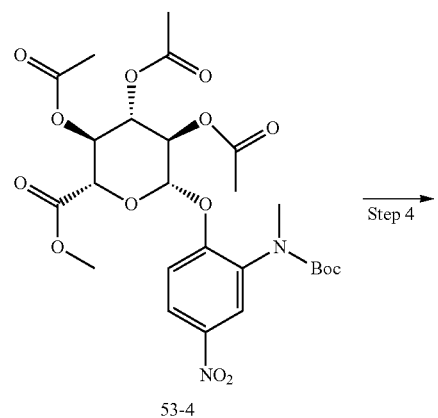
53-4

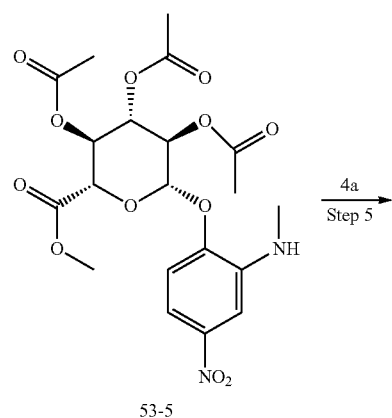
53-5

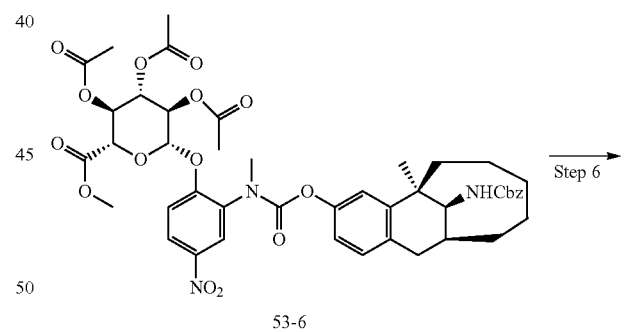
53-6

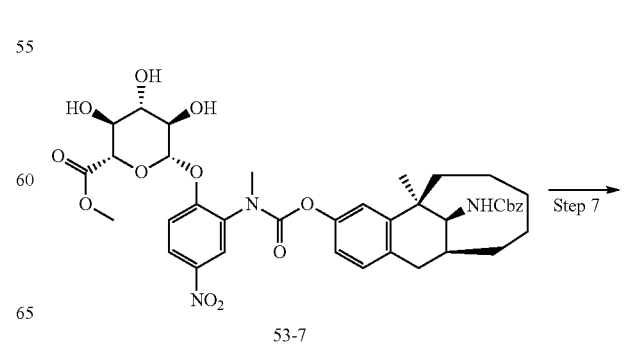
53-7

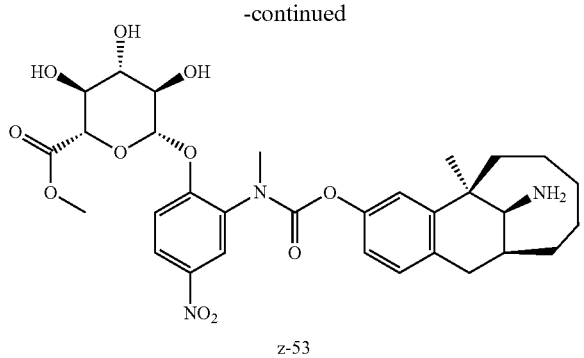

z-53

Step 1: To a 250 mL round bottom flask were added Compound 53-1 (5.1 g, 33.09 mmol), sodium bicarbonate (2.92 g, 34.76 mmol) and DMF (50 mL). After stirring at room temperature, methyl iodide (5.7 g, 40.16 mmol) was added and the mixture was stirred overnight at room temperature. The reaction was monitored by LC-MS until completion. The reaction solution was extracted with a water/EA system. The organic layer was dried, concentrated and then purified by combiflash (0-20% EA/n-hexane) to give a red oily Compound 53-2 (2.9 g, 52.2%). MS m/z (ESI): 169.0 [M+H]$^+$.

Step 2: To a 100 mL round bottom flask were added Compound 53-2 (2.9 g, 17.25 mmol), Boc$_2$O (7.53 g, 34.5 mmol), triethylamine (1.75 g, 17.29 mmol) and 30 mL of tetrahydrofuran and the mixture was stirred overnight at room temperature. The reaction was monitored by LC-MS until completion. The reaction solution was washed with a saturated ammonium chloride solution, extracted with EA, after which the organic layer was dried, concentrated and purified by combiflash (0-15% EA/hexane) to give Compound 53-3 as a yellow oil (4.7 g, 74.6%). MS m/z (ESI): 390.9 [M+Na]$^+$.

Step 3: To a 100 mL round-bottomed flask were added Compound 53-3 (400 mg, 1.491 mmol), 53.1 (730 mg, 1.838 mmol), silver oxide (1.05 g, 4.531 mmol), potassium carbonate (830 mg, 6 mmol) and acetonitrile (10 mL). The mixture was stirred at 50° C. for 3 hours. The reaction was monitored by LC-MS until completion. The reaction solution was filtered through celite and the filtrate was concentrated and purified by combiflash (0-40% EA/hexane) to give Compound 53-4 (570 mg, 59.4%) as a yellow oil. MS m/z (ESI): 607.0 [M+Na]$^+$.

Step 4: To a 100 mL round-bottom flask were added Compound 53-4 (510 mg, 0.872 mmol), 10 mL of dichloromethane and 1 mL of trifluoroacetic acid, and the mixture was stirred at room temperature overnight. The reaction was monitored by LC-MS until completion. The reaction solution was washed with saturated sodium bicarbonate and brine, and the organic layer was dried and concentrated to give 440 mg of Compound 53-5 as a yellow solid. MS m/z (ESI): 485.0 [M+H]$^+$.

Step 5: A 100 mL round bottom flask was loaded with Compound 53-5 (367 mg, 0.758 mmol), Compound 4a (1.1 g, 2.489 mmol), 10 mL of tetrahydrofuran and DIPEA (505 mg, 3.907 mmol), and the mixture was stirred at room temperature for 3 hours. The reaction was monitored by LC-MS until completion. 30 mL of EA was added to the reaction solution and washed with 1M hydrochloric acid (20 mL*2) and saturated brine (20 mL*1). The organic layer was dried, concentrated, and purified by combiflash (0-50% EA/n-hexane) to give a yellow solid Compound 53-6 (460 mg, 68.2%). MS m/z (ESI): 912.1 [M+Na]$^+$.

Step 6: To a 50 mL round bottom flask were added Compound 53-6 (340 mg, 0.382 mmol), 10 mL of methanol, and lithium hydroxide (200 mg, 4.766 mmol), and the mixture was stirred in an ice bath for 4 hours. The reaction was monitored by LC-MS until completion. The pH of the reaction solution was adjusted with 1M hydrochloric acid to 3-4, added with 30 mL of EA and extracted with EA (30 mL*2), after which the organic layer was dried and concentrated to obtain 300 mg of yellow solid Compound 53-7. MS m/z (ESI): 772.4 [M+Na]$^+$.

Step 7: A white solid Compound z-53 (35 mg, 39.8%) was prepared by using Compound 53-7 as a raw material and referring to the method of Step 2 in Example 8. MS m/z (ESI): 630.2 [M+H]$^+$; $^1$H NMR (400 MHz, DMSO-d$_6$) δ 8.35 (s, 1H), 8.20-8.25 (m, 2H), 7.44 (d, 1H), 6.86-7.06 (m, 3H), 5.40 (m, 1H), 4.17 (m, 1H), 3.62 (s, 3H), 3.31-3.46 (m, 4H), 3.16 (s, 3H), 3.06 (m, 1H), 2.62 (m, 1H), 2.21 (m, 1H), 1.91 (m, 1H), 1.61-1.72 (m, 3H), 1.32-1.40 (m, 3H), 1.28 (s, 3H), 1.11 (m, 1H), 0.64 (m, 2H).

Example 54

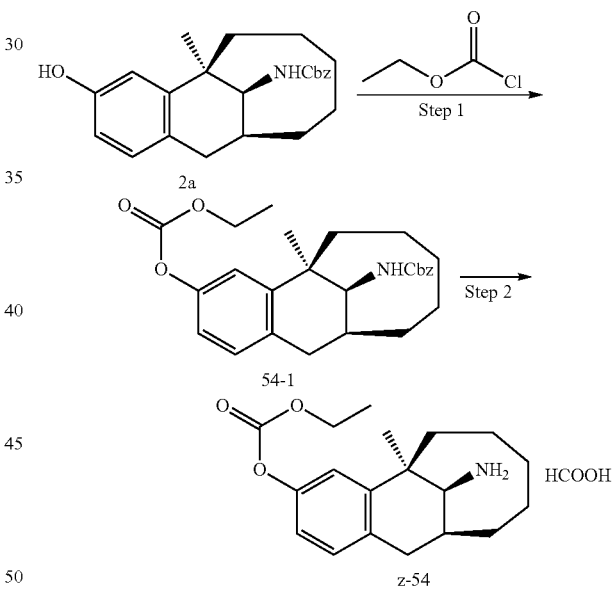

Step 1: To 5 mL of dry dichloromethane was added Compound 2a (218 mg, 0.575 mmol), ethyl chloroformate (186 mg, 1.726 mmol) and triethylamine (174 mg, 1.726 mmol) in an ice bath, and the mixture was stirred at room temperature for 2 hours. The reaction was monitored by LC-MS until completion. Dichloromethane and water were added to the system. The organic layer was separated, dried, and concentrated to give 295 mg of crude product of Compound 54-1 which was used directly for the next reaction. MS m/z (ESI): 451 [M+H]$^+$.

Step 2: A white solid Compound z-54 (54.5 mg, 32.8%) was prepared by using Compound 54-1 as a raw material and referring to the method of Step 2 in Example 8. MS m/z (ESI): 317 [M+H]$^+$.

Example 55

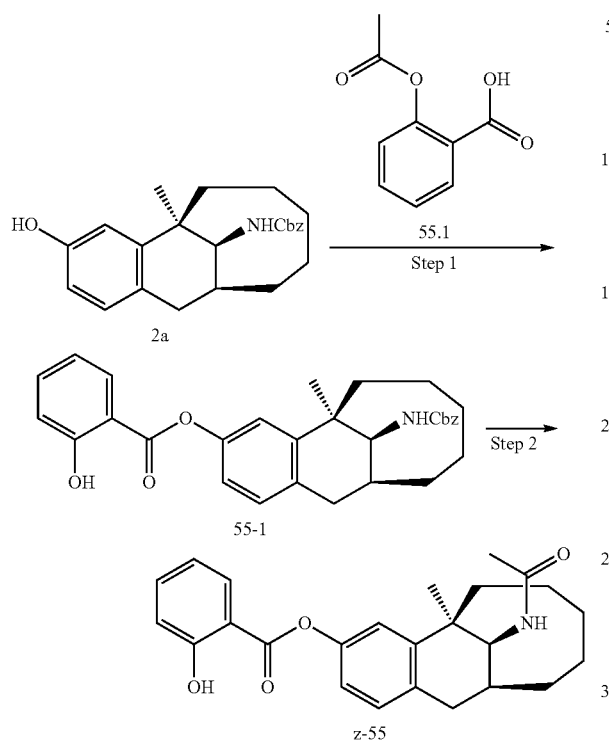

Step 1: The preparation method was the same as that of Compound 52-1, except that Compound 52.1 in the preparation method of 52-1 was replaced with Compound 55.1 and stirred overnight at room temperature under a nitrogen atmosphere and purified by combiflash (petroleum ether: EA=10:1) to give 293 mg of oily Compound 55-1. MS m/z (ESI): N/A.

Step 2: Compound z-55 (8.4 mg, 9.5%) was prepared by using Compound 55-1 as a raw material and referring to the method of Step 2 in Example 8. MS m/z (ESI): 408 [M+H]$^+$.

Example 56

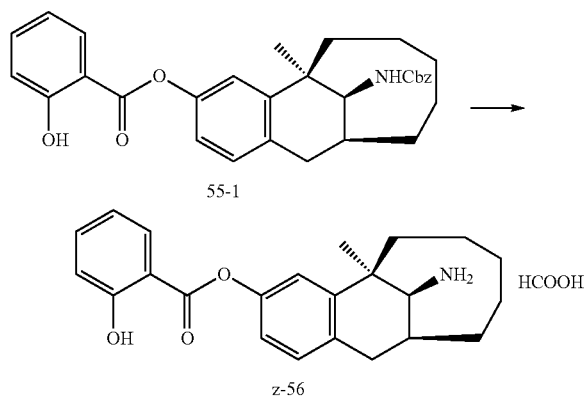

To Compound 55-1 (140 mg, 0.28 mmol) was added 1 ml of hydrobromic acid and 2 ml of acetic acid. The mixture was stirred at room temperature for 18 hours, concentrated, and purified by preparative high-performance liquid chromatography to give Compound z-56 (43.1 mg; 42%) as a white solid. MS m/z (ESI): 366 [M+H]$^+$.

Example 57

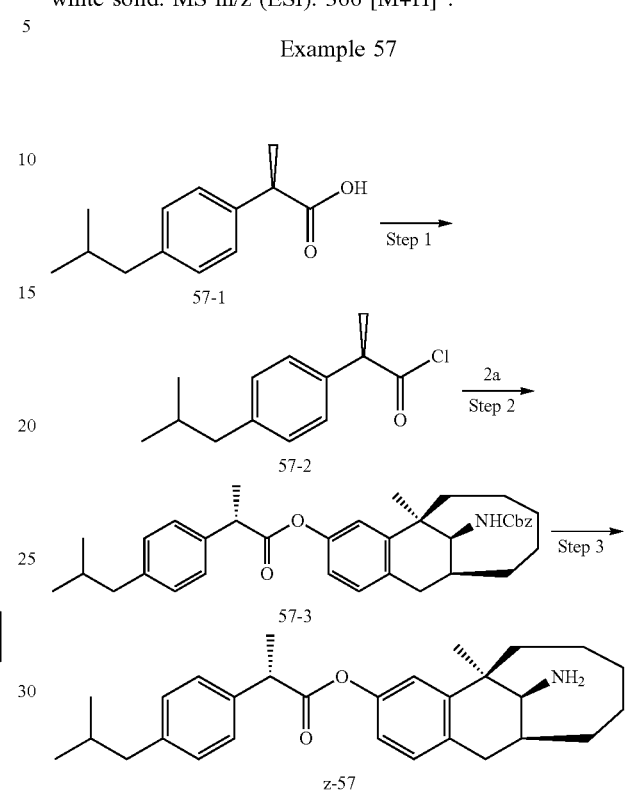

Step 1: Compound 57-1 (500 mg, 2.427 mmol) was dissolved in 10 mL of dry dichloromethane. After cooling in an ice bath, 5 mL of thionyl chloride was slowly added, and the mixture was stirred at 60° C. overnight. The reaction was monitored by LC-MS until completion. The reaction solution was concentrated to give 550 mg of oily Compound 57-2 which was used directly in the next Step. MS m/z (ESI): N/A.

Step 2: Compound 2a (250 mg, 1.12 mmol) and triethylamine (160 mg, 1.6 mmol) were dissolved in 5 mL of dry dichloromethane. After cooling in an ice bath, Compound 57-2 (250 mg, 0.66 mmol) was slowly added, and the mixture was stirred at room temperature for 6 hours. The reaction solution was concentrated and purified by combiflash (petroleum ether:EA=10:1) to give oil Compound 57-3 (377 mg, 59%). MS m/z (ESI): N/A.

Step 3: Compound z-57 (151.4 mg, 66.2%) was prepared by using Compound 57-3 as a raw material and referring to the method of Step 2 in Example 8. MS m/z (ESI): 434 [M+H]$^+$.

Example 58

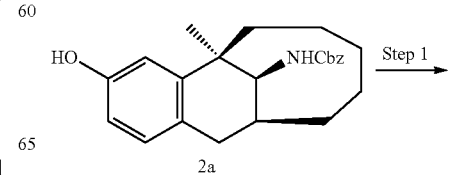

-continued

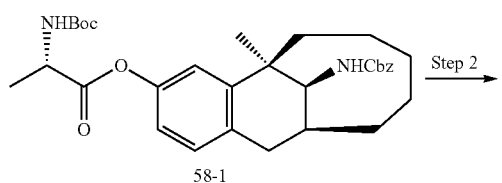# 58-1

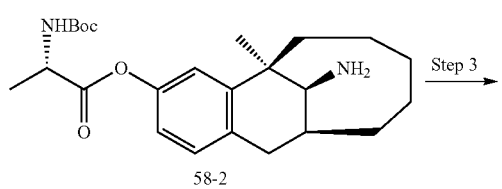# 58-2

Step 2: 200 mg of colorless oil Compound 58-2 was prepared by using Compound 58-1 as a raw material and referring to the method of Step 2 in Example 8. MS m/z (ESI): 417.3 [M+H]$^+$.

Step 3: To a 50 mL round bottom flask were added Compound 58-2 (200 mg, 0.48 mmol), 1,4-dioxane (10 mL) and hydrochloric acid/1,4-dioxane (3 mL, 4 M), and the mixture was stirred at room temperature overnight. The reaction solution was concentrated to remove the solvent and purified by preparative HPLC to give Compound z-58 (60 mg, 32.1%) as a white solid. MS m/z (ESI): 317.2 [M+H]$^+$.

Example 59

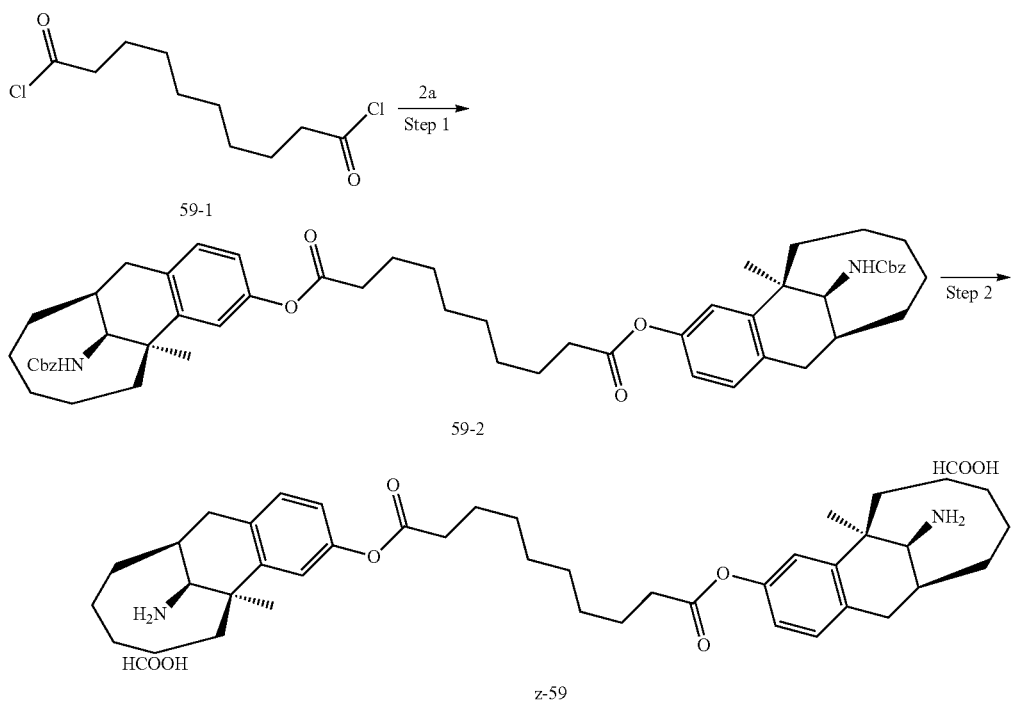

-continued

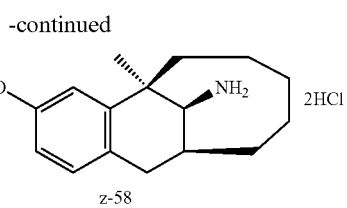# z-58

Step 1: The preparation method was the same as that of Compound 52-1, except that Compound 52.1 in the preparation method of 52-1 was replaced with (S)-2-(tert-butoxycarbonylamine) propionic acid. After purification by combiflash (0-10% EA/hexane), a white solid Compound 58-1 (265 mg, 91.4%) was obtained. MS m/z (ESI): 451.4 [M+H]$^+$.

Step 1: A 100 mL round bottom flask was loaded with Compound 2a (317 mg, 0.835 mmol), sodium hydride (50 mg, 1.254 mmol), 5 mL of dry tetrahydrofuran and 59-1 (100 mg, 0.418 mmol), and the mixture was stirred at room temperature for 2 hours. The reaction was monitored by LC-MS until completion. The reaction solution was extracted by EA/water system, the organic layers were combined, dried and concentrated to give 195 mg of Compound 59-2. MS m/z (ESI): N/A.

Step 2: Compound z-59 (27 mg, 29%) was prepared by using Compound 59-2 as a raw material and referring to the method of Step 2 in Example 8. MS m/z (ESI): N/A.

Example 60

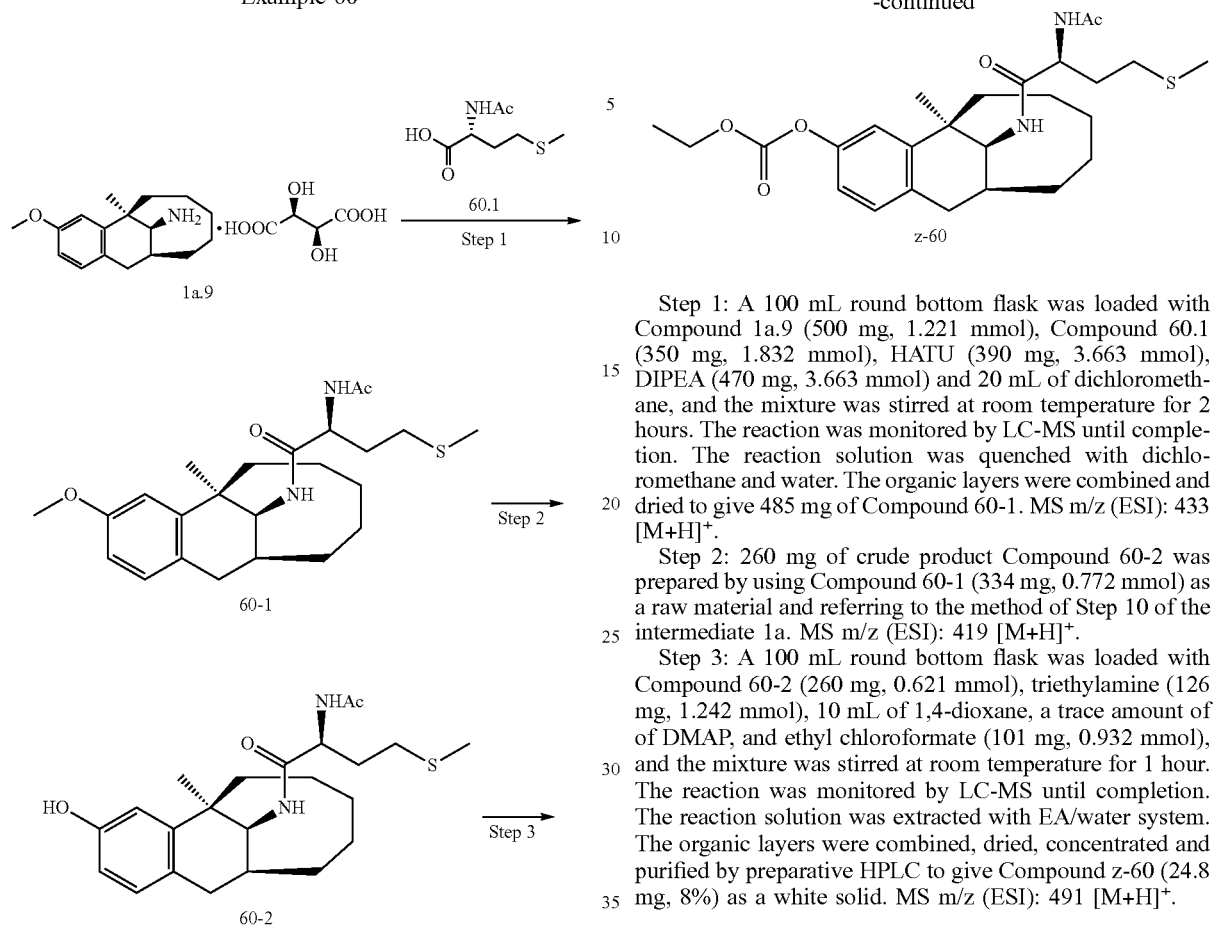

Step 1: A 100 mL round bottom flask was loaded with Compound 1a.9 (500 mg, 1.221 mmol), Compound 60.1 (350 mg, 1.832 mmol), HATU (390 mg, 3.663 mmol), DIPEA (470 mg, 3.663 mmol) and 20 mL of dichloromethane, and the mixture was stirred at room temperature for 2 hours. The reaction was monitored by LC-MS until completion. The reaction solution was quenched with dichloromethane and water. The organic layers were combined and dried to give 485 mg of Compound 60-1. MS m/z (ESI): 433 [M+H]+.

Step 2: 260 mg of crude product Compound 60-2 was prepared by using Compound 60-1 (334 mg, 0.772 mmol) as a raw material and referring to the method of Step 10 of the intermediate 1a. MS m/z (ESI): 419 [M+H]+.

Step 3: A 100 mL round bottom flask was loaded with Compound 60-2 (260 mg, 0.621 mmol), triethylamine (126 mg, 1.242 mmol), 10 mL of 1,4-dioxane, a trace amount of of DMAP, and ethyl chloroformate (101 mg, 0.932 mmol), and the mixture was stirred at room temperature for 1 hour. The reaction was monitored by LC-MS until completion. The reaction solution was extracted with EA/water system. The organic layers were combined, dried, concentrated and purified by preparative HPLC to give Compound z-60 (24.8 mg, 8%) as a white solid. MS m/z (ESI): 491 [M+H]+.

Example 61

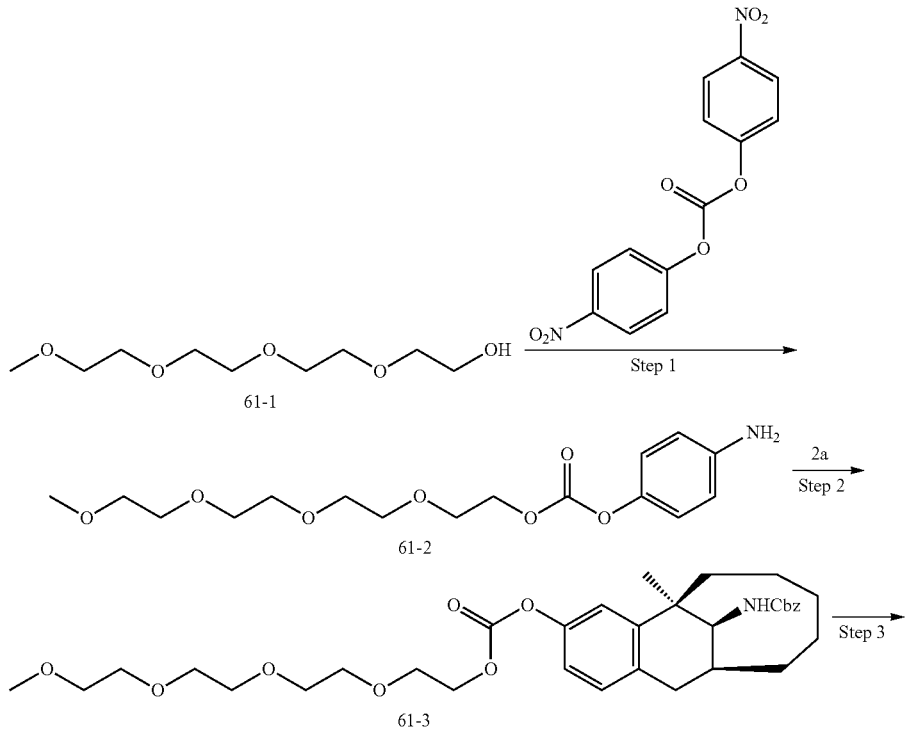

-continued

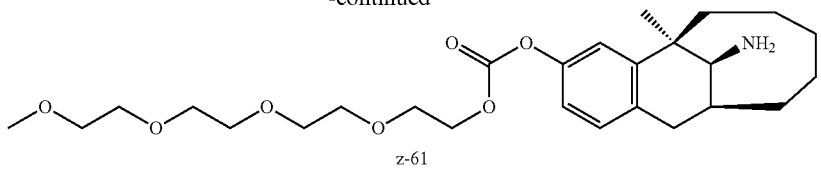

z-61

Step 1: The preparation method was the same as that of intermediate 3a, except that Compound 2a in the preparation method of 3a was replaced with Compound 61-1. After purification by combiflash, 826 mg of Compound 61-2 was obtained. MS m/z (ESI): N/A.

Step 2: A 100 mL round bottom flask was loaded with Compound 61-2 (826 mg, 2.212 mmol), Compound 2a (700 mg, 1.845 mmol), 15 mL of tetrahydrofuran and DMAP (249 mg, 2.083 mmol), respectively, and the mixture was stirred at room temperature overnight. The reaction was monitored by LC-MS until completion. After concentrated, the mixture was purified by combiflash, Compound 61-3 (923 mg, 68%) was obtained. MS m/z (ESI): 614 [M+H]$^+$.

Step 3: Compound z-61 (42.5 mg, 6%) was prepared by using Compound 61-3 as a raw material and referring to the method of Step 2 in Example 8. MS m/z (ESI): N/A.

Example 62

Step 1: To a 100 mL round bottom flask were added Compound 62-1 (1.631 g, 7.832 mmol), sodium hydride (469 mg, 11.748 mmol), Compound 62.1 (1 g, 8.615 mmol), and 30 mL of dry tetrahydrofuran and the mixture was stirred overnight at room temperature. After the solution was quenched by water, the organic layer was concentrated to obtain 2.54 g crude product of Compound 62-2.

Step 2: To a 250 mL round-bottom flask were added Compound 62-2 (2.54 g, 7.832 mmol), Compound 2a (1.486 g, 3.916 mmol), EDCI (2.432 g, 15.666 mmol), DIPEA (3.036 g, 23.491 mmol), DMAP (47.8 mg, 0.392 mmol) and 40 mL of tetrahydrofuran, and the mixture was stirred at room temperature overnight. The reaction solution was extracted with EA/water system, the organic layer was collected and washed with saturated brine. The organic layer was separated, dried, and concentrated. After purification by combiflash, 300 mg of Compound 62-3 was obtained. MS m/z (ESI): N/A.

Step 3: Compound z-62 (28 mg, 11.6%) was prepared by using Compound 62-3 as a raw material and referring to the method of Step 2 in Example 8. MS m/z (ESI): 552 [M+H]$^+$.

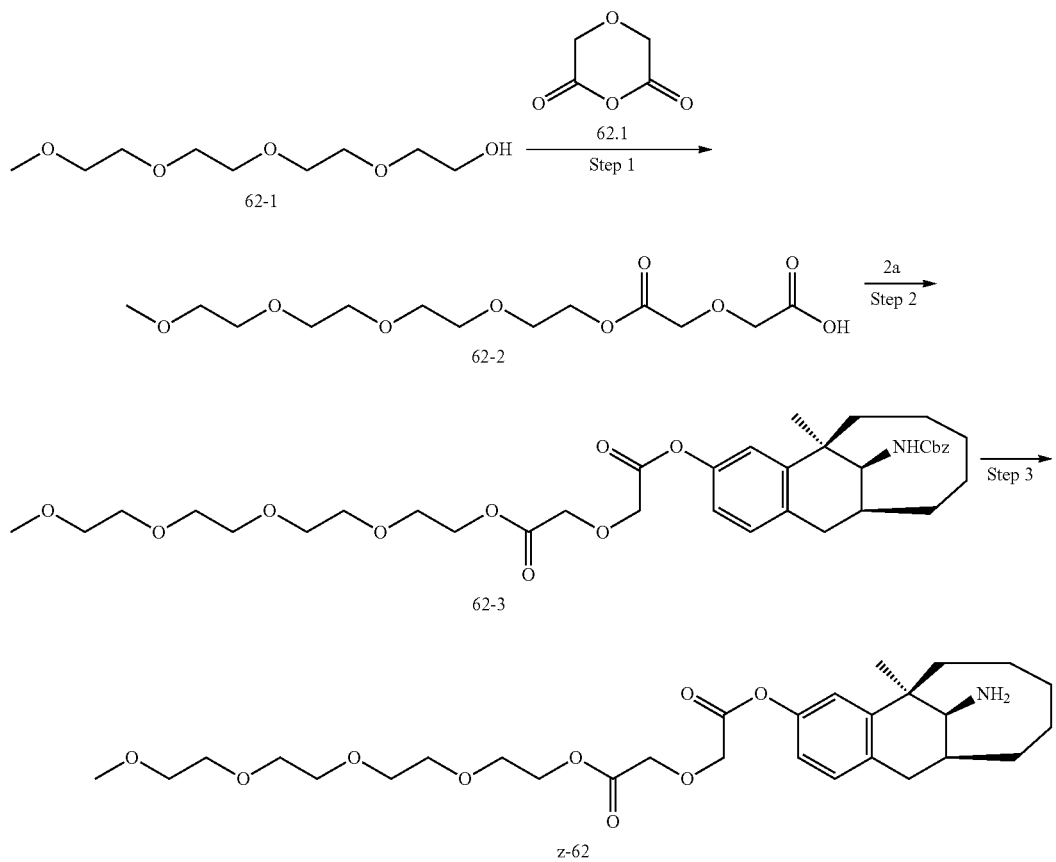

Example 63

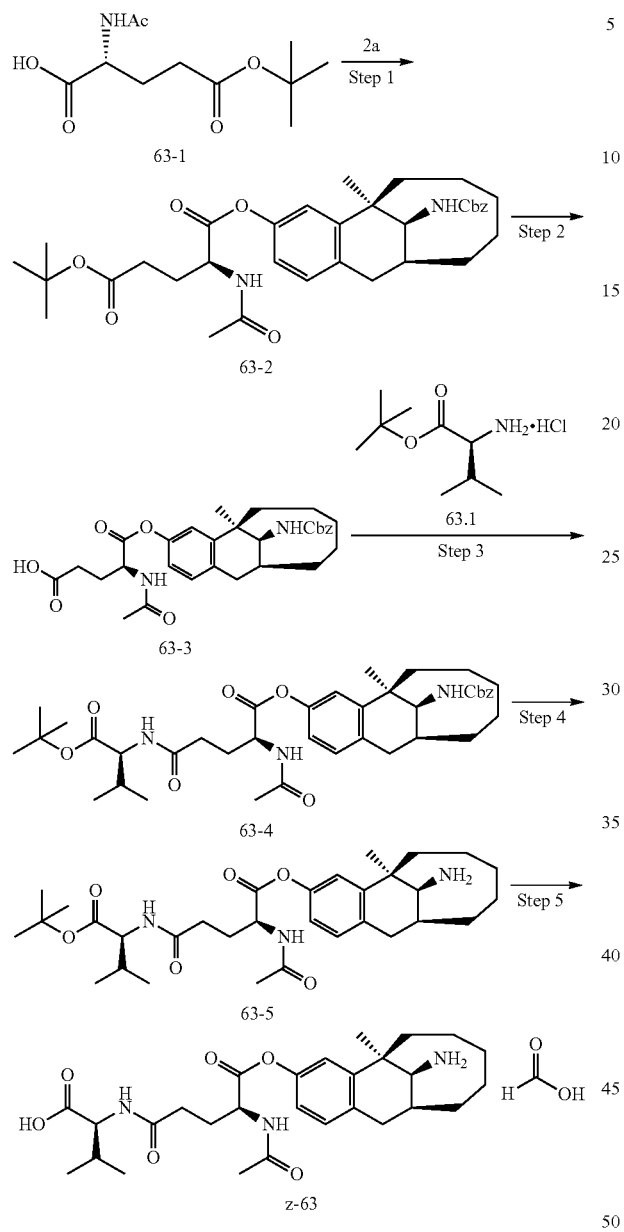

Step 1: The preparation method was the same as that of Compound 46-1, except that Compound 46.1 in the preparation method of 46-1 was replaced with Compound 63-1, and stirred at room temperature overnight. After purification by combiflash (0-40% EA/Hexane), a white solid Compound 63-2 (365 mg, 71.4%) was obtained. MS m/z (ESI): 629.4 [M+Na]$^+$. Step 2: 470 mg of oily Compound 63-3 was prepared by using Compound 63-2 as a raw material and referring to the method of Step 4 in Example 53. MS m/z (ESI): 551.3 [M+H]$^+$.

Step 3: A white solid Compound 63-4 (380 mg, 72.9%) was prepared by using Compound 63-3 as a raw material and dichloromethane as solvent and referring to the method of Step 1 in Example 52, and purification by combiflash (petroleum ether/EA/methanol=50/50/5). MS m/z (ESI): N/A.

Step 4: After the reaction solution was filtered and concentrated, 275 mg of white solid Compound 63-5 was prepared by using Compound 63-4 as a raw material and referring to the method of Step 2 in Example 8. MS m/z (ESI): 572.5 [M+H]$^+$.

Step 5: A white solid Compound z-63 (97.3 mg, 41.5%) was prepared by using Compound 63-5 as a raw material and referring to the method of Step 4 in Example 53, and concentration and purification by preparative HPLC of the reaction solution. MS m/z (ESI): 516.4 [M+H]$^+$.

Example 64

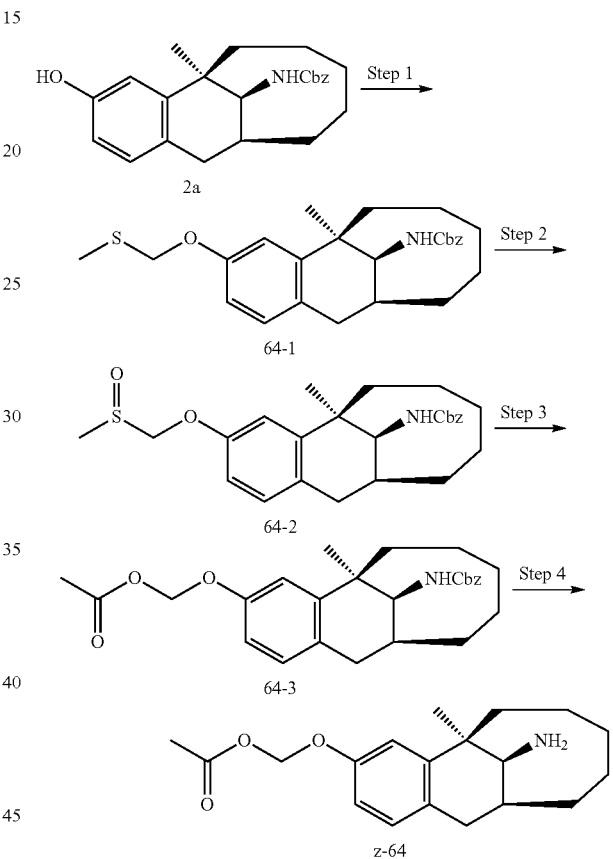

Step 1: A 50 mL round bottom flask were added with Compound 2a (506 mg, 1.333 mmol) and dried DMF (8 mL), added with sodium hydride (160 mg, 60%, 4 mmol) was in an ice bath, and then added with chloromethyl dimethyl sulfide (250 mg, 2.589 mmol) dropwise. The mixture was stirred while being slowly warmed to room temperature and reacted for 2 hours. The reaction was monitored by LC-MS until completion. The system was quenched with 30 mL of water and extracted with dichloromethane (30 mL*2), after which the organic layers were combined, washed with saturated brine (30 mL), dried and concentrated to give 1 g of yellow oily Compound 64-1. MS m/z (ESI): 440.3 [M+H]$^+$.

Step 2: A 50 mL round bottom flask were added with Compound 64-1 (187 mg, 0.425 mmol) and 5 mL of dry dichloromethane, added with m-CPBA (100 mg, 60%, 0.493 mmol) in an ice-bath, and stirred for 10 minutes. Saturated sodium bisulfite solution was added to the system to quench the reaction. The organic layer was separated, washed with a saturated sodium bicarbonate solution, concentrated and purified by combiflash (0-100% EA/n-hexane) to give Compound 64-2 (150 mg, 77.4%) as a colorless oil. MS m/z (ESI): 456.3 [M+H]$^+$.

Step 3: To a 50 mL round-bottom flask, Compound 64-2 (330 mg, 0.724 mmol), 10 mL of acetic anhydride and 2 drops of methanesulfonic acid were added, and the mixture was stirred at room temperature overnight. The reaction was monitored by LC-MS until completion. The reaction solution was concentrated to remove the solvent, and EA was added to the system to dissolve the residue, which was then washed with saturated sodium bicarbonate solution. The organic layer was concentrated to give 330 mg of Compound 64-3 as a yellow oil. MS m/z (ESI): 452.3 [M+H]$^+$.

Step 4: A white solid Compound z-64 (87 mg, 37.6%) was prepared by using Compound 64-3 as a raw material and referring to the method of Step 2 in Example 8. MS m/z (ESI): 318.2 [M+H]$^+$.

Example 65

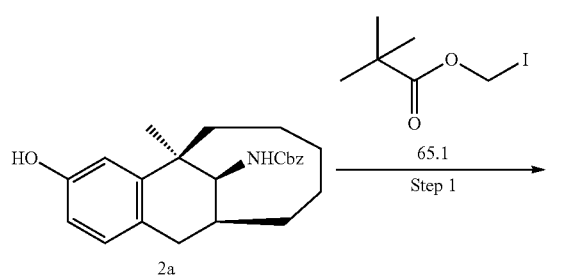

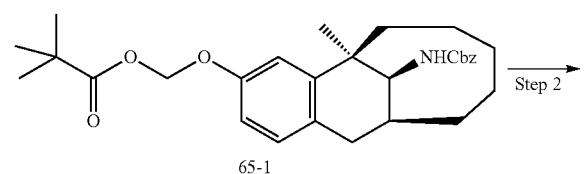

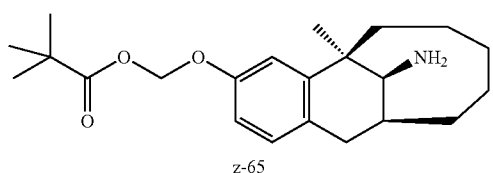

Step 1: A 100 mL round bottom flask was loaded with Compound 2a (500 mg, 1.318 mmol), Compound 65.1 (480 mg, 1.983 mmol), Bu$_4$NHSO$_4$ (450 mg, 1.325 mmol), potassium carbonate (550 mg, 3.979 mmol), 10 mL of dichloromethane and 10 mL of water. The mixture was stirred overnight at room temperature. The reaction was monitored by LC-MS until completion. The system was washed with water and extracted with dichloromethane. The organic layer was separated, dried and concentrated to give 750 mg of Compound 65-1 as a yellow oil. MS m/z (ESI): 392.2 [M+H]$^+$.

Step 2: A white solid Compound z-65 (203 mg, 37.2%) was prepared by using Compound 65-1 as a raw material and referring to the method of Step 2 in Example 8. MS m/z (ESI): 360.3 [M+H]$^+$.

Example 66

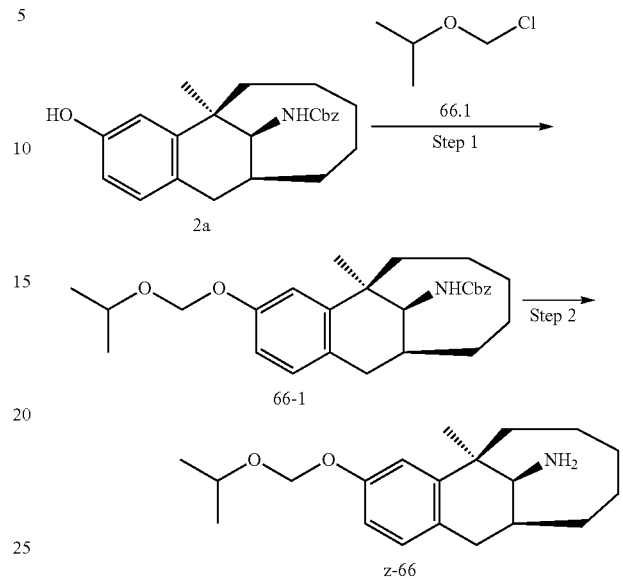

Step 1: The preparation method was the same as that of Compound 64-1, except that chloromethyl dimethyl sulfide in the preparation method of 64-1 was replaced with Compound 66.1, stirred at room temperature overnight, and purified by combiflash (0-10% EA/petroleum ether) to give a yellow oily Compound 66-1 (495 mg, 69%). MS m/z (ESI): N/A.

Step 2: A white solid Compound z-66 (207 mg, 52%) was prepared by using Compound 66-1 as a raw material and referring to the method of Step 2 in Example 8. MS m/z (ESI): 318.3 [M+H]$^+$.

Example 67

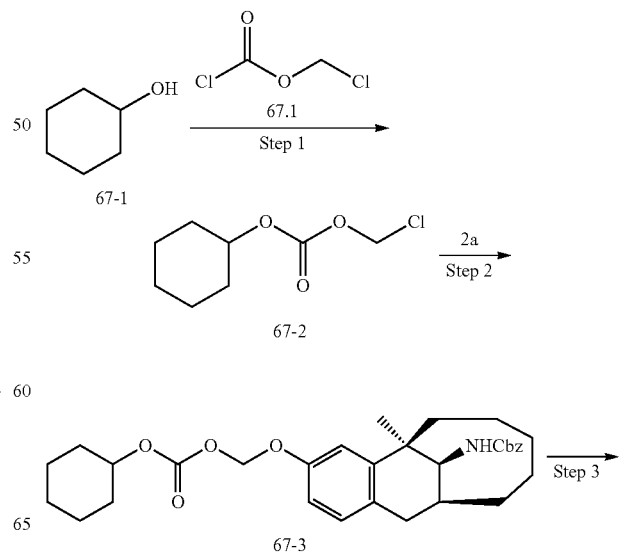

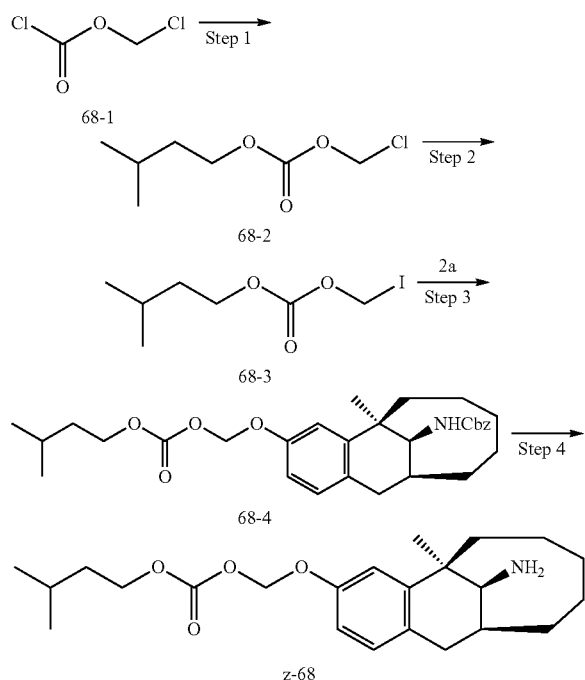

z-67

Step 1: Pyridine (948 mg, 11.98 mmol) was added to a solution of Compound 67-1 (600 mg, 5.99 mmol) and Compound 67.1 (772 mg, 5.99 mmol) in dichloromethane (10 mL). The mixture was stirred at room temperature overnight. The reaction solution was washed with water, after which the organic layer was dried, concentrated, and purified by combiflash (0-10% EA/petroleum ether) to give Compound 67-2 as a colorless oil (844 mg, 73%). MS m/z (ESI): N/A.

Step 2: The preparation method was the same as that of Compound 65-1, except that 65.1 in the preparation method of 65-1 was replaced with Compound 67-2, and 1 equivalent of sodium iodide was added, the mixture was stirred at 40° C. overnight and purified by Prep-HPLC to give a white solid Compound 67-3 (450 mg, 37%). MS m/z (ESI): 558.3 [M+H]$^+$. Step 3: A white solid Compound z-67 (254.2 mg, 75.5%) was prepared by using Compound 67-3 as a raw material and referring to the method of Step 2 in Example 8. MS m/z (ESI): 402.3 [M+H]$^+$.

Example 68

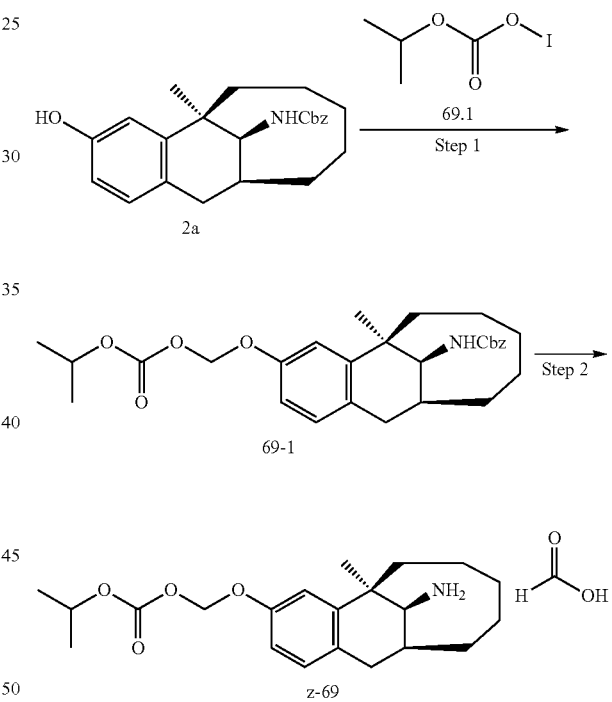

z-68

Step 1: The preparation method was the same as that of Compound 67-2, except that 67-1 in the preparation method of 67-2 was replaced with isopentanol, the mixture was stirred overnight at room temperature and purified by combiflash (0-10% EA/petroleum ether) to give Compound 68-2 (819 mg, 80%) as a yellow oil. MS m/z (ESI): N/A.

Step 2: Sodium iodide (830 mg, 5.536 mmol) was added to a solution of Compound 68-2 (500 mg, 2.768 mmol) in acetonitrile (5 mL) and the mixture was stirred under argon atmosphere at 40° C. overnight. The reaction solution was concentrated, and the residue was dissolved by adding dichloromethane to form a suspension. The inorganic salts were removed by filtration and the filtrate was concentrated to give 670 mg of Compound 68-3 as a yellow oil which was used directly for the next reaction.

Step 3: The preparation method was the same as that of Compound 65-1, except that 65.1 in the preparation method of 65-1 was replaced with Compound 68-3, the mixture was stirred at 40° C. for 2 days and purified by combiflash (0-10% EA/petroleum ether) to give Compound 68-4 (410 mg, 32%) as a colorless oil. MS m/z (ESI): 546.3 [M+Na]$^+$.

Step 4: A white solid Compound z-68 (115.8 mg, 38%) was prepared by using Compound 68-4 as a raw material and referring to the method of Step 2 in Example 7. MS m/z (ESI): 390.3 [M+H]$^+$.

Example 69

Step 1: A 100 mL round bottom flask was loaded with Compound 2a (500 mg, 1.318 mmol), Compound 69.1 (319 mg, 1.318 mmol), potassium carbonate (362 mg, 2.619 mmol) and 15 mL of acetonitrile, and the mixture was reacted at 80° C. for 8 hours. The reaction was monitored by LC-MS until completion. The mixture was extracted with EA/water, and the organic layers were combined and washed with saturated brine. After drying and concentrating, the mixture was purified to give Compound 69-1 (583 mg, 89%). MS m/z (ESI): N/A.

Step 2: A white solid Compound z-69 (98.5 mg, 23%) was prepared by using Compound 69-1 as a raw material and referring to the method of Step 2 in Example 8. MS m/z (ESI): 362 [M+H]$^+$.

Example 70

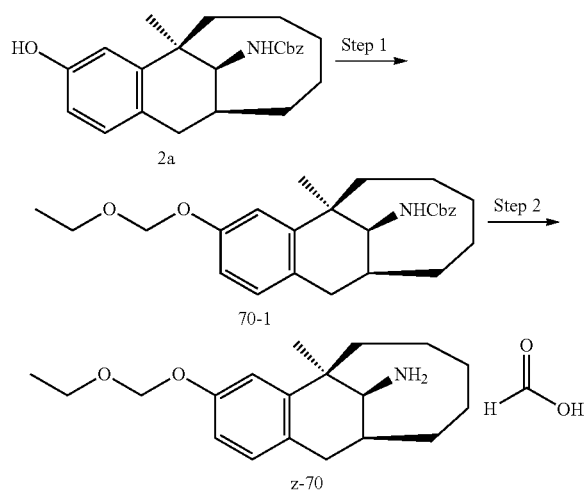

Step 1: To a 50 mL round bottom flask, Compound 2a (200 mg, 0.527 mmol), 10 mL of tetrahydrofuran, and sodium hydride (42 mg, 1.054 mmol) were added, and a solution of chloromethyl ether (60 mg, 0.632 mmol) in tetrahydrofuran (1 mL) was added dropwise in an ice bath, after which the mixture was reacted at room temperature for 1 hour. The reaction was monitored by LC-MS until completion. The system was quenched with water. After EA extraction, the organic layers were combined, washed with saturated brine, dried and concentrated to give a crude product of Compound 70-1 which was used directly for the next reaction. MS m/z (ESI): N/A.

Step 2: A white solid Compound z-70 (28.7 mg, 15%) was prepared by using Compound 70-1 as a raw material and referring to the method of Step 2 in Example 8. MS m/z (ESI): 304 [M+H]+.

Example 71

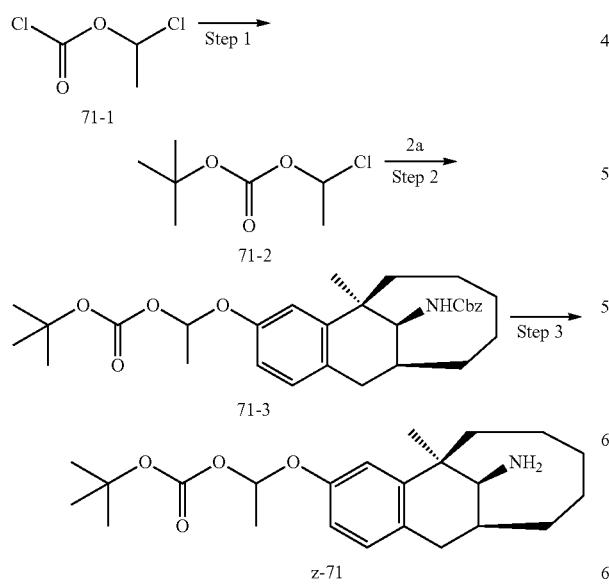

Step 1: A 250 mL round bottom flask was loaded with Compound 71-1 (5 g, 34.972 mmol), tert-butanol (2.592 g, 34.97 mmol), pyridine (5.535 g, 69.941 mmol) and 50 mL of dichloromethane, and the mixture was stirred at room temperature for 2 hours. The mixture was extracted with dichloromethane/water, and the organic layer was combined, washed, dried, concentrated and purified by combi-flash to give a colorless oil Compound 71-2 (3.458 g, 55%). MS m/z (ESI): N/A.

Step 2: The preparation method was the same as that of Compound 65-1, except that 65.1 in the preparation method of 65-1 was replaced with Compound 71-2, and 1 equivalent of sodium iodide was added. After purification by combi-flash, Compound 71-3 (1.2 g, 38.2%) was obtained. MS m/z (ESI): N/A.

Step 3: A white solid Compound z-71 (23.8 mg, 3%) was prepared by using Compound 71-3 as a raw material and referring to the method of Step 2 in Example 8. MS m/z (ESI): 390 [M+H]+.

Example 72

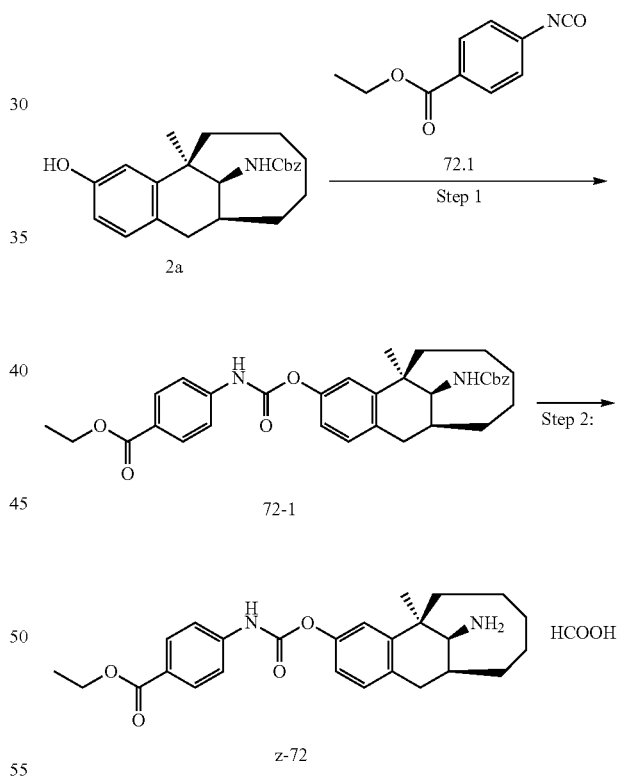

Step 1: The preparation method was the same as that of Compound 1-1, except that n-butyl isocyanate in the preparation method of 1-1 was replaced with Compound 72.1, and tetrahydrofuran was used as a solvent. 300 mg of crude product Compound 72-1 was obtained. MS m/z (ESI): 471 [M+H]+.

Step 2: A white solid Compound z-72 (50 mg, 21%) was prepared by using Compound 72-1 as a raw material and referring to the method of Step 2 in Example 8. MS m/z (ESI): 437 [M+H]+.

Example 73

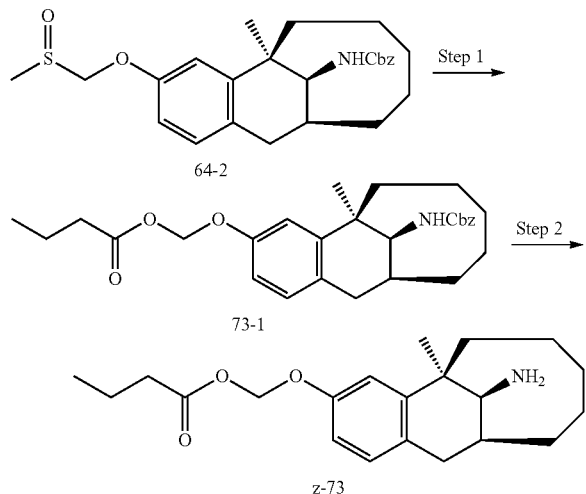

Step 1: The preparation method was the same as that of Compound 64-3, except that acetic anhydride in the preparation method of 64-3 was replaced with butyric anhydride. After purification by combiflash (0-15% EA/n-hexane), Compound 73-1 (760 mg, 98.9%) was obtained as a colorless oil. MS m/z (ESI): 502.3 [M+H]$^+$.

Step 2: A white solid Compound z-73 (240 mg, 43.9%) was prepared by using Compound 73-1 as a raw material and referring to the method of Step 2 in Example 8. MS m/z (ESI): 346.3 [M+H]$^+$.

Example 74

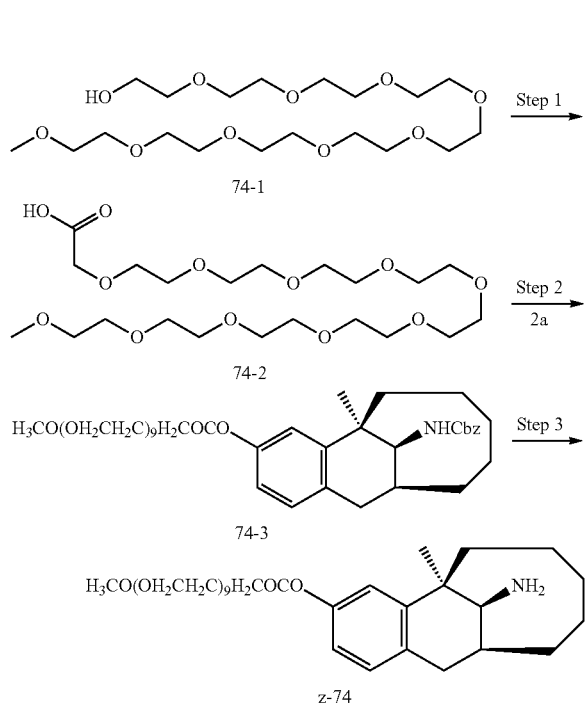

Step 1: The preparation method was the same as that of Compound 70-1, except that chloromethyl ether in the preparation method of 70-1 was replaced with tert-butyl bromoacetate, and then stirred overnight at room temperature to obtain 1.5 g of crude product Compound 74-2. MS m/z (ESI): N/A.

Step 2: The preparation method was the same as that of Compound 52-1, except that Compound 52.1 in the preparation method of 52-1 was replaced with Compound 74-2, and a trace amount of DMAP was added, stirred at room temperature for 1 hour, purified by combiflash (50% EA/hexane to 5% methanol/EA) and then purified by thin layer chromatography (EA:methanol=5:1) to give Compound 74-3 (650 mg, 71%) as a colorless oil. MS m/z (ESI): N/A.

Step 3: A white solid Compound z-74 (165 mg, 30.2%) was prepared by using Compound 74-3 as a raw material and referring to the method of Step 2 in Example 8. MS m/z (ESI): 714.5 [M+H]$^+$.

Example 75

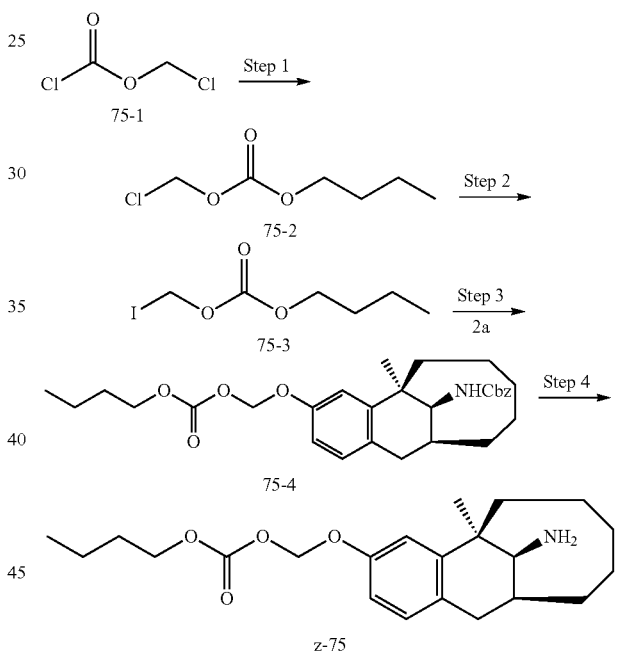

Step 1: The preparation method was the same as that of Compound 71-2, except that 71-1 and tert-butanol in the preparation method of 71-2 are replaced with 75-1 and n-butanol, respectively. After purification by combiflash, Compound 75-2 (3.678 g, 82%) was obtained. MS m/z (ESI): N/A.

Step 2: Compound 75-3 was prepared by using Compound 75-2 as a raw material and referring to the method of Step 2 in Example 68, wherein the mixture was stirred at 30° C. overnight under nitrogen atmosphere and concentrated to give 5.696 g of Compound 75-3, which was used directly for the next reaction.

Step 3: The preparation method was the same as that of Compound 69-1, except that 69.1 in the preparation method of 69-1 was replaced with 75-3. After purification by combiflash, Compound 75-4 (200 mg, 10%) was obtained. MS m/z (ESI): 510 [M+H]$^+$.

Step 4: A white solid Compound z-75 (370 mg, 74.6%) was prepared by using Compound 75-4 as a raw material and referring to the method of Step 2 in Example 7. MS m/z (ESI): 376.3 [M+H]⁺.

Example 76

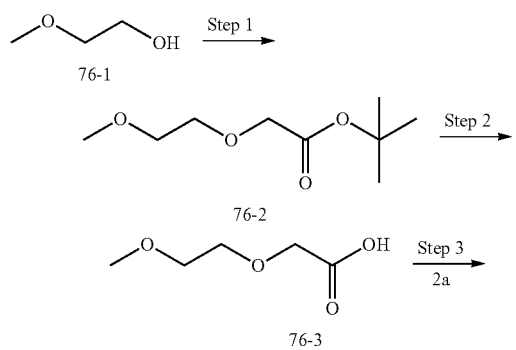

Step 1: The preparation method was the same as that of Compound 70-1, except that chloromethyl ether in the preparation method of 70-1 was replaced with tert-butyl bromoacetate, and a colorless oil Compound 76-2 (300 mg, 31.6%) was obtained after stirring at room temperature for 2 hours and purifying by combiflash (0-40% EA/hexane). MS m/z (ESI): N/A.

Step 2: The preparation method was the same as that of Compound 53-5, except that Compound 53-4 in the preparation method of 53-5 was replaced with Compound 76-2, and a yellow oil of Compound 76-3 (180 mg, 88.2%) was obtained after stirring at room temperature for 3 days. MS m/z (ESI): N/A.

Step 3: The preparation method was the same as that of Compound 74-3, except that Compound 74-2 in the preparation method of 74-3 was replaced with Compound 76-3, and a colorless oil of Compound 76-4 (590 mg, 88.7%) was obtained after purifying by combiflash (0-40% EA/Hexane). MS m/z (ESI): 496.3 [M+H]⁺.

Step 4: A white solid Compound z-76 (415 mg, 85.6%) was prepared by using Compound 76-4 as a raw material and referring to the method of Step 2 in Example 7. MS m/z (ESI): 362.3 [M+H]⁺.

Example 77

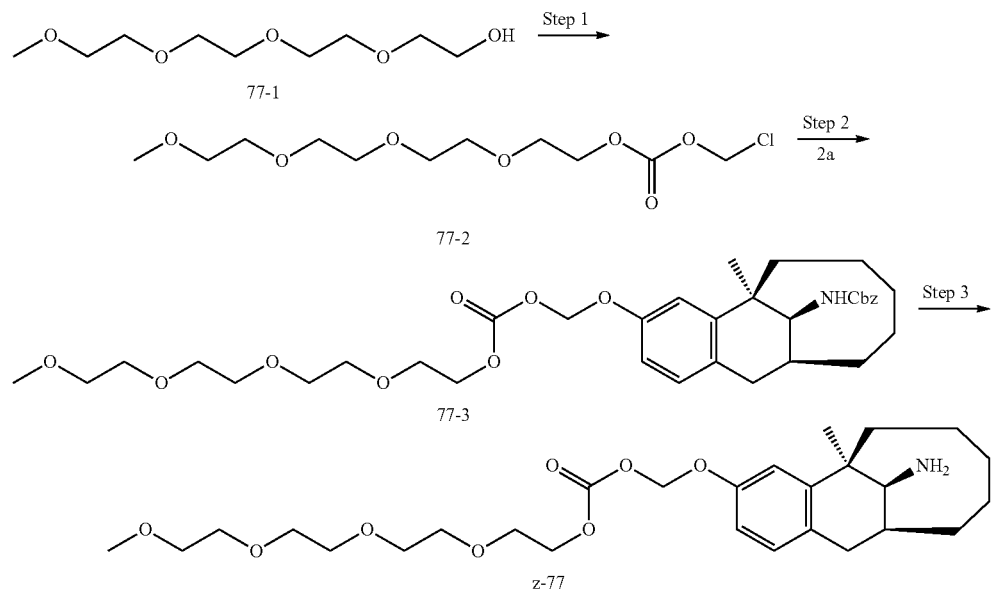

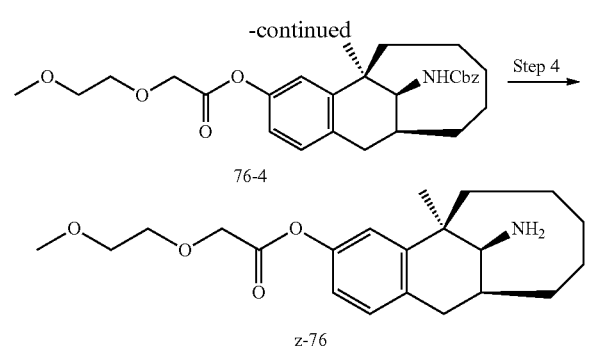

Step 1: The preparation method was the same as that of Compound 71-2, except that 71-1 and tert-butanol in the preparation method of 71-2 are replaced with 75-1 and 77-1, and stirred at room temperature overnight. The reaction was monitored by TLC until completion. Compound 77-2 (1.91 g, 83.8%) was obtained after purification by combiflash (0-100% EA/n-hexane). MS m/z (ESI): N/A.

Step 2: To a 100 mL round-bottom flask, Compound 77-2 (1.91 g, 6.351 mmol), sodium iodide (1.9 g, 12.676 mmol) and 20 mL of acetone were added, after which the mixture was stirred at 40° C. for 10 hours and then concentrated to remove the solvent. Compound 2a (1.5 g, 3.953 mmol), potassium carbonate (1.12 g, 8.104 mmol), 20 mL of dichloromethane, 20 mL of water, Bu₄NHSO₄ (2 g, 5.89 mmol) were added to the residue, after which the system was stirred at room temperature for 3 days, then raised to 40° C. and stirred for 1 day. The reaction was monitored by LC-MS until completion. The organic layer was separated, concentrated and purified by preparative HPLC to give a white solid of Compound 77-3 (533 mg, 21%). MS m/z (ESI): 666.4 [M+H]⁺.

Step 3: A white solid of Compound z-77 (390 mg, 84.8%) was prepared by using Compound 77-3 as a raw material and referring to the method of Step 2 in Example 7. MS m/z (ESI): 510.4 [M+H]⁺.

Example 78

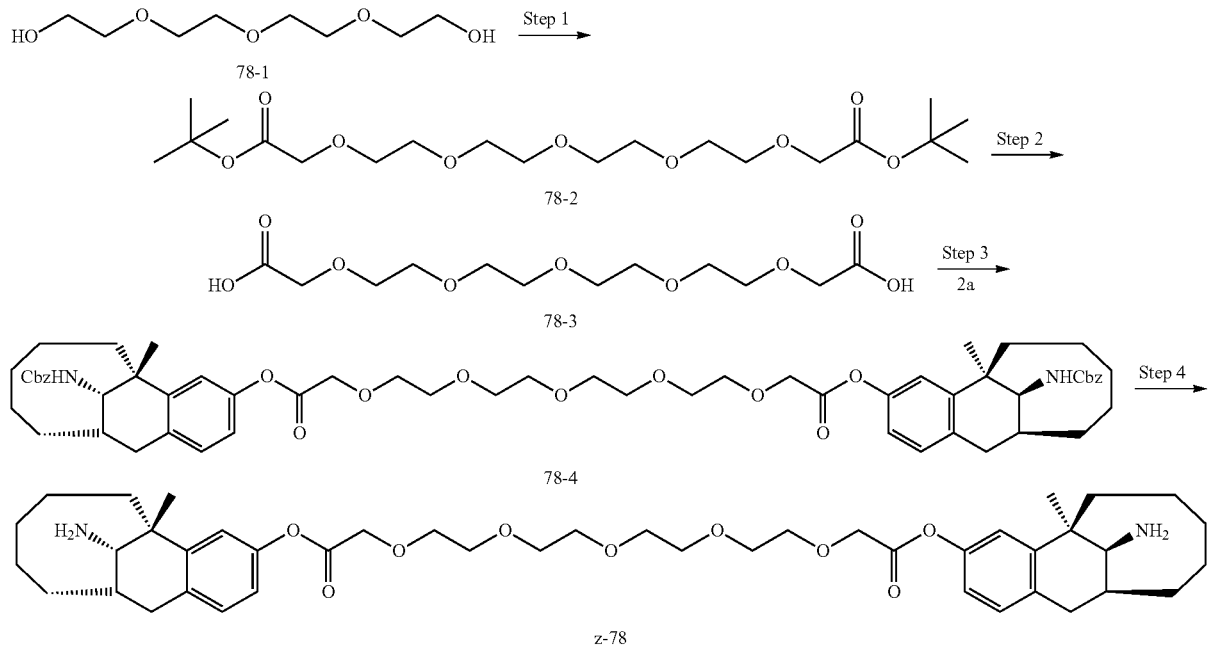

Step 1: The preparation method was the same as that of Compound 70-1, except that Compound 2a and chloromethyl ether in the preparation method of 70-1 were replaced with Compound 78-1 and tert-butyl bromoacetate, and a yellow oil Compound 78-2 (920 mg, 21.1%) was obtained after stirring at room temperature for 2 hours and purifying by combflash (0-80% EA/Hexane). MS m/z (ESI): 445.3 [M+Na]⁺.

Step 2: The preparation method was the same as that of Compound 53-5, except that Compound 53-4 in the preparation method of 53-5 was replaced with Compound 78-2. After stirring overnight at room temperature, the reaction was warmed to 40° C. and reacted for 2 days to give 640 mg of brown oily Compound 78-3. MS m/z (ESI): N/A.

Step 3: The preparation method was the same as that of Compound 74-3, except that Compound 74-2 in the preparation method of 74-3 was replaced with Compound 78-3, and a yellow oily Compound 78-4 (1.1 g, 94.4%) was obtained after stirring at room temperature for 2 hours and purifying by combiflash (0-10% EA/hexane). MS m/z (ESI): N/A.

Step 4: A white solid Compound z-78 (170 mg, 29.7%) was prepared by using Compound 78-4 as a raw material and referring to the method of Step 2 in Example 8. MS m/z (ESI): 765.5 [M+H]⁺.

Example 79

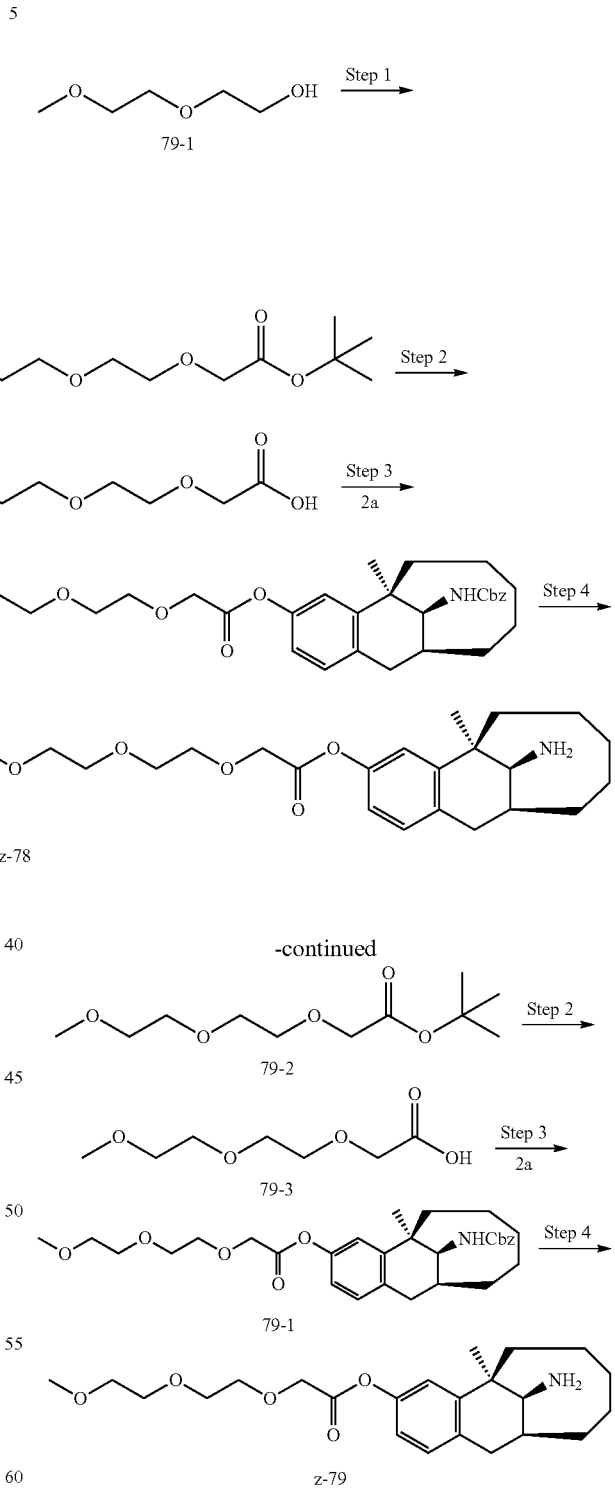

Step 1: The preparation method was the same as that of Compound 70-1, except that Compound 2a and chloromethyl ether in the preparation method of 70-1 were replaced with Compound 79-1 and tert-butyl bromoacetate, and a colorless oily Compound 79-2 (470 mg, 24.1%) was obtained after stirring at room temperature for 3 hours and purifying by combiflash (0-30% EA/n-hexane). MS m/z (ESI): N/A.

Step 2: The preparation method was the same as that of Compound 53-5, except that Compound 53-4 in the preparation method of 53-5 was replaced with Compound 79-2. 400 mg of yellow oily Compound 79-3 was obtained. MS m/z (ESI): 179.1 [M+H]⁺.

Step 3: The preparation method was the same as that of Compound 74-3, except that Compound 74-2 in the preparation method of 74-3 was replaced with Compound 79-3. After purification by combiflash (0-30% EA/n-hexane), a colorless oil Compound 79-4 (1 g, 92.2%) was obtained. MS m/z (ESI): 540.3 [M+H]⁺.

Step 4: A white solid Compound z-79 (325 mg, 43.2%) was prepared by using Compound 79-4 as a raw material and referring to the method of Step 2 in Example 8. MS m/z (ESI): 406.3 [M+H]⁺.

Example 80

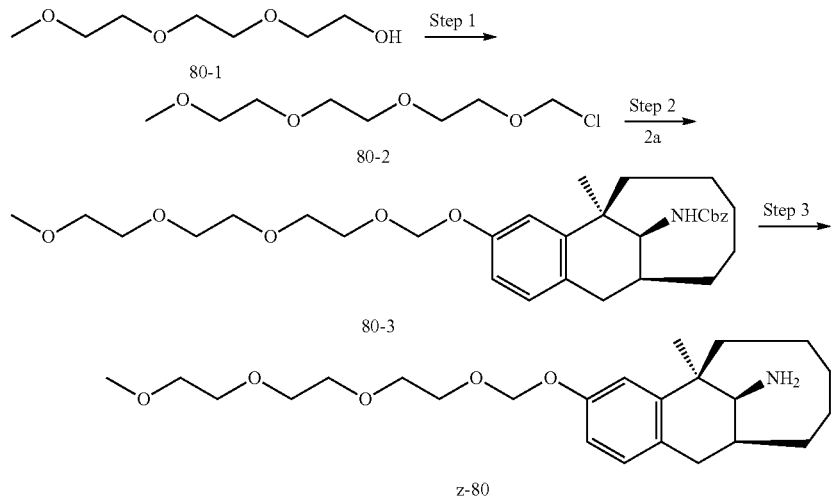

Step 1: The preparation method was the same as that of Compound 47-2, except that isobutanol in the preparation method of 47-2 was replaced with Compound 80-1. 2 g of crude product Compound 80-2 was obtained as a colorless oil. MS m/z (ESI): N/A.

Step 2: The preparation method was the same as that of Compound 47-3, except that Compound 47-2 in the preparation method of 47-3 was replaced with Compound 80-2. After purification by combiflash (0-50% EA/hexane), a colorless oil Compound 80-3 (810 mg, 88.8%) was obtained. MS m/z (ESI): 578.3 [M+H]⁺.

Step 3: A white solid Compound z-80 (577 mg, 84.7%) was prepared by using Compound 80-3 as a raw material and referring to the method of Step 2 in Example 7. MS m/z (ESI): 422.3 [M+H]⁺.

Example 81

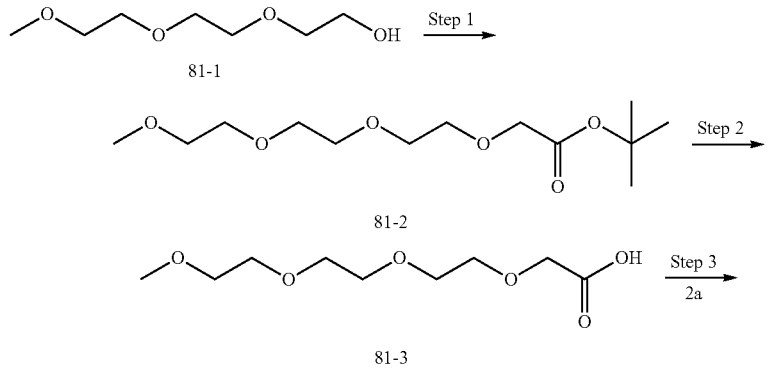

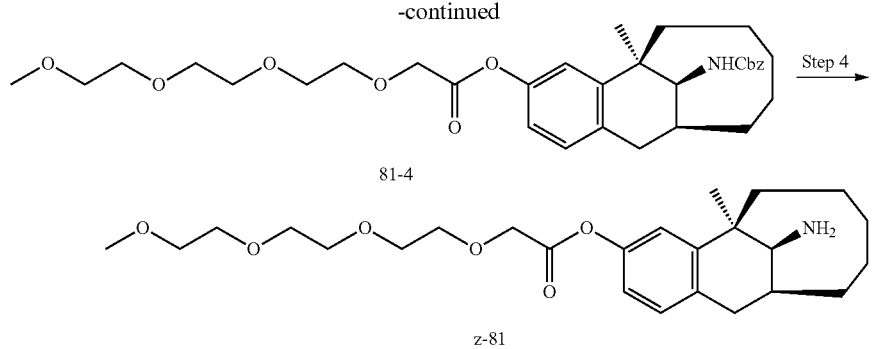

Step 1: The preparation method was the same as that of Compound 70-1, except that Compound 2a and chloromethyl ether in the preparation method of 70-1 are replaced with Compound 81-1 and tert-butyl bromoacetate, and stirred at room temperature overnight. The reaction was followed by TLC until the end of the reaction. After purification by combiflash (0-60% EA/hexane), Compound 81-2 (1.12 g, 59.6%) was obtained as a yellow oil. MS m/z (ESI): N/A.

Step 2: The preparation method was the same as that of Compound 53-5, except that Compound 53-4 in the preparation method of 53-5 was replaced with Compound 81-2, 1.55 g of a yellow oily Compound 81-3 was obtained after stirring at 40° C. overnight. MS m/z (ESI): 223.1 [M+H]+.

Step 3: The preparation method was the same as that of Compound 74-3, except that Compound 74-2 in the preparation method of 74-3 was replaced with Compound 81-3. A colorless oil Compound 81-4 (1.2 g, 63.2%) was obtained after reaction at room temperature for 30 minutes and purification by combiflash (0-50% EA/n-hexane). MS m/z (ESI): 584.3 [M+H]+.

Step 4: A white solid Compound z-81 (350 mg, 37.9%) was prepared by using Compound 81-4 as a raw material and referring to the method of Step 2 in Example 8. MS m/z (ESI): 450.4 [M+H]+.

Example 82

Step 1: The preparation method was the same as that of Compound 47-2, except that isobutanol in the preparation method of 47-2 was replaced with Compound 82-1. 2.6 g of crude product Compound 82-2 was obtained as a colorless oil. MS m/z (ESI): N/A. Step 2: The preparation method was the same as that of Compound 47-3, except that Compound 47-2 in the preparation method of 47-3 was replaced with Compound 82-2. After purification by combiflash, a colorless oil Compound 82-3 (890 mg, 93.9%) was obtained. MS m/z (ESI): 622.3 [M+Na]+.

Step 3: A white solid Compound z-82 (600 mg, 80.3%) was prepared by using Compound 82-3 as a raw material and referring to the method of Step 2 in Example 7. MS m/z (ESI): 466.4 [M+H]+.

Example 83

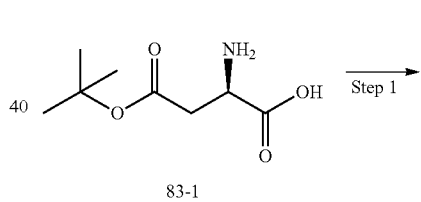

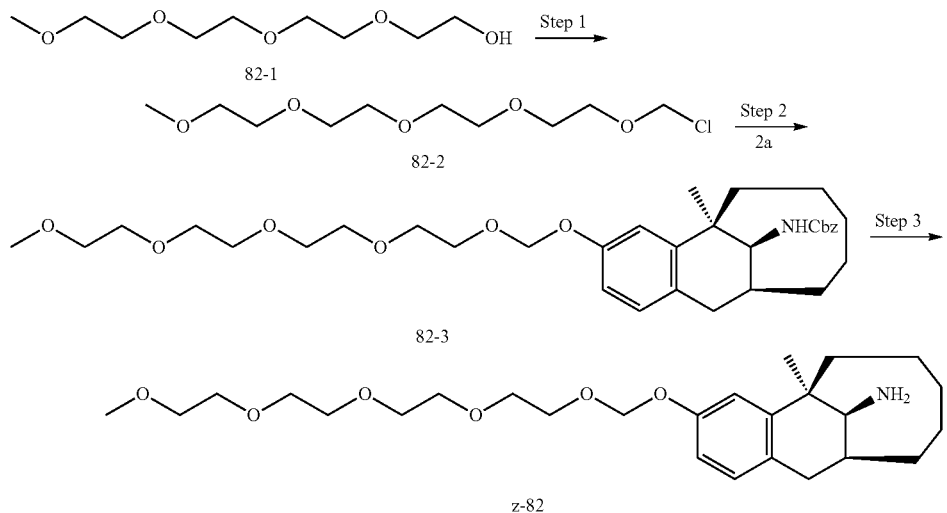

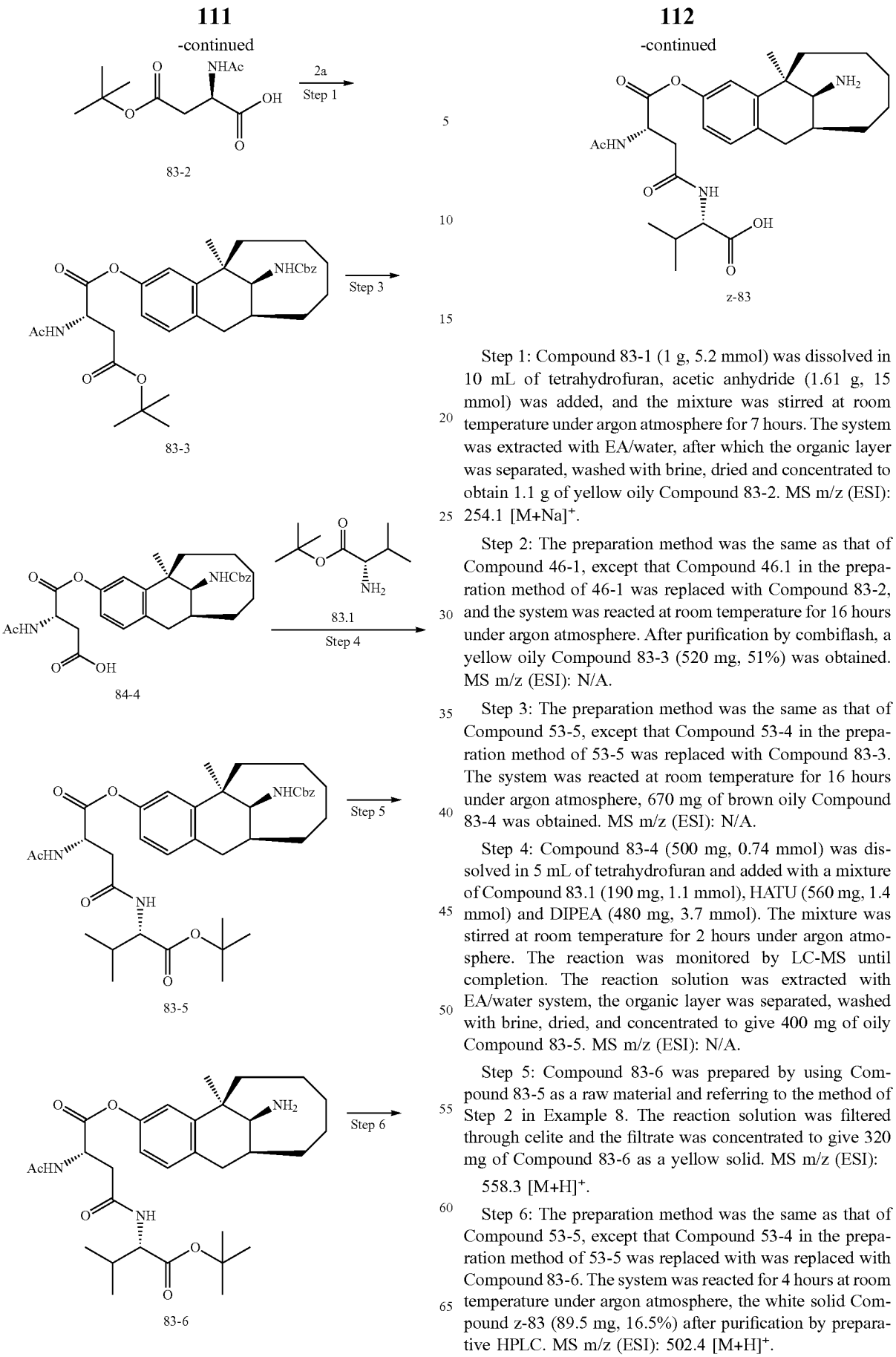

Step 1: Compound 83-1 (1 g, 5.2 mmol) was dissolved in 10 mL of tetrahydrofuran, acetic anhydride (1.61 g, 15 mmol) was added, and the mixture was stirred at room temperature under argon atmosphere for 7 hours. The system was extracted with EA/water, after which the organic layer was separated, washed with brine, dried and concentrated to obtain 1.1 g of yellow oily Compound 83-2. MS m/z (ESI): 254.1 [M+Na]$^+$.

Step 2: The preparation method was the same as that of Compound 46-1, except that Compound 46.1 in the preparation method of 46-1 was replaced with Compound 83-2, and the system was reacted at room temperature for 16 hours under argon atmosphere. After purification by combiflash, a yellow oily Compound 83-3 (520 mg, 51%) was obtained. MS m/z (ESI): N/A.

Step 3: The preparation method was the same as that of Compound 53-5, except that Compound 53-4 in the preparation method of 53-5 was replaced with Compound 83-3. The system was reacted at room temperature for 16 hours under argon atmosphere, 670 mg of brown oily Compound 83-4 was obtained. MS m/z (ESI): N/A.

Step 4: Compound 83-4 (500 mg, 0.74 mmol) was dissolved in 5 mL of tetrahydrofuran and added with a mixture of Compound 83.1 (190 mg, 1.1 mmol), HATU (560 mg, 1.4 mmol) and DIPEA (480 mg, 3.7 mmol). The mixture was stirred at room temperature for 2 hours under argon atmosphere. The reaction was monitored by LC-MS until completion. The reaction solution was extracted with EA/water system, the organic layer was separated, washed with brine, dried, and concentrated to give 400 mg of oily Compound 83-5. MS m/z (ESI): N/A.

Step 5: Compound 83-6 was prepared by using Compound 83-5 as a raw material and referring to the method of Step 2 in Example 8. The reaction solution was filtered through celite and the filtrate was concentrated to give 320 mg of Compound 83-6 as a yellow solid. MS m/z (ESI): 558.3 [M+H]$^+$.

Step 6: The preparation method was the same as that of Compound 53-5, except that Compound 53-4 in the preparation method of 53-5 was replaced with was replaced with Compound 83-6. The system was reacted for 4 hours at room temperature under argon atmosphere, the white solid Compound z-83 (89.5 mg, 16.5%) after purification by preparative HPLC. MS m/z (ESI): 502.4 [M+H]$^+$.

Example 84

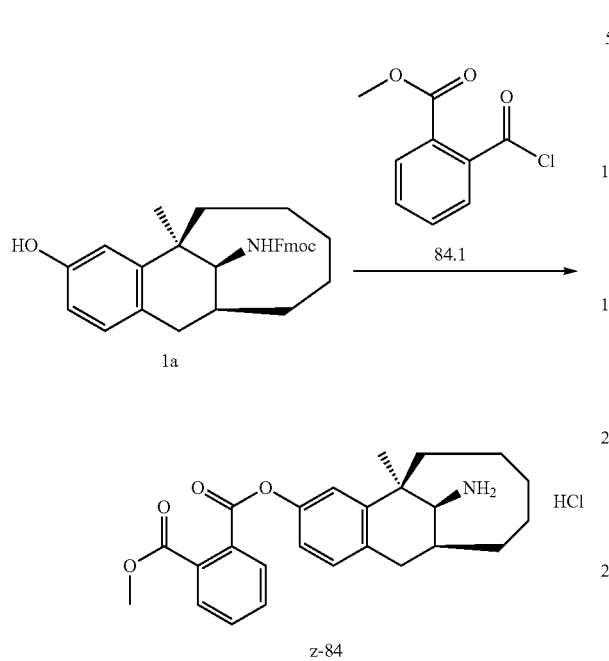

Step 1: To a 100 mL round bottom flask, Compound 1a (256 mg, 0.547 mmol), Compound 84.1 (120 mg, 0.604 mmol) and triethylamine (115 mg, 1.136 mmol) were added and the mixture was stirred overnight at room temperature. 1 mL of piperidine was added to the reaction solution, and stirred continuously at room temperature for 6 hours. The reaction was monitored by LC-MS until completion. The reaction solution was washed with saturated ammonium chloride and brine, the organic layer was dried, concentrated, and purified by Prep-HPLC to give a white solid Compound z-84 (40 mg, 16.5%). MS m/z (ESI): 408.2 [M+H]$^+$.

Example 85

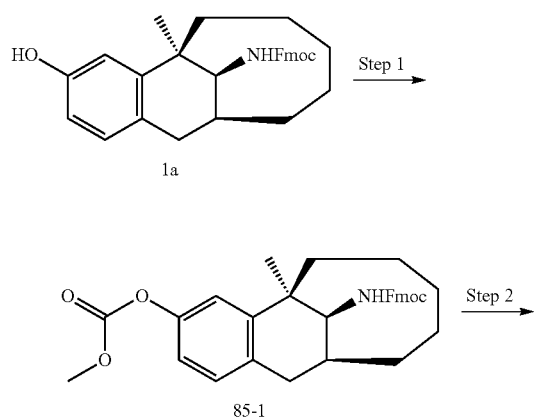

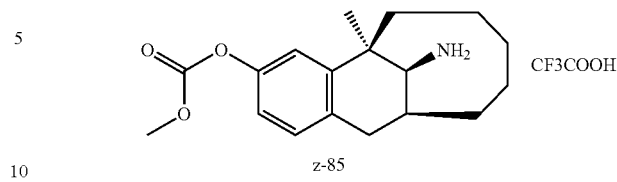

Step 1: The preparation method was the same as that of Compound 1-1, except that N-butyl isocyanate in the preparation method of 1-1 was replaced with methyl chloroformate, and stirred at room temperature for 7 hours. MS m/z (ESI): 526 [M+H]$^+$.

Step 2: Compound z-85 (3 mg, 2%) was prepared by using Compound 85-1 as a raw material and referring to the method of Step 2 of Example 1. MS m/z (ESI): 304 [M+H]$^+$.

Example 86

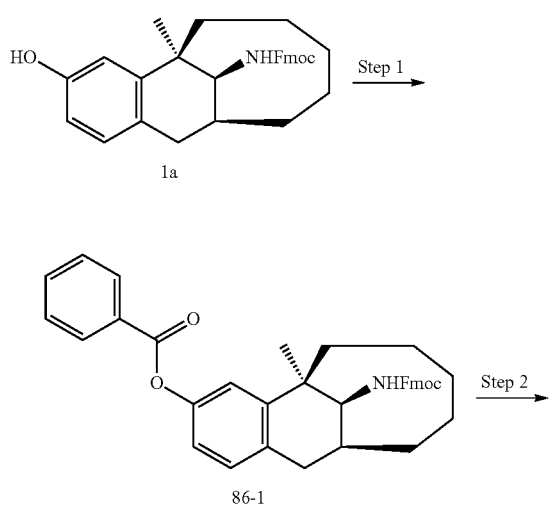

Step 1: The preparation method was the same as that of Compound 2-1, except that 4-methylpiperazine-1-carbonyl chloride in the preparation method of 2-1 was replaced with benzoyl chloride, and stirred at room temperature for 1.5 hours. MS m/z (ESI): 572 [M+H]$^+$.

Step 2: Compound z-86 (39.5 mg, 35%) was prepared by using Compound 86-1 as a raw material and referring to the method of Step 2 in Example 2. MS m/z (ESI): 350 [M+H]$^+$.

Example 87

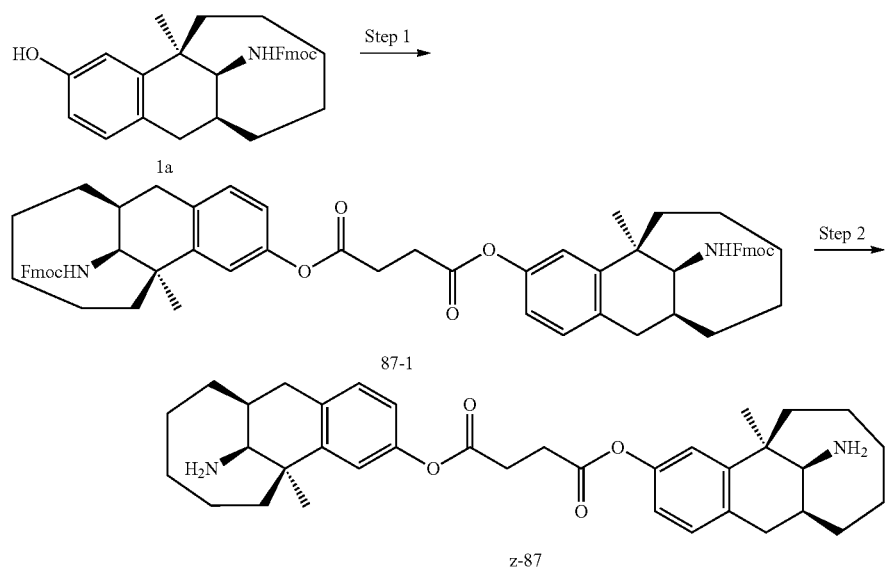

Step 1: Compound 1a (308 mg, 0.66 mmol), succinyl chloride (47 mg, 0.33 mmol) and triethylamine (130 mg, 1.32 mmol) were added to 4 mL of dry dichloromethane and reacted at room temperature for 6 hours. The reaction solution was extracted by EA/water system. The organic layer was separated and washed with brine, dried and concentrated, and purified by combiflash (petroleum ether: EA=3:1) to give 210 mg of oily Compound 87-1. MS m/z (ESI): N/A.

Step 2: Compound z-87 (9.6 mg, 8.1%) was prepared by using Compound 87-1 as a raw material and referring to the method of Step 2 in Example 1. MS m/z (ESI): 573 [M+H]$^+$.

Example 88

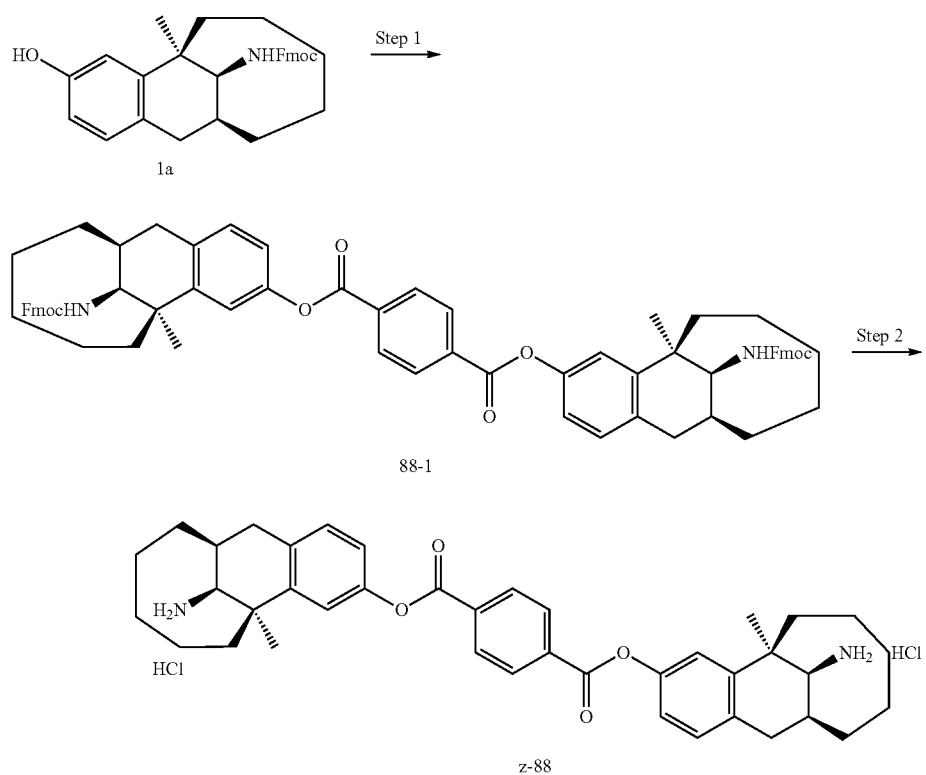

Step 1: The preparation method was the same as that of Compound 2-1, except that 4-methylpiperazine-1-carbonyl chloride in the preparation method of 2-1 was replaced with terephthaloyl chloride, and tetrahydrofuran was used as solvent. The reaction solution was extracted with EA/water system. The organic layer was separated, dried and concentrated to obtain 135 mg of crude product Compound 88-1. MS m/z (ESI): N/A.

Step 2: Compound z-88 (19.4 mg, 25%) was prepared by using Compound 88-1 as a raw material and referring to the method of Step 2 of Example 1. MS m/z (ESI): 621 [M+H]$^+$.

Example 89

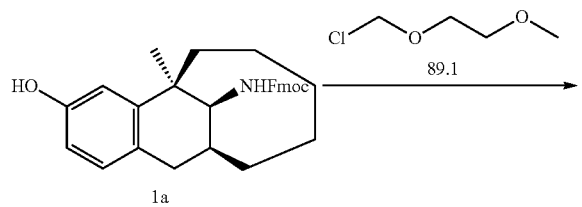

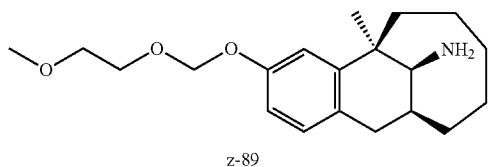

The preparation method was the same as that of Compound 70-1, except that Compound 2a and chloromethyl ether in the preparation method of 70-1 were replaced with Compound 1a and 89.1, and a white solid Compound z-89 (120 mg, 34.3%) was obtained after stirring at room temperature for 3 hours and purifying by preparative HPLC. MS m/z (ESI): 334.3 [M+H]$^+$.

Example 90

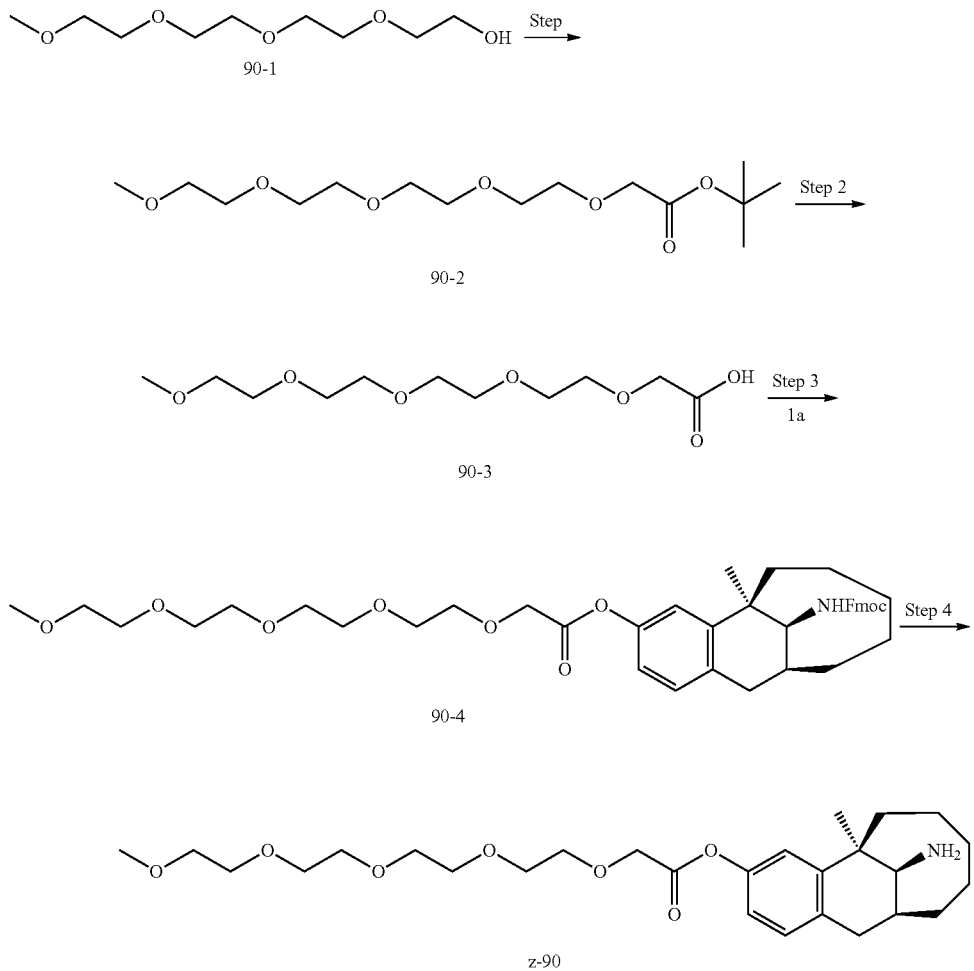

Step 1: The preparation method was the same as that of Compound 70-1, except that Compound 2a and chloromethyl ether in the preparation method of 70-1 are replaced with Compound 90-1 and tert-butyl bromoacetate, and a yellow oily Compound 90-2 (400 mg, 51.2%) was obtained after reacting in a ice bath for 2 hours and purifying by combiflash (0-50% EA/hexane). MS m/z (ESI): N/A.

Step 2: The preparation method was the same as that of Compound 53-5, except that Compound 53-4 in the preparation method of 53-5 was replaced with Compound 90-2, and 450 mg of brown oil Compound 90-3 was obtained after reacting at room temperature for 2 days. MS m/z (ESI): N/A.

Step 3: The preparation method was the same as that of Compound 62-3, except that Compound 2a and 62-2 in the preparation method of 62-3 were replaced with Compound 1a and 90-3, and a colorless oil Compound 90-4 (510 mg, 70.3%) was obtained after purification by combiflash (0-50% EA/hexane). MS m/z (ESI): N/A.

Step 4: To a 50 mL round bottom flask, Compound 90-4 (345 mg, 0.482 mmol), 8 mL of DMF and a trace amount of TBAF were added, and the mixture was stirred at room temperature for 3 hours. The reaction was monitored by LC-MS until completion. The reaction solution was concentrated and purified by Preparative High-Performance Liquid Chromatography to give a white solid Compound z-90 (31.6 mg, 12.2%). MS m/z (ESI): 494.4 [M+H]$^+$.

Example 91

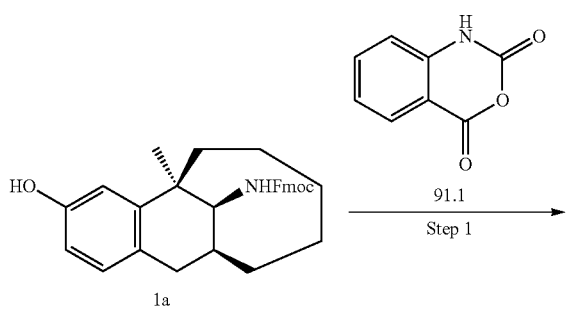

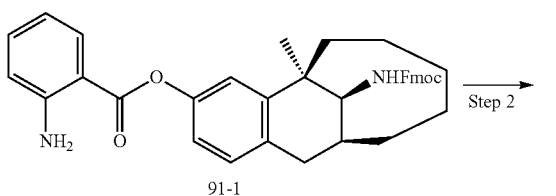

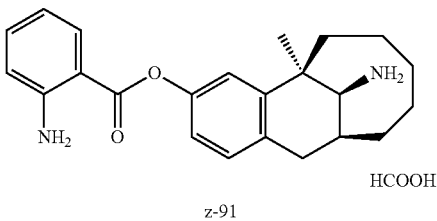

Step 1: To a solution of Compound 1a (200 mg, 0.43 mmol) in DMF (15 mL) was added Compound 91.1 (70 mg, 0.43 mmol) and DMAP (60 mg, 0.47 mmol). The system was warmed to 80° C. and stirred for 5 hours. After the reaction was complete, it was added with water, extracted with EA, washed with brine, dried and concentrated to obtain 100 mg of crude product Compound 91-1. MS m/z (ESI): N/A.

Step 2: Compound z-91 was prepared by using Compound 91-1 as a raw material and referring to the method of Step 2 of Example 1, a white solid Compound z-91 (20 mg, 12.8%) was obtained after stirring at room temperature for 6 hours. MS m/z (ESI): 365 [M+H]$^+$.

Example 92

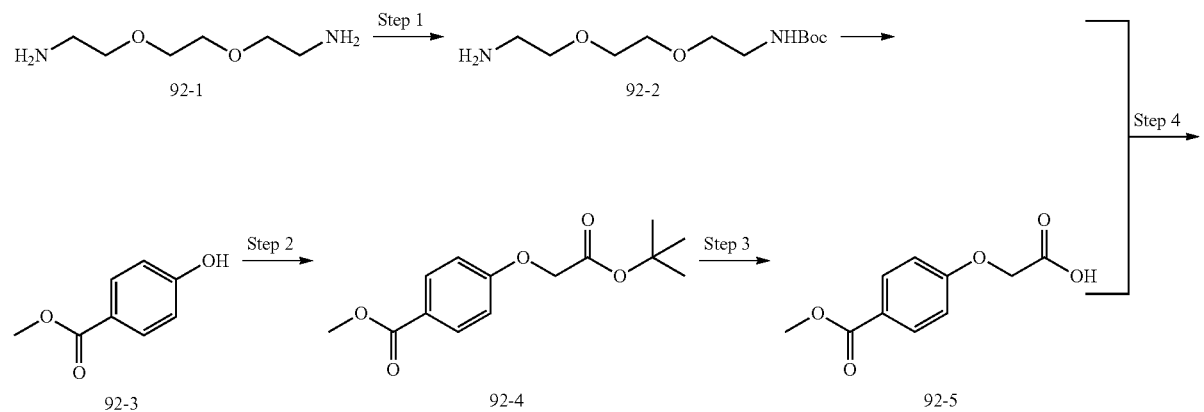

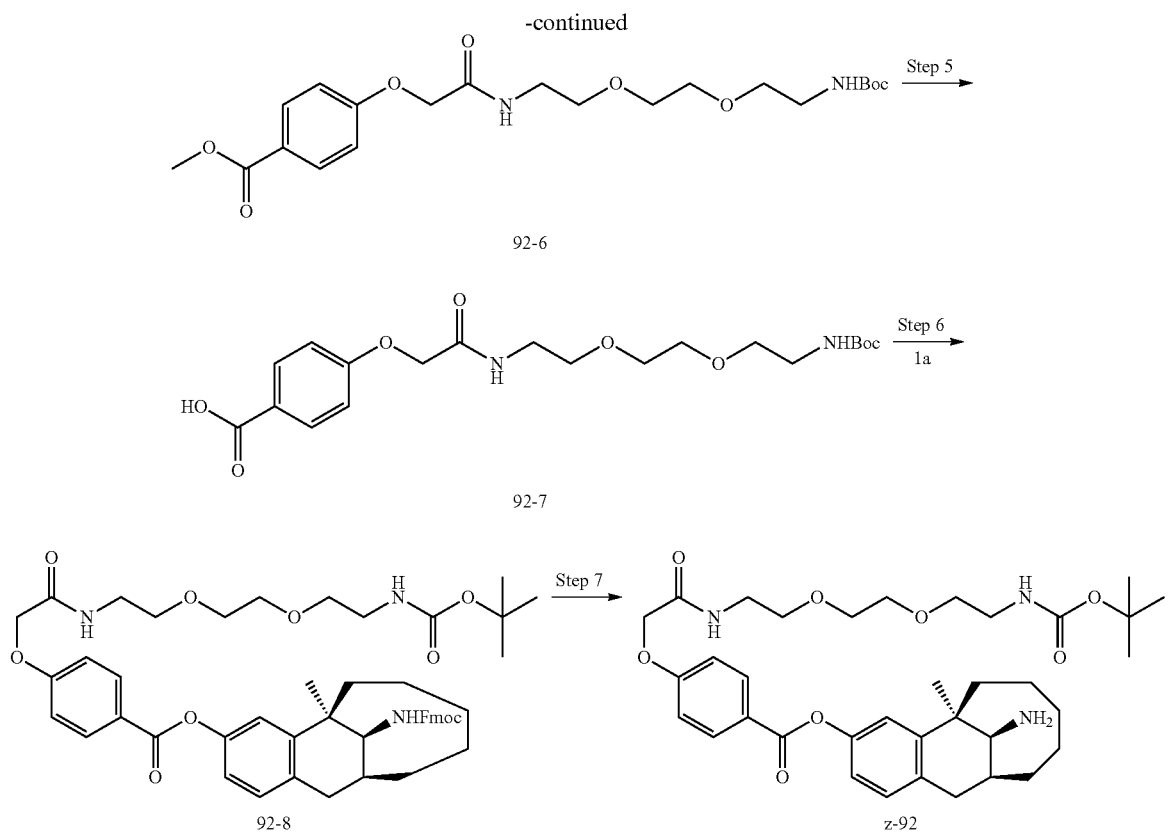

Step 1: To a 100 mL round-bottom flask, Compound 92-1 (2.05 g, 13.833 mmol), DIPEA (592 mg, 4.582 mmol) and 40 mL of dry dichloromethane were added, and Boc$_2$O (1 g, 4.582 mmol) in dichloromethane (20 mL) was added dropwise under ice-cooling. The mixture was stirred overnight at room temperature. After the reaction solution was concentrated, it was purified by combiflash (0-20% methanol/dichloromethane) to give 2 g of Compound 92-2 as a yellow oil. MS m/z (ESI): 249.2 [M+H]$^+$.

Step 2: A 100 mL round bottom flask was loaded with Compound 92-3 (810 mg, 5.32 mmol), tert-butyl bromoacetate (1.03 g, 5.31 mmol), potassium carbonate (1.13 g, 8.176 mmol) and 20 mL of acetone, and the mixture was stirred at 70° C. to 80° C. for 5 hours. The reaction was monitored by LC-MS until completion. The reaction solution was filtered and concentrated to give 1.5 g of crude product Compound 92-4 as a colorless oil. MS m/z (ESI): 267 [M+H]$^+$.

Step 3: The preparation method was the same as that of Compound 53-5, except that Compound 53-4 in the preparation method of 53-5 was replaced with Compound 92-4, and 1.25 g of solid Compound 92-5 was obtained after reacting at room temperature for 5 hours. MS m/z (ESI): 211.1 [M+H]$^+$.

Step 4: A 100 mL round bottom flask was loaded with Compound 92-2 (1.71 g, 6.89 mmol), Compound 92-5 (720 mg, 3.428 mmol), HATU (560 mg, 1.4 mmol), DIPEA (890 mg, 6.886 mmol) and 15 mL of tetrahydrofuran, and the mixture was stirred at room temperature for 1 hour. The reaction was monitored by LC-MS until completion. The reaction solution was extracted with EA/water system, after which the organic layer was separated, washed with saturated brine, dried, concentrated and purified by combiflash (0-100% EA/n-hexane) to give oily Compound 92-6 (1.37 g, 79.7%). MS m/z (ESI): 463.2 [M+Na]$^+$.

Step 5: To a 50 mL round-bottomed flask, Compound 92-6 (605 mg, 1.373 mmol), hydrated lithium hydroxide (115 mg, 2.741 mmol), 7 mL of tetrahydrofuran and 7 mL of water were added, and the mixture was stirred at room temperature for 2 days. The reaction was monitored by LC-MS until completion. The reaction solution was concentrated to remove tetrahydrofuran. The mixture was added with 30 mL of water and extracted with EA (30 mL*2). The aqueous layer was adjusted to pH 5-6 with 0.1N hydrochloric acid in an ice bath and extracted with EA (30 mL*3). The organic layer was separated, washed with saturated brine, dried and concentrated to give a white solid Compound 92-7 (350 mg, 59.8%). MS m/z (ESI): 449.2 [M+N]$^+$.

Step 6: The preparation method was the same as that of Compound 62-3, except that Compound 62-2 and 2a in the preparation method of 62-3 were replaced with Compound 92-7 and 1a. After purification by combiflash (0-80% EA/hexane), a white solid Compound 92-8 (235 mg, 62.2%) was obtained. MS m/z (ESI): 776.5 [M-Boc]$^+$.

Step 7: An oily Compound z-92 (93 mg, 60.8%) was prepared by using Compound 92-8 as a raw material and referring to the method of Step 2 of Example 1 after stirring at room temperature overnight. MS m/z (ESI): 654.5 [M+H]$^+$.

Example 93

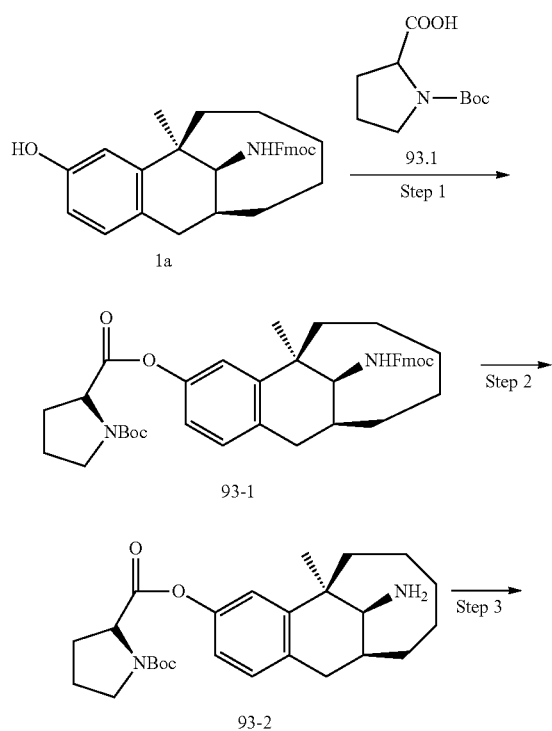

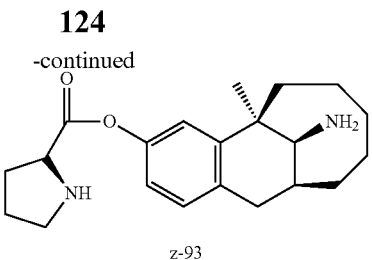

Step 1: The preparation method was the same as that of Compound 52-1, except that Compound 2a and 52.1 in the preparation method of 52-1 are replaced with Compound 1a and 93.1. 330 mg of white solid Compound 93-1 was obtained by combiflash. MS m/z (ESI): 565 [M-Boc]⁺.

Step 2: Compound 93-2 was prepared by using Compound 93-1 as a raw material and referring to the method of Step 2 of Example 1, and 200 mg of Compound 93-2 was obtained after stirring at room temperature for 3 hours and purifying by combiflash. MS m/z (ESI): 443 [M+H]⁺.

Step 3: To Compound 93-2 (200 mg, 0.452 mmol) was added 0.5 mL of hydrochloric acid/1,4-dioxane (4M) and 5 mL of dichloromethane, and the mixture was stirred at room temperature overnight. The reaction was monitored by LC-MS until completion. The reaction solution was concentrated and purified by preparative HPLC to give a white solid Compound z-93 (9.7 mg, 6.2%). MS m/z (ESI): 343.3 [M+H]⁺.

Example 94

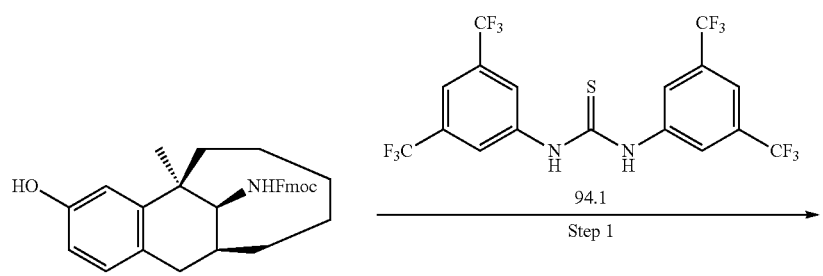

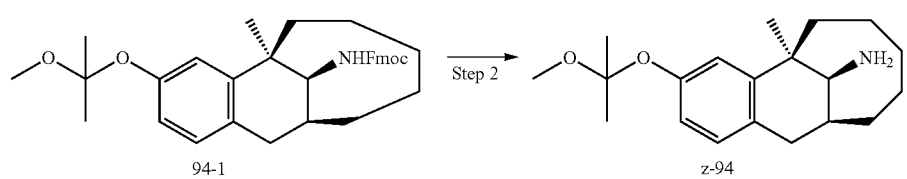

Step 1: Compound 1a (560 mg, 1.198 mmol), 3 mL of 2-methoxypropene, and a trace amount of Compound 94.1 were reacted in a sealed tube at 50° C. overnight. The reaction solution was concentrated and had the solvent was removed to give 700 mg of a crude product Compound 94-1 as a yellow oil. MS m/z (ESI): N/A.

Step 2: A yellow oily Compound z-94 (190 mg, 46.2%) was prepared by using Compound 94-1 as a raw material and referring to the method of Step 2 of Example 1 after stirring at room temperature for 5 hours. MS m/z (ESI): 318.4 [M+H]+.

Example 95

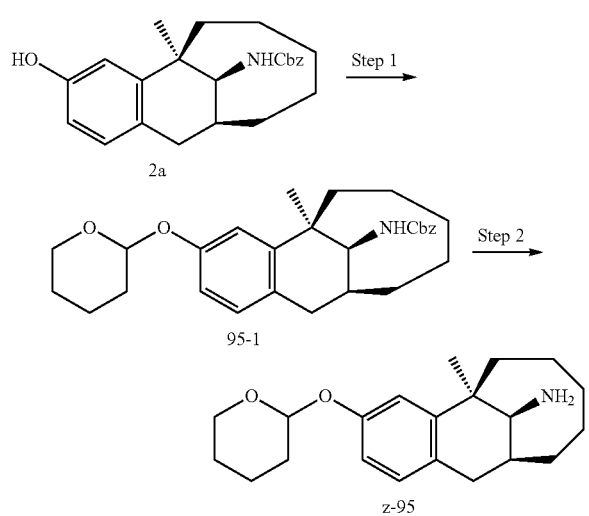

Step 1: The preparation method was the same as that of Compound 94-1, except that Compound 1a and 2-methoxypropene in the preparation method of 94-1 were replaced with Compound 2a and 3,4-dihydro-2H-pyran. The reaction solution was concentrated and purified by combiflash (0-10% EA/hexane) to give a colorless oil Compound 95-1 (515 mg, 84.3%). MS m/z (ESI): N/A.

Step 2: A colorless oil Compound z-95 (280 mg, 76.5%) was prepared by using Compound 95-1 as a raw material and referring to the method of Step 2 in Example 8. MS m/z (ESI): 330.3 [M+H]+.

Example 96

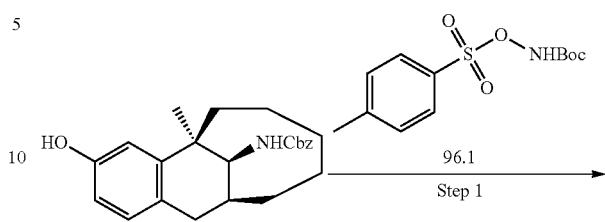

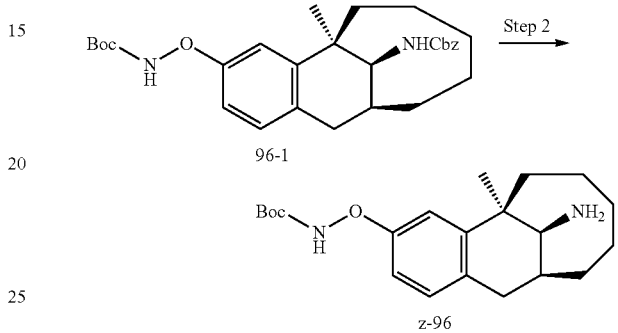

Step 1: To a 100 mL three-necked flask, Compound 2a (500 mg, 1.318 mmol) and 15 mL of tetrahydrofuran were added. After cooling in an ice/ethanol bath, LiHMDS (7 mL, 1M) was added dropwise. After stirring for 30 minutes, a solution of Compound 96.1 (1.9 g, 6.613 mmol) in tetrahydrofuran (5 mL) was added, the mixture was warmed to room temperature and stirred for 2 hours. The reaction was monitored by LC-MS until completion. The reaction was quenched by addition of water and extracted by EA, after which the organic layer was dried, concentrated, and purified by Prep-HPLC to give a white solid Compound 96-1 (143 mg, 23.4%). MS m/z (ESI): 439.3 [M-(t-Bu)]+.

Step 2: A white solid Compound z-96 (50 mg, 48.1%) was prepared by using Compound 96-1 as a raw material and referring to the method of Step 2 in Example 8. MS m/z (ESI): 361.3 [M+H]+.

Example 97

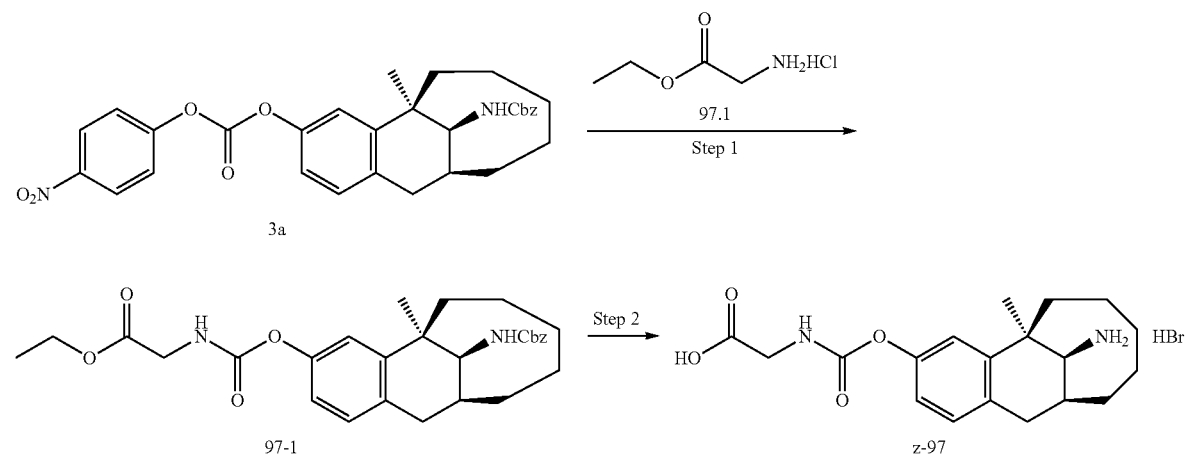

Step 1: The preparation method was the same as that of 3a, except that Compound 2a and bis(p-nitrophenyl) carbonate in the preparation method of 3a were replaced with Compound 3a and 97.1, After stirring at room temperature for 3 hours, the reaction solution was concentrated to give 370 mg of crude product of Compound 97-1 as a yellow oil. MS m/z (ESI): 509.3 [M+H]⁺.

Step 2: To a 50 mL three-necked flask, Compound 97-1 (370 mg, 0.727 mmol), 2 mL of hydrobromic acid and 4 mL of acetic acid were added, and the mixture was stirred at 50° C. for 5 hours. The reaction was monitored by LC-MS until completion. The reaction solution was concentrated and purified by preparative HPLC to give 22 mg of white solid Compound z-97. MS m/z (ESI): 347.2 [M+H]⁺; ¹H NMR (400 MHz, DMSO-d₆) δ 8.29 (s, 1H), 7.49 (m, 1H), 7.03 (d, 1H), 6.90 (d, 1H), 6.79-6.81 (dd, 1H), 4.16 (m, 2H), 3.25 (m, 1H), 3.06-3.09 (m, 1H), 2.60 (m, 1H), 2.27 (m, 1H), 1.84-1.87 (m, 1H), 1.64-1.78 (m, 3H), 1.35-1.50 (m, 3H), 1.31 (s, 3H), 1.12 (m, 1H), 0.66 (m, 2H).

Example 98

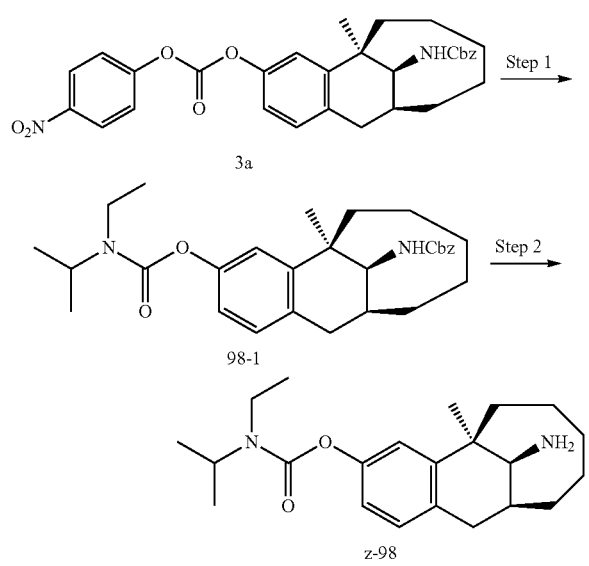

Step 1: The preparation method was the same as that of Compound 7-1, except that 2,5,8,11-tetraethylene glycol monomethyl ether-13-amine in the preparation method of 7-1 was replaced with N-ethylisopropylamine, and a colorless oil Compound 98-1 (222 mg, 82%) was obtained after stirring at room temperature for 8 hours and purifying by combiflash (0-15% EA/petroleum ether). MS m/z (ESI): 493 [M+H]⁺.

Step 2: Compound z-98 (73.4 mg, 41%) was prepared by using Compound 98-1 as a raw material and referring to the method of Step 2 in Example 8. MS m/z (ESI): 359.1 [M+H]⁺; ¹H NMR (400 MHz, DMSO-d₆) δ 7.07 (d, 1H), 6.95 (d, 1H), 6.83 (dd, 1H), 4.34-4.14 (m, 1H), 3.50-3.16 (m, 3H), 3.10 (dd, 1H), 2.66 (d, 1H), 2.29 (br. s., 1H), 1.97-1.87 (m, 1H), 1.81-1.60 (m, 3H), 1.53-1.38 (m, 3H), 1.35 (s, 3H), 1.26-1.08 (m, 10H), 0.78-0.61 (m, 2H).

Example 99

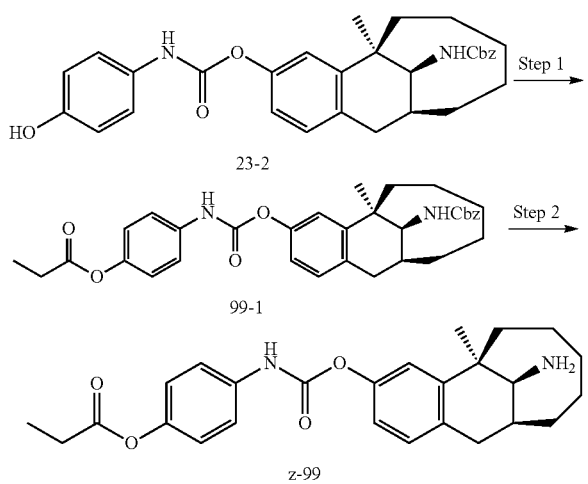

Step 1: The preparation method was the same as that of Compound 57-3, except that Compound 2a and 57-2 in the preparation method of 57-3 were replaced with Compound 23-2 and propionyl chloride, and a white solid Compound 99-1 (300 mg, 83.3%) was obtained after stirring for 1 hour in an ice bath and purifying by combiflash (0-30% EA/hexane). MS m/z (ESI): 571.0 [M+H]⁺.

Step 2: Compound z-99 (180 mg, 78.6%) was prepared by using Compound 99-1 as a raw material and referring to the method of Step 2 in Example 7. MS m/z (ESI): 437.0 [M+H]⁺; ¹H NMR (400 MHz, DMSO-d₆) δ 10.20 (s, 1H), 8.30 (s, 1H), 7.41-7.49 (m, 2H), 7.04-7.10 (m, 4H), 6.91-6.94 (m, 1H), 3.20 (m, 1H), 3.06-3.12 (m, 1H), 2.62 (m, 1H), 2.52-2.58 (m, 2H), 2.23 (m, 1H), 1.92 (m, 1H), 1.65-1.76 (m, 3H), 1.35-1.43 (m, 3H), 1.32 (s, 3H), 1.11 (m, 1H), 1.09 (t, 3H), 0.65 (m, 2H).

Example 100

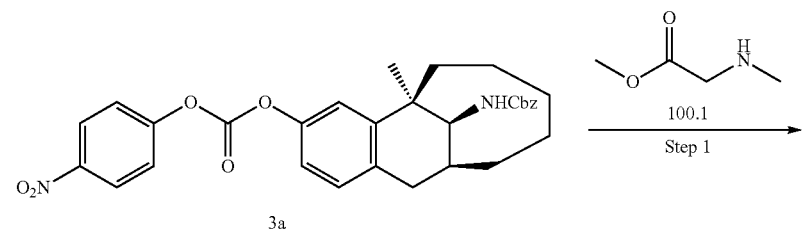

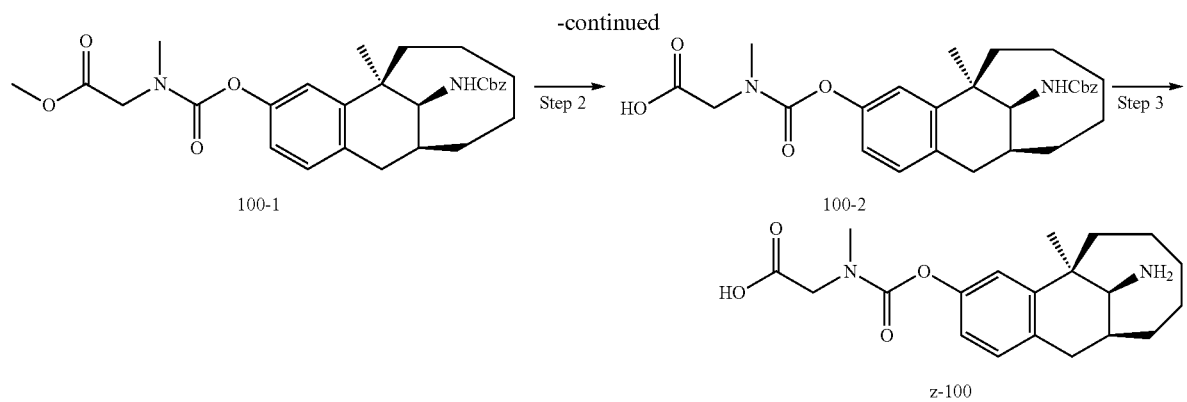

Step 1: The preparation method was the same as that of Compound 11-1, except that 2-methoxyethylamine in the preparation method of 11-1 was replaced with Compound 100.1. MS m/z (ESI): 509 [M+H]⁺.

Step 2: To a solution of Compound 100-1 (263 mg, 0.517 mmol) in 10 mL of methanol was added sodium hydroxide (2 mL, 1M) and the mixture was stirred at 40° C. for 3 hours. The reaction was monitored by LC-MS until completion. The methanol was removed, dissolved by addition of water, and adjusted to a pH of 2 with hydrochloric acid, and the mixture was filtered to obtain the cake which was Compound 100-1. MS m/z (ESI): 495.2 [M+H]⁺.

Step 3: Compound z-100 (129 mg, 78%) was prepared by using Compound 100-2 as a raw material and referring to the method of Step 2 in Example 7. MS m/z (ESI): 361.3 [M+H]⁺.

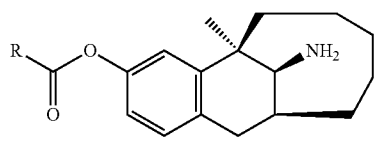

(I)

The target compounds of the examples are as shown in Formula (I), and the substituent R is shown in the following table.

General Steps:

Compounds z-101 to z-107, z-109 to z-129, z-131 to z-135, z-137, z-138, z-140 to z-144, and z-146 to z-157 are prepared by using 3a or 4a as raw materials and referring to a method similar to that of Example 7.

Compound z-108 is prepared by referring to a method similar to that of Example 54.

Compounds z-130, z-136, z-139, and z-145 are prepared by referring to a method similar with that of Example 100.

| Compound No. | R | MS [M + H]⁺ |
|---|---|---|
| z-101 | 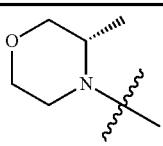 | 373 |
| z-102 | | 373 |
| z-103 | | 343 |
| z-104 | | 375 |
| z-105 | | 375 |
| z-106 | | 373 |
| z-107 | | 389 |
| z-108 | | 316 |

| Compound No. | R | MS [M + H]+ |
|---|---|---|
| z-109 | morpholine-piperidine | 442 |
| z-110 | tetrahydropyran-NH- | 373 |
| z-111 | 3-methoxyazetidine | 359 |
| z-112 | tetrahydropyran-N(Et)- | 401 |
| z-113 | Me2N-CH2CH2-N(Et)- | 388 |
| z-114 | 3-hydroxyazetidine | 345 |
| z-115 | cis-3-hydroxycyclobutyl-NH- | 359 |
| z-116 | thiomorpholine-1,1-dioxide | 407 |
| z-117 | oxetan-3-yl-NH- | 345 |
| z-118 | HOCH2CH2-NH- | 333 |

| Compound No. | R | MS [M + H]+ |
|---|---|---|
| z-119 | 5-methoxypyridin-2-yl-NH- | 396 |
| z-120 | methyl piperidine-4-carboxylate | 414 |
| z-121 | HOCH2CH2-N(Et)- | 361 |
| z-122 | 1-(hydroxymethyl)cyclopropyl-NH- | 359 |
| z-123 | 4-(dimethylamino)piperidine | 400 |
| z-124 | 4-hydroxypiperidine | 373 |
| z-125 | 4-acetylpiperazine | 400 |
| z-126 | (S)-1-hydroxypropan-2-yl-NH- | 347 |
| z-127 | HOCH2CH2-N(Me)- | 347 |
| z-128 | 4-(hydroxymethyl)piperidine | 387 |

-continued

| Compound No. | R | MS [M + H]+ |
|---|---|---|
| z-129 | 2-methylpiperazinyl | 372 |
| z-130 | piperidine-4-carboxylic acid | 401 |
| z-131 | 1-methylpiperidin-4-yl(ethyl)amino | 414 |
| z-132 | cyclopropyl(2-hydroxyethyl)amino | 373 |
| z-133 | cyclopropyl(2-methoxyethyl)amino | 387 |
| z-134 | bis(2-hydroxyethyl)amino | 377 |
| z-135 | methyl piperidine-3-carboxylate | 415 |
| z-136 | piperidine-3-carboxylic acid | 401 |
| z-137 | azetidin-1-yl | 329 |

-continued

| Compound No. | R | MS [M + H]+ |
|---|---|---|
| z-138 | 1,3-dihydroxypropan-2-ylamino | 363 |
| z-139 | proline | 387 |
| z-140 | (1-methylpiperidin-4-yl)amino | 386 |
| z-141 | oxetan-3-yl(methyl)amino | 359 |
| z-142 | oxetan-3-yl(ethyl)amino | 373 |
| z-143 | (5-hydroxypyridin-2-yl)amino | 382 |
| z-144 | 2-(dimethylamino)ethylamino | 360 |
| z-145 | 2-aminobenzoic acid | 409 |
| z-146 | (1-methylpiperidin-3-yl)(methyl)amino | 400 |
| z-147 | (5-methoxypyridin-2-yl)(methyl)amino | 410 |

-continued

| Compound No. | R | MS [M + H]+ |
|---|---|---|
| z-148 | 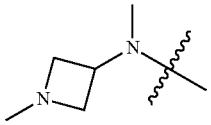 [SMILES: *N(C)C1CN(C)C1] | 372 |
| z-149 | 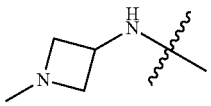 [SMILES: *NC1CN(C)C1] | 358 |
| z-150 | 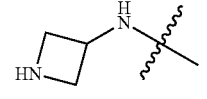 | 344 |
| z-151 | 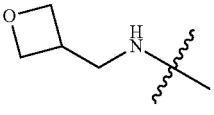 [SMILES: *NCC1COC1] | 359 |
| z-152 | 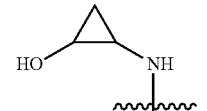 | 345 |
| z-153 | 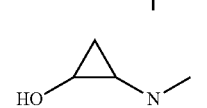 | 359 |
| z-154 | 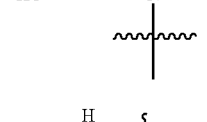 | 303 |
| z-155 |  | 359 |
| z-156 | 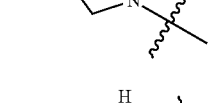 | 359 |
| z-157 | 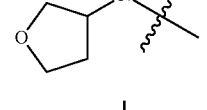 | 373 |
| z-158 | 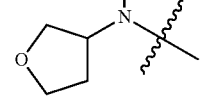 | 317 |

Assay 1: In Vivo Test of Rats

LC-MS/MS method was applied for the determination of the drug concentration in plasma at different times after the example compounds were administered via gavage to rats in order to study the pharmacokinetic behavior of the compounds of the disclosure in vivo in rats and evaluate their pharmacokinetic characteristics.

Procedures:

Test animals: healthy adult male SD rats (weight 200-300 g, 3, fasted), provided by SLAC company;

Administration and dosage: 16 mg/kg or 24 mg/kg, 10 mL/kg, 5% 1,2-propanediol (1,2-Propanediol, Shanghai Titan Technology Co., Ltd. Lot No.: P1057349)) was administered via oral gavage to SD rats;

Blood collection: firstly, the animals which were selected to meet the test requirements prior to administration were weighed and labelled. The rats were bound before the blood collection, about 150 μl of blood from each administered rat was taken at predetermined time points via orbital vein (blood was collected before administration and at 0.083, 0.25, 0.5, 1, 2, 4, 6, and 8 h after administration respectively, 9 time points in total). Blood was transferred to a 1.5 ml tube to which $K_2EDTA$ was added previously. The collected blood sample was put on wet ice, and centrifuged (2000 g, 5 min under 4° C.) to obtain plasma sample, the whole process of which was completed within 15 minutes after blood collection. All the samples were stored at approximately −70° C. until analysis.

LC/MS/MS method was applied to determine drug concentrations. At the same dose and administration, pharmacokinetic parameters of dezocine and some example compounds of the disclosure in rats are shown in Table 1 and Table 2, whereas $F_{rel}$ is the relative bioavailability, with the formula: $(AUC_{compound}/AUC_{dezocine})*100$, and mpk represents mg/kg.

TABLE 1

Pharmacokinetic parameters after oral administration of dezocine in rats (Dezocine dosed at 10 mpk)

| Compound | AUC(hr*ng/mL) |
|---|---|
| Dezocine | 58.6 |

TABLE 2

Pharmacokinetic parameters of dezocine after oral administration of test compounds in rats (Dosage is equivalent to 10 mpk of dezocine)

| Compound No. | AUC (hr*ng/mL) | $F_{rel}$(%) | Compound No. | AUC (hr*ng/mL) | $F_{rel}$(%) |
|---|---|---|---|---|---|
| z-62 | 107 | 183 | z-73 | 136 | 232 |
| z-64 | 152 | 259 | z-76 | 135 | 230 |
| z-65 | 88 | 150 | z-77 | 151 | 258 |
| z-66 | 114 | 195 | z-79 | 114 | 195 |
| z-69 | 163 | 278 | z-81 | 205 | 350 |
| z-70 | 116 | 198 | z-90 | 131 | 224 |
| z-71 | 83.4 | 142 | z-91 | 0 | 0 |
| z-94 | 90.1 | 154 | z-99 | 0 | 0 |
| z-7 | 140 | 239 | Z-12 | 220 | 375 |
| Z-14 | 99 | 169 | Z-17 | 268 | 457 |
| Z-19 | 115 | 196 | Z-26 | 109 | 186 |
| Z-32 | 132 | 225 | Z-38 | 134 | 229 |
| Z-39 | 146 | 249 | Z-40 | 222 | 379 |
| Z-49 | 133 | 227 | Z-98 | 110 | 188 |
| Z-103 | 126 | 215 | Z-113 | 150 | 256 |
| Z-114 | 92 | 157 | Z-117 | 104 | 177 |
| Z-127 | 103 | 176 | Z-137 | 140 | 239 |
| Z-150 | 0 | 0 | Z-158 | 135 | 230 |

By comparison between Table 1 and Table 2, it can be seen that, compared with the oral administration of dezocine, the compounds of the present disclosure have better pharmacokinetic properties greatly improved relative bioavailability, prolonged drug effect time by more than 2 times, reduced dosage and dosing frequency, and smaller side effects. In addition, the compound structure of the present disclosure has great influence on the pharmacokinetic properties, and the relative bioavailability is greatly reduced when the group attached to nitrogen is phenyl or pyridinyl.

Assay 2: Inhibition of hERG Potassium Ion Channel 2.1 Cell Culture 2.1.1 Cells used in this experiment were CHO cell lines transfected with hERG cDNA and stably expressing hERG channels (supplied by Sophion Bioscience, Denmark), with cell progeny being P15. Cells were cultured in medium containing the following ingredients Invitrogen): Ham's F12 medium, 10% (v/v) inactivated fetal bovine serum, 100 μl/ml hygromycin B, and 100 μl/ml Geneticin.

2.1.2 CHO hERG cells were grown in Petri dishes containing the above medium and cultured in an incubator of 5% $CO_2$ at 37° C. CHO hERG cells were transferred onto round glass plates in Petri dishes and grown on the same culture medium and culture conditions as above 24 h to 48 h prior to the electrophysiological experiments. The density of CHO hERG cells on each round glass plate must meet the requirements that the vast majority of cells are independent and separate.

2.2 Experimental Solution

The following solutions (recommended by Sophion) were used for electrophysiological recording. The reagents used in this test were provided by Sigma.

TABLE 3

Intracellular and extracellular fluid composition

| Reagents | Extracellular fluid (mM) | Intracellular fluid (mM) |
|---|---|---|
| $CaCl_2$ | 2 | 5.37 |
| $MgCl_2$ | 1 | 1.75 |
| KCl | 4 | 120 |
| NaCl | 145 | — |
| Glucose | 10 | — |
| HEPES | 10 | 10 |
| EGTA | — | 5 |
| Na-ATP | — | 4 |
| PH | 7.4 (adjusted with NaOH) | 7.25 (adjusted with KOH) |
| Osmotic pressure | Osmotic pressure ~305 mOsm | Osmotic pressure ~295 mOsm |

2.3 Electrophysiological Recording System

In this experiment, whole-cell current recording was performed using a manual patch clamp system (HEKA EPC-10 signal amplification and digital conversion system, purchased from HEKA Electronic, Germany). The round glass slide of which surface CHO hERG cells were grown on was placed in an electrophysiological recording slot under an inverted microscope. Extracellular fluid was perfused continuously in the recording slot (approximately 1 ml per minute). Conventional whole-cell patch clamp current recording technique was used in the experiment. Unless otherwise specified, the experiments were performed at normal room temperature (25° C.). Cell patch clamp at −80 mV. Cell patch clamp voltage was depolarized to +20 mV to activate hERG potassium channel, and to −50 mV after 5 sec to eliminate inactivation and generate tail currents. The tail current peak was used as a value for hERG current. When the hERG potassium current recorded in the above steps became steady under continuous perfusion of the extracellular fluid in the recording slot, the subject drug to be tested could be added to the perfusion until the inhibition of the hERG current by the drug reached a steady state. Typically, the most recent three consecutive current recording lines were generally used as a measure to determine whether the state was stable. After reaching a steady state, it was perfused with extracellular fluid for washing until the hERG current returned to the value before the drug adding. One or more drugs, or multiple concentrations of the same drug, could be tested on a single cell but it was necessary to rinse with extracellular fluid before testing a different drug. Cisapride (purchased from Sigma) was used as a positive control in the experiments to ensure normal quality of the cells used.

2.4 Treatment and Dilution of Compounds

The compound was first dissolved in DMSO to a concentration of 10 mM and then the compound was diluted 1000-fold to a final test concentration of 10 μM using extracellular fluid.

The final concentration of DMSO in the compound test solution was 0.1%. The test concentration of cisapride as a positive control was 0.1 μM. All stock solutions and test solutions were subjected to regular 5-10 minutes of sonication and shaking to ensure complete dissolution of the compound.

2.5 Data Analysis

The test data were analyzed by the data analysis software provided by HEKA Patchmaster (V2x73.2), Microsoft Excel and Graphpad Prism 5.0.

TABLE 4

Inhibition of hERG potassium ion channels by exemplary compounds of the disclosure

| Compound No. | hERG inhibition rate/10 μM | Compound No. | hERG inhibition rate/10 μM |
|---|---|---|---|
| Z-49 | 14.39% | Z-109 | 17.20% |
| Z-110 | 13.32% | Z-113 | 16.02% |
| Z-114 | 17.07% | Z-115 | 12.90% |
| Z-116 | 11.22% | Z-117 | 20.59% |
| Z-121 | 21.22% | Z-122 | 1.91% |
| Z-123 | 8.84% | Z-126 | 4.92% |
| Z-127 | 9.95% | Z-130 | 3.24% |
| Z-131 | 39.88% | Z-158 | 15.31% |
| Z-23 | 71.45% | Z-119 | 78% |

It can be seen from Table 4 that the exemplary compounds of the present disclosure had little inhibitory activity on the hERG potassium ion channel and thus a selective inhibitory effect on the potassium ion channel. In addition, the structures of the compounds of the present disclosure had a great influence on the inhibition of hERG. The inhibitory activity of hERG potassium ion channel was greatly enhanced when the linking group was phenyl or pyridinyl.

Assay 3: Inhibition of CYP Enzyme 1. 0.1 M potassium phosphate buffer (K-buffer), pH 7.4 was preheated;

100 mM K-Buffer: 9.5 mL Stock A and 40.5 mL Stock B were mixed, brought to a total volume of 500 mL with Milli-Q water, and titrated to pH 7.4 of KOH or $H_3PO_4$;

Stock A (1 M monobasic potassium phosphate): 136.5 g of monobasic potassium phosphate was dissolved in 1 L of Milli-Q water; and Stock B (1 M dibasic potassium phosphate): 174.2 g of dibasic potassium phosphate was dissolved in 1 L of Milli-Q water.

2. Serial dilutions of test compounds and reference inhibitors (400×) were prepared in a 96-well plate:

2.1 8 μL of 10 mM test compounds was transferred to 12 μL of ACN. 2.2 A separate inhibitor solution was prepared for reference: 8 μL of inhibitor DMSO stock was added with 12 μL of ACN.

2.3 A 1:3 serial dilution was prepared with a DMSO:ACN mixture (v/v: 40:60).

3. 4×NADPH cofactor (66.7 mg NADPH dissolved in 10 mL 0.1 M K-buffer, pH 7.4) was prepared.

4. 4× substrate (2 mL for each isoform) was prepared as indicated in the table below (Liver microsomes must be added on ice).

5. 0.2 mg/mL liver microsome solution (990 μL of 0.1 M K-buffer was added to each 10 μL of 20 mg/mL) was prepared on ice.

6. 200 μL of 0.2 mg/mL liver microsomes was added on ice to a 96-well plate and then 1 μL of test compound or reference compound was added into corresponding wells.

7. The following solutions were added to a 96-well plate (in duplicate) on ice:

7.1 30 μL of 2× test compounds and reference compound in 0.2 mg/mL liver microsome solution were added;

7.2 15 μL of 4× substrate solution was added.

8. The 96-well assay plate and NADPH solution were pre-heated at 37° C. for 5 minutes.

9. 15 μL of pre-heated 8 mM NADPH solution was added into the assay plates to initiate the reaction.

10. The 3A4 subtype was incubated at 37° C. for 5 min for.

11. The reaction was quenched by adding 120 μL of ACN containing an internal standard.

12. After quenching, the plates were shaked in a vibrator (IKA, MTS 2/4) for 5 min (600 rpm/min) and then centrifuged at 3, 750 rpm for 15 min (Allegra X-12R centrifuge).

13. After centrifugation, 50 μL of the supernatant from each well was taken into a 96-well plate containing 70 μL of wastons water and mixed for LC/MS analysis.

TABLE 5

Assay System for CYP3A4 inhibition

| CYP | Probe Substrate | Stock Conc. | Final Conc. (μM) | CYP | Selective Inhibitors | Stock Conc. | Final Highest Conc. (μM) | Liver Microsome Conc. (mg/mL) |
|---|---|---|---|---|---|---|---|---|
| 3A4 | 1 mM Midazolam (abbreviated as M) in ACN | 5 | | 3A4 | Ketoconazole | 2.5 mM in DMSO | 2.5 | 0.1 |

TABLE 6

Preparation methods for three types of subtype 3A4

| CYP | 2 mL | 1 mL | 500 uL |
|---|---|---|---|
| 3A4 | 20 μM in K-buffer: substrate (40 μL) + K-buffer(1960 μL) | 20 uM in K-buffer: substrate (20 μL) + K-buffer(980 μL) | 20 uM in K-buffer: substrate (10 μL) + K-buffer(490 μL) |

TABLE 7

Inhibitory effect of exemplary compounds of the disclosure on CYP3A4

| Compound No. | CYP3A4(M) inhibition rate/1 μM | Compound No. | CYP3A4(M) inhibition rate/1 μM |
|---|---|---|---|
| Z-2 | 19.8% | Z-14 | 49.5% |
| Z-19 | 33.6% | Z-49 | 7.28% |

TABLE 7-continued

Inhibitory effect of exemplary compounds of the disclosure on CYP3A4

| Compound No. | CYP3A4(M) inhibition rate/1 μM | Compound No. | CYP3A4(M) inhibition rate/1 μM |
|---|---|---|---|
| Z-100 | 1.6% | Z-109 | 6.6% |
| Z-110 | 28.0% | Z-111 | 45.7% |
| Z-113 | 28.6% | Z-114 | 11.8% |
| Z-115 | 18.0% | Z-116 | 14.2% |
| Z-117 | 23.8% | Z-118 | 8.8% |
| Z-121 | 38.7% | Z-122 | 17.0% |
| Z-123 | 0% | Z-124 | 19.6% |
| Z-125 | 18.1% | Z-126 | 3.6% |
| Z-127 | 17.4% | Z-128 | 41.9% |
| Z-129 | 4.0% | Z-130 | 13.0% |
| Z-131 | 26.7% | Z-134 | 4.8% |
| Z-135 | 21.3% | Z-136 | 0% |
| Z-137 | 45.3% | Z-138 | 0% |
| Z-140 | 8.7% | Z-141 | 30.8% |
| Z-144 | 22.2% | Z-146 | 3.1% |
| Z-147 | 77.7% | Z-35 | 88.1% |
| Z-23 | 89.2% | | |

It can be seen from Table 7 that the exemplary compounds of the present disclosure had little inhibitory activity on CYP3A4, while the structures of the compounds of the present disclosure had relatively great influence on the inhibition of CYP3A4. When the group attached to nitrogen was phenyl or pyridinyl, the inhibitory activity on CYP3A4 was greatly increased.

All publications mentioned herein are incorporated by reference as if each individual document was cited as a reference, as in the present application. It should also be understood that, after reading the above teachings of the present disclosure, those skilled in the art can make various changes or modifications, equivalents of which falls in the scope of claims as defined in the appended claims.

What is claimed is:

1. A compound of Formula (I), or a pharmaceutically acceptable salt, solvate, or stereoisomer thereof:

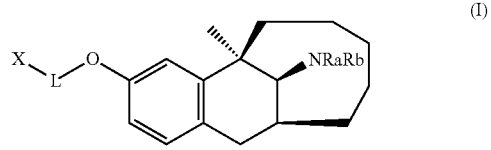

(I)

wherein,

L is —CO— or —$(C(R_4R_5)_2)_k$—; k is 1, 2 or 3;

X is —$N(R_1R_2)$, —$OR_3$ or —$CH_2O$—$((CH_2)_r$—$O)_t$—$CH_3$; r is 2, 3 or 4; t is 1, 2, 3, 4, 5, 6, 7, 8 or 9;

$R_a$ and $R_b$ are each independently hydrogen, methyl, —CHO, —$C(O)OC_{1-10}$ alkyl or —$C(O)C_{1-10}$ alkyl;

$R_4$ and $R_5$ are each independently hydrogen or methyl;

$R_1$ and $R_2$ are each independently hydrogen, $C_{1-10}$ alkyl, $C_{3-8}$ cycloalkyl, $C_{6-10}$ aryl, 5 to 6 membered single heteroaryl ring, 4 to 6 membered saturated single heterocycle, spiro, spiroheterocycle, bridged ring, bridged heterocycle or —((CH$_2$)$_n$—O)$_m$—CH$_3$; wherein n is 2, 3 or 4; m is 1, 2, 3, 4, 5, 6, 7, 8 or 9;

or $R_1$ and $R_2$, together with the nitrogen atom to which they are attached, form a 4 to 6 membered saturated single heterocycle;

$R_3$ is $C_{1-10}$ alkyl, $C_{3-8}$ cycloalkyl, —((CH$_2$)$_p$—O)$_q$—CH$_3$, —C(O)O—((CH$_2$)$_p$—O)$_q$—CH$_3$, —C(O)OC$_{1-10}$ alkyl, —C(O)OC$_{3-8}$ cycloalkyl, —C(O)C$_{1-10}$ alkyl; wherein p is 2, 3 or 4; q is 1, 2, 3 or 4; and the alkyl, cycloalkyl, alkoxy, alkynyl, aryl, 4 to 6 membered saturated single heterocycle, 5 to 6 membered single heteroaryl ring, spiro, spiroheterocycle, bridged ring, and bridged heterocycle are unsubstituted or substituted with 1, 2 or 3 substituents selected from the group consisting of NR$_{a0}$R$_{b0}$, halogen, acetyl, hydroxy, hydroxymethyl, hydroxyethyl, carboxyl, $C_{1-8}$ alkyl, $C_{1-8}$ alkoxy, halogenated $C_{1-8}$ alkyl, $C_{3-8}$ cycloalkyl, $C_{3-8}$ cycloalkoxy, $C_{2-10}$ alkenyl, $C_{2-10}$ alkynyl, halogenated $C_{1-8}$ alkoxy, $C_{6-10}$ aryl, 4 to 6 membered saturated single heterocycle, —C(O)C$_{1-10}$ alkyl, —C(O)OC$_{1-10}$ alkyl, —OC(O)C$_{1-10}$ alkyl, —CONR$_{a0}$R$_{b0}$; and, R$_{a0}$ and R$_{b0}$ are each independently hydrogen, $C_{1-8}$ alkyl, and $C_{1-8}$ alkyl substituted with $C_{1-8}$ alkoxy.

2. The compound or a pharmaceutically acceptable salt, solvate, or stereoisomer thereof of claim 1, wherein R$_a$ and R$_b$ are hydrogen.

3. The compound or a pharmaceutically acceptable salt, solvate, or stereoisomer thereof of claim 1, wherein $R_1$ is hydrogen, $C_{1-10}$ alkyl, $C_{3-8}$ cycloalkyl or —((CH$_2$)$_{n1}$—O)$_{m1}$—CH$_3$;

$R_2$ is $C_{1-10}$ alkyl, $C_{3-8}$ cycloalkyl, $C_{6-10}$ aryl, 5 to 6 membered single heteroaryl ring, 4 to 6 membered saturated single heterocycle, spiro, spiroheterocycle, bridged ring, bridged heterocycle or —((CH$_2$)$_{n2}$—O)$_{m2}$—CH$_3$; wherein n1 and n2 are each independently 2, 3 or 4; and, m1 and m2 are each independently 1, 2, 3, 4, 5, 6, 7, 8 or 9;

or $R_1$ and $R_2$, together with the nitrogen atom to which they are attached, form a 4 to 6 membered saturated single heterocycle; and the alkyl, cycloalkyl, aryl, 4 to 6 membered saturated single heterocycle, 5 to 6 membered single heteroaryl ring, spiro, spiroheterocycle, bridged ring, and bridged heterocycle are unsubstituted or substituted with 1, 2 or 3 substituents selected from the group consisting of NR$_{a0}$R$_{b0}$, halogen, acetyl, hydroxy, hydroxymethyl, hydroxyethyl, carboxyl, $C_{1-8}$ alkyl, $C_{1-8}$ alkoxy, halogenated $C_{1-8}$ alkyl, $C_{3-8}$ cycloalkyl, $C_{3-8}$ cycloalkoxy, $C_{2-10}$ alkenyl, $C_{2-10}$ alkynyl, halogenated $C_{1-8}$ alkoxy, $C_{6-10}$ aryl, 4 to 6 membered saturated single heterocycle, —C(O)C$_{1-10}$ alkyl, —C(O)OC$_{1-10}$ alkyl, —OC(O)C$_{1-10}$ alkyl, and —CONR$_{a0}$R$_{b0}$; and, R$_{a0}$ and R$_{b0}$ are each independently hydrogen, $C_{1-8}$ alkyl, and $C_{1-8}$ alkyl substituted with $C_{1-8}$ alkoxy.

4. The compound or a pharmaceutically acceptable salt, solvate, or stereoisomer thereof of claim 1, wherein $R_1$ and $R_2$ are each independently hydrogen, $C_{1-10}$ alkyl, and $C_{3-8}$ cycloalkyl; and the alkyl or cycloalkyl is unsubstituted or substituted with 1, 2 or 3 substituents selected from the group consisting of NR$_{a0}$R$_{b0}$, hydroxy, hydroxymethyl, carboxyl, $C_{2-10}$ alkenyl, $C_{1-8}$ alkoxy, 4 to 6 membered saturated single heterocycle, and —C(O)OC$_{1-10}$ alkyl; and, R$_{a0}$ and R$_{b0}$ are each independently hydrogen, $C_{1-8}$ alkyl, and $C_{1-8}$ alkyl substituted with $C_{1-8}$ alkoxy.

5. The compound or a pharmaceutically acceptable salt, solvate, or stereoisomer thereof of claim 1, wherein $R_1$ is hydrogen, $C_{1-10}$ alkyl or $C_{3-8}$ cycloalkyl; $R_2$ is —CH(R$_{11}$)—C(O)OC$_{1-10}$ alkyl or —CH(R$_{11}$)—C(O)OH; and, R$_{11}$ is hydrogen or $C_{1-3}$ alkyl.

6. The compound or a pharmaceutically acceptable salt, solvate, or stereoisomer thereof of claim 1, wherein $R_1$ is hydrogen, $C_{1-10}$ alkyl, $C_{3-8}$ cycloalkyl or —((CH$_2$)$_{n1}$—O)$_{m1}$—CH$_3$; $R_2$ is —((CH$_2$)$_{n2}$—O)$_{m2}$—CH$_3$; wherein n1 and n2 are each independently 2, 3 or 4; and, m1 and m2 are each independently 1, 2, 3, 4, 5, 6, 7, 8 or 9.

7. The compound or a pharmaceutically acceptable salt, solvate, or stereoisomer thereof of claim 1, wherein $R_1$ is hydrogen, $C_{1-10}$ alkyl or $C_{3-8}$ cycloalkyl; $R_2$ is $C_{6-10}$ aryl;

the aryl is unsubstituted or substituted with 1, 2 or 3 substituents selected from the group consisting of halogen, hydroxy, carboxyl, $C_{1-8}$ alkyl, $C_{1-8}$ alkoxy, —OC(O)C$_{1-10}$ alkyl, —CONR$_{a0}$R$_{b0}$; R$_{a0}$, R$_{b0}$ are each independently hydrogen, $C_{1-8}$ alkyl, and $C_{1-8}$ alkyl substituted with $C_{1-8}$ alkoxy; and the cycloalkyl is unsubstituted or substituted with one substituent selected from the group consisting of hydroxy and hydroxymethyl.

8. The compound or a pharmaceutically acceptable salt, solvate, or stereoisomer thereof of claim 1, wherein $R_1$ is hydrogen, $C_{1-10}$ alkyl or $C_{3-8}$ cycloalkyl; and $R_2$ is 5 to 6 membered single heteroaryl ring; and the 5 to 6 membered single heteroaryl ring is unsubstituted or substituted with 1, 2 or 3 substituents selected from the group consisting of halogen, hydroxy, carboxyl, $C_{1-8}$ alkyl, $C_{1-8}$ alkoxy, —OC(O)C$_{1-10}$ alkyl, and —CONR$_{a0}$R$_{b0}$; and, R$_{a0}$ and R$_{b0}$ are each independently hydrogen, $C_{1-8}$ alkyl, and $C_{1-8}$ alkyl substituted with $C_{1-8}$ alkoxy.

9. The compound or a pharmaceutically acceptable salt, solvate, or stereoisomer thereof of claim 1, wherein $R_1$ is hydrogen, $C_{1-10}$ alkyl or $C_{3-8}$ cycloalkyl; and $R_2$ is 4 to 6 membered saturated single heterocycle; and the 4 to 6 membered saturated single heterocycle is unsubstituted or substituted with 1, 2 or 3 substituents selected from the group consisting of NR$_{a0}$R$_{b0}$, acetyl, hydroxy, hydroxymethyl, hydroxyethyl, carboxyl, $C_{1-8}$ alkyl, $C_{1-8}$ alkoxy, $C_{6-10}$ aryl, 4 to 6 membered saturated single heterocycle, —C(O)C$_{1-10}$ alkyl, —C(O)OC$_{1-10}$ alkyl; and, R$_{a0}$ and R$_{b0}$ are each independently hydrogen, $C_{1-8}$ alkyl, and $C_{1-8}$ alkyl substituted with $C_{1-8}$ alkoxy.

10. The compound or a pharmaceutically acceptable salt, solvate, or stereoisomer thereof of claim 1, wherein $R_1$ and $R_2$, together with the nitrogen atom to which they are attached, form a 4 to 6 membered nitrogen-containing saturated single heterocycle; and the 4 to 6 membered nitrogen-containing saturated single heterocycle is unsubstituted or substituted with 1, 2 or 3 substituents selected from the group consisting of NR$_{a0}$R$_{b0}$, acetyl, hydroxy, hydroxymethyl, carboxyl, $C_{1-8}$ alkyl, $C_{1-8}$ alkoxy, $C_{6-10}$ aryl, 4 to 6 membered saturated single heterocycle, —C(O)C$_{1-10}$ alkyl, and —C(O)OC$_{1-10}$ alkyl; R$_{a0}$ and R$_{b0}$ are each independently hydrogen, $C_{1-8}$ alkyl, and $C_{1-8}$ alkyl substituted with $C_{1-8}$ alkoxy.

11. The compound or a pharmaceutically acceptable salt, solvate, or stereoisomer thereof of claim 1, wherein $R_1$ is hydrogen, $C_{1-10}$ alkyl or $C_{3-8}$ cycloalkyl; and, $R_2$ is spiro, spiroheterocycle, bridged ring or bridged heterocycle.

12. The compound or a pharmaceutically acceptable salt, solvate, or stereoisomer thereof of claim 1, wherein L is —CO—; X is —N(R$_1$R$_2$), —OR$_3$ or —CH$_2$O—((CH$_2$)—O)$_r$—CH$_3$; and, r, t, R$_1$, R$_2$, and R$_3$ are as defined in claim 1.

13. The compound or a pharmaceutically acceptable salt, solvate, or stereoisomer thereof of claim 1, wherein L is —CO—; X is —N(R$_1$R$_2$); and, R$_1$ and R$_2$ are as defined in claim 1.

14. The compound or a pharmaceutically acceptable salt, solvate, or stereoisomer thereof of claim 1, wherein L is —CO—; X is —OR$_3$ or —CH$_2$O—((CH$_2$)$_r$—O)$_t$—CH$_3$; and, r, t, and R$_3$ are as defined in claim 1.

15. The compound or a pharmaceutically acceptable salt, solvate, or stereoisomer thereof of claim 1, wherein L is —(C(R$_4$R$_5$)$_2$)$_k$—; X is —OR$_3$; and, k, R$_3$, R$_4$, and R$_5$ are as defined in claim 1.

16. The compound or a pharmaceutically acceptable salt, solvate, or stereoisomer thereof of claim 1, the compound of Formula (I) is selected from the group consisting of:

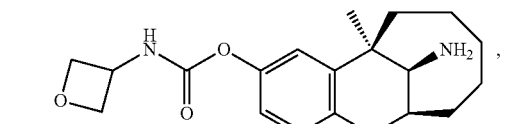,

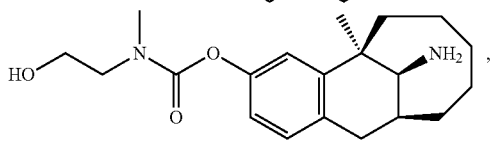,

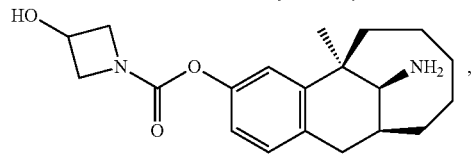,

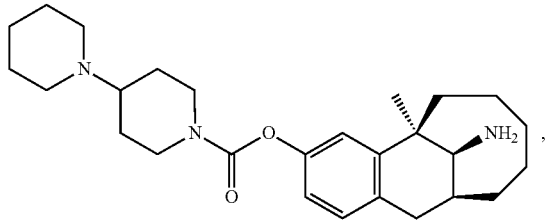,

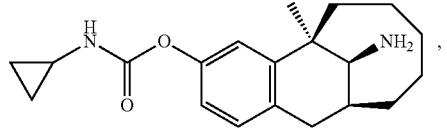,

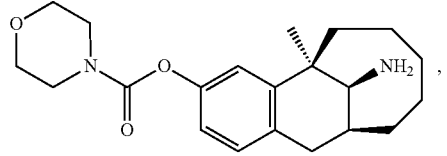,

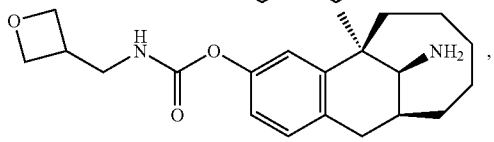,

-continued

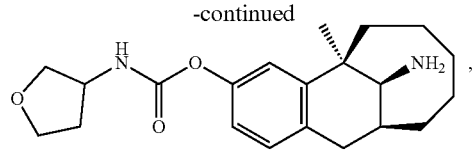,

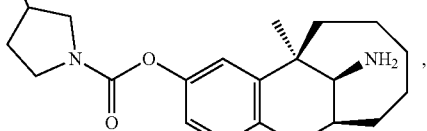,

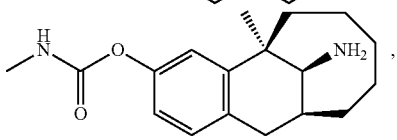,

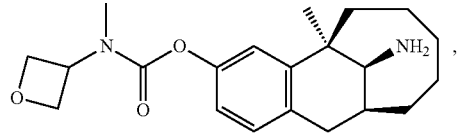,

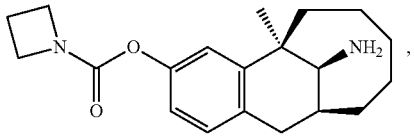,

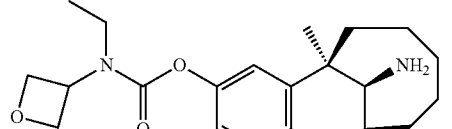,

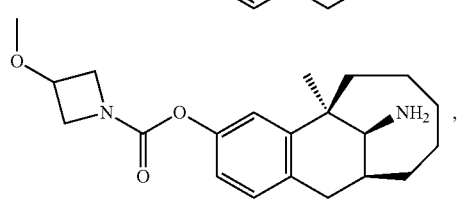, and

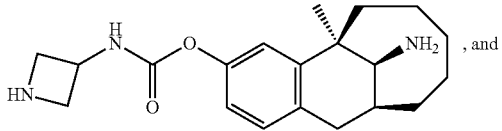

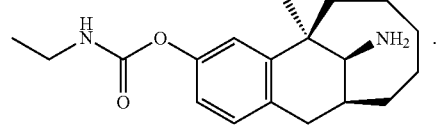.

17. A pharmaceutical composition, comprising the compound or a pharmaceutically acceptable salt, solvate, or stereoisomer thereof of claim 1; and a pharmaceutically acceptable carrier.

18. A method for treating pain, comprising: administering to a subject in need a therapeutically effective amount of the compound or a pharmaceutically acceptable salt, solvate, or stereoisomer thereof of claim 1.

19. A method for treating pain, comprising: administering to a subject in need a therapeutically effective amount of the pharmaceutical composition of claim 17.

* * * * *